US008614332B2

(12) United States Patent
Ryono et al.

(10) Patent No.: US 8,614,332 B2
(45) Date of Patent: *Dec. 24, 2013

(54) SUBSTITUTED PYRAZOLYLAMIDES USEFUL AS GLUCOKINASE ACTIVATORS

(75) Inventors: Denis E. Ryono, Minneapolis, MN (US); Peter T. W. Cheng, Princeton, NJ (US); Scott A. Bolton, Newtown, PA (US); Sean Chen, Princeton, NJ (US); Yan Shi, Flourtown, PA (US); Wei Meng, Pennington, NJ (US); Joseph A. Tino, Lawrenceville, NJ (US); Richard B. Sulsky, West Trenton, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/397,123

(22) Filed: Feb. 15, 2012

(65) Prior Publication Data
US 2012/0142636 A1   Jun. 7, 2012

Related U.S. Application Data

(63) Continuation of application No. 13/012,351, filed on Jan. 24, 2011, now Pat. No. 8,153,677, which is a continuation of application No. 11/769,964, filed on Jun. 28, 2007, now Pat. No. 7,910,747.

(60) Provisional application No. 60/818,912, filed on Jul. 6, 2006.

(51) Int. Cl.
C07D 231/00   (2006.01)

(52) U.S. Cl.
USPC .......... 548/375.1; 544/408; 548/953

(58) Field of Classification Search
USPC ............... 544/408; 548/375.1, 953
See application file for complete search history.

(56) References Cited

U.S. PATENT DOCUMENTS

| | | | |
|---|---|---|---|
| 6,320,050 B1 | 11/2001 | Bizzarro et al. | |
| 2006/0135578 A1 | 6/2006 | Momose et al. | |
| 2008/0009465 A1* | 1/2008 | Ryono et al. | 514/85 |

FOREIGN PATENT DOCUMENTS

| | | |
|---|---|---|
| EP | 1 074 556 A1 | 7/2001 |
| WO | WO 00/58293 | 10/2000 |
| WO | WO 02/08209 | 1/2002 |
| WO | WO 02/46173 | 6/2002 |
| WO | WO 03/015774 | 2/2003 |
| WO | WO 03/095438 | 11/2003 |
| WO | WO 2004/063194 | 7/2004 |
| WO | WO 2004/072031 | 8/2004 |
| WO | WO 2004/072066 | 8/2004 |
| WO | WO2004/013139 A2 | 12/2004 |
| WO | WO 2005/028488 | 3/2005 |
| WO | WO 2005/044801 | 5/2005 |
| WO | WO 2005/054200 | 6/2005 |
| WO | WO 2005/056530 | 6/2005 |
| WO | WO 2005/080359 | 9/2005 |
| WO | WO 2005/080360 | 9/2005 |
| WO | WO 2005/103021 | 11/2005 |
| WO | WO 2005/121110 | 12/2005 |
| WO | WO 2006/016174 | 2/2006 |
| WO | WO 2006/016178 | 2/2006 |
| WO | WO 2006/016194 | 2/2006 |
| WO | WO 2006/040528 | 4/2006 |
| WO | WO 2006/040529 | 4/2006 |
| WO | WO 2006/058923 | 6/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/060448 | 5/2007 |

OTHER PUBLICATIONS

Hackam, et al. JAMA, 296(14), 2006, 1731-1732.*
Sarabu, R. Expert Opinion: Therapeutic Patents, 18(7), 2008, 759-768.*
Fyfe, M. C. T. et al., "Glucokinase activator PSN-GK1 displays enhanced antihyperglycaemic and insulinotropic actions", Diabetologia, 50(6), pp. 1277-1287, (2007).
Guertin, K.R. et al., "Small molecule glucokinase activators as glucose lowering agents: A new paradigm for diabetes therapy", Current Medicinal Chemistry, 13(15), pp. 1839-1843, (2006).

(Continued)

Primary Examiner — Douglas M Willis
(74) Attorney, Agent, or Firm — Burton Rodney

(57) ABSTRACT

Compounds are provided which are phosphonate and phosphinate activators and thus are useful in treating diabetes and related diseases and have the structure

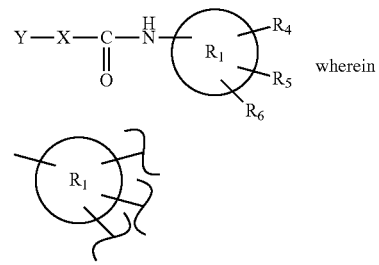

wherein is a heteroaryl ring;
$R_4$ is —$(CH_2)_n$—Z—$(CH_2)_m$—PO(OR$_7$)(OR$_8$),
—$(CH_2)_n$Z—$(CH_2)_m$—PO(OR$_7$)R$_9$,
—$(CH_2)_n$—Z—$(CH_2)_m$—OPO(OR$_7$)R$_9$,
—$(CH_2)_n$Z—$(CH_2)_m$—OPO(R$_9$)(R$_{10}$), or
—$(CH_2)_n$Z—$(CH_2)_m$—PO(R$_9$)(R$_{10}$);
$R_5$ and $R_6$ are independently selected from H, alkyl and halogen;
Y is $R_7(CH_2)_s$ or is absent; and
X, n, Z, m, $R_4$, $R_5$, $R_6$, $R_7$, and s are as defined herein;
or a pharmaceutically acceptable salt thereof.
A method for treating diabetes and related diseases employing the above compounds is also provided.

18 Claims, No Drawings

(56) References Cited

OTHER PUBLICATIONS

Johnson, D. et al., "Glucose-dependent Modulation of Insulin Secretion and Intracellular Calcium Ions by GKA50—a Glucokinase Activator", Diabetes, 56, pp. 1694-1702 (2007).

McKerrecher, D. et al., "Design of a potent, soluble glucokinase activator with excellent in vivo efficacy", Bioorg. Med. Chem. Lett., 16, pp. 2705-2709 2006).

Sarabu, R. et al., "Targeting glucokinase activation for the treatment of type 2 diabetes—A status review", Current Opinion in Drug Discovery and Development, 8(5), pp. 631-637, (2005).

Baboulene, M. et al, "Reactivity of diethyl 3-bromo-2-oxopropyl Phosphonate in the Hantzsch Reaction", Phosphorus and Sulfur and the Related Elements, Gordon and Breach—Harwood Academic, vol. 5, No. 1, (1978), pp. 87-94.

Endova, M. et al., "Transprotection of n-Benzoylated Nucleobase Derivatives by Dialkylaminomethylene Group", Nucleosides & Nucleotides, Marcel Dekker, Inc. US., vol. 16, No. 12, (1997), pp. 2151-2164.

Holy, A. et al., "Synthesis of N-(2-Phosphonylmethoxyethyl) Derivatives of Heterocyclic Bases", Collection of Czechoslovak Chemical Communications, Institute of Organic Chemistry & Biochemistry, Prague, CZ, vol. 54, No. 8, (1989) pp. 2190-2210.

Rosenberg, I. et al., "Acyclic Nucleotide Analogs. IV. Phosphonylmethoxyalkyl and Phosphonylalkyl Derivatives of Adenine", Collection of Czechoslovak Chemical Communications, Institute of Organic Chemistry & Biochemistry, Prague, CZ, vol. 53, (1988), pp. 2753-2777.

Rumthao, S. et al., "Design, Synthesis, and Evaluation of Oxyanion-hole Selective inhibitor Substituents for the S1 Subsite of Factor Xa", Bioorganic & Medicinal Chemistry Letters, Oxford, GB, vol. 14, No. 20, (2004), pp. 5165-5170.

Jordan, V. C. Nature Reviews: Drug Discovery, 2, 2003, p. 205.

Dorwald, F. Zaragoza. Side Reactions in Organic Synthesis: A Guide to Successful Synthesis Design, Weinheim: WILEY-VCH Verlag GmbH & Co. KGaA, 2005, Preface.

Wermuth, Camille G. The Practice of Medicinal Chemistry—Chapter 13: Molecular Variations Based on Isosteric Replacements, London: Academic Press United, 1996, pp. 203-237.

Dang, Qun (Max), "Organophosphonic acids as drug candidates," Expert Opin. Ther. Patents (2006), 16(3), pp. 343-348.

European Search Report issued Apr. 1, 2011.

McKerrecher, et al., "Discovery, synthesis and biological evaluation of novel glucokinase activators," Bio Med Chem Lett 15 (2005), pp. 2103-2106.

McKerrecher, et al., "Design of a potent, soluble glucokinase activator with excellent in vivo efficacy," Bio Med Chem Lett 16 (2006), pp. 2705-2709.

Waring, et al., "Overcoming retinoic acid receptor-α based testicular toxicity in the optimisation of glucokinase activators," Med. Chem. Comm. 2 (2011), pp. 771-774.

Pike, et al., "Design of a potent, soluble glucokinase activator with increased pharmacokinetic half-life," Bio Med Chem Lett 21 (2011), pp. 3467-3470.

\* cited by examiner

SUBSTITUTED PYRAZOLYLAMIDES USEFUL AS GLUCOKINASE ACTIVATORS

This application is a continuation of U.S. application Ser. No. 13/012,351 filed on Jan. 24, 2011 (now allowed), which is a continuation of U.S. application Ser. No. 11/769,964 filed on Jun. 28, 2007, now issued as U.S. Pat. No. 7,910,747 on Mar. 22, 2011, which claims priority to U.S. Provisional Application No. 60/818,912 filed Jul. 6, 2006, whose contents are hereby incorporated by reference.

FIELD OF THE INVENTION

The present invention relates to novel phosphonate and phosphinate compounds which are activators of the enzyme glucokinase and thus are useful in treating diabetes, and to a method for treating diabetes, especially Type II diabetes, using such compounds.

BACKGROUND OF THE INVENTION

The enzyme glucokinase (GK), which is mainly found in pancreatic β-cells and liver parenchymal cells, catalyzes the conversion of glucose to glucose-6-phosphate, which is the first step in the metabolism of glucose. Glucokinase is also a rate-controlling enzyme for glucose metabolism in pancreatic β-cells and liver parenchymal cells, which play an important role in whole-body glucose homeostasis.

Liag, Y. et al., (Biochem. J., 1995, 309:167-173) report the finding that Type II (maturity-onset) diabetes of the young (MODY-2) is caused by loss of function mutations in the glucokinase gene, which suggests that glucokinase also functions as a glucose sensor in humans. Thus, compounds that activate glucokinase and thus increase the sensitivity of the glucokinase sensor system and thereby cause increase in insulin secretion will be useful in the treatment of hyperglycemia and Type II diabetes.

Glucokinase activators have been demonstrated to be effective in enhancing: 1) the effect of glucose on insulin release from isolated rat and human pancreatic islets, and 2) the glucose induction of pancreatic islet glucokinase in isolated cultured rat islets (e.g. Matschinsky, F. M. et al., Diabetes, 2006, 55:1, and ("Glucokinase and Glycemic Disease, from Basics to Novel Therapeutics", published by Karger, 2004; F. M. Matschinsky and M. A. Magnuson, eds., Ch. 6, pp. 360-378). In diabetic animal model studies, glucokinase activators have been demonstrated to stimulate insulin release, enhance glycogen synthesis and reduce hepatic glucose production in pancreatic clamp studies. Importantly, glucokinase activators have been demonstrated to dose-dependently lower blood glucose levels in different standard animal models of type 2 diabetes, such as the ob/ob mouse, db/db mouse and Zucker in acute single-dose studies and also effectively improved the glucose excursion in both normal C57/BL6J and ob/ob mice in oral glucose tolerance tests (e.g. in "Glucokinase and Glycemic Disease, from Basics to Novel Therapeutics", published by Karger, 2004; F. M. Matschinsky and M. A. Magnuson, eds., Ch. 6, pp. 360-378 as well as Fyfe, M. C. et al., Diabetologia, 2007, 50:1277).

Glucokinase activators have also demonstrated antidiabetic efficacy in chronic animal models of type II diabetes. For instance, in a 9-day study in ob/ob mice, a glucokinase activator improved the overall glucose profile while showing comparable antihyperglycemic effects in oral glucose tolerance tests at the beginning and end of the study (Fyfe, M. C. et al., Diabetologia, 2007, 50:1277). In another instance, in a chronic 40-week study, a glucokinase activator prevented the development of hyperglycemia in diet-induced obese mice which were glucose intolerant. The diet-induced obese mice treated with a glucokinase activator showed marked improvement in the glucose excursion in an oral glucose tolerance test at the end of the study relative to the control group ("Glucokinase and Glycemic Disease, from Basics to Novel Therapeutics", published by Karger, 2004; F. M. Matschinsky and M. A. Magnuson, eds., Ch. 6, pp. 360-378).

SUMMARY OF THE INVENTION

In accordance with one aspect of the invention, compounds are provided having the structure I

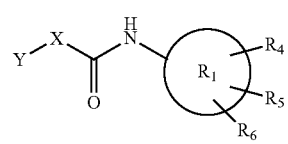

wherein $R_1$ is a heteroaryl substituted by $R_4$ and optionally substituted with one or two substituents $R_5$ and/or $R_6$, wherein the heteroaryl possesses a nitrogen atom adjacent to the atom joining said heteroaryl group to

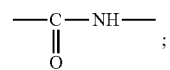

$R_4$ is —$(CH_2)_n$—Z—$(CH_2)_m$—PO$(OR_7)(OR_8)$,
or —$(CH_2)_nZ$—$(CH_2)_m$—PO$(OR_2)R_9$,
or —$(CH_2)_n$—Z—$(CH_2)_m$—O—PO$(OR_2)R_9$,
or —$(CH_2)_nZ$—$(CH_2)_m$—O—PO—$(R_9)R_{10}$,
or —$(CH_2)_nZ$—$(CH_2)_m$—PO$(R_9)R_{10}$;

$R_7$ and $R_8$ are the same or different and are independently selected from hydrogen and alkyl;

$R_9$ and $R_{10}$ are the same or different and are independently selected from alkyl, aryl, arylalkyl, heteroaryl and heteroarylalkyl, any of which may be optionally substituted;

additionally, $R_7$ and $R_8$ can be cyclized into a ring

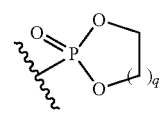

where q=1-3;

similarly, $R_7$ and $R_9$ can be cyclized into a ring

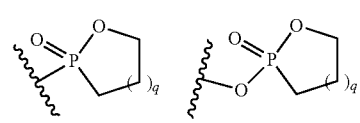

where q=1-3, or where q=1-3;

similarly, $R_9$ and $R_{10}$ can be cyclized into a ring

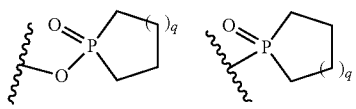

where q=1-3; or where q=1-3;

Z is selected from a bond, alkylene and alkenylene, each of which may be optionally substituted (e.g. hydroxy, alkoxy, aminoalkyl, aminoaralkyl, aminoheteroaralkyl, aminoaryl, aminoheteroaryl or carboxy);

m is 0, 1 or 2;

n is 0, 1 or 2;

and Z may be O, S, $SO_2$ when m is 1 or 2, n is 0, 1, or 2;

$R_5$ and $R_6$ are the same or different and are independently selected from hydrogen, alkyl, halogen or carboxyl, or is absent;

X is selected from

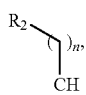 X-1

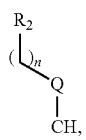 X-2

 X-3

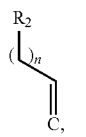 X-4

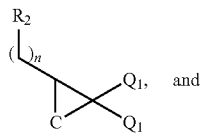 X-5 a bond; X-6 and when Y is absent, X is selected from

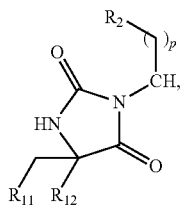 X-7

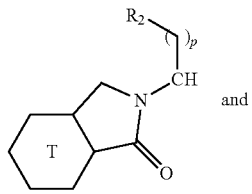 X-8 and

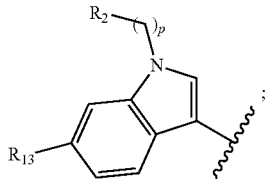 X-9

$R_2$ is selected from hydrogen, alkyl, cycloalkyl, heterocyclyl, aryl, heteroaryl, alkynyl, and alkenyl (all of which may be optionally substituted);

p is 0 or 1;

Q is selected from O, $S(O)_q$ and CO, where q is 0, 1 or 2;

$Q_1$ is selected from hydrogen and fluorine;

$R_{11}$ is selected from hydrogen, lower alkyl, cycloalkyl, aryl and heteroaryl;

$R_{12}$ is selected from hydrogen, and lower alkyl, or $R_{11}$ and $R_{12}$ together with the carbon atom to which they are attached form a cycloalkyl ring of 5 to 7 carbon atoms;

$R_{13}$ is selected from halo, nitro, amino, cyano, methyl, trifluoromethyl, hydroxy, methoxy, trifluoromethoxy, methylthio, methylsulfinyl and methylsulfonyl;

T is selected from aryl and heteroaryl, each of which may be optionally substituted;

Y is $R_3$—$(CH_2)_s$—, or is absent;

where $R_3$ is aryl or heteroaryl, each of which may be optionally substituted;

s is 0 or 1;

all stereoisomers thereof, a prodrug ester thereof or a pharmaceutically acceptable salt thereof.

Preferably in compounds of formula I

X is

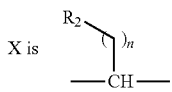

where more preferably n is 1, and $R_2$ is a cycloalkyl, preferably cyclopentyl or cyclohexyl, or $R_2$ is a heterocyclyl group such as cycloalkyl with an embedded hetero atom such as an oxygen atom or a sulfur atom, for example tetrahydropyran, tetrahydrofuran,

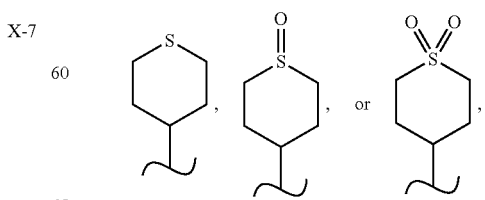

preferably tetrahydropyran;

Y is aryl or heteroaryl or is absent, still more preferably aryl, more preferably phenyl, still more preferably

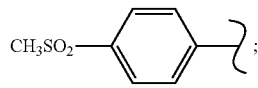

or X is a bond and Y is

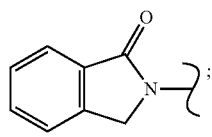

$R_4$ is $(CH_2)_n-Z-(CH_2)_m-PO(OR_7)(OR_8)$ wherein Z is alkylene or alkenylene, wherein n is 0, m is 0 and Z is a bond, $-CH_2-$, $-CH_3-CH=CH-$, $-CH_2CH_2-$ or

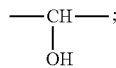

and
$R_5$ and $R_6$ are each H;
$R_7$ is H or alkyl; and
$R_8$ is H or alkyl.
The moiety

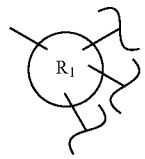

is preferably

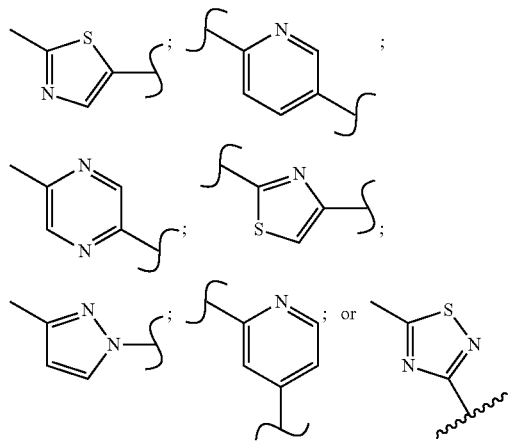

$R_4$ is more preferably

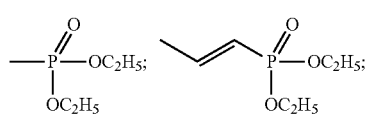

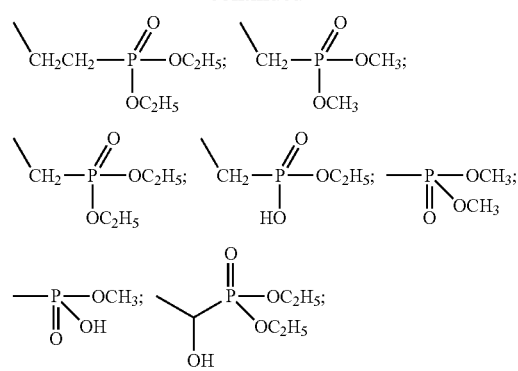

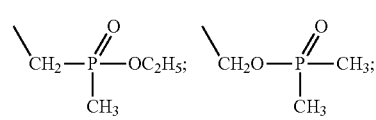

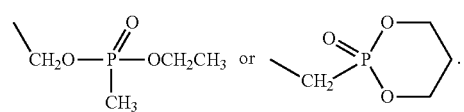

Preferred embodiments of Y—X—CO— wherein X is X-1 include, but are not limited to:

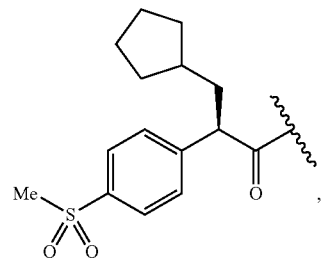

(a)

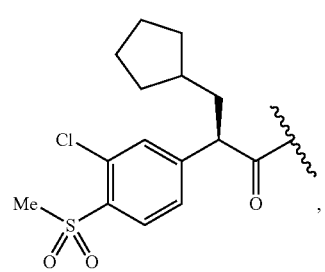

(b)

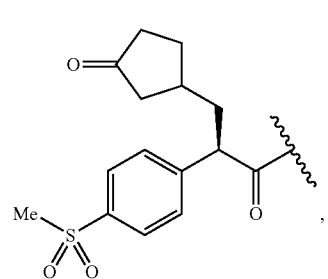

(c)

and

-continued
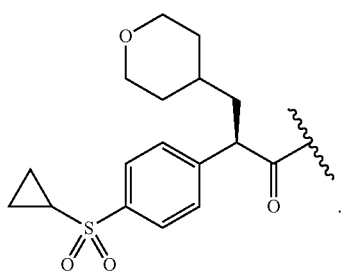
(d)
Preferred embodiments of Y—X—CO— wherein X=X-2 include, but are not limited to:
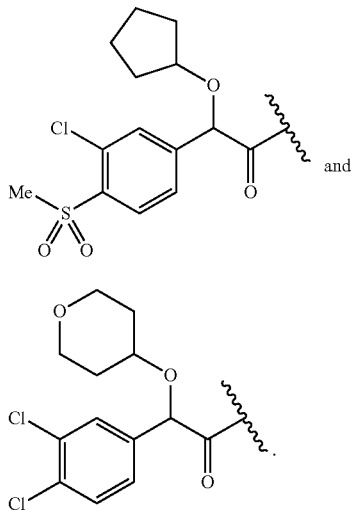
(e)
(f)
Preferred embodiments of Y—X—CO— wherein X=X-3 include, but are not limited to:
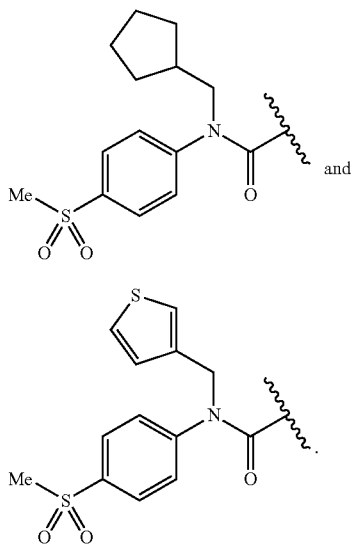
(g)
(h)
Preferred embodiments of Y—X—CO— wherein X=X-4 include, but are not limited to:
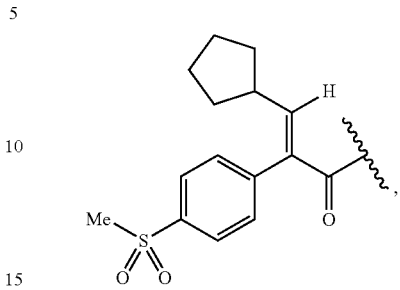
(i)
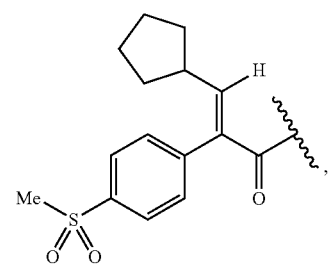
(j)
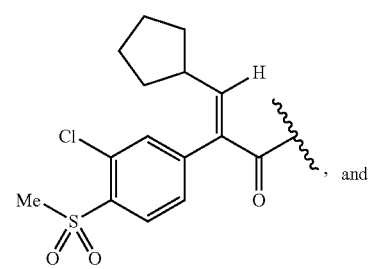
(k)
Preferred embodiments of Y—X—CO— wherein X=X-5 include, but are not limited to:
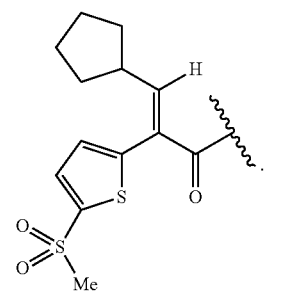
(l)
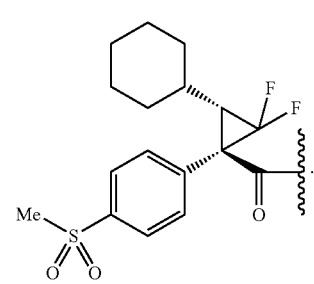
(m)

Preferred embodiments of Y—X—CO— wherein X=X-6 (wherein X is a bond) include, but are not limited to:
(n)
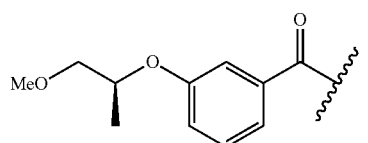
(o)
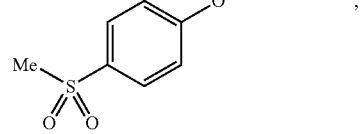
(p)
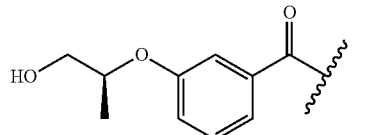
(q)
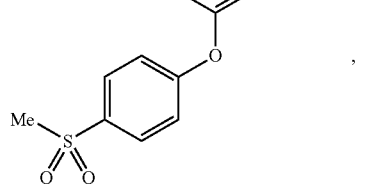
(r)
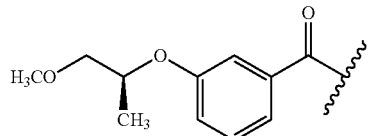
(s)
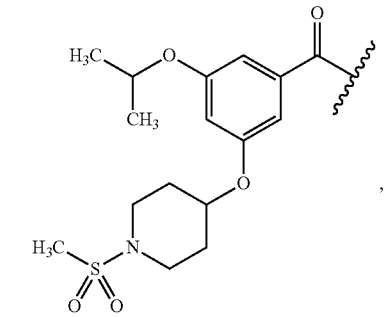
(t)
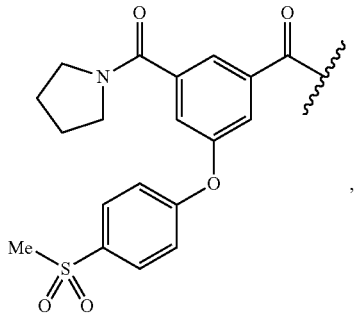
(u)
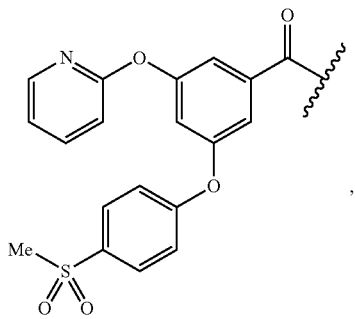
(v)
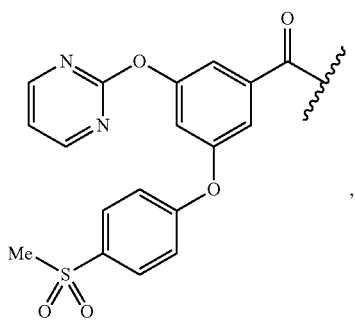
, and
(w)
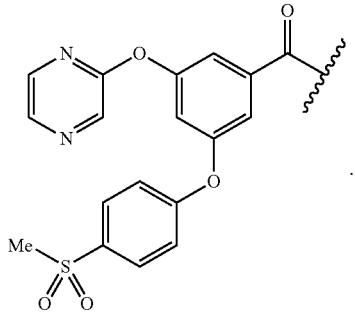
.

Preferred embodiments of Y—X—CO— wherein X=X-7 include, but are not limited to:
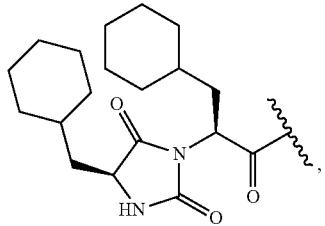
(x)
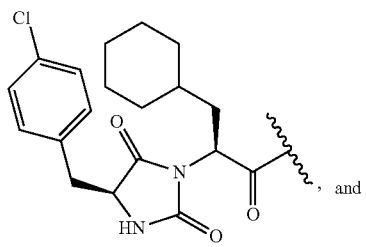
(y)
, and
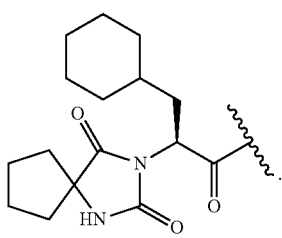
(z)
Preferred embodiments of Y—X—CO— wherein X=X-8 include, but are not limited to:
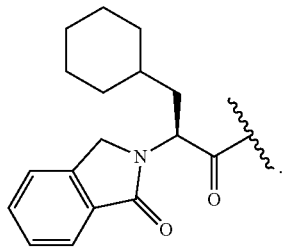
(aa)
Preferred embodiments of Y—X—CO— wherein X=X-9 include, but are not limited to:
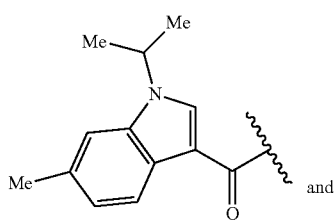
(ab)
and
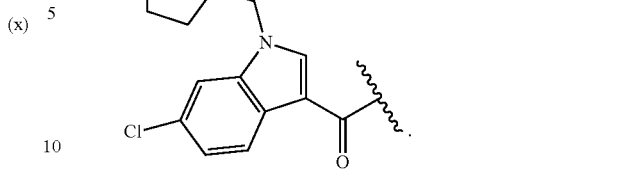
(ac)
Examples of preferred compounds in accordance with the present invention include, but are not limited to, the following:
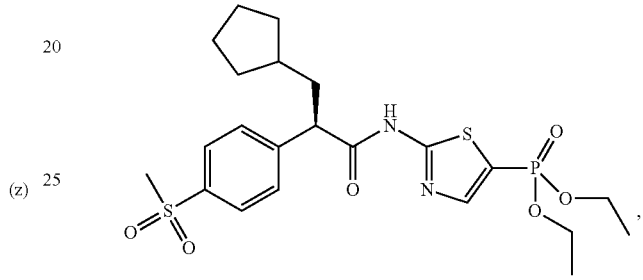
,
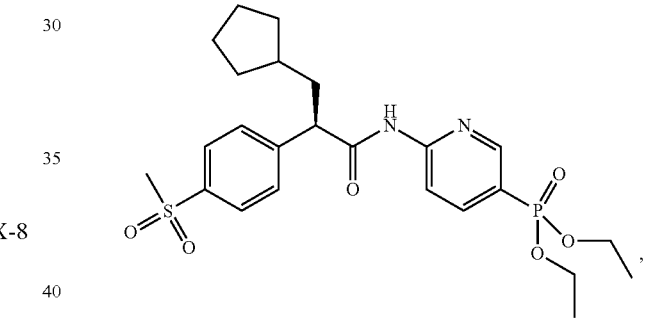
,
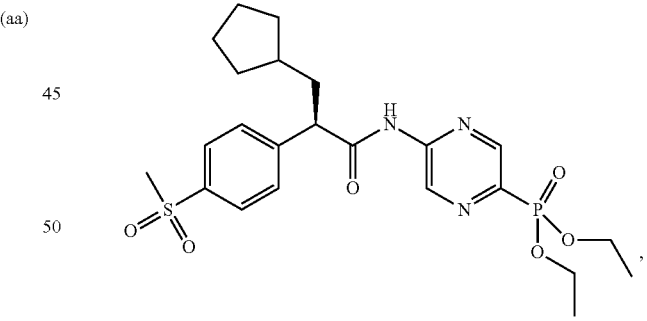
,
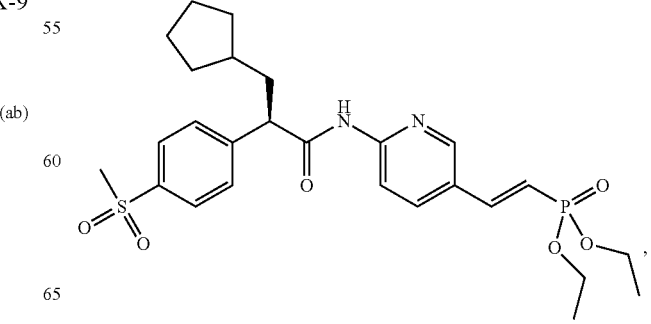
, 13
-continued
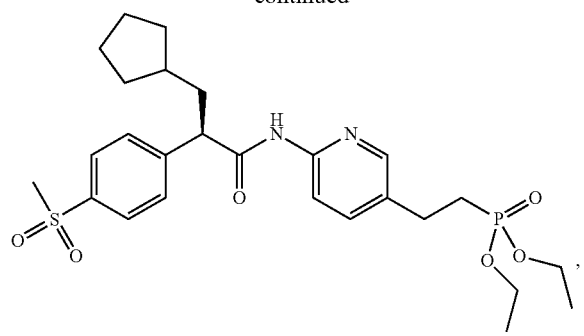
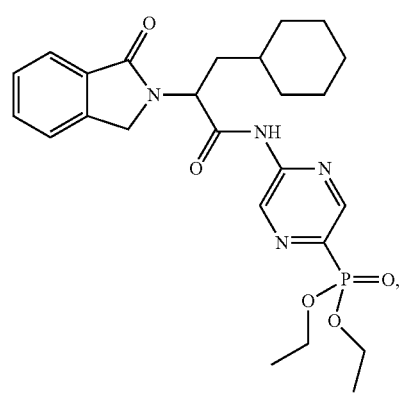
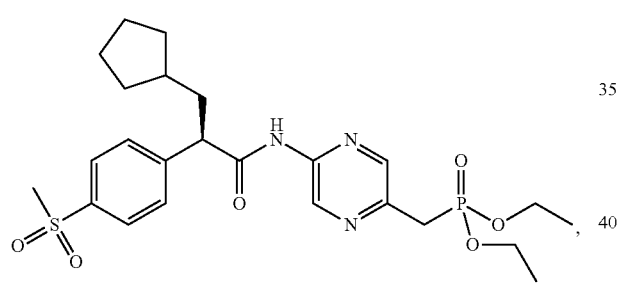
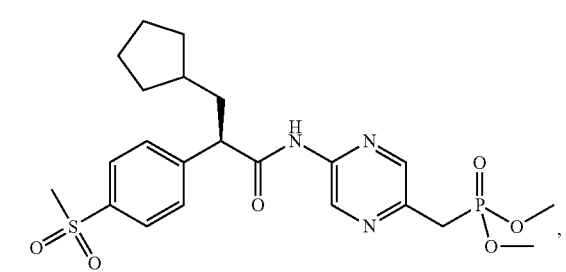
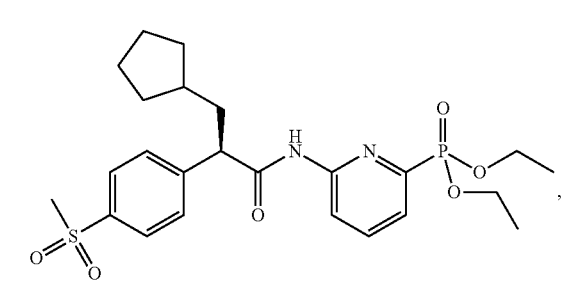
14
-continued
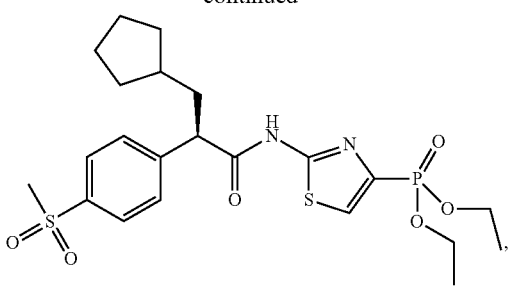
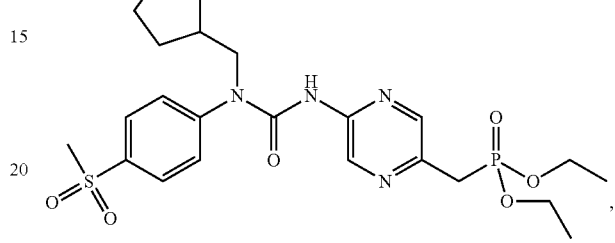
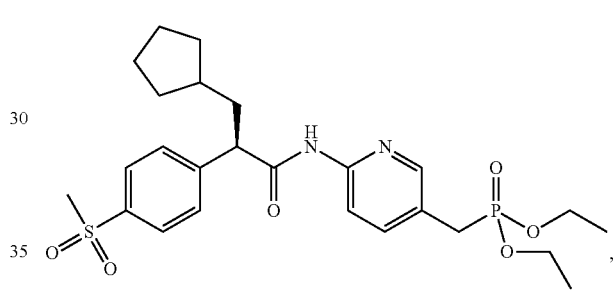
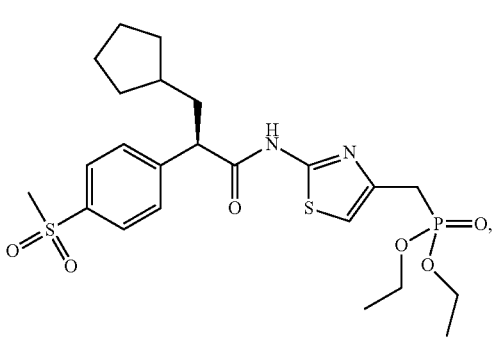
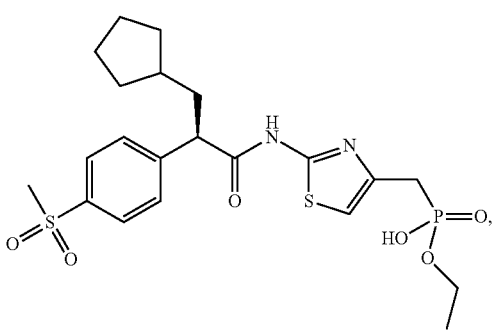

15
-continued
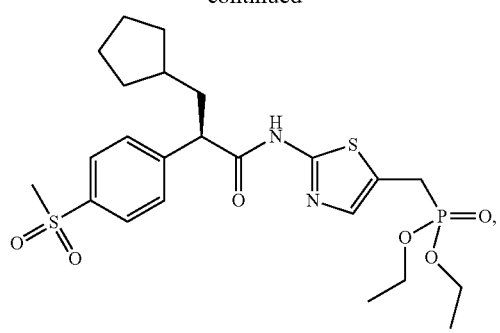
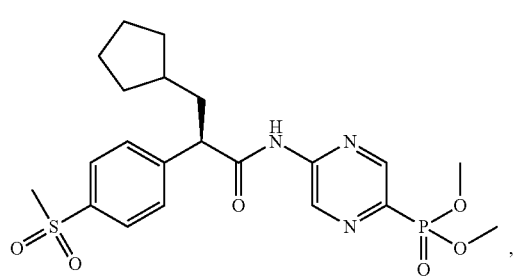
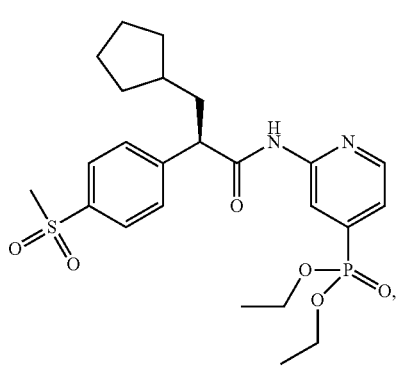
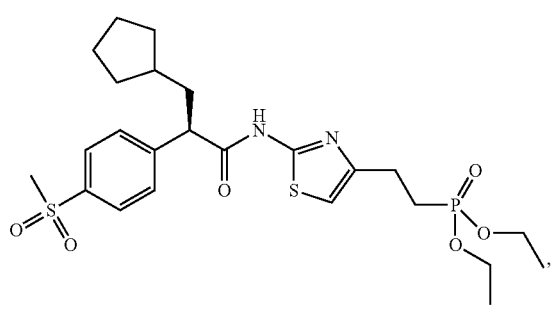
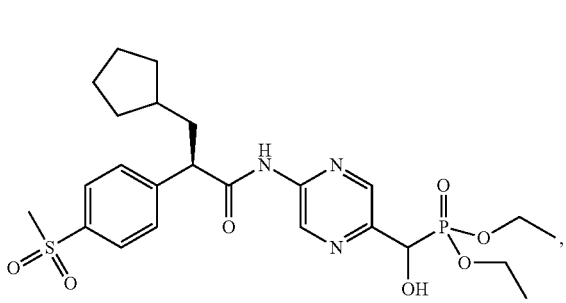
16
-continued
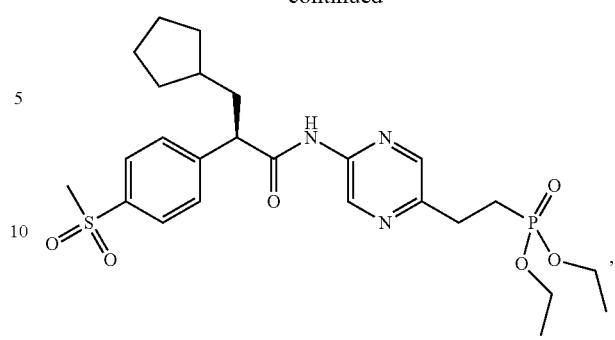
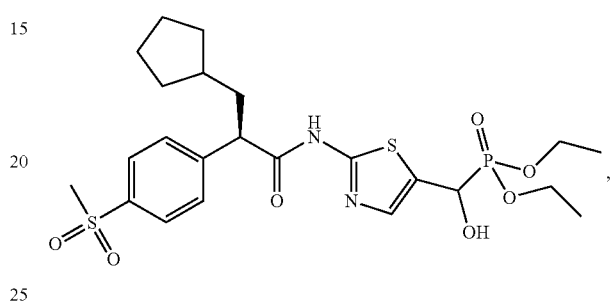
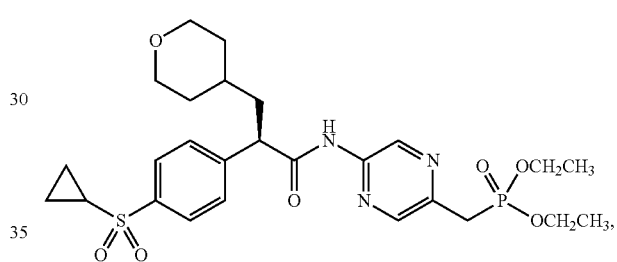
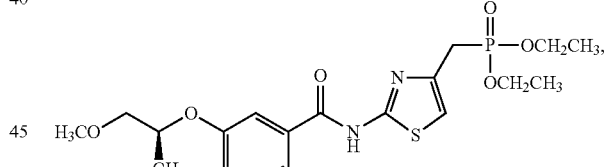
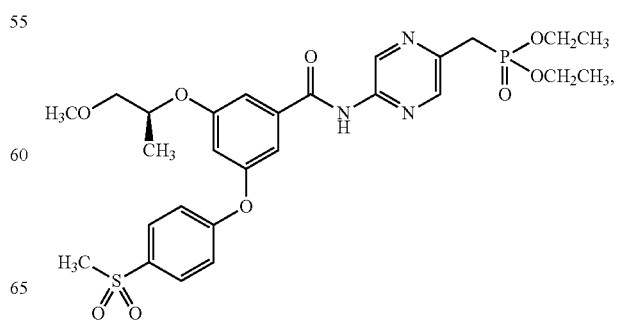

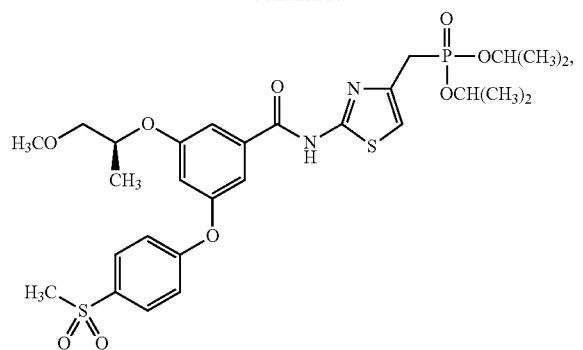
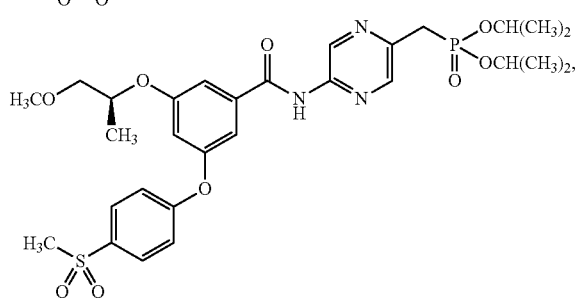
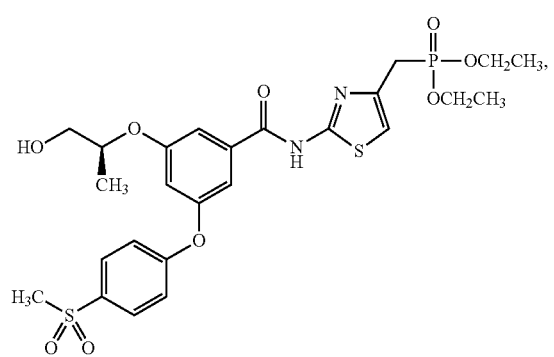
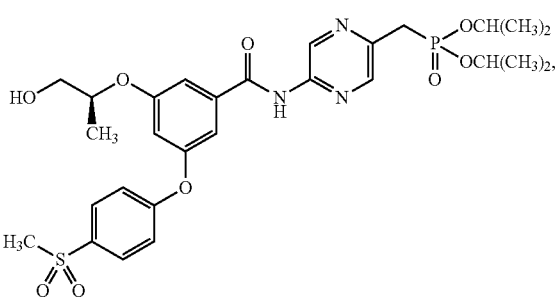
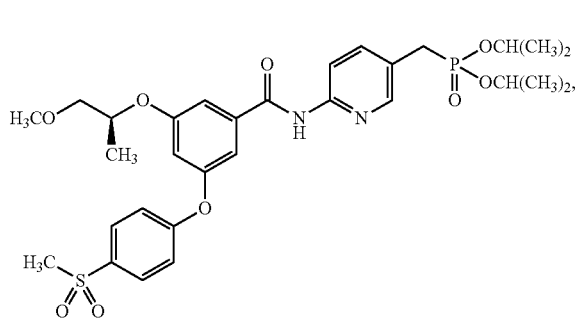
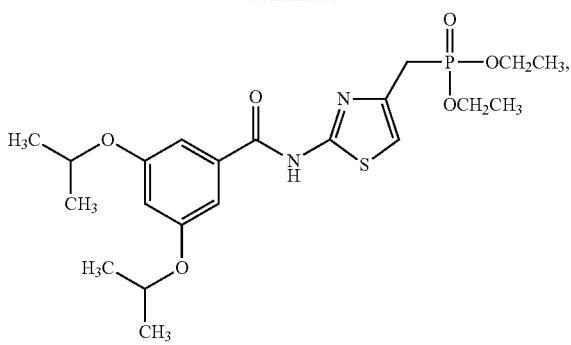
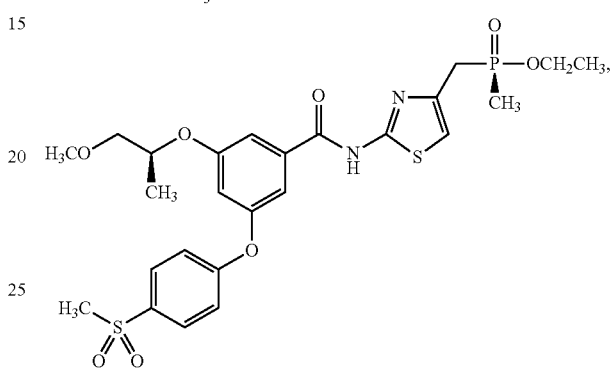
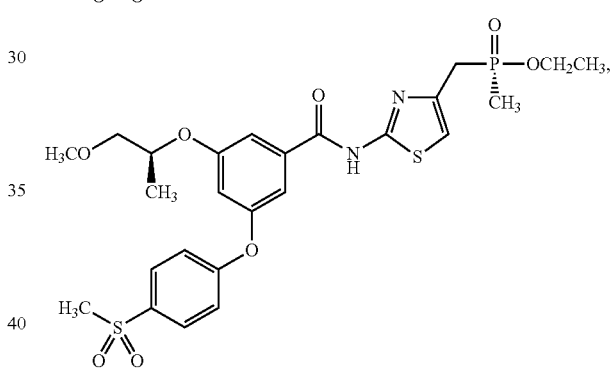
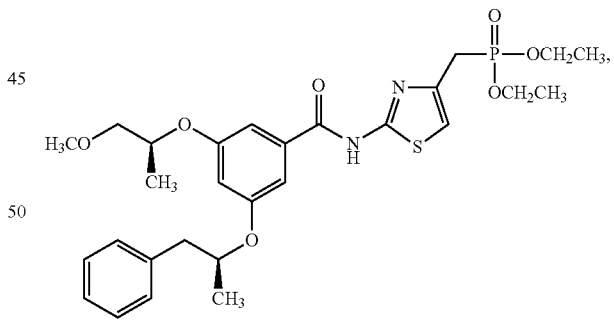
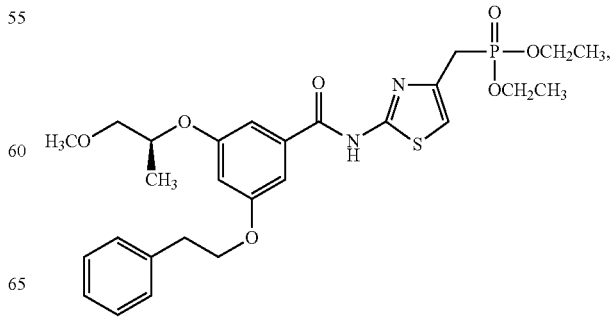

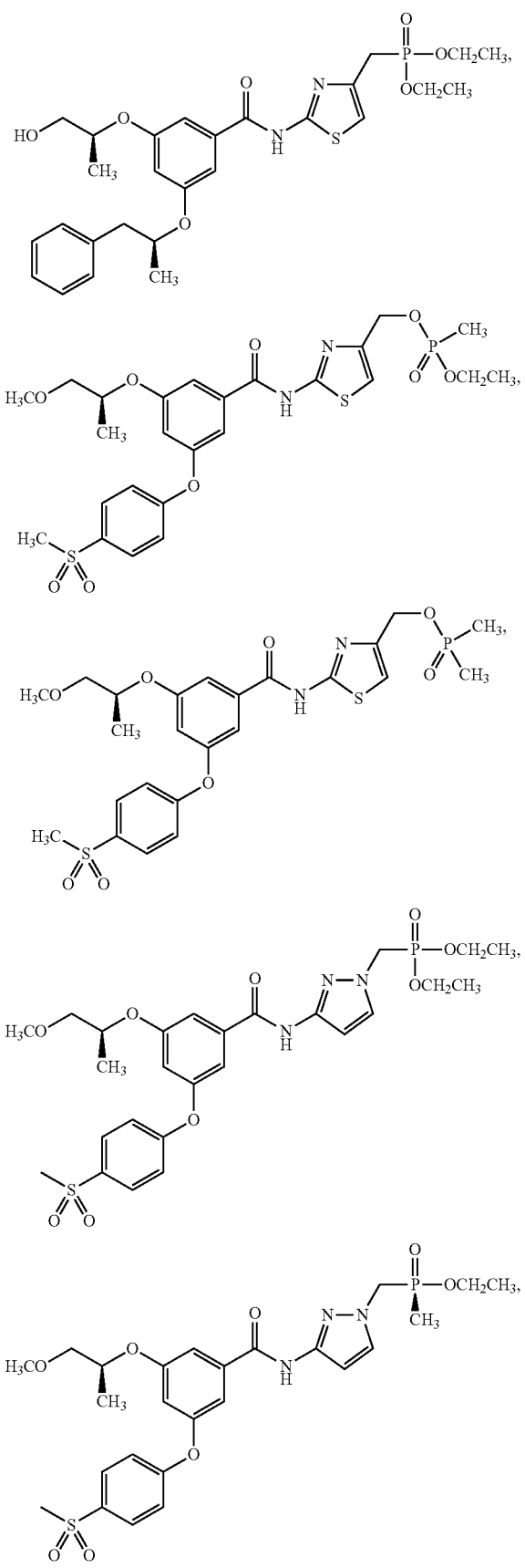
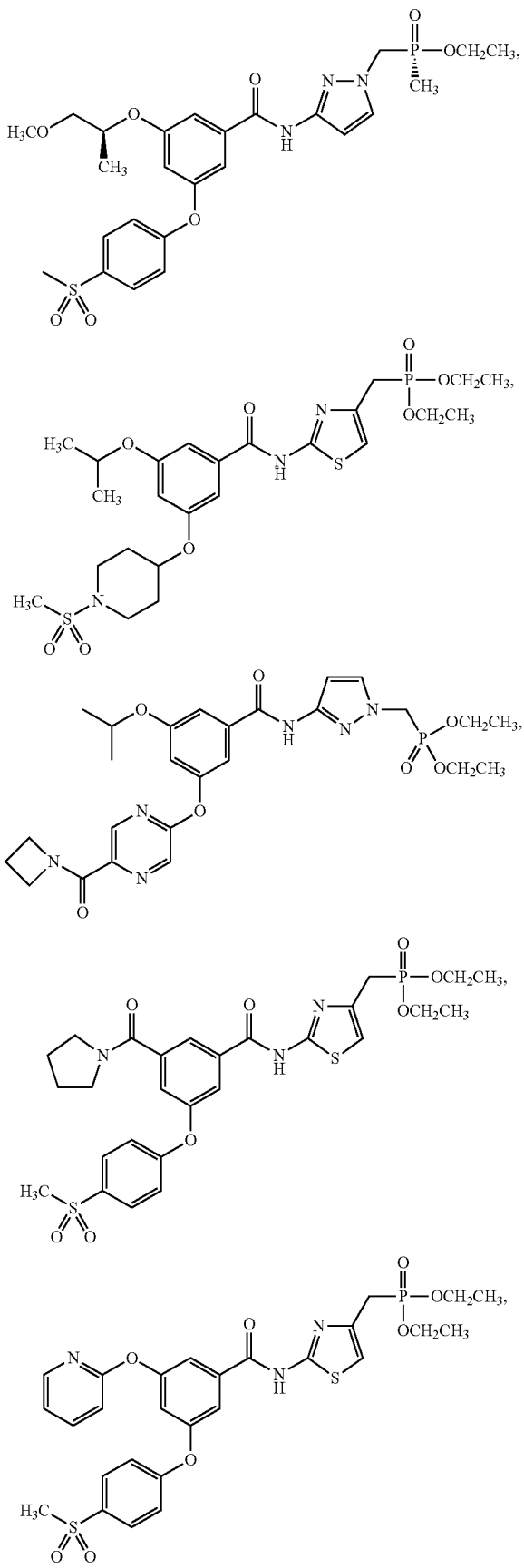

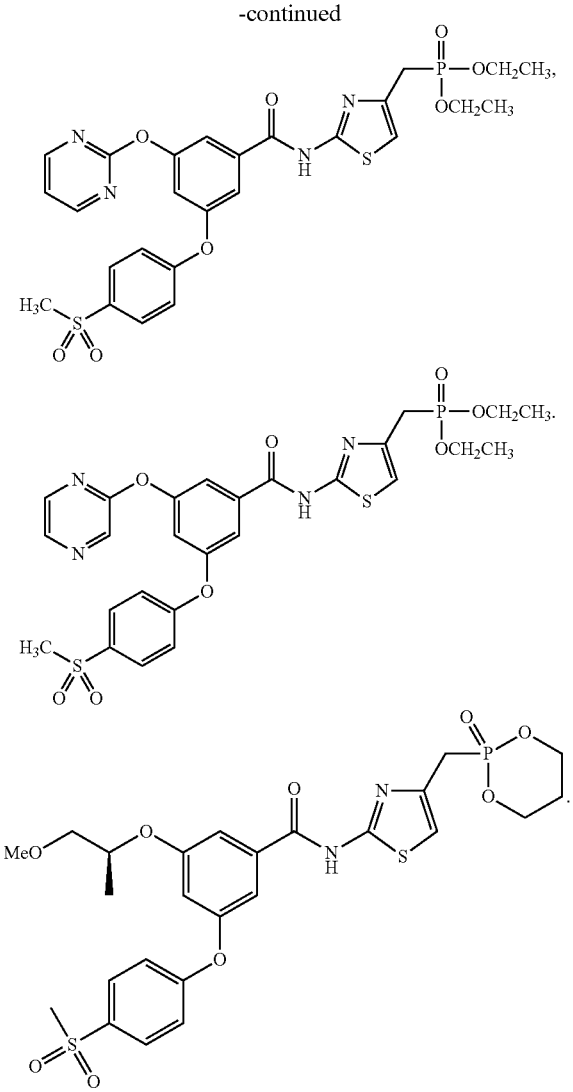

The compounds of the present invention activate or enhance the activity of the enzyme glucokinase. Consequently, the compounds of the present invention may be used in the treatment of multiple diseases or disorders associated with a deficit of glucokinase, such as diabetes and related conditions, microvascular complications associated with diabetes, the macrovascular complications associated with diabetes, cardiovascular diseases, Metabolic Syndrome and its component conditions, and other maladies. Examples of diseases or disorders associated with deficit in activity of the enzyme glucokinase that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

The present invention provides for compounds of formula I, pharmaceutical compositions employing such compounds, and for methods of using such compounds. In particular, the present invention provides a pharmaceutical composition containing a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with deficit in the activity of the enzyme glucokinase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other therapeutic agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

In another embodiment, compounds of the present invention are selected from the compounds exemplified in the examples.

In another embodiment, the present invention relates to pharmaceutical compositions which include of a therapeutically effective amount of a compound of the present invention, alone or, optionally, in combination with a pharmaceutically acceptable carrier and/or one or more other agent(s).

In another embodiment, the present invention relates to methods of enhancing the activity of the enzyme glucokinase which includes the step of administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with deficit in the activity of the enzyme glucokinase which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the deficit in activity of the enzyme glucokinase that can be prevented, inhibited, or treated according to the present invention include, but are not limited to, are those diseases or disorders set out above.

In another embodiment, the present invention relates to a method for preventing, inhibiting, or treating the progression or onset of diabetes, hyperglycemia, obesity, dyslipidemia, hypertension, and cognitive impairment which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

DETAILED DESCRIPTION OF THE INVENTION

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms, and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "lower alkyl," "alkyl," or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, wherein $R_a$ and $R_b$ are the same or different and are independently selected from hydrogen, alkyl, alkenyl, $CO_2H$, $CO_2(alkyl)$, $C_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of $(C_{1-6})$alkyl, $(C_{2-6})$alkenyl, hydroxy, halogen, cyano, nitro, $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}alkyl)$, —$S(C_{1-6}alkyl)$, —$NH_2$, $NH(C_{1-6}alkyl)$, $N(C_{1-6}alkyl)_2$, $N(CH_3)_3^+$, $SO_2(C_{1-6}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$, $C_{3-7}$cycloalkyl, phenyl, benzyl, phenylethyl, phenyloxy, benzyloxy, naphthyl, a four to seven membered heterocylo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

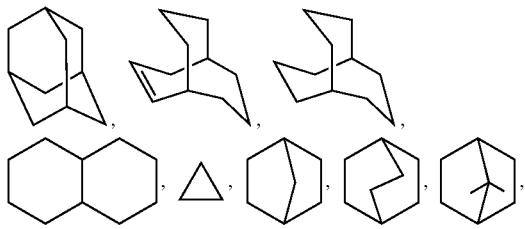

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatri-enyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio, and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

Unless otherwise indicated, the term "aryl" as employed herein alone or as part of another group refers to monocyclic and bicyclic aromatic groups containing 6 to 10 carbons in the ring portion (such as phenyl, biphenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings) for example

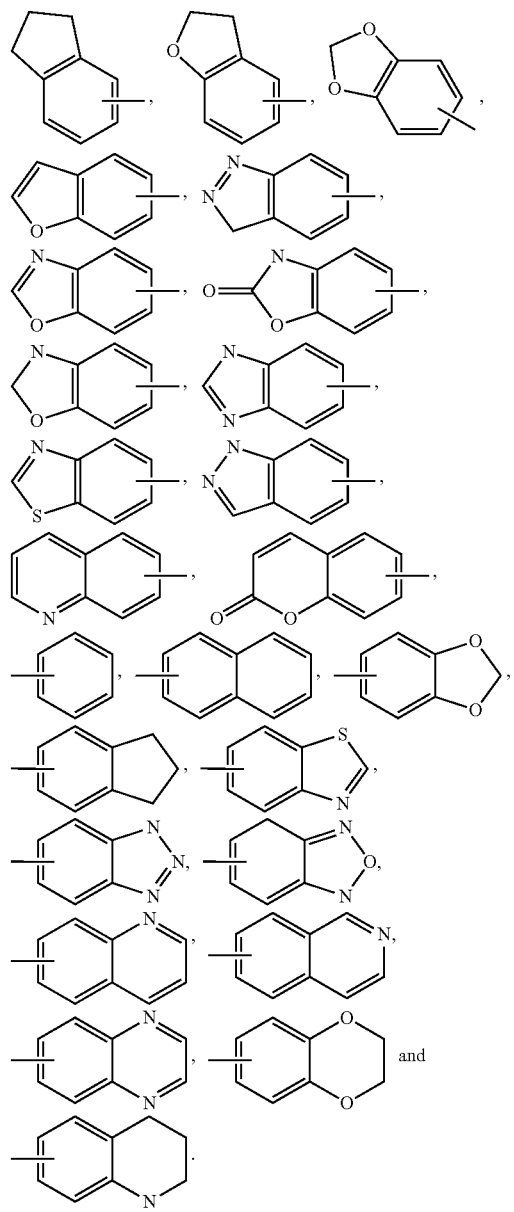

The aryl group may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfon-aminocarbonyl, $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, or $-NR_a(C_{1-4}alkylene)CO_2R_b$, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of ($C_{1-4}$alkyl, ($C_{2-4}$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$. and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R_3$ groups or substituents for $R_3$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

The term "acyl" alone or as part of another group refers to a carbonyl group linked to an organic radical, more particularly, the group $C(=O)R_e$, as well as the bivalent groups $-C(=O)-$ or $-C(=O)R_e-$, which are linked to organic radicals. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The term "heterocyclo" or "heterocyclic" or "heterocyclyl" or "cycloheteroalkyl" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S, or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N-OH, =N-O-alkyl, aryl, cycloalkyl, heterocyclo, and/or heteroaryl, wherein $R_a$, $R_b$, and $R_c$ are as defined above for substituted alkyl groups, and are also in turn optionally substituted as recited above. When a heterocyclo is substituted with a further ring, said ring in turn is optionally substituted with one to two of ($C_{1-4}$)alkyl, ($C_{2-4}$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like. Exemplary bicyclic heterocyclo groups include quinuclidinyl.

Preferred heterocyclo groups in compounds of formula (I) include

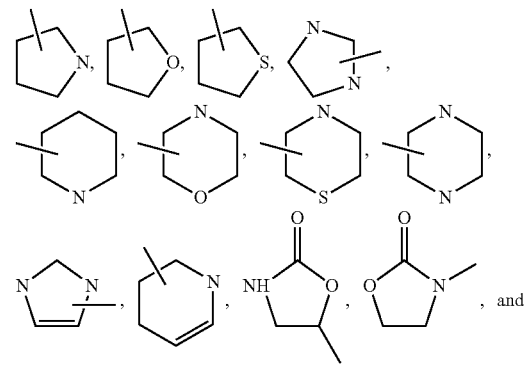

-continued

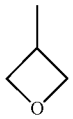

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated, and may include aryl, cycloalkyl, heteroaryl or cycloheteroaryl. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents which may be any of the substituents set out for alkyl and can be selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)$ $R_b$, $SO_3H$, —$PO(OH)_2$, —$C(=O)R_a$, —$CO_2R_a$, —$C(=O)$ $NR_aR_b$, —$C(=O)(C_{1-4}alkylene)NR_aR_b$, —$C(=O)NR_a$ $(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of ($C_{1-4}$alkyl, ($C_{2-4}$alkenyl, halogen, hydroxy, cyano, nitro, $CF_3$, O ($C_{1-4}$alkyl), $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)$ $(C_{1-4}alkylene)NH(alkyl)$, and/or $C(=O)(C_{1-4}alkylene)N$ $(C_{1-4}alkyl)_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

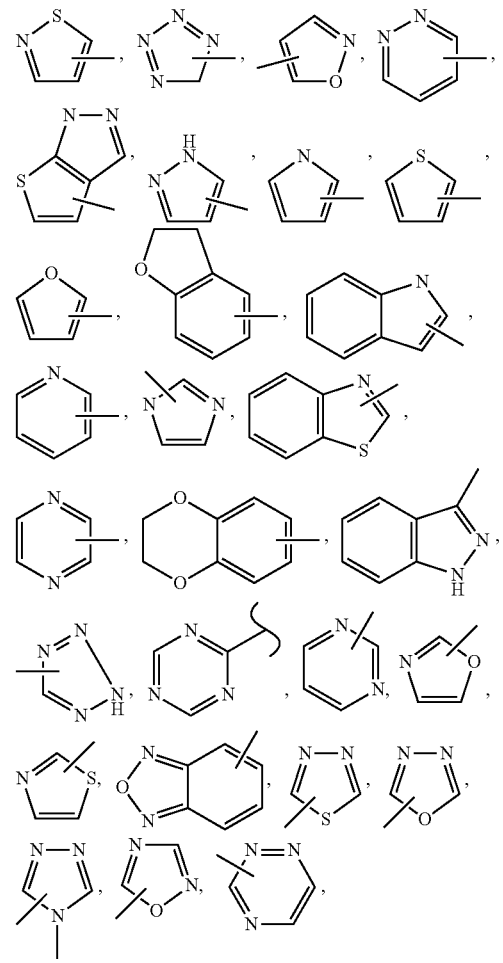

and the like.

The term "heterocyclylalkyl" or "heterocycloalkyl" or "cycloheteroalkylakyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an —OH group.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

The terms pharmaceutically acceptable "salt" and "salts" may refer to basic salts formed with inorganic and organic bases. Such salts include ammonium salts; alkali metal salts, such as lithium, sodium, and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts." Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid, or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric, or citric acid, such as amino acids, (for example aspartic or glutamic acid or lysine or arginine), or benzoic acid, or with organic sulfonic acids, such as ($C_1$-$C_4$) alkyl or arylsulfonic acids, which are unsubstituted or substituted, for example by halogen, for example methanesulfonic acid or p-toluenesulfonic acid.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Any compound that can be converted in vivo to provide the bioactive agent (i.e., the compound of formula I) is a prodrug within the scope and spirit of the invention.

The term "prodrug" denotes a compound which, upon administration to a subject, undergoes chemical conversion by metabolic or chemical processes to yield a compound of the formula, and/or a salt and/or solvate thereof. For example, compounds containing a carboxy group can form physiologically hydrolyzable esters which serve as prodrugs by being hydrolyzed in the body to yield formula compounds per se. Such prodrugs are preferably administered orally since hydrolysis in many instances occurs principally under the influence of the digestive enzymes. Parenteral administration may be used where the ester per se is active, or in those instances where hydrolysis occurs in the blood.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl, or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

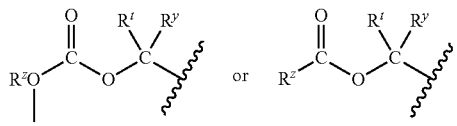

wherein $R^z$, $R^t$, and $R^y$ are H, alkyl, aryl, or arylalkyl; however, $R^zO$ cannot be HO.

Examples of such prodrug esters include

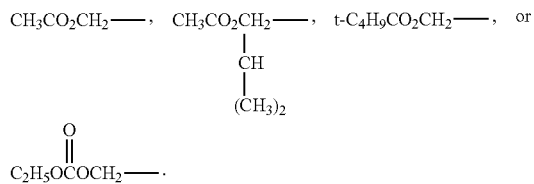

Other examples of suitable prodrug esters include

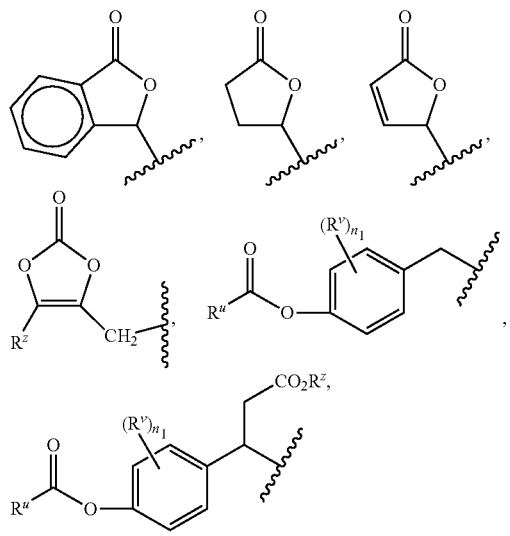

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl, or alkoxyl, and $n_1$ is 0, 1, or 2.

The term "tautomer" refers to compounds of the formula I and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to treat or prevent diabetes and/or obesity.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Synthesis

Compounds of formulae I and Ia may be prepared as shown in the following reaction schemes and the description thereof, as well as relevant literature procedures that may be used by one skilled in the art. Exemplary reagents and procedures for these reactions appear hereinafter and in the working Examples. Protection and deprotection in the Schemes below may be carried out by procedures generally known in the art (see, for example, Greene, T. W. and Wuts, P. G. M., Protecting Groups in Organic Synthesis, $3^{rd}$ Edition, 1999 [Wiley]).

The synthesis of amide compounds of formula I wherein X=

X-1

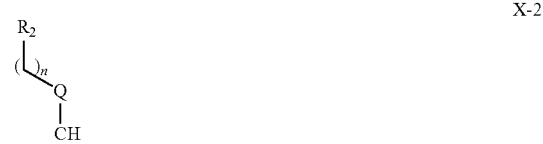

X-2

X-4

X-5

X-6 bond, and when Y is absent,

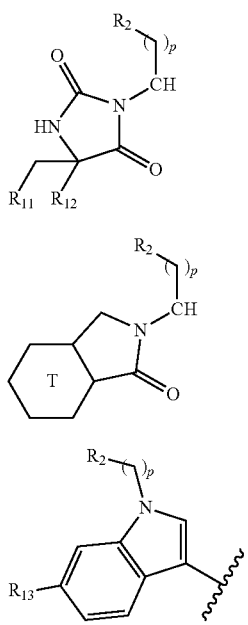

is described in Scheme 1. The carboxylic acid 1 is coupled with amine 2 followed standard literature conditions, such as: (1) the use of oxalyl chloride with catalytic DMF to form the acid chloride intermediate followed by subsequent reaction with amine 2 in the presence of an amine base; or (2) the treatment of a mixture of 1 and 2 with a coupling reagent such as DEPBT (Li et al., Org. Lett., 1999, 1:91). Where the heteroaromatic ring $R_1$ is depicted in Scheme 1 and in all subsequent schemes described below, the optional ring substituents $R_5$ and $R_6$ may be present.

SCHEME 1

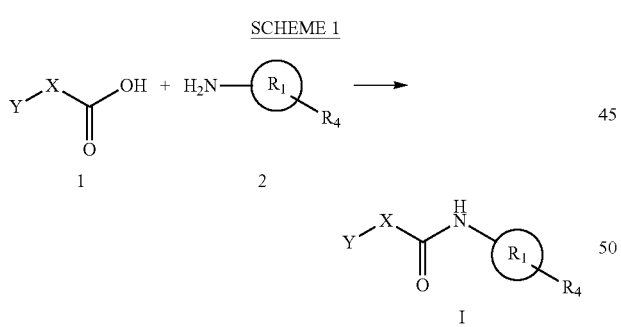

Procedures for the synthesis of pertinent examples of carboxylic acid 1 can be found in the literature (references include, but are not limited to, the following PCT Intl. Applications: for X-1, WO 2000/058293, WO 2001/083465, WO 2001/085706, WO 2001/085707, WO 2002/046173, WO 2003/095438, WO 2004/052869, WO 2004/072031, WO 2004/063194, WO 2004/072066, WO 2005/103021, WO 2006/016194, WO 2006/016174, WO 2006/016178; for X-2, WO 2002/008209, WO 2004/063194; for X-4, WO 2001/044216, WO 2004/072031, WO 2004/072066, WO 2004/063194, WO 2002/014312, WO 2005/103021, WO 2006/016194; for X-5, WO 2004/063179; for X-6, WO 2003/000262, WO 2003/000267, WO 2003/080585, WO 2003/015774, WO 2004/045614, WO 2004/046139, WO 2004/076420, WO 2005/121110; WO 2006/040528, WO 2006/040529, WO 2006/125972, WO 2007/007040, WO 2007/007041, WO 2007/007042, WO 2007/0017649; for X-7, WO 2001/083478; for X-8, WO 2002/048106; for X-9, WO 2004/031179.

The synthesis of urea compounds of formula I wherein

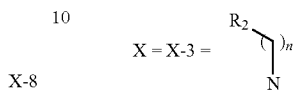

is described in Scheme 2. The amine 3 may be treated with a reagent such as carbonyldiimidazole, 4-nitrophenylchloroformate, phosgene, or a phosgene derivative such as diphosgene or triphosgene, followed by the addition of amine 2 to afford the desired urea product of formula I. Alternatively, amine 2 may be first treated with a reagent such as carbonyldiimidazole (or other like reagents as described above), followed by addition of amine 3 to provide ureas of formula I-A.

SCHEME 2

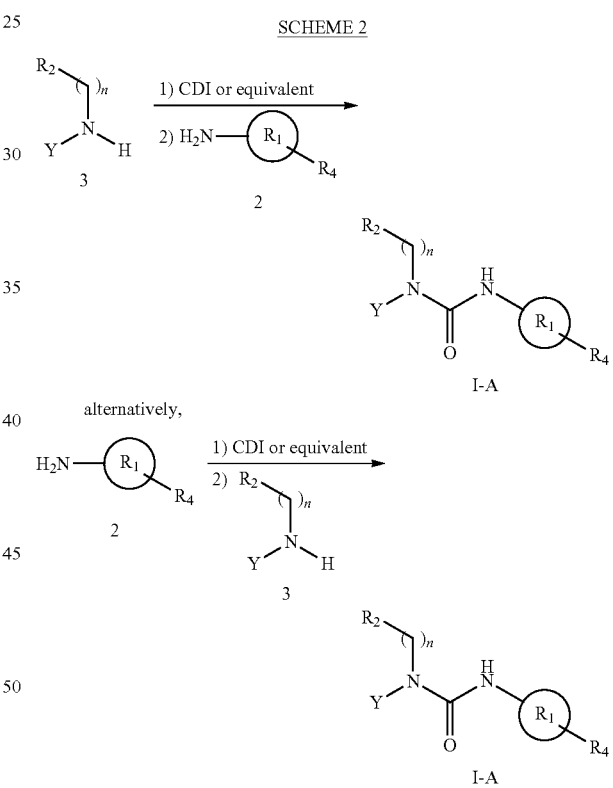

Procedures for the synthesis of pertinent examples of amine 3 are available in the literature (references include PCT Int. Applications WO2003/055482 and WO2004/002481; and Castellano et al., Bioorg. Med. Chem. Lett. 2005, 15:1501).

Scheme 3 describes a general approach to the synthesis of amine 2A wherein

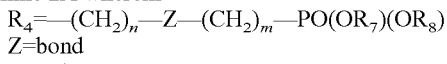

Z=bond m and n=0 i.e., where the resulting phosphonate group is directly attached to the heteroaromatic ring, $R_1$. A protected amino-substituted heteroaryl 4 with a suitably activated hydrogen substituent is deprotonated with a strong base such as LDA or n-butyllithium. The resulting anion is reacted with a dialkylchlorophosphate 5 resulting in direct attachment of the phosphonate group to $R_1$. Removal of the protecting groups provides amine 2A. Alternatively, the halo-substituted heteroaryl 6 can also be converted to the same anionic intermediate via halogen-metal exchange by reaction with a base such as n-butyllithium. This approach can also be extended to the synthesis of phosphinic acids by the use of a reagent such as N,N-diethylchloromethylphosphonamide to react with the anion intermediate (Rumthao et al., *Bioorg. Med. Chem. Lett.*, 2004, 14:5165-5170). As an example, the protected thiazole amine 7 may be deprotonated as shown in Scheme 3 using a base such as LDA or n-BuLi and phosphonylated as described to give, after deprotection, the 5-phosphonate-substituted thiazole amine 2B (South et al., *J. Het. Chem.*, 1991, 28:1017).

The reactions described in Scheme 3 above and Schemes 4, 5, 6, 7 and 8 below may also be conducted on compounds wherein the group Y—X—CO— has already been acylated to the amine 2 and where the chemistry is allowed by compatible structure in Y—X—CO— and/or the use of appropriate protecting groups.

Scheme 4 describes another approach to the synthesis of amine 2A. The protected heteroaryl amine 8 containing a substituent such as bromo, iodo or triflate is coupled to dialkylphosphite 9 in the presence of a catalytic amount of palladium(0) catalyst, such as tetrakis-triphenylphosphine palladium(0) to provide, after deprotection, the phosphonate substituted heteroaryl amine 2A (Hirao et al., *Synthesis*, 1981, 56-57). The use of the reagent 10 in this reaction provides the corresponding phosphinate 2C (Rumthao et al., *Bioorg. Med. Chem. Lett.*, 2004, 14:5165-5170). As an example, the reaction between the bromo pyridine 11 and dialkylphosphite 9 catalyzed by $Pd(Ph_3P)_4$ provides the phosphonylated pyridine compound I-B. Compound II is obtained by coupling acid 1 to 5-bromo-2-aminopyrazine in the manner described in Scheme 1.

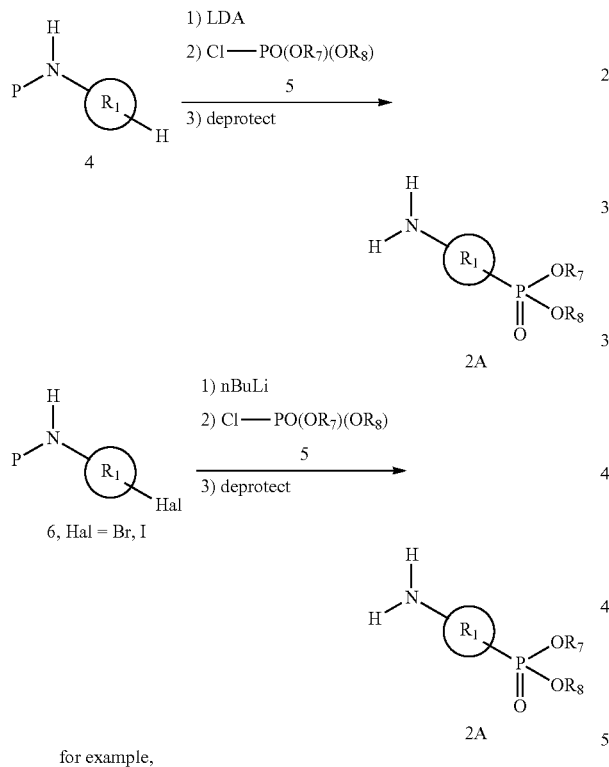

SCHEME 3

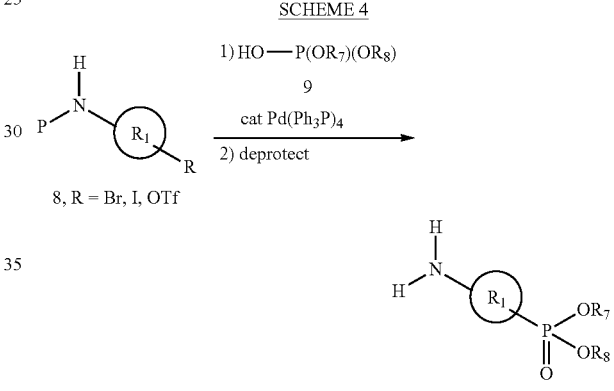

SCHEME 4

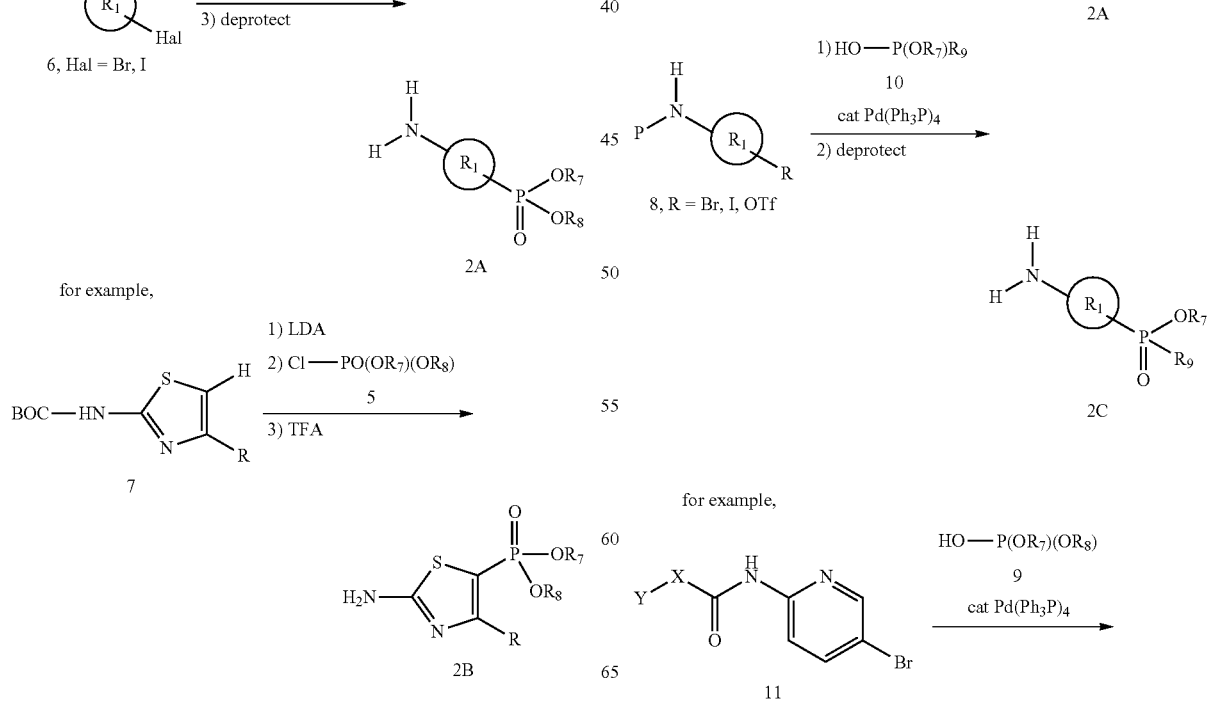

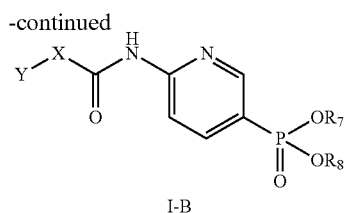

I-B

Scheme 5 describes the synthesis of compounds of formula I in which
$R_4 = -(CH_2)_n - Z - (CH_2)_m - PO(OR_7)(OR_8)$
Z=alkene or ethylene
m and n=0
thus connecting the phosphonate group to the heteroaromatic ring with a two-carbon linker. A suitably protected heteroaryl amine 8 is coupled to vinyl phosphonate 12 in the presence of catalytic amounts of a Pd(II) catalyst such as Pd(OAc)$_2$ and phosphine ligand such as tri-o-tolylphosphine to give a protected vinyl phosphonate intermediate product (Xu et al., *Synthesis*, 1983, 556-558). Removal of protecting groups yields the vinyl phosphonate amine 2D which is converted to I-D, the corresponding compound of formula I wherein Z=alkene (vinyl) by the manner described in Schemes 1 and 2. Hydrogenation in the presence of catalytic Pd(0) of 2D and 1D provides the corresponding ethylene (two-carbon) linked phosphonate compounds, 2E and 1-E. As mentioned earlier, these transformations can be conducted on a fully elaborated intermediate such as described conversion of aminopyrazine amide 11 to the vinyl phosphonate substituted pyrazine product I-F.

SCHEME 5

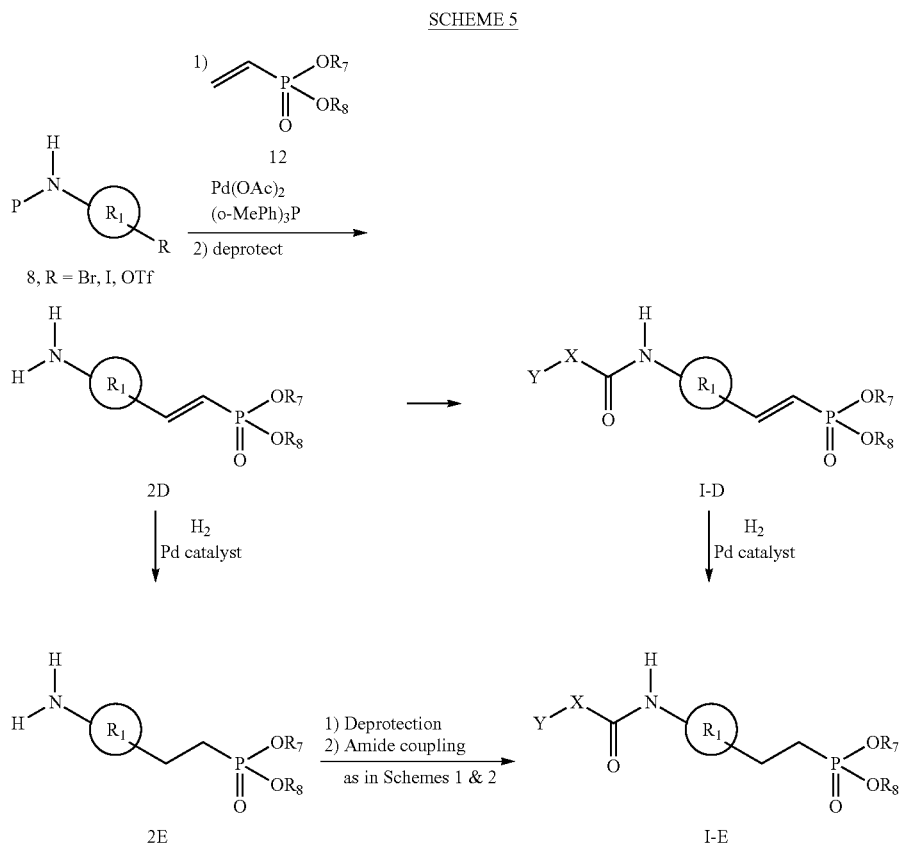

for example,

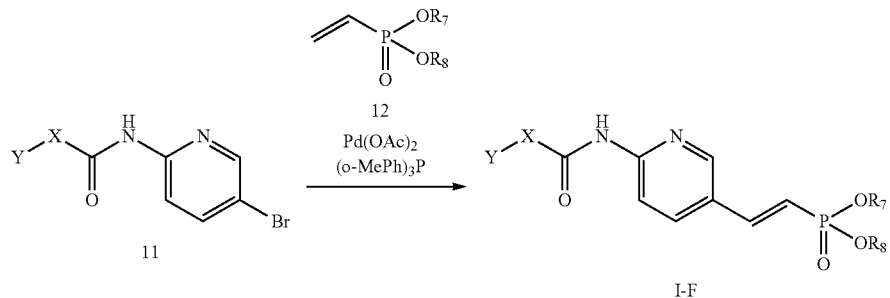

Scheme 6 describes the synthesis of compounds of formula I in which the phosphonate or phosphinate groups in $R_4$ are incorporated using the Arbusov (Engel, R., Handbook of Organophosphorus Chemistry, 1992 [Marcel Dekker]) or Michaelis-Becker (Engel, R., Handbook of Organophosphorus Chemistry, 1992 [Marcel Dekker]) reactions. In the Arbusov reaction, the alkyl halide 13 is heated with the trialkylphosphite 14 to yield, after removal of protecting groups, amine 2F Amine 2F is converted to compounds of formula IG by means described in Schemes 1 and 2. When carried out using $R_9P(OR_7)_2$ instead of the trialkylphosphite 14, the corresponding phosphinic ester product is obtained (i.e., where $R_4=\!\!-\!\!(CH_2)_n\!\!-\!\!Z\!\!-\!\!(CH_2)_m\!\!-\!\!PO\!\!-\!\!(R_9)(OR_7)$ (Kapustin et al., *Org. Lett.*, 2003, 5:3053-3057). In the Michaelis-Becker reaction, compound 13 is reacted with dialkylphosphite 15 in the presence of base to yield, after removal of protecting groups, amine 2F Amine 2F can be converted to compounds of formula I-G by means described in Schemes 1 and 2. As an example, the Boc-protected 5-bromomethylpyrazine can heated with trialkylphosphite 14 to give, after removal of the Boc group, the phosphonomethyl-substituted pyrazine amine 2G, which can be converted to compounds of formula I as described above.

3034-3047). The aminothiazoles 2H and 21 may be converted to compounds of formula I by means described in Scheme 1 and 2.

SCHEME 7

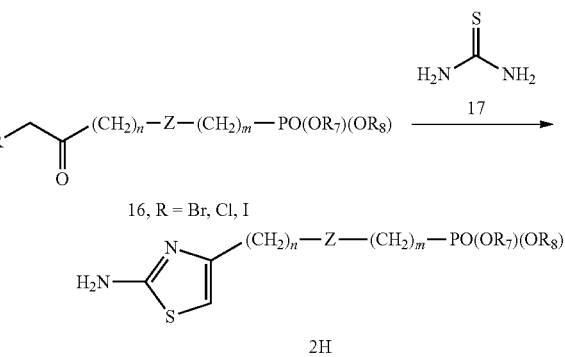

SCHEME 6

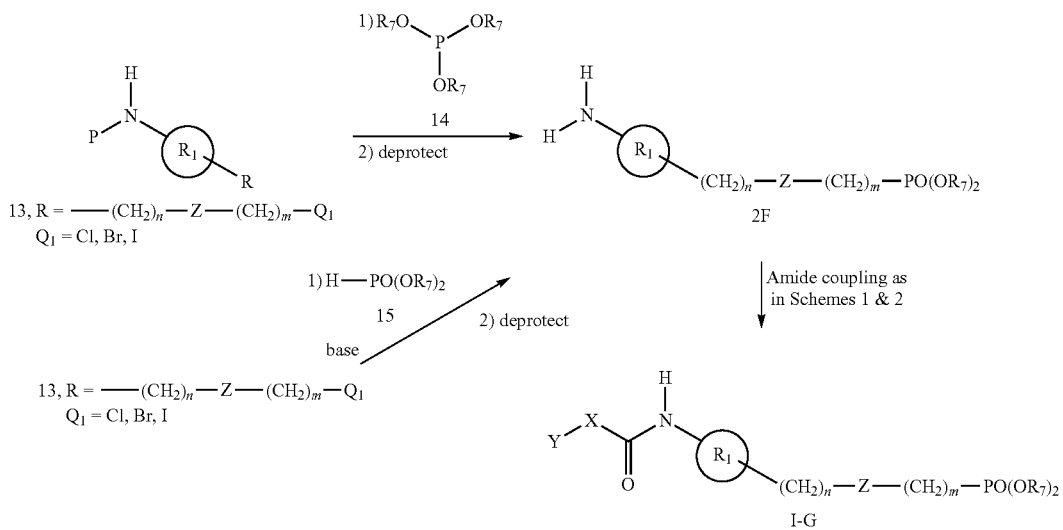

for example,

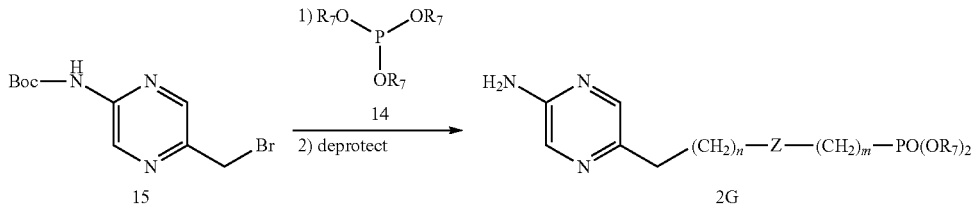

Scheme 7 describes the synthesis compounds of formula I in which the $R_1$ heteroaromatic ring is a thiazole. In this scheme, the phosphonate or phosphinate group in incorporated into an acyclic precursor to the formation of the heteroaromatic ring. In a standard Hantzsch thiazole synthesis, haloketone 16 is reacts with thiourea 17 to form the 4-substituted, 2-aminothiazole 2H. As an example, acetylphosphonic acid 18 is treated with bromine to form the α-haloketone 19. The reaction of 19 with thiourea 17 affords the 5-phosphono-2-aminothiazole 21 (Ohler et al., *Chem. Ber.*, 1984, 117:

-continued for example,

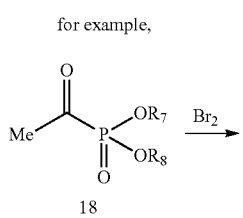

-continued

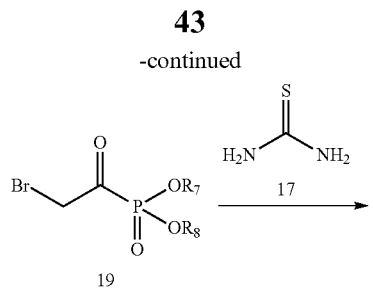

19

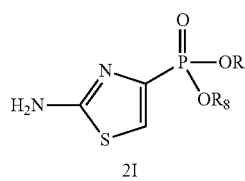

21

Scheme 8 describes the synthesis of compounds of formula I in which $R_4$=—$(CH_2)_n$—Z—$(CH_2)_m$-PO($OR_7$)($OR_8$)

Z=CH(OH)

m=0, 1 n=0, 1, 2 i.e., compounds in which $R_4$ contains a hydroxy-substituted methylene [Z=CH(OH)] positioned between the heteroaromatic ring $R_1$ and the phosphonate group. In equation (1), reaction of dialkylphosphite 9 with aldehyde 22 in the presence of a base such as triethylamine or DBN gives the hydroxyphosphonate product I-H (Caplan et al., *J. Chem. Soc. Perkin* 1,2000, 3:421-437), representing a compound of formula I in which Z=CH(OH), n=0, 1, 2 and m=0. In equation (2), alkyl phosphonate 23 is treated with a base such as n-BuLi, followed by addition of aldehyde 22 gives the hydroxyphosphonate product I-I (Mikolajczyk et al., *Synthesis*, 1984, 691-694), representing a compound of formula I in which Z=CH(OH), n=0, 1, 2 and m=1. As examples, the pyrazine 24 and thiazole 25 are converted as shown to the corresponding hydroxyphosphonates, I-J and I-K.

SCHEME 8

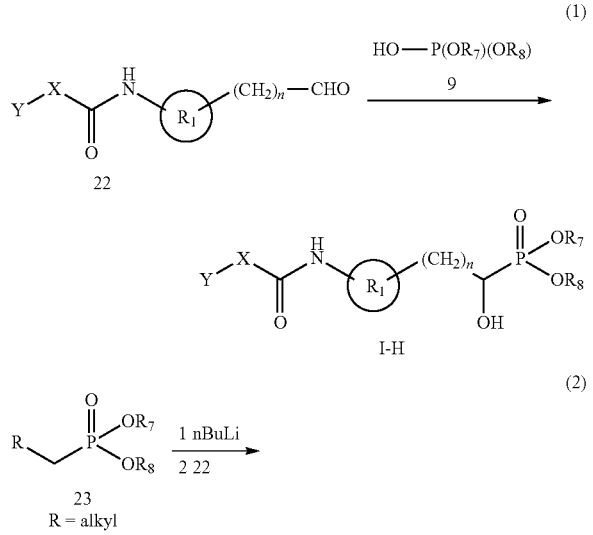

-continued

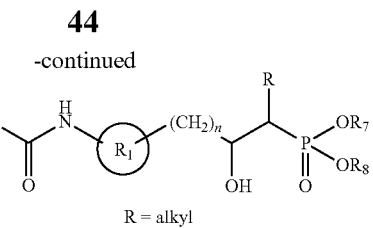

R = alkyl
I-I for example,

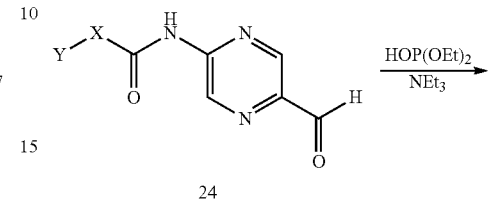

24

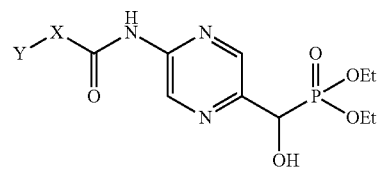

I-J

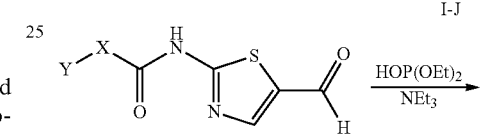

25

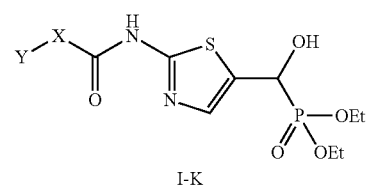

I-K

Scheme 9 describes the synthesis of compounds of formula I in which $R_4$=—$(CH_2)_n$—Z—$(CH_2)_m$—PO($OR_7$)($OR_8$)

Z=CH($OR_9$)

m=0 n=0, 1, 2 i.e., compounds in which $R_4$ contains a alkoxy-substituted methylene [Z=CH($OR_9$)] positioned between the heteroaromatic ring $R_1$ and the phosphonate group. In equation (1), the hydroxylphosphonate products of Scheme 8 may be alkylated with suitable active alkyl halides 26 to give the alpha-alkoxy phosphonates I-L (Wrobleski et al., *Tetrahedron Asymmetry*, 2002, 13:845-850). Alternatively, equation (2) depicts the rhodium-catalyzed insertion reaction of alcohols 28 with alpha-diazo phosphonates 27 which also provides compounds I-L (Cox, G. et al., *Tetrahedron*, 1994, 50:3195-3212; Moody, C. et al., *Tetrahedron Asymmetry*, 2001, 12:1657-1661). The preparation of alpha-diazo phosphonates 28 has been described by direct diazo transfer to the corresponding ketone 29a (Regitz, M., *Tetrahedron Lett.*, 1968, 9:3171-3174). Alternatively, the diazo phosphonates 28 can be obtained via base-catalyzed decomposition of the alpha-toluenesulfonylhydrazides derived from the corresponding keto phosphonates 29b (Marmor, R. et al., *J. Org. Chem.*, 1971, 36:128-136). The alpha-keto phosphonates 29a may be synthesized directly from alpha-hydroxy phosphonates (1-H) by oxidation using a reagent such as $CrO_3$ (Kaboudin, B. et al., Tetrahedron Lett., 2000, 41:3169-2171). Alternatively, the Arbusov reaction between an acid chloride and trialkylphosphite yields the corresponding alpha-keto phosphonate (Marmor, R., et al., *J. Org. Chem.*, 1971, 36:128-136). Methods for the synthesis of phosphonates such as 29a have been described above.

SCHEME 9

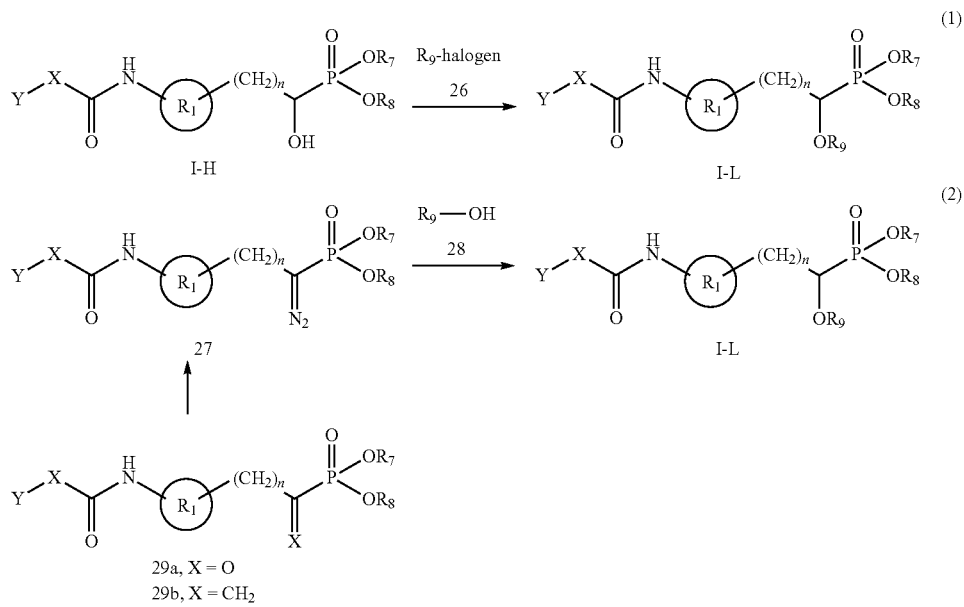

Scheme 10 describes the synthesis of compounds of formula I in which $R_4 = -(CH_2)_n - Z - (CH_2)_m - PO(OR_7)(OR_8)$
$Z = CH(NHR_9)$
$m = 0$
$n = 0, 1, 2$ i.e., compounds in which $R_4$ contains an amino-substituted methylene [$Z=CH(NHR_9)$] positioned between the heteroaromatic ring $R_1$ and the phosphonate group. In Scheme 10, aldehyde 22 can be reacted with a dialkylphosphite 9 and amine 30 to give the alpha-amino substituted phosphonate I-M by conducting the reaction in the presence of silica gel and microwave irradiation (Zhan et al., *Chem. Lett.*, 2005, 34:1042-1043). Other methods involve preformation of the corresponding imine resulting from condensation of the aldehyde 22 and amine 30, which is followed by reaction with the dialkylphosphite 9 in the presence of various catalysts such as Lewis acids (Laschat and Kunz, *Synthesis*, 1992, 90). Furthermore, other catalysts may be used for the one-pot synthesis described in Scheme 10 (for example, use of SmI$_2$ is described in Xu et al., *Eur. J. Org. Chem.*, 2003, 4728).

SCHEME 10

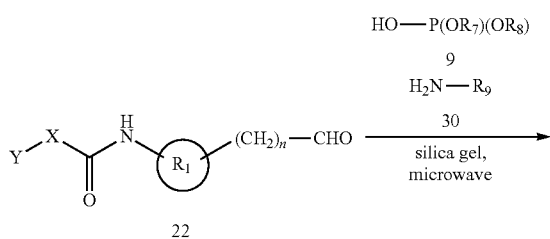

-continued

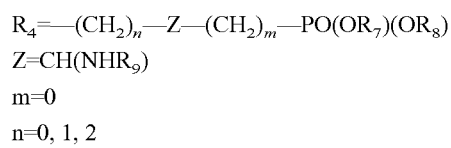
I-M

Scheme 11 describes the synthesis of compounds of formula I in which $R_4 = -(CH_2)_n - Z - (CH_2)_m - O - PO(OR_7)R_9$
and $-(CH_2)_n Z - (CH_2)_m - O - PO - R_9 R_{10}$.

Reaction of the alcohol precursor 31 with the a phosphonyl chloride 32 or phosphinyl chloride 33 in the presence of a base such as pyridine or triethylamine yields the phosphonate compound I-N (equation 1) or the phosphinate compound I-O (equation 2). In addition to the reaction shown for the synthesis of phosphonates I-N, other methods include the direct esterification of a phosphonic acid or the use of the Mitsunobu reaction (Saady et al., *Tetrahedron Lett.*, 1995, 36:2239-2242). The preparation of phosphinic esters of dimethylphosphinic acid (I-O wherein $R_9$ and $R_{10}$=Me) has been described using dimethylphosphinyl chloride and tetrazole in the presence of pyridine to produce an intermediate phosphinyl tetrazolide (PCT Intl. Application WO 2000/078763).

SCHEME 11

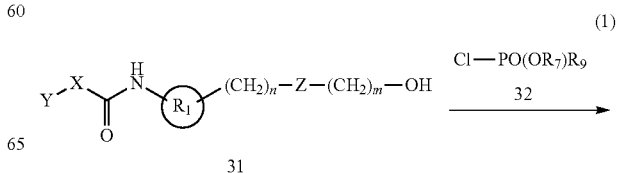

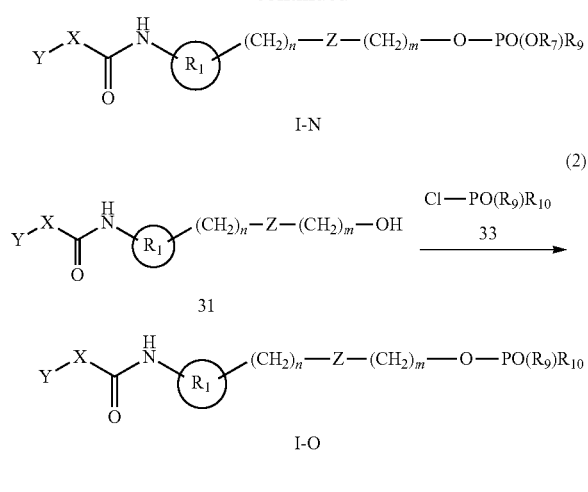

Scheme 12 describes the synthesis of compounds of formula I in which $R_4 = -(CH_2)_n - Z - (CH_2)_m - O - PO(OR_7)R_9$ and $-(CH_2)_n Z-(CH_2)_m - O - PO-(R_9)R_{10}$, and Z=S or $SO_2$, and m=1 or 2, and n=0, 1 or 2.

Reaction of a suitably activated halogen-substituted heteroaromatic intermediate 8 with potassium thiocyanate gives the thiocyanate intermediate 34. At this point, protecting groups may be removed and the resulting amino heteroaromatic compound coupled with acid 1 using standard means such as EDC-HOBt to give intermediate 35. Treatment of thiocyanate 35 with $NaBH_4$ yields the corresponding thiol intermediate which is alkyated with the substituted halide 36 to give compounds of formula I wherein Z=S (I-P). Treatment of the product I-P with oxidizing agents such as hydrogen peroxide or oxone gives compounds of formula I wherein $Z=SO_2$ (I-Q). As an example, treatment of the HBr salt of 2-amino-5-bromothiazole (37) with, for instance, potassium thiocyanate, affords thiocyanate 38. The amino-thiocyanate product is acylated with acid 1 using standard means to give the amide 39. Reduction of the thiocyanate group of 39 with a reagent such as $NaBH_4$, followed by alkylation of the resulting free thiol with iodomethyl phosphonate 40 gives phosphonate compounds of formula I where Z=S, m=1 and n=0 (I-P).

SCHEME 12

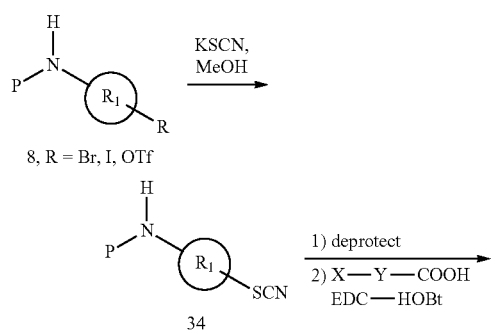

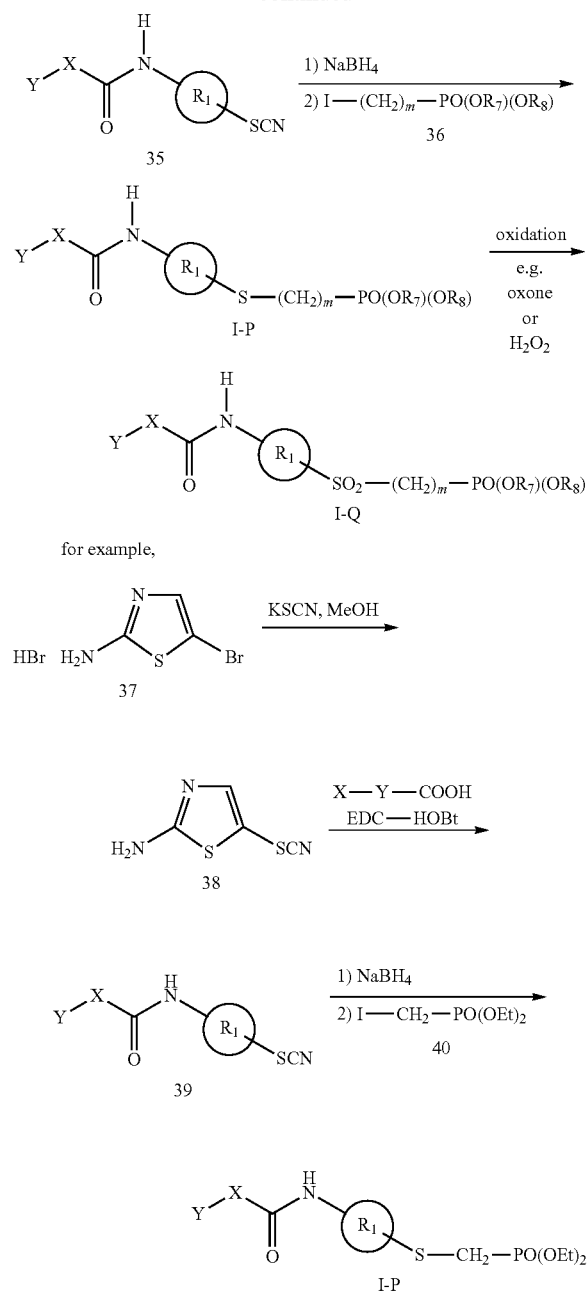

Scheme 13 describes the synthesis of compounds of formula I in which $R_4 = -(CH_2)_n - Z - (CH_2)_m - O - PO(OR_7)R_9$ and $-(CH_2)_n Z-(CH_2)_m - O - PO-(R_9)R_{10}$, and Z=O, and m=1 or 2, and n=0, 1 or 2.

Reaction of a suitably activated halogen-substituted heteroaromatic intermediate 41 with the hydroxy substituted phosphonate intermediate 42 in the presence of silver oxide yields I-R, the phosphonate compound of formula I in which Z=O, m=1 or 2, and n=0, 1 or 2 (Flor et al., *J. Med. Chem.*, 1999, 42:2633-2640).

SCHEME 13

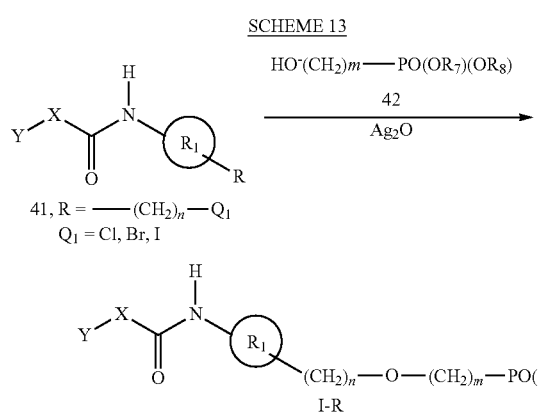

Scheme 14 describes a general synthesis of amine 2D, where the phosphonate or phosphinate moiety (here illustrated by a phosphonate) is linked to the heterocycle R1 by a nitrogen atom rather than a carbon atom. A protected (Pro) amino-heterocyle such as 43 can be deprotonated with a base followed by alkylation with an appropriate halide containing the phosphonate/phosphinate moiety followed by deprotection to give amine 2D. This is illustrated by the example of the N-Boc protected triazole 44, which is deprotonated with a base (e.g. NaH), then alkylated with an iodomethyl phosphonate 45. Deprotection of the N-Boc group then furnishes the aminotriazole phosphonate 46. On the other hand, in certain cases, the amino-heterocycle does not need to be protected, as illustrated in the case of the pyrazole 47, which can be deprotonated with a base such as KOtBu and alkylated preferentially on the ring nitrogen with electrophiles such as an iodomethyl phosphonate 45 to form product 48.

SCHEME 14

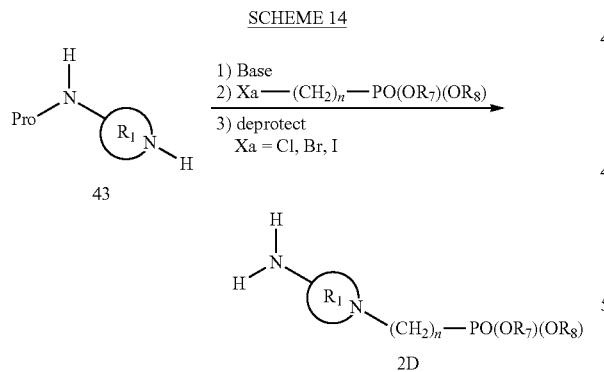

for example,

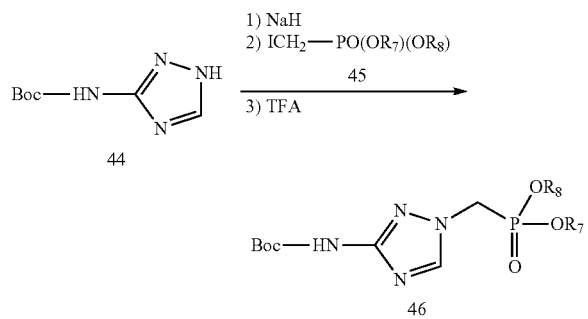

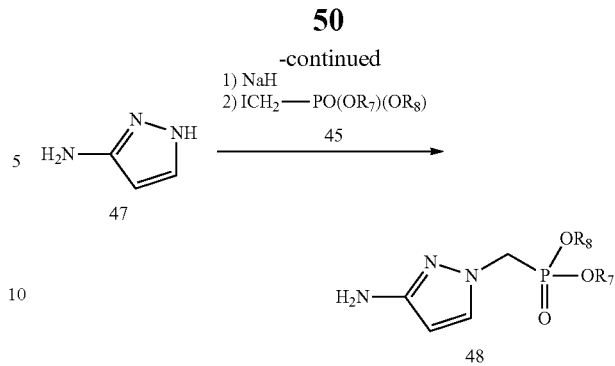

An alternative representative approach to N-alkylated phosphonates/phosphinates is shown in Scheme 15 Amine 43 can be deprotonated with an appropriate base and reacted with an iodide such as 49 (containing a functional group Xa, e.g. Cl, Br, OTs) to give the N-alkylated heterocycle 51. Alternatively, amine can be reacted with an iodide such as 50 (containing e.g., a protected hydroxyl group $OP_2$, which can subsequently be deprotected and converted to a halide via known methods, e.g. $Ph_3P/CBr_4$) to provide the N-alkylated heterocycle 51. This intermediate then can be reacted with either a trialkyl phosphate (Arbusov reaction) as described in Scheme 6 to provide a phosphonate, or, as shown here. When halide 51 is reacted with the phosphonite 52, the product is the corresponding phosphinic ester 2E (reference: Kapustin et al., *Org. Lett.,* 2003, 5:3053-3057).

SCHEME 15

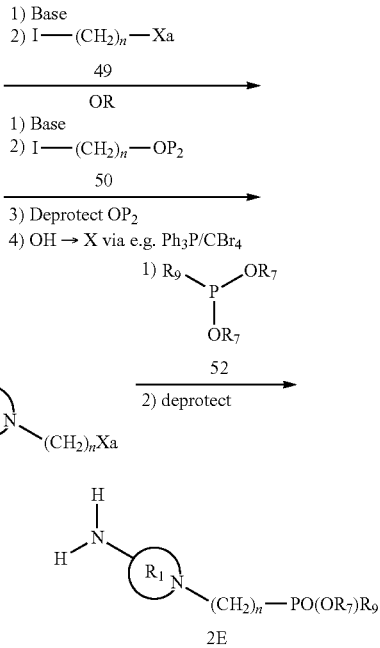

Scheme 16 describes the synthesis of compounds of formula I-S which contain cyclic phosphonate esters. The phosphonate diester of intermediate amine 2F is protected (e.g. as a tert-butyl carbamate or as a benzyl carbamate) to give the phosphonate 53, which is dealkylated with an agent such as bromotrimethylsilane. The resulting bis-trimethylsilyl phosphonic acid ester is reacted directly with oxalyl chloride to give the phosphoryl dichloride 54. Intermediate 54 is converted to the desired cyclic phosphonate 55 by reaction with an appropriate diol 54a in the presence of a base (reference: Notter et al., *Bioorg. Med. Chem. Lett.,* 2007, 17:113-117). Deprotection of 55 gives the corresponding amine, which is then readily converted to compounds of formula I-S by the methods previously described in Schemes 1 and 2.

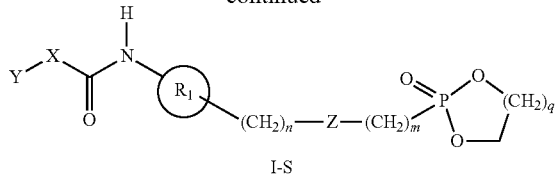

I-S

Similarly, Scheme 17 describes the synthesis of compounds of formula I-T which contain cyclic phosphine oxides. The phosphoryl dichloride 54 can be reacted with a Grignard reagent formed from a dibromide 56 and magnesium to provide the cyclic phosphine oxide 57 (ref: R. Polniaszek. et. al., *J. Org. Chem.,* 1991, 56:3137-3146). Deprotection of 57 gives the corresponding amine, which is then converted to compounds of formula I-T by the methods previously described in Schemes 1 and 2.

SCHEME 16

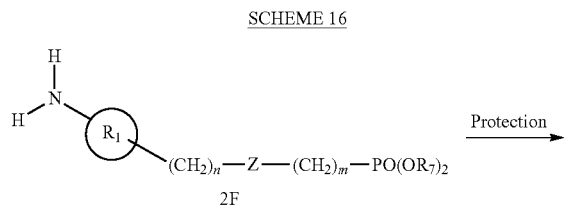

SCHEME 17

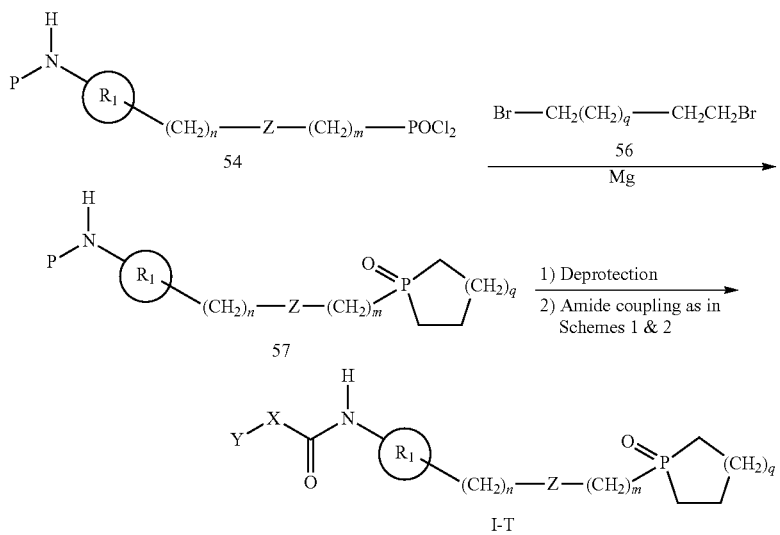

Scheme 18 describes the synthesis of compounds of formula I-U which contain cyclic phosphinates. Ethyl dichlorophosphate is reacted with a Grignard reagent formed from a dibromide 56 and magnesium to give the cyclic phosphinate ester 58 (ref: R. Polniaszek et. al., *J. Org. Chem.,* 1991, 56:3137-3146). Ester 58 is dealkylated (e.g. with bromotrimethylsilane). The resulting trimethylsilyl phosphonic acid ester is reacted directly with a chlorinating agent (e.g. oxalyl chloride) to give the phosphoryl chloride 59, which is then reacted with alcohol 31 in the presence of a base to give compounds of formula I-U.

-continued

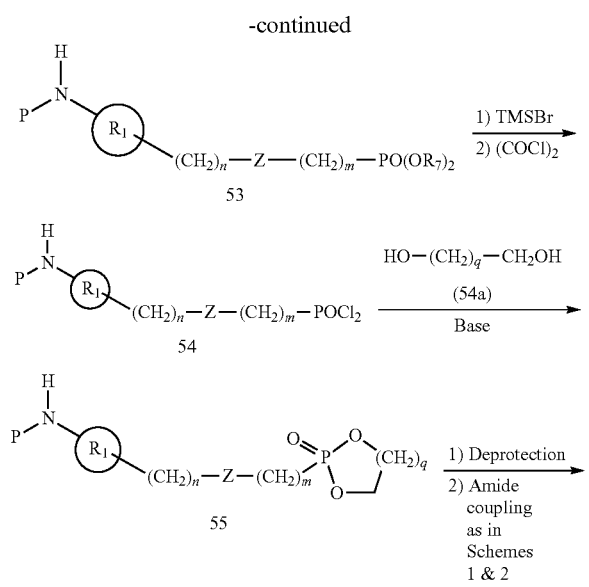

SCHEME 18

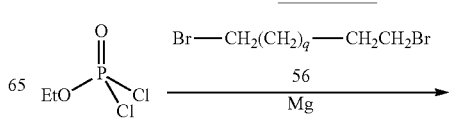

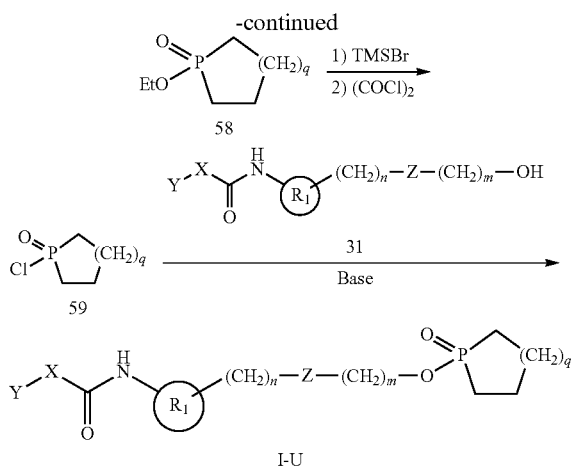

Utilities and Combinations

A. Utilities

The compounds of the present invention possess activity as enhancers of activity of the enzyme glucokinase, and, therefore, may be used in the treatment of diseases associated with glucokinase activity.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

Metabolic Syndrome or "Syndrome X" is described in Ford, et al., *J. Am. Med. Assoc.*, 2002, 287:356-359 and Arbeeny et al., *Curr. Med. Chem.—Imm., Endoc. & Metab. Agents*, 2001, 1:1-24.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other enhancers of activity of glucokinase or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-infective agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-ischemic agents, anti-cancer agents, anti-cytotoxic agents, anti-restenotic agents, anti-pancreatic agents, lipid lowering agents, appetite suppressants, memory enhancing agents, and cognitive agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones (PPARgamma agonists): ciglitazone, pioglitazone, troglitazone, rosiglitazone; non-thiazolidinedione PPAR-gamma agonists; selective PPARgamma modulators (SPPARMs; e.g. metaglidasen from Metabolex); PPAR-alpha agonists; PPAR alpha/gamma dual agonists; PPAR delta agonists, PPARalpha/gamma/delta pan agonists; SGLT2 inhibitors; dipeptidyl peptidase-IV (DPP4) inhibitors; aldose reductase inhibitors; RXR agonists: JTT-501, MX-6054, DRF2593, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's farglitazar (GI-262570), englitazone (CP-68722, Pfizer), or darglitazone (CP-86325, Pfizer), isaglitazone (MIT/J&J), JTT-501 (JPNT/P&U), L-895645 (Merck), R-119702 (Sankyo/WL), N,N-2344 or balaglitazone (Dr. Reddy/NN), or YM-440 (Yamanouchi).

Suitable PPAR alpha/gamma dual agonists include muraglitazar (Bristol-Myers Squibb), tesaglitazar (Astra/Zeneca), naveglitazar (Lilly/Ligand); AVE-0847 (Sanofi-Aventis); TAK-654 (Takeda), as well as those disclosed by Murakami et al, "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", Diabetes 47:1841-1847 (1998), WO 01/21602 and U.S. Pat. No. 6,414,002, the disclosure of which is incorporated herein by reference, employing dosages as set out therein, which compounds designated as preferred are preferred for use herein. Suitable PPARdelta agonists include, for example, GW-501516 (Glaxo). Suitable PPARalpha/gamma/delta pan agonists include, for example, GW-677954 (Glaxo).

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptin (Bristol-Myers Squibb), vildagliptin (Novartis) and sitagliptin (Merck) as well as those disclosed in WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36):11597-11603, 1999, TSL-225 (tryptophyl-1,2,3,4-tetrahydroisoquinoline-3-carboxylic acid) as disclosed by Yamada et al., Bioorg. & Med. Chem. Lett., 8:1537-1540 (1998), 2-cyanopyrrolidides and 4-cyanopyrrolidides, as disclosed by Ashworth et al., Bioorg. & Med. Chem. Lett., Vol. 6, No. 22, pp. 1163-1166 and 2745-2748 (1996), employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1 (1-36) amide, GLP-1(7-36) amide, GLP-1 (7-37) (as disclosed in U.S. Pat. No. 5,614,492 to Habener), as well as AC2993 (Amylin), and LY-315902 (Lilly).

Other anti-diabetic agents that can be used in combination with compounds of the invention include ergoset and D-chiroinositol.

Suitable anti-ischemic agents include, but are not limited to, those described in the Physician's Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, cholesterol ester transfer protein inhibitors (e.g., torcetrapib (Pfizer)), and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983, and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440; and related statin compounds disclosed in U.S. Pat. No. 5,753,675; pyrazole analogs of mevalonolactone derivatives, as disclosed in U.S. Pat. No. 4,613,610; indene analogs of mevalonolactone derivatives, as disclosed in PCT application WO 86/03488; 6-[2-(substituted-pyrrol-1-yl)alkyl)pyran-2-ones and derivatives thereof, as disclosed in U.S. Pat. No. 4,647,576; Searle's SC-45355 (a 3-substituted pentanedioic acid derivative) dichloroacetate; imidazole analogs of mevalonolactone, as disclosed in PCT application WO 86/07054; 3-carboxy-2-hydroxy-propane-phosphonic acid derivatives, as disclosed in French Patent No. 2,596,393; 2,3-disubstituted pyrrole, furan and thiophene derivatives, as disclosed in European Patent Application No. 0221025; naphthyl analogs of mevalonolactone, as disclosed in U.S. Pat. No. 4,686,237; octahydronaphthalenes, such as disclosed in U.S. Pat. No. 4,499,289; keto analogs of mevinolin (lovastatin), as disclosed in European Patent Application No. 0142146 A2; and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin, and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp. 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2:1-40 (1996).

In addition, other squalene synthetase inhibitors suitable for use herein include the terpenoid pyrophosphates disclosed by P. Ortiz de Montellano et al, J. Med. Chem., 1977, 20:243-249, the farnesyl diphosphate analog A and presqualene pyrophosphate (PSQ-PP) analogs as disclosed by Corey and Volante, J. Am. Chem. Soc., 1976, 98:1291-1293, phosphinylphosphonates reported by McClard, R. W. et al, J.A.C.S., 1987, 109:5544 and cyclopropanes reported by Capson, T. L., Ph.D. dissertation, June, 1987, Dept. Med. Chem. U of Utah, Abstract, Table of Contents, pp. 16, 17, 40-43, 48-51, Summary.

The fabric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24:9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1):77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1):16-30; "RP 73163: a bioavailable alkylsulfinyl-diphenylimidazole ACAT inhibitor", Smith, C., et al, Bioorg. Med. Chem. Lett. (1996), 6(1):47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3):204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, Chemtracts: Org. Chem. (1995), 8(6):359-62, or TS-962 (Taisho Pharmaceutical Co. Ltd.).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitors for use in combination with the compounds of the invention include SCH48461 (Schering-Plough), as well as those disclosed in Atherosclerosis 115:45-63 (1995) and J. Med. Chem. 41:973 (1998).

Examples of suitable ileal Na$^+$/bile acid cotransporter inhibitors for use in combination with the compounds of the invention include compounds as disclosed in Drugs of the Future, 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120:1199-1206, and Cornicelli et al, "15-Lipoxygenase and its Inhibition: A Novel Therapeutic Target for Vascular Disease", Current Pharmaceutical Design, 1999, 5:11-20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, and those discussed in D. L. Hertzog, Expert Opin. Ther. Patents, 2004, 14:1435-1452.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson), or axokine (Regeneron), with sibutramine and topiramate being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., HP-228); leptin or mimentics; 11-beta-hydroxysteroid dehydrogenase type-1 inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators; and monoclonal antibodies. Additional anti-cancer agents are disclosed in EP 1177791. The compounds of the invention may also be used in conjunction with radiation therapy.

Examples of suitable memory enhancing agents, anti-dementia agents, or cognitive agents for use in combination with the compounds of the present invention include, but are not limited to, donepezil, rivastigmine, galantamine, memantine, tacrine, metrifonate, muscarine, xanomelline, deprenyl, and physostigmine.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules, or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules, or powders. The dose for adults is between 0.25 and 2,000 mg per day, preferably between 1 and 500 mg, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

ABBREVIATIONS

The following abbreviations are employed in the Examples and elsewhere herein:
Ph=phenyl
Bn=benzyl
t-Bu=tertiary butyl
i-Bu=iso-butyl
Me=methyl
Et=ethyl
Pr=propyl
iPr=isopropyl
Bu=butyl
AIBN=2,2'-Azobisisobutyronitrile
TMS=trimethylsilyl
TMSCHN$_2$=(trimethylsilyl)diazomethane
TMSN$_3$=trimethylsilyl azide
TBS=tert-butyldimethylsilyl
FMOC=fluorenylmethoxycarbonyl
Boc or BOC=tert-butoxycarbonyl
Cbz=carbobenzyloxy or carbobenzoxy or benzyloxycarbonyl
THF=tetrahydrofuran
Et$_2$O=diethyl ether
hex=hexanes
EtOAc=ethyl acetate
DMF=dimethyl formamide
MeOH=methanol
EtOH=ethanol
DCM=dichloromethane
i-PrOH=isopropanol
DMSO=dimethyl sulfoxide
DME=1,2 dimethoxyethane
DMA=N,N-dimethylacetylamide
DCE=1,2 dichloroethane
HMPA=hexamethyl phosphoric triamide
HOAc or AcOH=acetic acid
TFA=trifluoroacetic acid
DIEA or DIPEA or i-Pr$_2$NEt or Hunig's Base=diisopropylethylamine
TEA or Et$_3$N=triethylamine
NMM=N-methyl morpholine
NBS=N-bromosuccinimide
NCS=N-chlorosuccinimide
DMAP=4-dimethylaminopyridine
DEPBT=3-diethoxyphosphoryloxy-1,2,3-benzotriazin-4[3H]-one
mCPBA=3-chloroperoxybenzoic acid
NaBH$_4$=sodium borohydride
NaBH(OAc)$_3$=sodium triacetoxyborohydride
NaN$_3$=sodium azide
DIBALH=diisobutyl aluminum hydride
LiAlH$_4$=lithium aluminum hydride
n-BuLi=n-butyllithium
Oxone®=monopersulfate
Pd/C=palladium on carbon
PXPd$_2$=Dichloro(chlorodi-tert-butylphosphine)palladium (II) dimer or [PdCl$_2$(t-Bu)$_2$PC1]$_2$
PtO$_2$=platinum oxide
KOH=potassium hydroxide
NaOH=sodium hydroxide
LiOH=lithium hydroxide
LiOH.H$_2$O=lithium hydroxide monohydrate
HCl=hydrochloric acid
H$_2$SO$_4$=sulfuric acid
H$_2$O$_2$=hydrogen peroxide
Al$_2$O$_3$=aluminum oxide
K$_2$CO$_3$=potassium carbonate
Cs$_2$CO$_3$=cesium carbonate
NaHCO$_3$=sodium bicarbonate
ZnBr$_2$=zinc bromide
MgSO$_4$=magnesium sulfate Na₂SO₄=sodium sulfate
KSCN=potassium thiocyanate
NH₄Cl=Ammonium chloride
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H₂O=1-hydroxybenzotriazole hydrate
HOAT=1-Hydroxy-7-azabenzotriazole
PyBOP reagent or BOP reagent=benzotriazol-1-yloxy-tris (dimethylamino) phosphonium hexafluorophosphate
NaN(TMS)₂=sodium hexamethyldisilazide or sodium bis(trimethylsilyl)amide
Ph₃P=triphenylphosphine
Pd(OAc)₂=Palladium acetate
(Ph₃P)₄Pd°=tetrakis triphenylphosphine palladium
Pd₂(dba)₃=tris(dibenzylacetone)dipalladium
DPPF=1,1'-Bis(diphenylphosphino)ferrocene
HATU=2-(7-aza-1H-benzotriazole-1-yl)-1,1,3,3-tetramethyluronium hexafluorophosphate, 2-(3H-[1,2,3]triazolo[4,5-b]pyridin-3-yl)-1,1,3,3-tetramethylisouronium hexafluorophosphate(V)
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
H₂=hydrogen
Ar=argon
N₂=nitrogen
Equiv=equivalent(s)
min=minute(s)
h or hr=hour(s)
L=liter
mL=milliliter
μL=microliter
g=gram(s)
mg=milligram(s)
mol=moles
mmol=millimole(s)
meq=milliequivalent
RT or R.T.=room temperature
AT=ambient temperature
sat or sat'd=saturated
aq.=aqueous
TLC=thin layer chromatography
HPLC=high performance liquid chromatography
HPLC R$_t$=HPLC retention time
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLES

The following working Examples serve to better illustrate, but not limit, some of the preferred embodiments of the present invention.

General

The term HPLC refers to a Shimadzu high performance liquid chromatography with one of following methods:

Method A: YMC or Phenomenex C18 5 micron 4.6×50 mm column using a 4 minute gradient of 0-100% solvent B [90% MeOH:10% H₂O:0.2% H₃PO₄] and 100-0% solvent A [10% MeOH:90% H₂O:0.2% H₃PO₄] with 4 mL/min flow rate and a 1 min. hold, an ultra violet (uv) detector set at 220 nm.

Method B: Phenomenex S5 ODS 4.6×30 mm column, gradient elution 0-100% B/A over 2 min (solvent A=10% MeOH/H₂O containing 0.1% TFA, solvent B=90% MeOH/H₂O containing 0.1% TFA), flow rate 5 mL/min, UV detection at 220 nm.

Method C: YMC S7 ODS 3.0×50 mm column, gradient elution 0-100% B/A over 2 min (solvent A=10% MeOH/H₂O containing 0.1% TFA, solvent B=90% MeOH/H₂O containing 0.1% TFA), flow rate 5 mL/min, UV detection at 220 nm.

The term prep HPLC refers to an automated Shimadzu HPLC system using a mixture of solvent A (10% MeOH/90% H₂O/0.2% TFA) and solvent B (90% MeOH/10% H₂O/0.2% TFA). The preparative columns are packed with YMC or Phenomenex ODS C18 5 micron resin or equivalent.

The following Examples are illustrative of preferred compounds of the invention.

Example 1

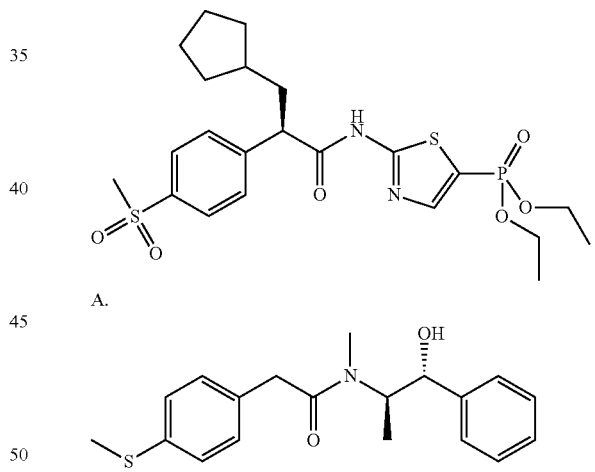

A.

Trimethylacetyl chloride (3.83 mL; 31.1 mmol) was added dropwise to a −10° C. mixture of 4-methylthio-phenylacetic acid (5.40 g; 29.6 mmol) and K₂CO₃ (12.3 g; 88.8 mmol) in acetone (40 mL), while maintaining the temperature at <−10° C. After 10 min at −10° C., the reaction was warmed to 0° C. After 10 min at 0° C., the reaction was cooled to −10° C. (1R,2R)-(−)-pseudoephedrine (7.34 g; 44.4 mmol) was added. After 10 min at −10° C., the reaction mixture was allowed to warm to RT. After 4 h, the reaction was partitioned between EtOAc (60 mL) and H₂O (30 mL). The aqueous phase was extracted with EtOAc (30 mL). All organic phases were combined, washed with brine (30 mL), dried (MgSO₄) and concentrated in vacuo. The crude product was recrystallized from warm EtOAc/hexanes to afford Part A compound (7.3 g; 75%) as a crystalline solid.

B.

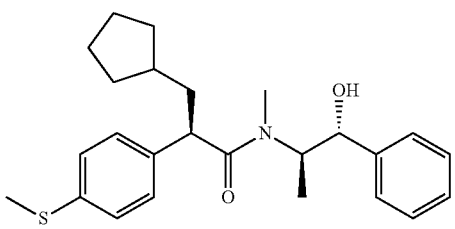

A solution of Part A compound (7.0 g; 21.27 mmol) in THF (51 mL) was added over 45 min to a −70° C. solution of LiN(TMS)$_2$ (44.7 mL of a 1.0 M solution in THF; 44.7 mmol) while keeping the internal temperature below −65° C. After addition the reaction mixture was stirred at −70° C. for 15 min and then allowed to warm to 0° C. After 20 min at 0° C. the reaction was re-cooled to −70° C. A solution of cyclopentylmethyl iodide (6.70 g; 31.91 mmol) in DMPU (5.4 mL; 44.68 mmol) was added. The reaction was stirred at −70° C. for 30 min and then allowed to warm to RT. After 20 h the reaction mixture was quenched by addition of sat. aqueous NH$_4$Cl (20 mL). The solution was extracted with EtOAc (175 mL). The organic phase was isolated, washed with sat. NH$_4$Cl (50 mL) and brine (50 mL), dried (MgSO$_4$) and concentrated. The crude product was purified by flash chromatography (SiO$_2$; continuous gradient from 0 to 90% solvent B over 75 min, where solvent A=hexanes and solvent B=EtOAc) to give Part B compound (6.94 g; 79%).

C.

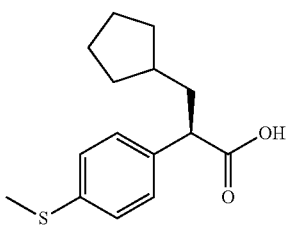

A solution of Part B compound (5.44 g; 13.22 mmol) in 1,4 dioxane (24 mL) was treated with 9 N aqueous H$_2$SO$_4$ (15 mL). The reaction mixture was then heated at 105° C. After 20 h heating was stopped and the solution was cooled to RT. H$_2$O (100 mL) was added to precipitate the product. The solid was isolated by filtration and dried in vacuo to give Part C compound (3.40 g; 97%).

D.

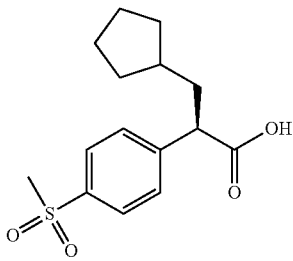

Oxone® (17.64 g; 28.70 mmol) was added to a mixture of Part C compound (3.30 g; 12.48 mmol) in 2-propanol (90 mL) and H$_2$O (45 mL). After 20 h at RT the 2-propanol was removed in vacuo. The aqueous solution was extracted with EtOAc (175 mL). The organic phase was washed with H$_2$O (50 mL) and brine (50 mL), dried (MgSO$_4$) and concentrated in vacuo to give Part D compound (3.60 g; 97%) as a white solid. (Part D compound was prepared by a slight modification of the procedure found in Patent WO 02/46173).

E.

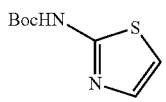

Di-tert-butyl dicarbonate (2.40 g; 11.00 mmol) was added to a solution of 2-aminothiazole (1.00 g; 9.99 mmol) in THF (5 mL). TEA (1.67 mL; 11.98 mmol) was added followed by a catalytic amount of 4-DMAP (2.0 mg). After 4 h the reaction mixture was concentrated in vacuo. The residue was partitioned between EtOAc (20 mL) and 0.1 N aqueous HCl (15 mL). The organic phase was washed with brine (15 mL), dried (MgSO$_4$) and concentrated in vacuo. The crude product was chromatographed (SiO$_2$; continuous gradient from 0 to 100% solvent B over 25 min; hold at 100% solvent B for 5 min, where solvent A=hexanes and solvent B=EtOAc) to give Part E compound (0.77 g; 39%) as a white solid.

F.

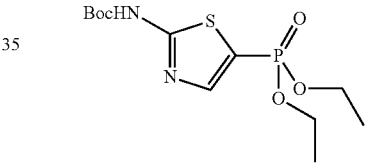

A −78° C. solution of LDA (1.44 mL of a 2.0 M solution in THF/heptane/ethylbenzene; 2.88 mmol) was cannulated into a −78° C. solution of Part A compound (0.25 g; 1.25 mmol) in THF (4 mL). After 30 min a solution of ClPO$_3$Et$_2$ (270 µL; 1.87 mmol) in THF (0.5 mL) was slowly added. The reaction mixture was allowed to slowly warm to RT overnight. After 16 h the reaction was quenched by addition of H$_2$O (0.5 mL). The solution was partitioned between EtOAc (5 mL) and brine (5 mL). The organic phase was dried (MgSO$_4$) and concentrated in vacuo. The crude product chromatographed (SiO$_2$; continuous gradient from 0 to 100% solvent B over 10 min, hold at 100% solvent B for 10 min, where solvent A=hexanes and solvent B=EtOAc) to give Part F compound (0.12 g; 29%).

G.

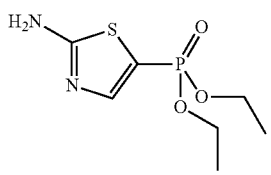

TFA (0.40 mL) was added to a 0° C. solution of Part B compound (0.12 g; 0.37 mmol) in DCM (0.80 mL). After addition was complete the reaction mixture was allowed to warm to RT and stirred at RT for 4 h. Volatiles were removed in vacuo, and the residue was dissolved in EtOAc (3 mL). The EtOAc solution was washed with sat. aqueous NaHCO$_3$ (3 mL). The aqueous layer was extracted with EtOAc (2 mL). The combined organic extracts were dried (MgSO$_4$) and concentrated in vacuo to give Part G compound (83.0 mg; 96%).

H.

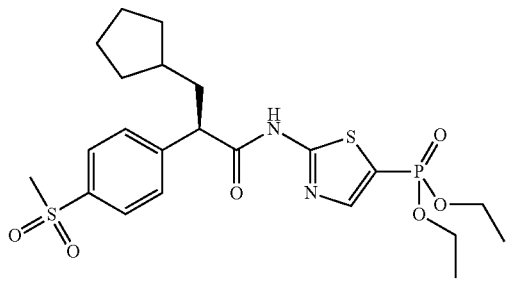

DEPBT (47.8 mg; 0.16 mmol) was added to a solution of Part D compound (23.7 mg; 0.08 mmol) and Part G compound (20.8 mg; 0.09 mmol) in THF (0.40 mL). DIPEA (27.0 uL; 0.16 mmol) was added. After 24 h at RT the reaction mixture was concentrated in vacuo. The residue was dissolved in EtOAc (3 mL). The EtOAc layer was washed with 1 N aqueous HCl (2 mL), H$_2$O (2 mL), sat. aqueous NaHCO$_3$ (2×2 mL) and brine (2 mL), dried (MgSO$_4$) and concentrated in vacuo. The crude product was dissolved in DCM (3 mL). The solution was stirred with aminomethylated polystyrene resin (40 mg; to remove unreacted activated ester) for 20 min and then filtered. The filtrate was concentrated in vacuo. The residue was purified by preparative HPLC (YMC reverse phase ODS-A-5u 30×100 mm column; flow rate=40 mL/min, 10 to 100% solvent B over 12 min, hold to 16 min, where solvent A=90:10:0.1 H$_2$O:MeOH:TFA and solvent B=90:10:0.1 MeOH:H$_2$O:TFA) to give the title compound (15 mg; 37%) as a colorless solid. [M+H]$^+$=515.2; $^1$H NMR (400 MHz, CD$_3$OD): δ 1.19 (m, 2H), 1.33 (m, 6H), 1.50 (m, 2H), 1.64 (m, 3H), 1.80 (m, 2H), 1.89 (m, 1H), 2.23 (m, 1H), 3.10 (s, 3H), 4.00 (t, 1H), 4.12 (m, 4H), 7.69 (d, 2H), 7.89 (d, J=4.8 Hz, 1H), 7.93 (d, 2H).

Example 2

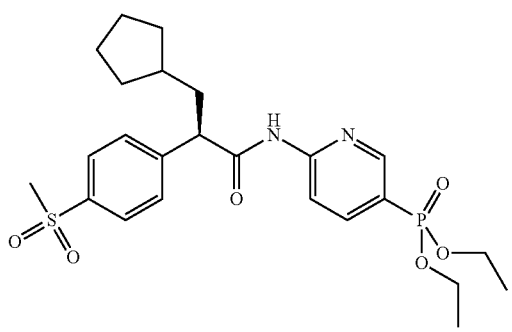

A.

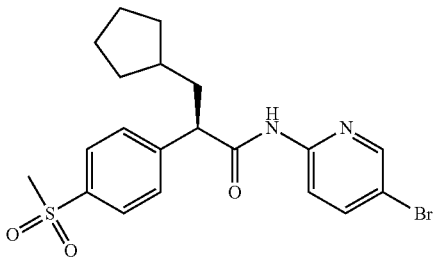

Oxalyl chloride (2.0 M in DCM) (0.68 mL; 1.35 mmol) was added to a mixture of Example 1 Part D compound (200 mg; 0.68 mmol) in DCM (1 mL). DMF (5 μL) was added. Gas evolution occurred. After 2 h at RT the reaction mixture was concentrated in vacuo. The residue was stripped from CHCl$_3$ (2×2 mL), then was dissolved in DCM (2.5 mL). The solution was cooled to 0° C. and 2-amino-5-bromopyridine (175 mg; 1.01 mmol) was added followed by pyridine (82 uL; 1.01 mmol). The reaction mixture was stirred at RT for 16 h, then was concentrated in vacuo. The residue was partitioned between EtOAc (5 mL) and 0.1 N aqueous HCl (4 mL). The organic phase was washed with brine (4 mL), dried (MgSO$_4$), and concentrated in vacuo. The crude product was chromatographed (SiO$_2$; continuous gradient from 0 to 80% solvent B over 18 min, where solvent A=hexanes and solvent B=EtOAc) to give Part A compound (250 mg; 82%).

B.

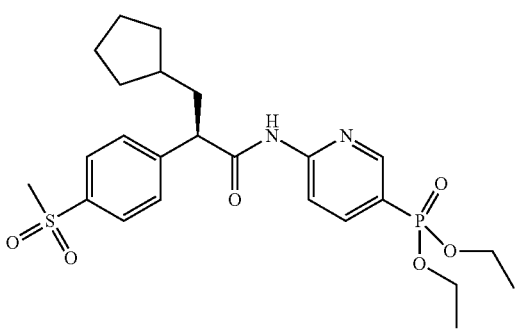

THF (degassed) (0.50 mL) was added to Part A compound (28.9 mg; 0.064 mmol) and (Ph$_3$P)$_4$Pd° (14.8 mg; 0.013 mmol). H(O)P(OEt)$_2$ (10.3 μL; 0.079 mmol) was added followed by TEA (13.7 μL; 0.098 mmol). The vessel was capped and the reaction mixture was heated at 75° C. for 9 h, then was cooled to RT and concentrated in vacuo. The crude product was purified by preparative HPLC (YMC reverse phase ODS-A-5u 30×100 mm column; flow rate=40 mL/min, 20 to 100% solvent B over 12 min, hold at 100% solvent B for 17 min, where solvent A=90:10:0.1 H$_2$O:MeOH:TFA and solvent B=90:10:0.1 MeOH:H$_2$O:TFA) to give title compound (18 mg; 55%) as an amorphous solid. [M+H]$^+$=509.2; $^1$H NMR (400 MHz, CD$_3$OD): δ 1.19 (m, 2H), 1.32 (t, 6H), 1.51 (m, 2H), 1.64 (m, 3H), 1.84 (m, 3H), 2.22 (m, 1H), 3.09 (s, 3H), 4.02 (t, 1H), 4.12 (m, 4H), 7.70 (d, 2H), 7.92 (d, 2H), 8.08 (ddd, 1H), 8.26 (dd, 1H), 8.60 (dd, 1H).

Example 3

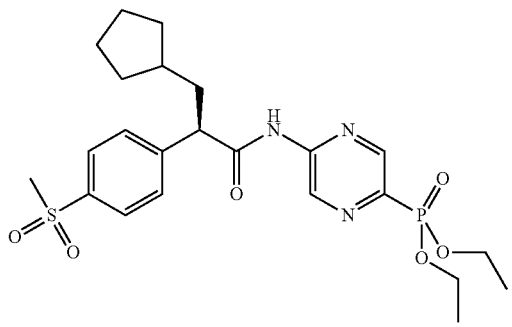 [SMILES: CCOP(=O)(OCC)c1cnc(NC(=O)[C@H](CC2CCCC2)c2ccc(S(C)(=O)=O)cc2)cn1]

The title compound (14.3 mg; 44%; yellow amorphous solid) was synthesized from 5-bromo-2-pyrazinamine employing the procedure described in Example 2. [M+H]$^+$=510.2; $^1$H NMR (400 MHz, CD$_3$OD): δ 1.19 (m, 2H), 1.33 (t, 6H), 1.51 (m, 2H), 1.64 (m, 3H), 1.84 (m, 3H), 2.22 (m, 1H), 3.09 (s, 3H), 4.03 (t, 1H), 4.21 (m, 4H), 7.71 (d, 2H), 7.92 (d, 2H), 8.71 (s, 1H), 9.59 (s, 1H).

Example 4

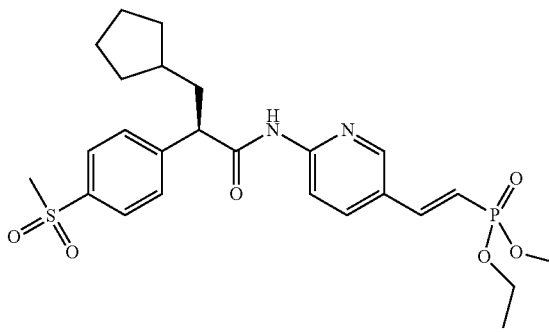

CH$_3$CN (150 μL) was added to a mixture of Example 2 Part A compound (30 mg; 0.066 mmol), Pd(OAc)$_2$ (0.30 mg; 0.0013 mmol) and tri-o-tolylphosphine (0.80 mg; 0.0026 mmol). Diethyl vinylphosphate (10.7 uL; 0.083 mmol) was added followed by TEA (27.7 uL; 0.199 mmol). The reaction mixture was heated at 95° C. for 4 h, then was cooled to RT. The solution was partitioned between EtOAc (3 mL) and brine (2 mL). The organic phase was dried (MgSO$_4$) and concentrated in vacuo. The residue was chromatographed (SiO$_2$; continuous gradient from 0 to 100% solvent B over 12 min, hold at 100% for 8 min, where solvent A=hexanes and solvent B=EtOAc) to give the title compound (24 mg; 68%) as an amorphous solid. [M+H]$^+$=535.3; $^1$H NMR (400 MHz, CDCl$_3$): δ 1.15 (m, 2H), 1.36 (t, 6H), 1.48 (m, 2H), 1.61 (m, 3H), 1.74 (m, 2H), 1.92 (m, 1H), 2.23 (m, 1H), 3.05 (s, 3H), 3.68 (t, 1H), 4.14 (m, 4H), 6.25 (t, 1H), 7.42 (d, J=22.4 Hz, 2H), 7.59 (d, 2H), 7.85 (dd, 1H), 7.92 (d, 2H), 8.23 (s, 1H), 8.24 (d, 2H), 8.31 (d, 1H).

Example 5

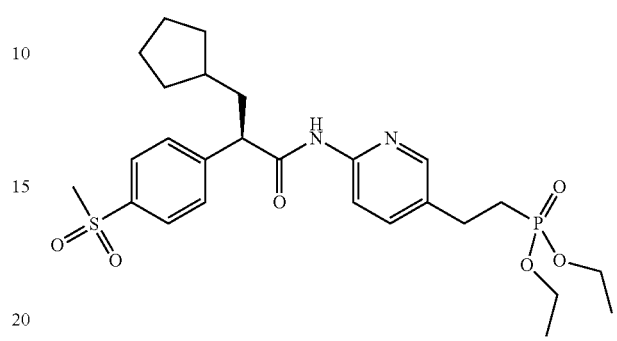

10% Pd/C (5 mg) was added to a solution of Example 4 compound (20 mg; 0.037 mmol) in MeOH (0.30 mL). A H$_2$ atmosphere was introduced via balloon. After 8 h the reaction mixture was filtered. The catalyst was rinsed with MeOH (1.5 mL) and the combined filtrates were concentrated in vacuo. The crude product was chromatographed (SiO$_2$; continuous gradient from 0 to 100% solvent B over 6 min, hold at 100% solvent B for 15 min, where solvent A=hexanes and solvent B=EtOAc) to give the title compound (14.5 mg; 73%) as a colorless solid. [M+H]$^+$=537.2; $^1$H NMR (400 MHz, CDCl$_3$): δ 1.13 (m, 2H), 1.31 (t, 6H), 1.47 (m, 2H), 1.61 (m, 2H), 1.74 (m, 3H), 1.90 (m, 1H), 2.00 (m, 2H), 2.21 (m, 1H), 2.87 (m, 2H), 3.05 (s, 3H), 3.65 (t, 1H), 4.10 (m, 4H), 7.56 (dd, 1H), 7.58 (d, 2H), 7.90 (d, 2H), 8.08 (d, 1H), 8.13 (d, 1H), 8.20 (s, 1H).

Example 6

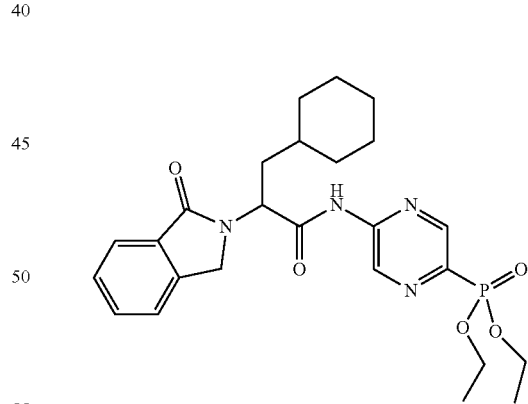

A.

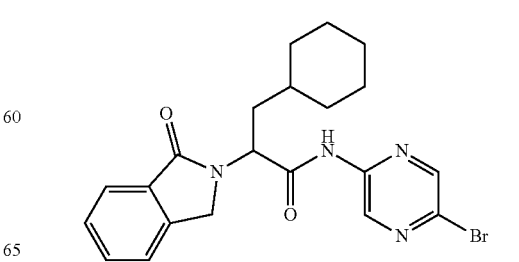

To a 0° C. solution of (S)-3-Cyclohexyl-2-(1-oxo-1,3-dihydroisoindol-2-yl)-propionic acid (144 mg, 0.5 mmol, prepared as described in WO 2002/048106) and oxalyl chloride (0.38 mL of a 2 M solution in DCM; 0.75 mmol) in DCM (1 mL) under Ar was added DMF (1 drop). After 30 min, the reaction was allowed to warm to RT and was stirred at RT for 4 h. Volatiles were removed in vacuo; the crude acid chloride was re-dissolved in DCM (3 mL). 5-Bromo-2-aminopyrazine (130 mg, 0.75 mmol) and pyridine (0.061 mL, 0.75 mmol) were added to the acid chloride solution cooled in an ice bath under Ar. The reaction mixture was allowed to warm to room temperature overnight, then was diluted with DCM (6 mL) and rinsed with 0.5 N aqueous HCl (1 mL, 2×), water (1 mL), sat. aqueous NaHCO$_3$ (1 mL), brine (1 mL), then dried (MgSO$_4$) and concentrated in vacuo. The residue was chromatographed (40 g SiO$_2$, 0-50% EtOAc-hexanes gradient) gave 188 mg (84%) of racemic Part A compound.

B.

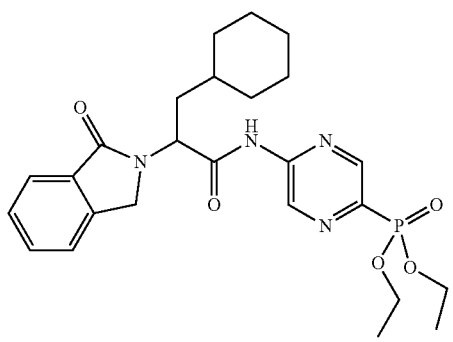

THF (degassed) (0.40 mL) was added to a reaction flask containing Part A compound (25.0 mg; 0.056 mmol) and (Ph$_3$P)$_4$Pd(0) (12.9 mg; 0.011 mmol). Diethyl phosphite (8.72 uL; 0.068 mmol) was added followed by TEA (10.9 uL; 0.078 mmol). The reaction vessel was capped and the reaction mixture was heated at 85° C. for 6 h, then cooled to RT and concentrated in vacuo. The residue was partitioned between EtOAc (2 mL) and brine (1.5 mL). The organic phase was isolated, dried (MgSO$_4$) concentrated in vacuo. The crude product was purified by preparative HPLC (YMC reverse phase ODS-A-5u 30×100 mm column; flow rate=40 mL/min., 45 to 100% solvent B over 12 min, hold to 16 min, where solvent A=90:10:0.1 H$_2$O:MeOH:TFA and solvent B=90:10:0.1 MeOH:H$_2$O:TFA) to give title compound (8 mg; 29%; colorless solid) as a racemic mixture. [M+H]$^+$=501.3; $^1$H NMR (400 MHz, CDCl$_3$): δ 1.00 (m, 2H), 1.20 (m, 4H), 1.35 (m, 6H), 1.65 (m, 3H), 1.85 (m, 3H), 2.05 (m, 1H), 4.22 (m, 4H), 4.54 (q, 2H), 5.23 (t, 1H), 7.50 (m, 3H), 7.60 (dd, 1H), 7.92 (d, 1H), 8.75 (s, 1H), 9.52 (s, 1H), 9.62 (s, 1H).

Example 7

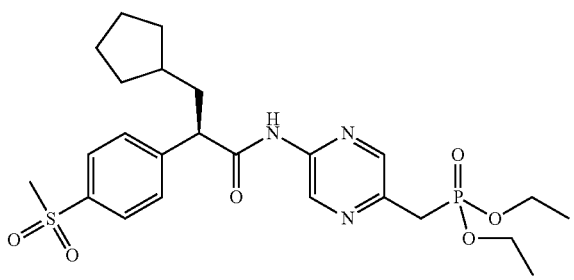

A.

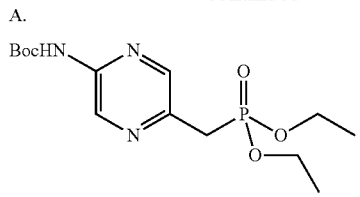

(EtO)$_3$P (0.60 mL; 3.47 mmol) was added to a reaction flask containing a solution of tert-butyl 5-(bromomethyl) pyrazin-2-ylcarbamate (*Bioorg. Med. Chem. Lett.*, 2002, 12:1203-1208) (125 mg; 0.434 mmol) in THF (1.0 mL). The reaction vessel was capped and the reaction mixture was heated at 80° C. for 16 h, then was cooled to RT and concentrated in vacuo. The crude product was chromatographed (SiO$_2$; continuous gradient from 0 to 100% solvent B over 8 min, hold at 100% solvent B for 8 min, where solvent A=hexanes and solvent B=EtOAc) to give Part A compound (145 mg; 96%).

B.

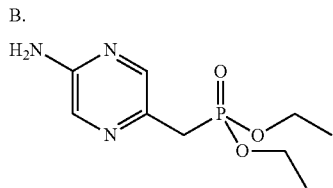 [SMILES: CCOP(=O)(Cc1cnc(N)cn1)OCC]

TFA (0.30 mL) was added to a cold (0° C.) solution of Part A compound (144 mg; 0.417 mmol) in DCM (1.2 mL). The reaction mixture was then stirred at RT for 16 h, then was concentrated in vacuo. The residue was partitioned between EtOAc (4 mL) and sat. aqueous NaHCO$_3$ (3 mL). The organic phase was isolated, washed with brine (3 mL), dried (MgSO$_4$), and concentrated in vacuo to give Part B compound (51 mg; 50%).

C.

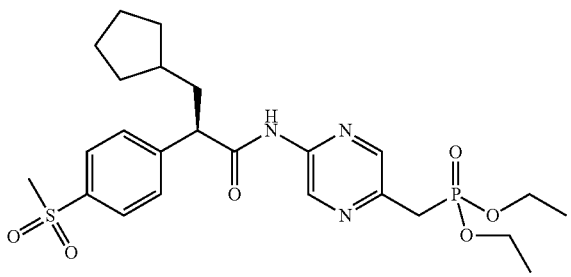

Oxalyl chloride (0.84 uL of a 2.0 M solution in DCM; 0.168 mmol) was added to a mixture of Example 1 Part D compound (25 mg; 0.084 mmol) in DCM (0.15 mL). DMF (5 µL) was added. Gas evolution occurred. After 1.5 h at RT the reaction mixture was concentrated in vacuo. The residue was stripped from CHCl$_3$ (2×0.8 mL). The crude acid chloride was then dissolved in DCM (0.25 mL). Part B compound (24.8 mg; 0.101 mmol) was added followed by pyridine (10.2 uL; 0.126 mmol). After stirring for 16 h at RT the reaction was concentrated in vacuo. The residue was partitioned between EtOAc (4 mL) and brine (2 mL). The organic phase was dried (MgSO$_4$) and concentrated in vacuo. The crude product was purified by preparative HPLC (YMC reverse phase ODS-A-5u 30×100 mm column; flow rate=40 mL/min, 10 to 100% solvent B over 12 min, hold to 16 min, where solvent A=90:10:0.1 H$_2$O:MeOH:TFA and solvent B=90:10:0.1 MeOH:H$_2$O:TFA) to give the title compound (18 mg; 41%) as an amorphous solid. [M+H]$^+$=524.4; $^1$H NMR (400 MHz, CD$_3$OD): δ 1.18 (m, 2H), 1.27 (t, 6H), 1.51 (m, 2H), 1.64 (m, 2H), 1.72 (m, 1H), 1.83 (m, 3H), 2.22 (m, 1H), 3.09 (s, 3H), 3.46 (d, 2H), 4.00 (t, 1H), 4.09 (m, 4H), 7.70 (d, 2H), 7.92 (d, 2H), 8.32 (s, 1H), 9.30 (s, 1H).

Example 8

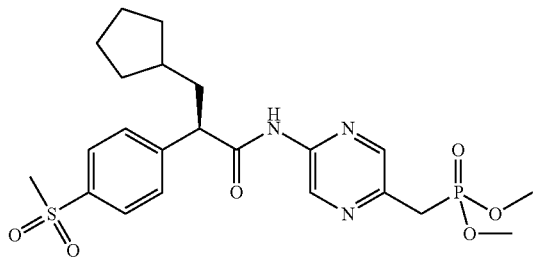 [SMILES: COP(=O)(Cc1cnc(NC(=O)[C@H](CC2CCCC2)c2ccc(S(C)(=O)=O)cc2)cn1)OC]

The title compound (11 mg; 19%; colorless solid) was synthesized from trimethylphosphite employing the sequence described for the synthesis of Example 7. [M+H]$^+$=496.3; $^1$H NMR (400 MHz, CD$_3$OD): δ 1.19 (m, 2H), 1.51 (m, 2H), 1.64 (m, 2H), 1.72 (m, 1H), 1.84 (m, 3H), 2.23 (m, 1H), 3.09 (s, 3H), 3.50 (d, 2H), 3.73 (s, 3H), 3.76 (s, 3H), 4.00 (t, 1H), 7.69 (d, 2H), 7.91 (d, 2H), 8.31 (s, 1H), 9.29 (s, 1H).

Example 9

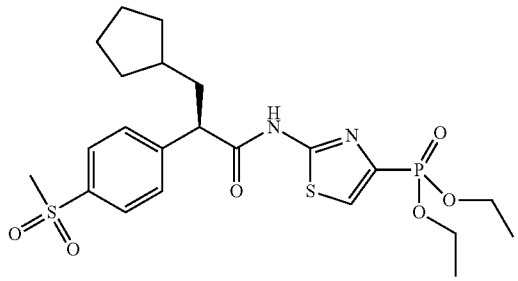

A.

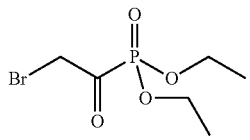

A solution of bromine (145 uL; 2.82 mmol) in CCl$_4$ (5 mL) was added dropwise to a 0° C. solution of acetyl-phosphonic acid di-ethyl ester (0.508 g; 2.82 mmol) in CCl$_4$ (5 mL). The reaction mixture was then stirred at RT for 2 h, then was concentrated in vacuo. The residue was chromatographed (SiO$_2$; continuous gradient from 0 to 100% solvent B over 10 min, hold at 100% solvent B for 10 min, where solvent A=hexanes and solvent B=EtOAc) to give Part A compound (250 mg; 34%).

B.

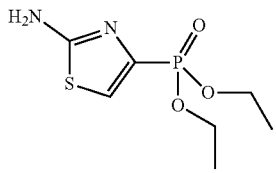

Thiourea (43.9 mg; 0.577 mmol) was added to a solution of Part A compound (135 mg 0.52 mmol) in EtOH (1.0 mL). The reaction mixture was stirred at RT for 48 h, then was concentrated in vacuo. The residue was partitioned between EtOAc (5 mL) and sat. aqueous NaHCO$_3$ (3 mL). The organic phase was isolated, washed with brine (3 mL), dried (MgSO$_4$) and concentrated in vacuo. The residue was chromatographed (SiO$_2$; continuous gradient from 0 to 100% solvent B over 2 min, hold at 100% solvent B for 10 min, where solvent A=hexanes and solvent B=EtOAc) to give Part B compound (22 mg; 18%).

C.

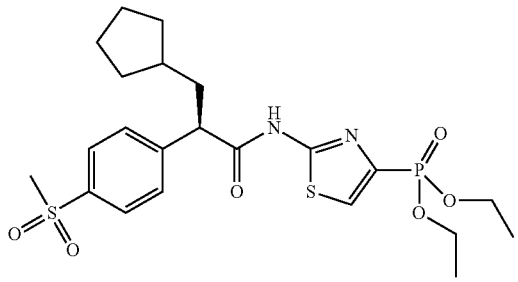

DEPBT (50 mg; 0.168 mmol) was added to a stirred solution of Example 1 Part D compound (25 mg; 0.084 mmol) and Part B compound (21.9 mg; 0.093 mmol) in THF (0.40 mL). DIPEA (28.4 uL; 0.168 mmol) was added. After 96 h at RT the reaction mixture was concentrated in vacuo. The residue was dissolved in EtOAc (3 mL). The EtOAc solution was washed with brine (2 mL), dried (MgSO$_4$), filtered, and concentrated in vacuo. The crude product was purified by preparative HPLC (YMC reverse phase ODS-A-5u 30×100 mm column; flow rate=40 mL/min, 20 to 100% solvent B over 12 min, hold to 15 min, where solvent A=90:10:0.1 H$_2$O:MeOH:TFA and solvent B=90:10:0.1 MeOH:H$_2$O:TFA) to give title compound (13 mg; 30%) as a white solid. [M+H]$^+$=515.2; $^1$H NMR (400 MHz, CD$_3$OD): δ 1.18 (m, 2H), 1.31 (m, 6H), 1.51 (, 2H), 1.64 (m, 3H), 1.81 (m, 2H), 1.88 (m, 1H), 2.23 (m, 1H), 3.10 (s, 3H), 3.96 (t, 1H), 4.14 (m, 4H), 7.68 (d, 2H), 7.86 (d, J=4.95 Hz, 1H), 7.93 (d, 2H).

Example 10

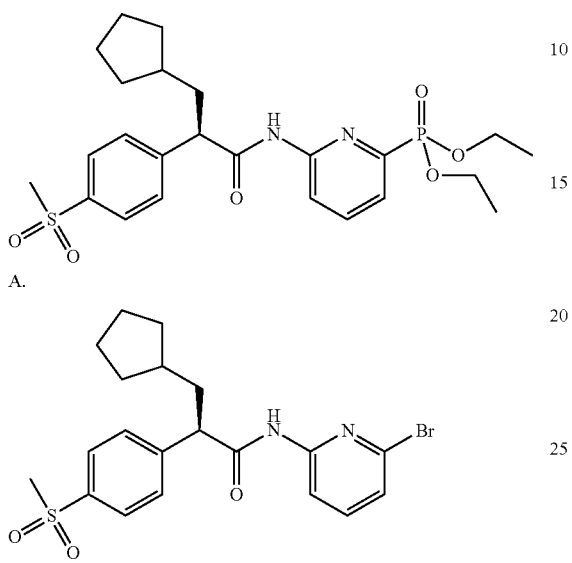

A.

B.

DEPBT (162 mg; 0.540 mmol) was added to a stirred solution of Example 1 Part D compound (80 mg; 0.270 mmol) and 2-amino-6-bromopyridine (51.4 mg; 0.297 mmol) in THF (1.0 mL). DIPEA (91.0 uL; 0.540 mmol) was added. After 48 h at RT more 2-amino-6-bromopyridine (93.0 mg; 0.537 mmol) was added. After an additional 48 h the reaction mixture was concentrated in vacuo. The residue was partitioned between EtOAc (6 mL) and 0.1 N aqueous HCl (3 mL). The organic phase was washed with brine (3 mL), dried (MgSO$_4$) and concentrated in vacuo. The crude product was purified by preparative HPLC (YMC reverse phase ODS-A-5u 30×100 mm column; flow rate=40 mL/min, 35 to 100% solvent B over 10 min, hold to 13 min, where solvent A=90:10:0.1 H$_2$O:MeOH:TFA and solvent B=90:10:0.1 MeOH:H$_2$O:TFA) to give Part A compound (16 mg; 13%).

B.

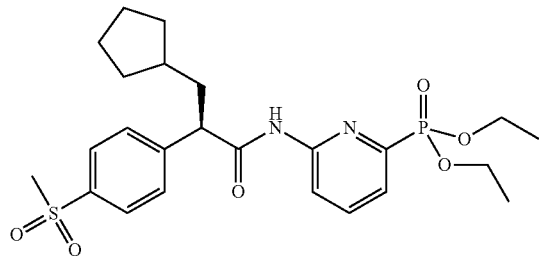

THF (degassed) (0.50 mL) was added to a reaction flask containing Part A compound (14.0 mg; 0.031 mmol) and (Ph$_3$P)$_4$Pd(0) (7.2 mg; 0.006 mmol). Diethyl phosphite (4.8 uL; 0.037 mmol) was added followed by Et$_3$N (6.0 µL; 0.043 mmol). The reaction vessel was capped and the reaction mixture was heated at 75° C. for 12 h, then was cooled to RT. The reaction mixture was concentrated in vacuo. The crude product was purified by preparative HPLC (YMC reverse phase ODS-A-5u 20×100 mm column; flow rate=40 mL/min., 20 to 100% solvent B over 12 min, hold to 15 min, where solvent A=90:10:0.1 H$_2$O:MeOH:TFA and solvent B=90:10:0.1 MeOH:H$_2$O:TFA) to give the title compound (3.6 mg; 23%) as a colorless solid. [M+H]$^+$=509.3; $^1$H NMR (400 MHz, CD$_3$OD): δ 1.20 (m, 2H), 1.33 (m, 6H), 1.53 (m, 2H), 1.65 (m, 2H), 1.72 (m, 1H), 1.83 (m, 3H), 2.22 (m, 1H), 3.09 (s, 3H), 4.01 (t, 1H), 4.19 (m, 4H), 7.61 (t, 1H), 7.71 (d, 2H), 7.91 (m, 3H), 8.32 (d, 1H).

Example 11

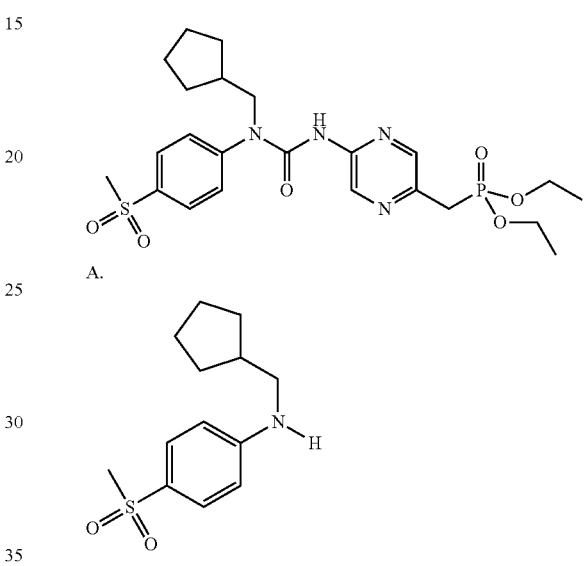

A.

To a 0° C. mixture of 4-methylsulfonylaniline, hydrochloride (1.06 g, 5.10 mmol), cyclopentane carboxaldehyde (0.5 g, 5.10 mmol), and Et$_3$N (1 mL, 7.14 mmol) in 20 mL of dichloroethane was added NaBH(OAc)$_3$ (1.51 g, 7.14 mmol). The reaction was allowed to warm to RT and stirred at RT for two days, then was treated with excess sat. aqueous NaHCO$_3$. The aqueous layer was extracted with EtOAc. The organic extract was rinsed with brine, dried (MgSO$_4$) and concentrated in vacuo. Purification by flash chromatography (120 g silica gel, continuous gradient from 0-100% EtOAc-hexanes) gave Part A compound (904 mg, 70% yield).

B.

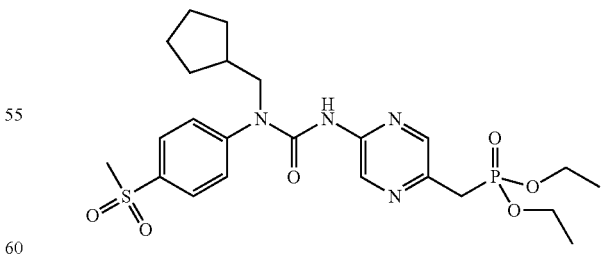

Part 1: 4-Nitrophenylchloroformate (49.3 mg; 0.245 mmol) was added to a cold (0° C.) solution of Example 7 Part B compound (60 mg; 0.245 mmol). Pyridine 20.8 µL; 0.257 mmol) was added. The reaction mixture was stirred at RT for 1 h, then was concentrated in vacuo to give the crude carbamate.

Part 2: The crude carbamate was dissolved in CH₃CN (1.0 mL). Part A compound (62 mg; 0.245 mmol) was added. The reaction mixture was heated at 40° C. for 2 h, then was cooled to RT and concentrated in vacuo. The crude product was chromatographed (SiO₂; continuous gradient from 0 to 100% solvent B over 4 min, switch to solvent C, hold at 100% solvent C for 8 min, where solvent A=hexanes, solvent B=EtOAc and solvent C=10% MeOH in EtOAc) to give title compound (30 mg; 23%—two steps) as an amorphous solid. [M+H]⁺=525.3; ¹H NMR (400 MHz, CD₃OD): δ 1.28 (t, 8H), 1.54 (m, 2H), 1.67 (m, 4H), 2.10 (m, 1H), 3.17 (s, 3H), 3.45 (d, 2H), 3.83 (d, 2H), 4.09 (m, 4H), 7.65 (d, 2H), 8.05 (d, 2H), 8.19 (s, 1H), 9.12 (s, 1H).

Example 12

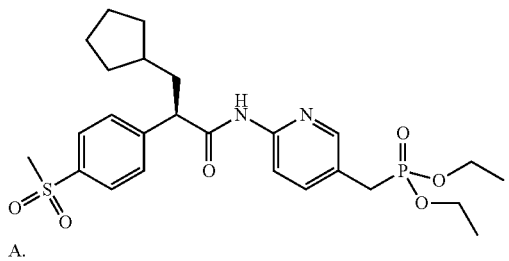

A.

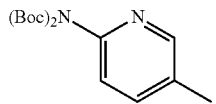

DIPEA (8.05 mL; 46.24 mmol) was added to a cold (0° C.) solution of 2-amino-5-picoline (2.50 g; 23.12 mmol) in DCM (30 mL). A solution of di-tert-butyl dicarbonate (12.61 g; 57.80 mmol) in DCM (17 mL) was added followed by 4-DMAP (2.82 g; 23.12 mmol). The reaction mixture was then stirred at RT for 16 h, then was concentrated in vacuo to half volume. The solution was diluted with EtOAc (125 mL). The organic solution was washed with sat. aqueous NH₄Cl (3×45 mL), brine (45 mL), sat. aqueous NaHCO₃ (2×45 mL) and brine (45 mL). The solution was then dried (MgSO₄) and concentrated in vacuo. The crude product was chromatographed (SiO₂; continuous gradient from 15 to 20% EtOAc in hexanes) to give Part A compound (2.70 g; 38%).

B.

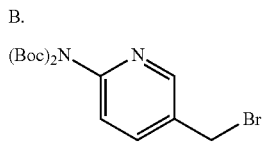

N-bromosuccinimide (1.56 g; 8.76 mmol) was added to a solution of Part A compound (2.70 g; 8.76 mmol) in CCl₄ (40 mL). Benzoyl peroxide (0.21 g; 0.88 mmol) was added. The reaction mixture was heated to reflux (80° C.) for 7 h, then was cooled to RT. The reaction mixture was filtered and the filtrate was concentrated in vacuo. The crude product was chromatographed (SiO₂; 5% EtOAc in DCM) to give Part B compound (1.48 g; 44%). (*Bioorg. Med. Chem. Lett,* 2004, 14:2227-2231).

C.

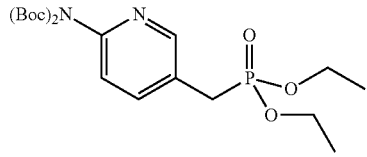

Triethylphosphite (1.2 mL; 6.97 mmol) was added to a solution of Part B compound (0.45 g; 1.16 mmol) in THF (2.5 mL). The reaction vessel was capped and the reaction mixture was heated at 80° C. for 16 h, then was cooled to RT. The solution was concentrated in vacuo. The crude product was chromatographed (SiO₂; continuous gradient from 0 to 100% solvent B over 8 min, hold at 100% solvent B for 6 min, where solvent A=hexanes and solvent B=EtOAc) to give Part C compound (0.52 g; 100%).

D.

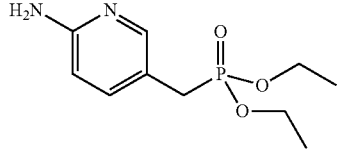

TFA (1.5 mL) was added to a cold (0° C.) solution of Part C compound (0.52 g; 1.17 mmol) in DCM (3 mL). The reaction mixture was then stirred at RT for 3 h, then was concentrated in vacuo. The residue was partitioned between CHCl₃ (10 mL) and sat. aqueous NaHCO₃ (8 mL). The aqueous phase was extracted with CHCl₃ (8 mL). The combined organic extracts were dried (MgSO₄) and concentrated in vacuo to give Part D compound (0.25 g; 88%).

E.

Oxalyl chloride (2.0 M in DCM) (104 µL; 0.208 mmol) was added to a 0° C. solution of Example 1 Part D compound (30.9 mg; 0.104 mmol) in DCM (0.3 mL). DMF (5 µL) was added. Gas evolution occurred. After 1 h at RT the reaction mixture was concentrated in vacuo. The residue was stripped from CHCl₃ (2×1 mL). The crude acid chloride was dissolved in DCM (0.42 mL). Part D compound (25.5 mg; 0.104 mmol) was added followed by pyridine (12.6 uL; 0.156 mmol). After stirring for 16 h the reaction was concentrated in vacuo. The residue was partitioned between EtOAc (5 mL) and brine (4 mL). The organic phase was dried (MgSO₄) and concentrated in vacuo. The crude product was purified by preparative HPLC (YMC reverse phase ODS-A-5u 30×100 mm column; flow rate=40 mL/min, 20 to 100% solvent B over 15 min, hold to 20 min, where solvent A=90:10:0.1 H₂O:MeOH:TFA and solvent B=90:10:0.1 MeOH:H₂O:TFA) to give the title compound (19 mg; 34%) as an amorphous solid. [M+H]⁺=523.4; ¹H NMR (400 MHz, CD₃OD): δ 1.20 (m, 2H), 1.27 (t, 6H), 1.51 (m, 2H), 1.65 (m, 2H), 1.71 (m, 1H), 1.85 (m, 3H), 2.21 (m, 1H), 3.10 (s, 3H), 3.30 (d, 2H), 3.98 (t, 1H), 4.07 (m, 4H), 7.70 (d, 2H), 7.92 (m, 4H), 8.23 (s, 1H).

Example 13

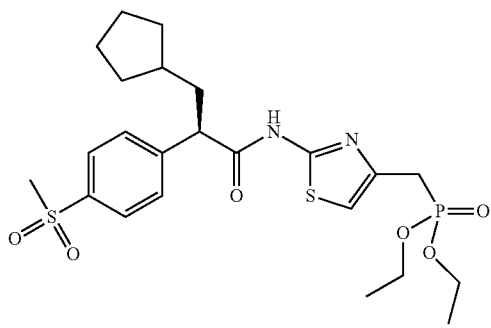

A.

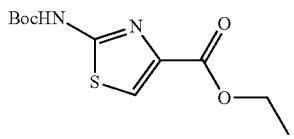

A solution of di-tert-butyl dicarbonate (11.3 g; 51.83 mmol) in THF (50 mL) was added to a cold (0° C.) solution of ethyl 2-aminothiazole-4-carboxylate (8.59 g; 49.36 mmol) in THF (150 mL). TEA (7.57 mL; 54.30 mmol) was added followed by a catalytic amount of 4-DMAP (30 mg). The reaction mixture was stirred at RT for 16 h, then was concentrated in vacuo. The residue was portioned between EtOAc (300 mL) and 0.5 N aqueous HCl (250 mL). The organic phase was washed with brine (150 mL), dried (MgSO₄) and concentrated in vacuo to give Part A compound (12.38 g; yield given below in Part B). The crude product was used in the next step without further purification.

B.

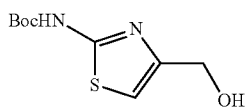

A solution of LiAlH₄ (1.0 M in THF) (48.0 mL; 48.0 mmol) was added to a cold (0° C.) solution of Part A compound (12.38 g; 45.3 mmol) in THF (130 mL). After 3 h at 0° C. the reaction was carefully quenched by dropwise addition of H₂O (5 mL). After 10 min, 5 N aqueous NaOH (2.5 mL) was added. After another 10 min, the solution was concentrated in vacuo. The residue was partitioned between EtOAc (300 mL) and H₂O (200 mL). The aqueous phase was extracted with EtOAc (100 mL). The combined organic phases were dried (MgSO₄) and concentrated in vacuo. The crude product was chromatographed (SiO₂; continuous gradient from 0 to 100% solvent B over 16 min, hold at 100% solvent B for 5 min, where solvent A=hexanes and solvent B=EtOAc) to give Part B compound (8.67 g; 67%—two steps).

C.

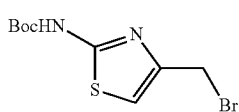

Method 1: A solution of methanesulfonyl chloride (318 µL; 4.10 mmol) in DCM (3 mL) was slowly added to a 0° C. solution of Part B compound (900 mg; 3.91 mmol) and TEA (600 µL; 4.30 mmol) in DCM (10 mL). After 25 min of stirring the reaction mixture was diluted with acetone (13 mL). LiBr (2.03 g; 23.46 mmol) was added. The reaction was stirred at RT for 1 h, then was diluted with sat. aqueous NH₄Cl (20 mL) and extracted with Et₂O (2×40 mL). The combined organic extracts were washed with sat. aqueous NH₄Cl (2×20 mL) and brine (20 mL). The solution was dried (MgSO₄) and concentrated in vacuo to give Part C compound (1.03 g; 89%). The crude product was taken forward without further purification.

Method 2: N-Boc thiourea (428 mg; 2.427 mmol) was added to a solution of 1,3-dibromoacetone (524 mg; 2.427 mmol) in acetone (9.7 mL). After 24 h at RT the reaction mixture was concentrated in vacuo to give Part C compound (0.78 g; Quant.) as a brown foam. The crude product was taken forward without further purification.

D.

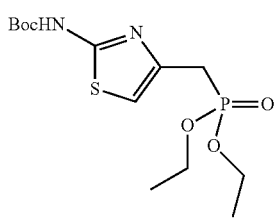

Triethyl phosphite (3.6 mL; 20.96 mmol) was added to a solution of Part C compound (878 mg; 2.99 mmol) in THF (6 mL). The reaction vessel was capped and the reaction mixture was heated at 80° C. for 16 h, then was cooled to RT. The solution was concentrated in vacuo. The crude product was chromatographed (SiO₂; continuous gradient from 0 to 100% solvent B over 8 min, hold at 100% solvent B for 10 min, where solvent A=hexanes and solvent B=EtOAc) to give Part D compound (0.86 g; 82%).

E.

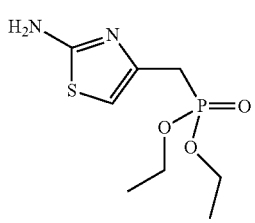

TFA (3.0 mL) was added to a 0° C. solution of Part D compound (0.86 g; 2.45 mmol) in DCM (7 mL). The reaction mixture was stirred at RT for 2.5 h, then was concentrated in vacuo. The residue was partitioned between EtOAc (15 mL) and sat. aqueous NaHCO₃ (10 mL). The aqueous phase was extracted with EtOAc (10 mL). The combined organic extracts were dried (MgSO₄) and concentrated in vacuo to give Part E compound (488 mg; 80%). ¹H NMR (400 MHz, CDCl₃) δ 6.17 (1H, d, J=3.95 Hz), 5.85 (2H, br. s.), 3.92-4.05 (4H, m), 3.08 (2H, d, J=21.09 Hz), 1.18 (6H, t, J=7.03 Hz).

F.

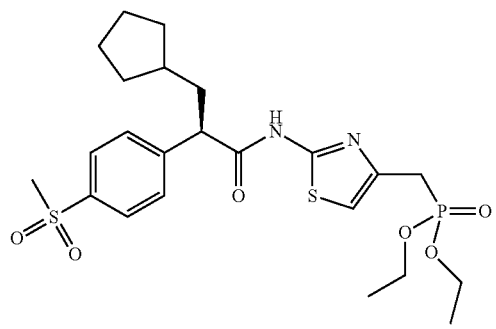

Oxalyl chloride (2.0 M in DCM) (0.63 mL; 1.26 mmol) was added to a 0° C. mixture of Example 1 Part D compound (250 mg; 0.844 mmol) in DCM (2.5 mL). DMF (10 uL) was added. Gas evolution occurred. After 1.5 h at RT the reaction mixture was concentrated in vacuo. The residue was stripped from CHCl₃ (2×3 mL). The crude acid chloride was dissolved in DCM (3.0 mL). Part E compound (253 mg; 1.013 mmol) was added followed by pyridine (205 uL; 2.532 mmol). After 2 h at RT the reaction was concentrated in vacuo. The residue was partitioned between EtOAc (15 mL) and 0.5 N aqueous HCl (10 mL). The organic phase was washed with 0.5 N aqueous HCl (10 mL) and brine (10 mL). The solution was dried (MgSO₄), and concentrated in vacuo. The crude product was chromatographed (SiO₂; continuous gradient from 0 to 100% solvent B over 3 min, hold at 100% solvent B for 14 min, where solvent A=hexanes and solvent B=EtOAc) to give the title compound (0.40 g; 89%) as an amorphous solid. [M+H]⁺=529.2; ¹H NMR (400 MHz, CD₃OD): δ 1.18 (m, 2H), 1.26 (t, 6H), 1.51 (m, 2H), 1.64 (m, 3H), 1.83 (m, 3H), 2.22 (m, 1H), 3.09 (s, 3H), 3.31 (d, 2H), 3.95 (t, 1H), 4.07 (m, 4H), 6.89 (d, J=4.03 Hz, 1H), 7.67 (d, 2H), 7.92 (d, 2H).

Example 14

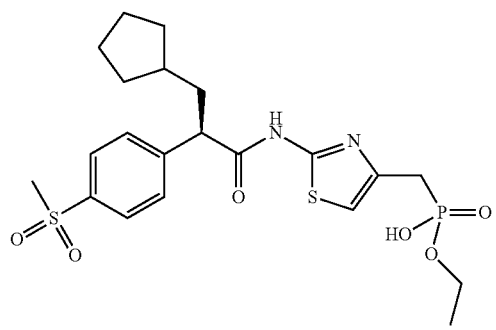 [SMILES: CCOP(=O)(O)Cc1csc(NC(=O)[C@H](CC2CCCC2)c2ccc(S(C)(=O)=O)cc2)n1]

1 N aqueous NaOH (136 uL; 0.136 mmol) was added to a solution of Example 13 Part F compound (50.5 mg; 0.096 mmol) in EtOH (100 μL). The reaction mixture was heated at 80° C. for 48 h, then was cooled to RT and concentrated in vacuo. The crude product was purified by preparative HPLC (YMC reverse phase ODS-A-5u 30×100 mm column; flow rate=40 mL/min, 10 to 100% solvent B over 16 min, hold to 20 min, where solvent A=90:10:0.1 H₂O:MeOH:TFA and solvent B=90:10:0.1 MeOH:H₂O:TFA) to give the title compound (12.5 mg; 26%) as an amorphous solid. [M+H]⁺=501.1; ¹H NMR (400 MHz, CDCl₃): δ 1.13 (m, 2H), 1.30 (t, 3H), 1.48 (m, 2H), 1.60 (m, 3H), 1.78 (m, 2H), 1.90 (m, 1H), 2.23 (m, 1H), 3.04 (s, 3H), 3.28 (d, 2H), 4.05 (m, 3H), 6.68 (d, 1H), 7.68 (d, 2H), 7.88 (d, 2H).

Example 15

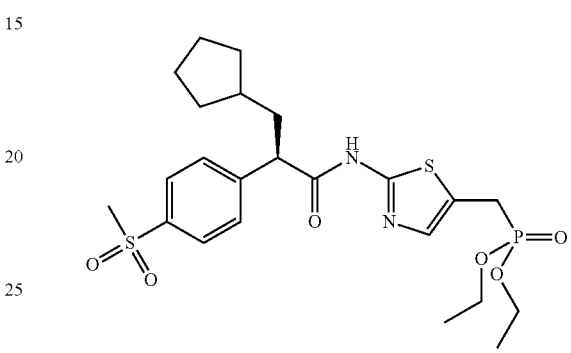

A.

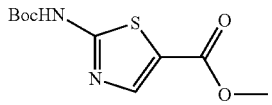

A solution of di-tert-butyl dicarbonate (1.66 g; 7.59 mmol) in THF (10 mL) was added to a 0° C. solution of methyl 2-aminothiazole-5-carboxylate (1.20 g; 7.59 mmol) in THF (20 mL). TEA (1.11 mL; 7.97 mmol) was added followed by a catalytic amount of 4-DMAP (10 mg). The reaction mixture was then stirred at RT for 20 h, then was concentrated in vacuo. The residue was partitioned between EtOAc (80 mL) and 0.2 N aqueous HCl (40 mL). The organic phase was washed with brine (40 mL), dried (MgSO₄) and concentrated in vacuo to give Part A compound (1.70 g; yield given below in Part B). The crude product was taken forward without further purification.

B.

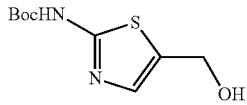

A solution of LiAlH₄ (7.60 mL of a 1.0 M solution in THF); 7.60 mmol) was added to a 0° C. solution of Part A compound (1.70 g; 6.58 mmol) in THF (30 mL). The reaction mixture was stirred at RT for 1 h, then was cooled to 0° C. and carefully quenched by dropwise addition of H₂O (0.76 mL). After 10 min, 5 N aqueous NaOH (0.38 mL) was added. After another 10 min, the solution was filtered through a pad of Celite and the filtrate was concentrated in vacuo. The crude product was chromatographed (SiO₂; continuous gradient from 0 to 100% solvent B over 13 min, hold at 100% solvent B for 6 min, where solvent A=hexanes and solvent B=EtOAc) to give Part B compound (0.80 g; 46%—two steps).

C.

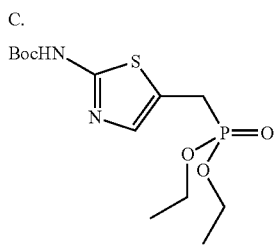

Part 1: Thionyl chloride (253 µL; 3.47 mmol) was added to a 0° C. mixture of Part B compound (200 mg; 0.869 mmol) in DCM (0.40 mL). The reaction mixture was stirred at 0° C. for 2 h then was concentrated vacuo to give the crude chloride.

Part 2: The crude chloride was dissolved in THF (3.0 mL). $(EtO)_3P$ (1.20 mL; 6.95 mmol) was added. The reaction mixture was heated at 80° C. for 16 h, then was cooled to RT and concentrated in vacuo. The crude product was chromatographed ($SiO_2$; continuous gradient from 0 to 100% solvent B over 8 min, switch to solvent C, hold at 100% solvent C for 7 min, where solvent A=hexanes, solvent B=EtOAc and solvent C=3% MeOH in EtOAc) to give Part C compound (270 mg; 89%—two steps).

D.

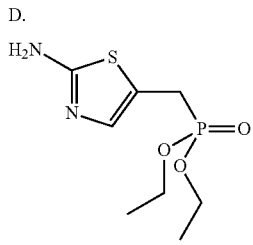

TFA (0.80 mL) was added to a 0° C. solution of Part C compound (0.31 g; 0.885 mmol) in DCM (2.4 mL). The reaction mixture was stirred at RT for 3 h then was concentrated in vacuo. The residue was partitioned between $CHCl_3$ (10 mL) and sat. aqueous $NaHCO_3$ (10 mL). The aqueous phase was extracted with $CHCl_3$ (10 mL). The combined organic extracts were dried ($MgSO_4$) and concentrated in vacuo to give Part D compound (198 mg; 89%).

E.

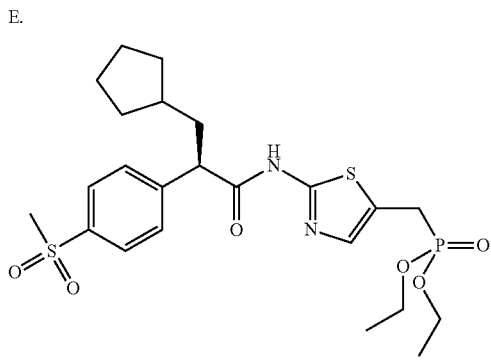

Oxalyl chloride (2.0 M in DCM) (101 uL; 0.202 mmol) was added to a 0° C. mixture of Example 1 Part D compound (40 mg; 0.135 mmol) in DCM (0.35 mL). DMF (6 uL) was added. Gas evolution occurred. The reaction mixture was then stirred at RT for 1.5 h then was concentrated in vacuo. The residue was stripped from $CHCl_3$ (2×1 mL). The crude acid chloride was dissolved in DCM (0.45 mL). Part D compound (47.3 mg; 0.189 mmol) was added followed by pyridine (33.0 uL; 0.405 mmol). After 4 h at RT the reaction was concentrated in vacuo. The residue was partitioned between EtOAc (6 mL) and brine (4 mL). The organic phase was dried ($MgSO_4$) and concentrated in vacuo. The crude product was purified by preparative HPLC (YMC reverse phase ODS-A-5u 30×100 mm column; flow rate=40 mL/min, 15 to 100% solvent B over 10 min, hold to 15 min, where solvent A=90:10:0.1 $H_2O$:MeOH:TFA and solvent B=90:10:0.1 MeOH:$H_2O$:TFA) to give the title compound (46 mg; 65%) as a white solid. $[M+H]^+=529.1$; $^1H$ NMR (400 MHz, $CD_3OD$): δ 1.18 (m, 2H), 1.29 (t, 6H), 1.49 (m, 2H), 1.63 (m, 3H), 1.80 (m, 3H), 2.22 (m, 1H), 3.09 (s, 3H), 3.43 (d, 2H), 3.96 (t, 1H), 4.09 (m, 4H), 7.26 (d, J=4.4 Hz, 1H), 7.67 (d, 2H), 7.92 (d, 2H).

Example 16

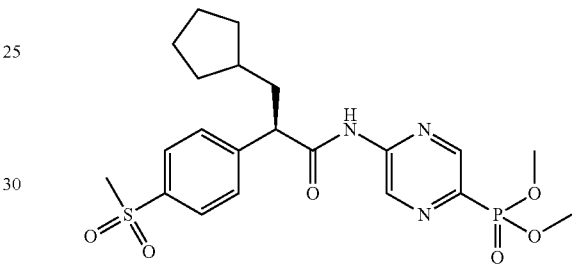

A.

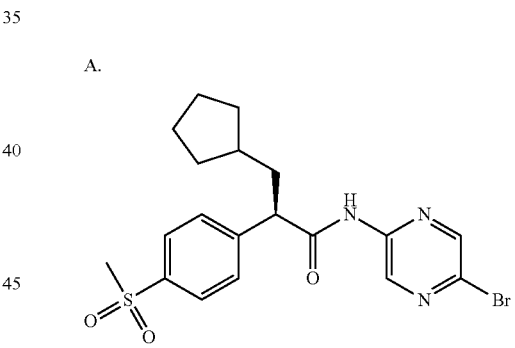

Oxalyl chloride (169 µL of a 2 M solution in DCM; 0.338 mmol) was added to a mixture of Example 1 Part D compound (50 mg; 0.169 mmol) in DCM (0.35 mL). The solution was cooled to 0° C. DMF (5 uL) was added. Gas evolution occurred. After 2 h at RT the reaction mixture was concentrated in vacuo. The residue was stripped from $CHCl_3$ (2×1 mL). The crude acid chloride was dissolved in DCM (0.5 mL). 5-bromo-2-pyrazinamine (44 mg; 0.253 mmol) was added followed by pyridine (20.5 uL; 0.253 mmol). The reaction mixture was stirred at RT for 3 h, then was concentrated in vacuo. The residue was partitioned between EtOAc (6 mL) and brine (4 mL). The organic phase was dried ($MgSO_4$) and concentrated in vacuo. The crude product was chromatographed ($SiO_2$; continuous gradient from 0 to 30% solvent B over 30 min, then 30% to 65% solvent B over 5 min, then hold at 65% solvent B for 5 min, where solvent A=hexanes and solvent B=EtOAc) to give Part A compound (64 mg; 84%).

B.

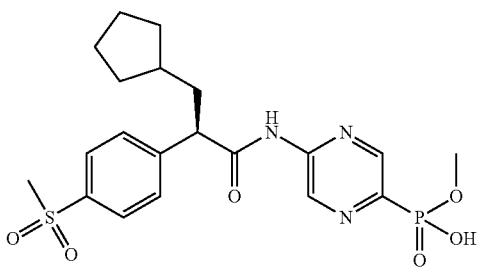

A solution of Part A compound (44 mg; 0.097 mmol) in THF (degassed) (0.50 mL) was added to a reaction flask containing (Ph$_3$P)$_4$Pd(0) (22.4 mg; 0.019 mmol). (MeO)$_3$P (11.6 µL; 0.126 mmol) was added followed by TEA (21.6 µL; 0.155 mmol). The reaction vessel was capped and the reaction mixture was heated at 75° C. for 6 h, then was cooled to RT and concentrated in vacuo. The crude product was purified by preparative HPLC (YMC reverse phase ODS-A-5u 30×100 mm column; flow rate=40 mL/min, 15 to 100% solvent B over 10 min, hold to 13 min, where solvent A=90:10:0.1 H$_2$O:MeOH:TFA and solvent B=90:10:0.1 MeOH:H$_2$O:TFA) to give Part B compound (17 mg; 38%).

C.

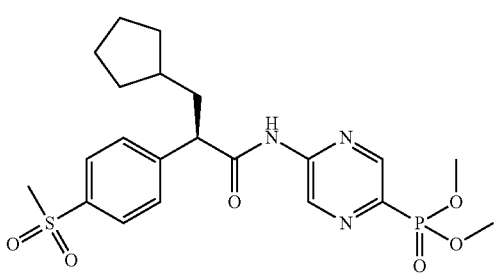

TMSCHN$_2$ (2.0 M in hexane) (73 µL; 0.145 mmol) was added to a mixture of Part B compound (17 mg; 0.036 mmol) in Et$_2$O (75 µL) and THF (250 µL). After stirring at RT for 1 h the reaction mixture was concentrated in vacuo. The crude product was purified by preparative HPLC (YMC reverse phase ODS-A-5u 20×100 mm column; flow rate=20 mL/min., 20 to 100% solvent B over 10 min, hold to 15 min, where solvent A=90:10:0.1 H$_2$O:MeOH:TFA and solvent B=90:10:0.1 MeOH:H$_2$O:TFA) to give the title compound (9 mg; 51%) as a colorless solid. [M+H]$^+$=482.2; $^1$H NMR (400 MHz, CD$_3$OD): δ 1.19 (m, 2H), 1.51 (m, 2H), 1.64 (m, 3H), 1.83 (m, 3H), 2.22 (m, 1H), 3.09 (s, 3H), 3.83 (d, 3H), 3.86 (d, 3H), 4.04 (t, 1H), 7.70 (d, 2H), 7.92 (d, 2H), 8.71 (s, 1H), 9.59 (s, 1H).

Example 17

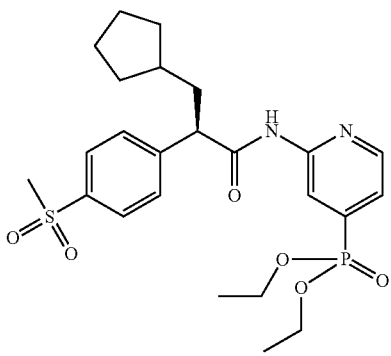

A.

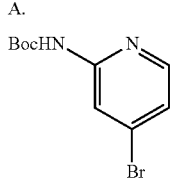

TEA (311 uL; 2.23 mmol) was added to a mixture of 4-bromo-picolinic acid (450 mg; 2.23 mmol) in toluene (6.7 mL). Diphenylphosphoryl azide (480 uL; 2.23 mmol) was added and the reaction was stirred for 30 min at RT, after which tert-butanol (427 uL; 4.46 mmol) was added. The reaction mixture was heated at 90° C. for 2 h, then was cooled to RT. The solution was diluted with EtOAc (15 mL), washed with 10% aqueous Na$_2$CO$_3$ (3×3 mL) and brine (10 mL), dried (MgSO$_4$) and concentrated in vacuo. The crude product was chromatographed (SiO$_2$; continuous gradient from 0 to 75% solvent B over 15 min, where solvent A=hexanes and solvent B=EtOAc) to give Part A compound (0.39 g; 65%).

B.

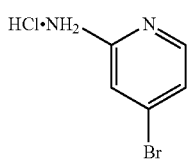

HCl (1 mL of a 4.0 M solution in 1,4 dioxane) was added to a reaction vessel containing Part A compound (106.5 mg; 0.390 mmol). After stirring at RT for 20 h the reaction mixture was concentrated in vacuo. The crude product was stirred with hexanes (3 mL). The HCl salt of Part B compound (81 mg; 100%) was isolated by filtration.

C.

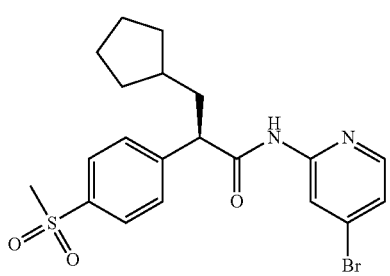

Oxalyl chloride (152 µL of a 2 M solution in DCM; 0.304 mmol) was added to a mixture of Example 1 Part D compound (60 mg; 0.202 mmol) in DCM (0.4 mL). The solution was cooled to 0° C. DMF (7 µL) was added. Gas evolution occurred. After 2 h at RT the reaction mixture was concentrated in vacuo. The residue was stripped from CHCl$_3$ (2×1 mL). The crude acid chloride was then dissolved in DCM (0.5 mL). Part B compound (53 mg; 0.253 mmol) was added followed by pyridine (49 uL; 0.606 mmol). The reaction mixture was stirred at RT for 2 h then was concentrated in vacuo. The residue was partitioned between EtOAc (8 mL) and brine (4 mL). The organic phase was dried (MgSO$_4$) and concentrated in vacuo. The crude product was chromatographed (SiO$_2$; continuous gradient from 0 to 100% solvent B over 10 min, where solvent A=hexanes and solvent B=EtOAc) to give Part C compound (72 mg; 79%).

D.

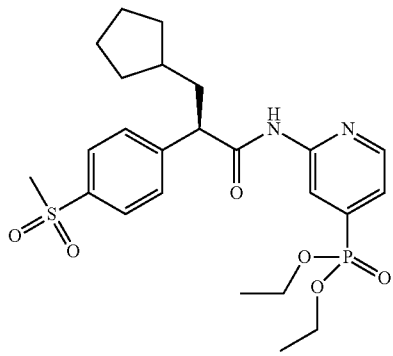

A solution of Part C compound (66 mg; 0.146 mmol) in THF (degassed) (0.38 mL) was added to a reaction flask containing $(Ph_3P)_4Pd(0)$ (34 mg; 0.029 mmol). $H(O)P(OEt)_2$ (21 μL; 0.161 mmol) was added followed by TEA (24.4 μL; 0.175 mmol). The reaction vessel was capped and the reaction mixture was heated at 75° C. for 16 h, then was cooled to RT and concentrated in vacuo. The crude product was purified by preparative HPLC (YMC reverse phase ODS-A-5u 30×100 mm column; flow rate=40 mL/min, 35 to 100% solvent B over 12 min, hold to 14 min, where solvent A=90:10:0.1 $H_2O$:MeOH:TFA and solvent B=90:10:0.1 MeOH:$H_2O$:TFA) to give the title compound (49 mg; 66%) as a white solid. [M+H]$^+$=509.1; $^1$H NMR (400 MHz, CD$_3$OD): δ 1.19 (m, 2H), 1.34 (m, 6H), 1.52 (m, 2H), 1.65 (m, 3H), 1.84 (m, 3H), 2.23 (m, 1H), 3.09 (s, 3H), 4.01 (t, 1H), 4.16 (m, 4H), 7.38 (dd, 1H), 7.71 (d, 2H), 7.92 (d, 2H), 8.47 (m, 2H).

Example 18

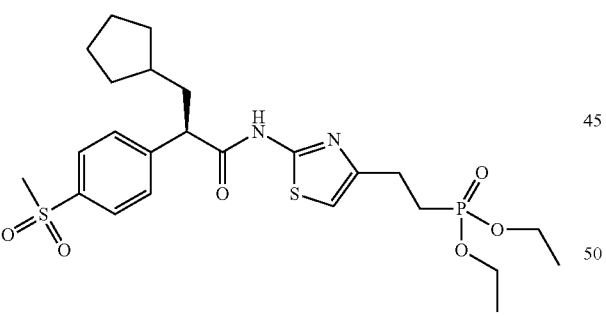

A.

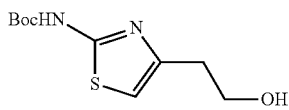

A solution of di-tert-butyl dicarbonate (1.03 g; 4.73 mmol) in toluene (15 mL) was added to a reaction vessel containing (ethyl 2-(2-aminothiazol-4-yl)acetate (0.80 g; 4.30 mmol). The reaction mixture was heated at 85° C. for 24 h, then was cooled to RT and concentrated in vacuo to give Part A compound (1.14 g; quant. yield). The crude compound was carried forward without further purification.

B.

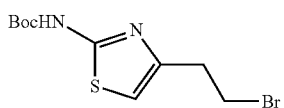

A solution of LiAlH$_4$ (4.30 mL of a 1 M solution in THF; 4.40 mmol) was added to a 0° C. solution of crude Part A compound (1.14 g; 3.98 mmol) in THF (13 mL). The reaction mixture was stirred at 0° C. for 2 h, then was carefully quenched by dropwise addition of sat. aqueous NH$_4$Cl (0.6 mL). The solution was partitioned between EtOAc (20 mL) and brine (10 mL). The organic phase was washed with brine (10 mL), dried (MgSO$_4$) and concentrated in vacuo. The crude product was chromatographed (SiO$_2$; continuous gradient from 0 to 100% solvent B over 8 min, hold at 100% solvent B for 8 min, where solvent A=hexanes and solvent B=EtOAc) to give Part B compound (0.42 g; 43%).

C.

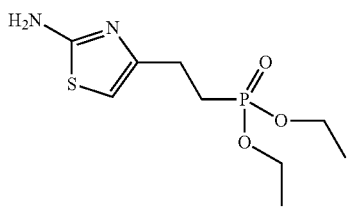

A solution of $CH_3SO_2Cl$ (140 μL; 1.81 mmol) in DCM (1.7 mL) was added to a 0° C. solution of Part B compound (0.42 g; 1.72 mmol) and TEA (264 uL; 1.89 mmol) in DCM (4.0 mL). After 30 min at 0° C. the reaction mixture was diluted with acetone (5.7 mL). LiBr (896 mg; 10.32 mmol) was added. The reaction was stirred at RT for 1 h, then was partitioned between Et$_2$O (10 mL) and sat. aqueous NH$_4$Cl (10 mL). The organic phase was washed with sat. aqueous NH$_4$Cl (10 mL) and brine (10 mL), dried (MgSO$_4$) and concentrated in vacuo to give Part C compound (0.50 g; 94%).

D.

Part 1: Part C compound (0.50 g; 1.63 mmol) was dissolved in neat $(EtO)_3P$ (1.0 mL). The reaction mixture was heated at 130° C. for 2 h; at this point analytical HPLC showed multiple peaks. The reaction was cooled to RT and concentrated in vacuo. The crude product was chromatographed (SiO$_2$; continuous gradient from 0 to 100% solvent B over 7 min, switch to solvent C, hold at 100% solvent C for 7 min, where solvent A=hexanes, solvent B=EtOAc and solvent C=3% MeOH in EtOAc). The compound was not pure at this point (65% purity).

Part 2: To a 0° C. solution of the impure intermediate from Part 1 in DCM (0.8 mL) was added TFA (0.4 mL). The reaction was allowed to warm to RT and stirred at RT for 2 h, then was concentrated in vacuo. The residue was partitioned between EtOAc (10 mL) and sat. aqueous NaHCO$_3$ (10 mL).

The organic phase was dried (MgSO$_4$) and concentrated in vacuo to give Part D compound (73 mg; 17%—two steps). (65% purity).

E.

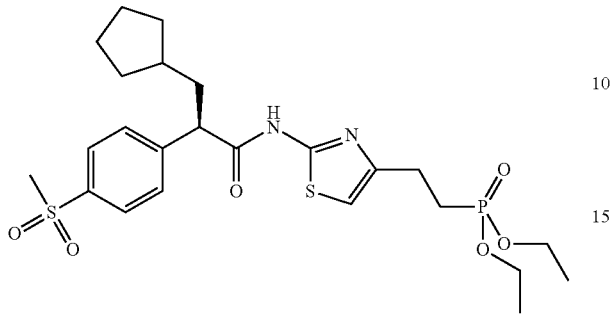

Oxalyl chloride (2.0 M in DCM) (78 μL; 0.155 mmol) was added to a mixture of Example 1 Part D compound (33 mg; 0.111 mmol) in DCM (0.25 mL). The solution was cooled to 0° C. DMF (7 μL) was added. Gas evolution occurred. After 1.5 h at RT the reaction mixture was concentrated in vacuo. The residue was stripped from CHCl$_3$ (2×0.8 mL). The crude acid chloride was dissolved in DCM (0.25 mL). Part D compound (38 mg; 0.144 mmol) was added followed by pyridine (27 uL; 0.333 mmol). The reaction mixture was stirred at RT for 2 h, then was concentrated in vacuo. The residue was partitioned between EtOAc (8 mL) and 0.5 N aqueous HCl (4 mL). The organic phase was washed with brine (4 mL), dried (MgSO$_4$), and concentrated in vacuo. The crude product was purified by preparative HPLC (YMC reverse phase ODS-A-5u 30×100 mm column; flow rate=40 mL/min, 20 to 100% solvent B over 10 min, hold to 14 min, where solvent A=90:10:0.1 H$_2$O:MeOH:TFA and solvent B=90:10:0.1 MeOH:H$_2$O:TFA) to give title compound (29 mg; 48%) as an amorphous solid. [M+H]$^+$=543.0; $^1$H NMR (400 MHz, CD$_3$OD): δ 1.19 (m, 2H), 1.27 (t, 6H), 1.50 (m, 2H), 1.63 (m, 3H), 1.81 (m, 3H), 2.20 (m, 3H), 2.87 (m, 2H), 3.09 (s, 3H), 3.95 (t, 1H), 4.06 (m, 4H), 6.77 (s, 1H), 7.67 (d, 2H), 7.92 (d, 2H).

Example 19

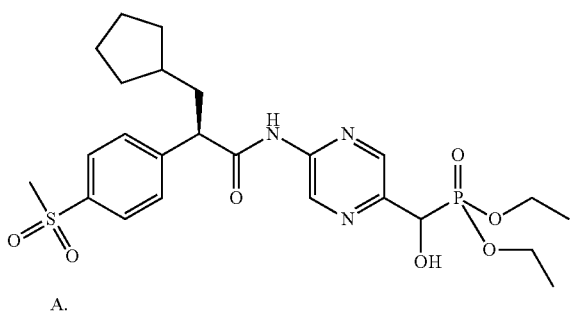

A.

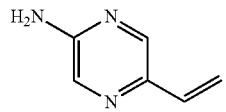

DMF (20 mL) was added to a reaction flask containing 5-bromo-2-pyrazinamine (1.00 g; 5.75 mmol), (Ph$_3$P)$_4$Pd(0) (199 mg; 0.173 mmol) and LiCl (853 mg; 20.13 mmol). DIPEA (2.50 mL; 14.38 mmol) was added followed by tributyl(vinyl)tin (2.52 mL; 8.62 mmol). The reaction mixture was heated at 120° C. for 4 h, then was cooled to RT. A solution of aqueous sat. KF (20 mL) was added. After stirring for 16 h the mixture was diluted with EtOAc (80 mL) and filtered through Celite. The filtrate was washed with H$_2$O (80 mL), dried (MgSO$_4$) and concentrated in vacuo. The crude product was chromatographed (SiO$_2$; continuous gradient from 0 to 100% solvent B over 13 min, hold at 100% for 4 min, where solvent A=hexanes and solvent B=EtOAc) to give Part A compound (0.41 g; 59%).

B.

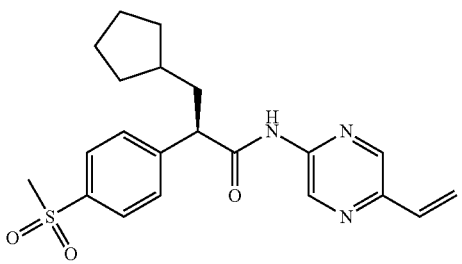

Oxalyl chloride (127 μL of a 2 M solution in DCM; 0.253 mmol) was added to a mixture of Example 1 Part D compound (50 mg; 0.169 mmol) in DCM (0.5 mL). The solution was cooled to 0° C. DMF (7 μL) was added. Gas evolution occurred. After 1.5 h at RT the reaction mixture was concentrated in vacuo. The residue was stripped from CHCl$_3$ (2×1 mL). The crude acid chloride was then dissolved in DCM (0.6 mL). Part A compound (24.5 mg; 0.202 mmol) was added followed by pyridine (41 uL; 0.507 mmol). The reaction mixture was stirred at RT for 1.5 h, then was concentrated in vacuo. The crude product was chromatographed (SiO$_2$; continuous gradient from 0 to 100% solvent B over 12 min, hold at 100% solvent B for 3 min, where solvent A=hexanes and solvent B=EtOAc) to give Part B compound (70 mg; 100%).

C.

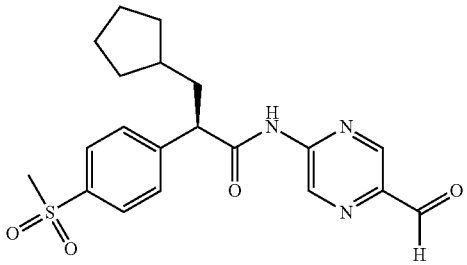

Acetic acid (15 μL) was added to a solution of Part B compound (70 mg; 0.175 mmol) in DCM (0.50 mL). The solution was cooled to −78° C. (dry ice/acetone). Ozone was bubbled through the solution until it turned light blue (~4 min). The dry ice/acetone bath was removed and the reaction was allowed to warm to RT. After 5 min of stirring at RT the solution was diluted with DCM (3 mL). Sat. aqueous NaHCO$_3$ (3 mL) was added (emulsion formed). The mixture was concentrated in vacuo to remove DCM. The aqueous solution was then extracted with EtOAc (4 mL). The organic phase was dried (MgSO₄) and concentrated in vacuo to give Part C compound (55 mg; 78%).

D.

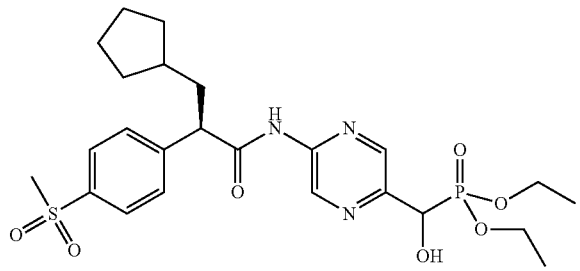

Diethyl phosphite (8.0 μL; 0.062 mmol) was added to a solution of Part C compound (25 mg; 0.062 mmol) in THF (0.30 mL). TEA (8.68 uL; 0.062 mmol) was then added. After 8 h at RT the solution was concentrated in vacuo. The crude product was purified by preparative HPLC (YMC reverse phase ODS-A-5u 30×100 mm column; flow rate=40 mL/min, 15 to 100% solvent B over 15 min, hold to 20 min, where solvent A=90:10:0.1 H₂O:MeOH:TFA and solvent B=90:10: 0.1 MeOH:H₂O:TFA) to give the title compound (15 mg; 45%; amorphous solid) as a 1:1 mixture of diastereomers. [M+H]⁺=540.2; ¹H NMR (400 MHz, CDCl₃): δ 1.15 (m, 2H), 1.31 (m, 6H), 1.48 (m, 2H), 1.62 (m, 3H), 1.78 (m, 2H), 1.93 (m, 1H), 2.22 (m, 1H), 3.88 (m, 1H), 4.20 (m, 4H), 5.13 (dd, 1H), 7.63 (d, 2H), 7.89 (d, 2H), 8.34 (d, 1H), 9.11 (d, 1H), 9.43 (s, 1H).

Example 20

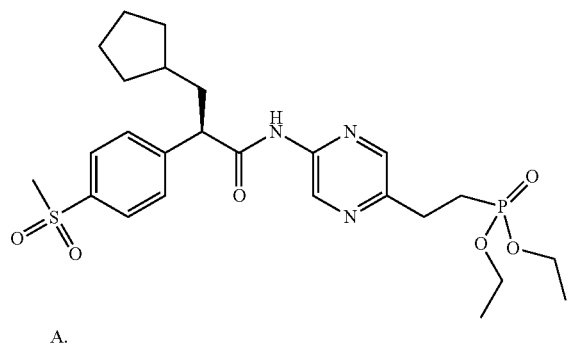

A.

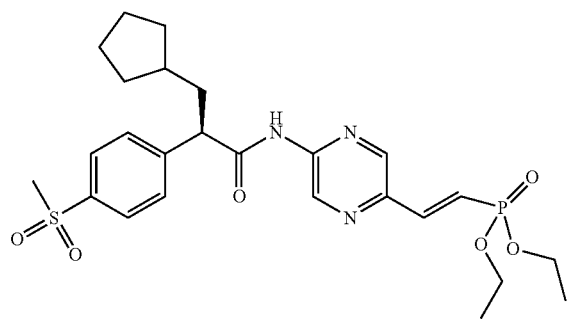

A solution of Example 19 Part C compound (26 mg; 0.065 mmol) in DCM (150 uL) was added to a solution of CH₂(PO₃Et₂)₂ (16.2 μL; 0.065 mmol) in 5 N aqueous NaOH (150 μL). After 1 h at RT the reaction mixture was partitioned between DCM (3 mL) and H₂O (2 mL). The organic phase was dried (MgSO₄) and concentrated in vacuo to give Part A compound (35 mg; 100%).

B.

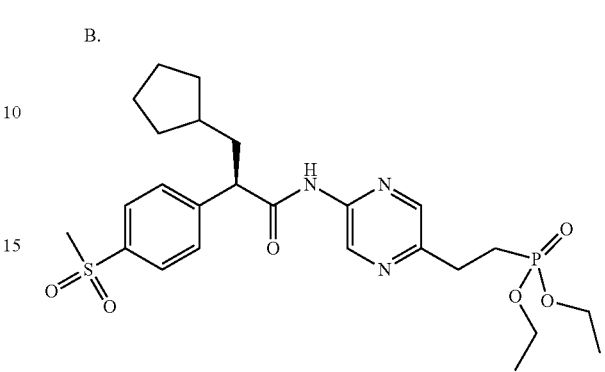

10% Pd/C (3 mg) was added to a solution of Part A compound (35 mg; 0.065 mmol) in MeOH (0.30 mL). A H₂ atmosphere was introduced via balloon. After 6 h the reaction mixture was filtered and the filtrate was concentrated in vacuo. The crude product was purified by preparative HPLC (YMC reverse phase ODS-A-5u 30×100 mm column; flow rate=40 mL/min, 20 to 100% solvent B over 11 min, hold to 15 min, where solvent A=90:10:0.1 H₂O:MeOH:TFA and solvent B=90:10:0.1 MeOH:H₂O:TFA) to give title compound (11 mg; 31%) as an amorphous solid. [M+H]⁺=538.2; ¹H NMR (400 MHz, CDCl₃): δ 1.15 (m, 2H), 1.30 (m, 8H), 1.48 (m, 2H), 1.61 (m, 3H), 1.76 (m, 2H), 1.93 (m, 1H), 2.22 (m, 3H), 3.05 (s, 3H), 3.74 (m, 1H), 4.09 (m, 4H), 7.61 (d, 2H), 7.92 (d, 2H), 8.08 (s, 1H), 8.29 (s, 1H), 9.44 (s, 1H).

Example 21

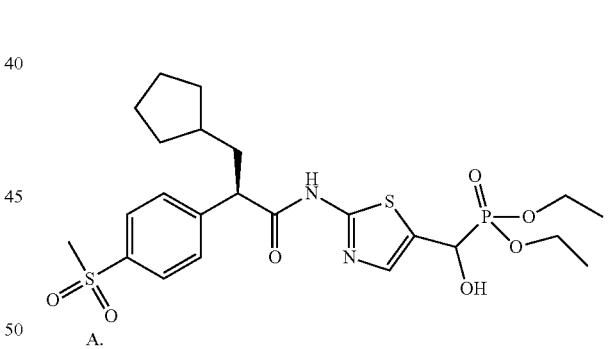

A.

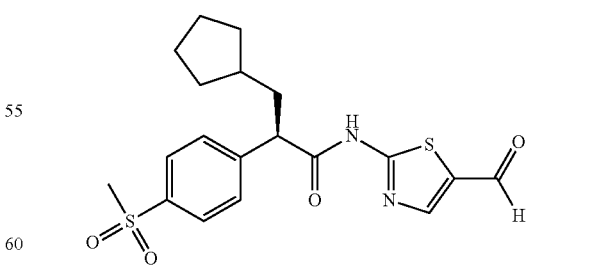

Oxalyl chloride (203 μL of a 2 M solution in DCM; 0.406 mmol) was added to a 0° C. mixture of Example 1 Part D compound (80 mg; 0.270 mmol) in DCM (0.70 mL). DMF (10 uL) was added. Gas evolution occurred. The reaction mixture was stirred at RT for 1.5 h, then was concentrated in vacuo. The residue was stripped from CHCl₃ (2×2 mL). The crude acid chloride was dissolved in DCM (0.90 mL). 2-amino-5-formylthiazole (45.0 mg; 0.351 mmol) was added followed by pyridine (66.0 uL; 0.810 mmol). After 16 h at RT the reaction was concentrated in vacuo. The crude product was chromatographed (SiO₂; continuous gradient from 0 to 100% solvent B over 6 min, hold at 100% solvent B for 8 min, where solvent A=hexanes and solvent B=EtOAc) to give Part A compound (27 mg; 25%).

B.

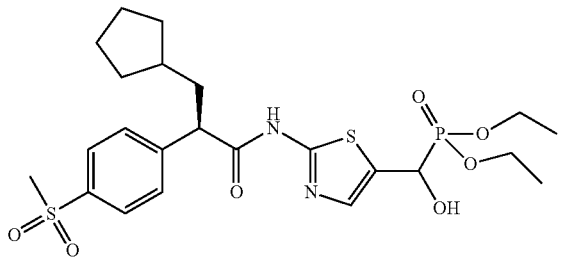

H(O)P(OEt)₂ (8.9 µL; 0.069 mmol) was added to a solution of Part A compound (27 mg; 0.066 mmol) in THF (0.30 mL). TEA (9.6 µL; 0.069 mmol) was added. The reaction mixture was stirred at RT for 20 h, after which more H(O)P(OEt)₂ (8.89 uL; 0.069 mmol) and TEA (9.62 uL; 0.069 mmol) were added along with THF (0.10 mL). After 20 h the reaction was heated at 45° C. for 16 h, then was cooled to RT. After two weeks at RT the residue which had formed was purified by preparative HPLC (YMC reverse phase ODS-A-5u 30×100 mm column; flow rate=40 mL/min, 15 to 100% solvent B over 20 min, where solvent A=90:10:0.1 H₂O:MeOH:TFA and solvent B=90:10:0.1 MeOH:H₂O:TFA) to give the title compound (27 mg; 75%; amorphous solid) as a 1:1 mixture of diastereomers. [M+H]⁺=540.2; ¹H NMR (400 MHz, CDCl₃): δ 1.16 (m, 2H), 1.32 (m, 6H), 1.49 (m, 2H), 1.62 (m, 3H), 1.78 (m, 2H), 1.95 (m, 1H), 2.24 (m, 1H), 3.04 (s, 3H), 4.01 (t, 1H), 4.21 (m, 4H), 5.18 (d, 1H), 7.37 (s, 1H), 7.65 (d, 2H), 7.91 (d, 2H).

Example 22

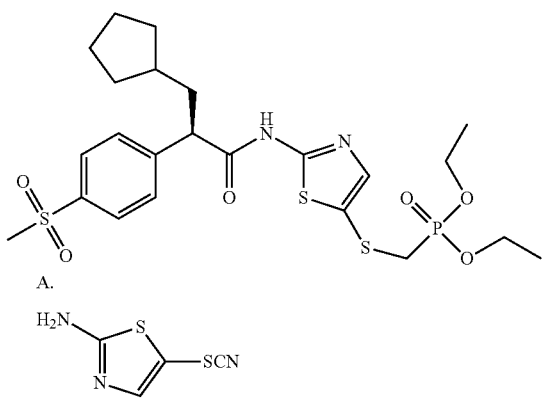

A.

To a solution of 2-amino-5-bromothiazole hydrobromide (10.0 g, 38.4 mmol) in MeOH (50 mL) was added KSCN (15.0 g, 160 mmol). The reaction mixture was stirred at RT for 18 h, then was concentrated in vacuo, and H₂O (40 mL) was added to the residue. The mixture was adjusted to pH 12 with 1N aqueous NaOH. A precipitate was formed, which was collected by suction filtration, and washed with H₂O (3×) and Et₂O (3×). The solid was dried in vacuo for 18 h to give Part A compound as a brown solid (2.8 g, 47%).

B.

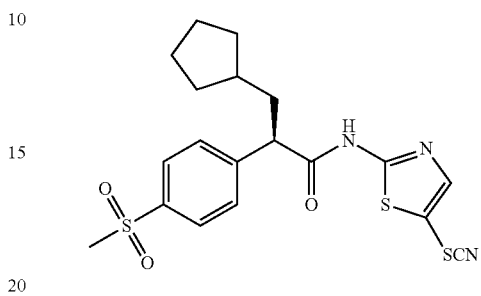

To a solution of Part A thiocyanate (800 mg, 5.09 mmol) and Example 1D (1.51 g, 5.09 mmol) in THF (20 mL) was added DEPBT (3.05 g, 10.18 mmol) and iPr₂NEt (1.8 mL, 10.18 mmol). The reaction mixture was stirred at RT for 18 h, then was concentrated in vacuo. The residue was taken up in EtOAc and brine, and extracted with EtOAc (3×). The combined organic extracts were washed with 1N aqueous HCl, H₂O, 5% aqueous NaHCO₃, H₂O, and brine, dried (MgSO₄), and concentrated in vacuo. The residue was chromatographed (SiO₂; continuous gradient 10% EtOAc/Hex to 100% EtOAc/Hexane) to give Part B compound (927 mg, 42%) as an orange solid.

C.

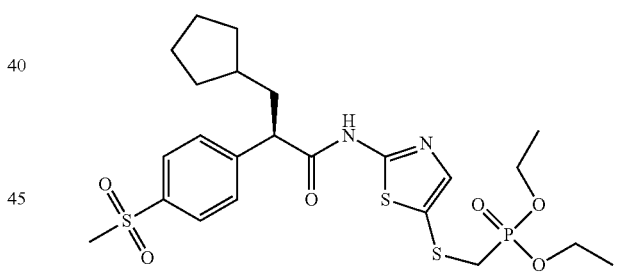

To a 0° C. solution of thiocyanate B (50 mg, 0.11 mmol) in absolute EtOH (2 mL) was added NaBH₄ (7 mg, 0.22 mmol). The mixture was stirred at 0° C. for 1 h, after which excess NaBH₄ was cautiously quenched with acetone (0.5 mL). The mixture was warmed to RT, and was added to a flask charged with ICH₂PO₃Et₂ (41 mg, 0.15 mmol). The reaction was stirred at RT for 18 h, then was concentrated in vacuo. The residue was purified by preparative HPLC (Phenomenex Luna 5u C18 21.2×100 mm column; detection at 220 nm; flow rate=20 mL/min; continuous gradient from 70% A to 100% B over 8 min+7 min hold time at 100% B, where A=90:10:0.1 H₂O:MeOH:TFA and B=90:10:0.1 MeOH:H₂O:TFA) to provide the title compound (25.1 mg, 39% yield) as an off white lyophilate. [M+H]⁺=561.1; ¹H NMR (400 MHz, DMSO-D6): δ 7.83 (d, J=8.4, 2H), 7.58 (d, J=8.3, 2H), 7.51 (s, 1H), 3.92 (m, 5H), 3.15 (s, 2H), 3.12 (s, 3H), 2.09-1.36 (m, 11H), 1.12 (m, 6H).

Example 23

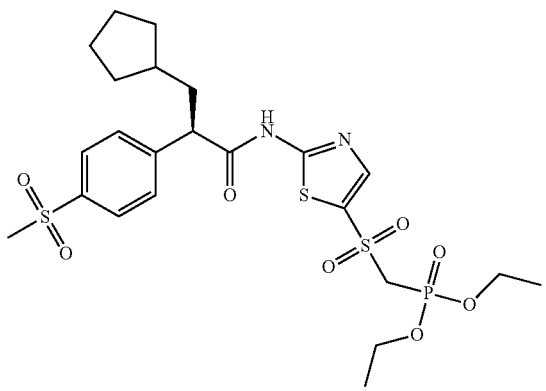 [SMILES: CCOP(=O)(CS(=O)(=O)c1cnc(NC(=O)[C@H](CC2CCCC2)c2ccc(S(C)(=O)=O)cc2)s1)OCC]

To a solution of Example 22 compound (20 mg, 0.04 mmol) in MeOH (1 mL) and THF (1 mL) was added p-toluenesulfonyl imidazole (24 mg, 0.11 mmol), 30% aqueous $H_2O_2$ (0.02 mL, 0.14 mmol), and 1N aqueous NaOH (1.0 mL). The reaction was stirred at RT for 3 h, then was concentrated in vacuo. The residue was purified by preparative HPLC (Phenomenex Luna 5u C18 21.2×100 mm column; detection at 220 nm; flow rate=20 mL/min; continuous gradient from 70% A to 100% B over 8 min+7 min hold time at 100% B, where A=90:10:0.1 $H_2O$:MeOH:TFA and B=90:10:0.1 MeOH:$H_2O$:TFA) to provide the title compound (12 mg, 57% yield) as a white lyophilate. $[M+H]^+$=593.2; $^1H$ NMR (400 MHz, DMSO-D6): δ 8.00 (s, 1H), 7.84 (d, J=8.4, 2H), 7.59 (d, J=8.4, 2H), 4.08-3.94 (m, 5H), 3.13 (s, 2H), 3.10 (s, 3H), 2.02-1.10 (m, 11H), 1.10-1.06 (m, 6H).

Example 24

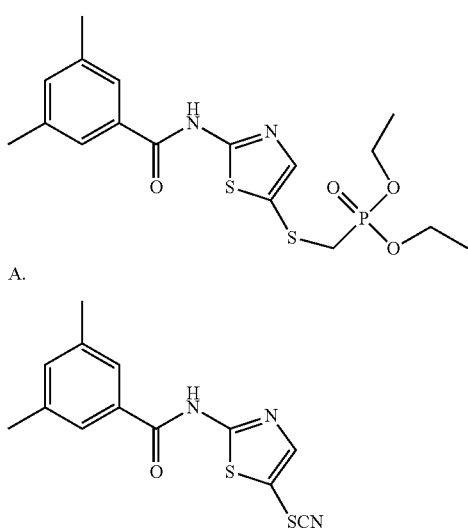

A.

To a solution of 3,5-dimethylbenzoic acid (800 mg, 5.3 mmol) in $CH_2Cl_2$ (20 mL) was added oxalyl chloride (0.51 mL, 5.8 mmol) and DMF (0.1 mL). The reaction mixture was stirred at RT for 2 h, then was concentrated in vacuo. The residue was taken up in THF (20 mL), and Example 22 Part A amine (922 mg, 5.8 mmol) and pyridine (0.86 mL, 10.6 mmol) were added. The mixture was stirred at RT for 18 h, then was diluted with EtOAc (60 mL), washed with $H_2O$ and brine, and extracted with EtOAc (2×). The combined organic extracts were dried ($MgSO_4$) and concentrated in vacuo. The residue was chromatographed (10% EtOAc/Hex to 100% EtOAc/Hexane) to give Part A compound (770 mg, 51% yield) as a brown solid.

B.

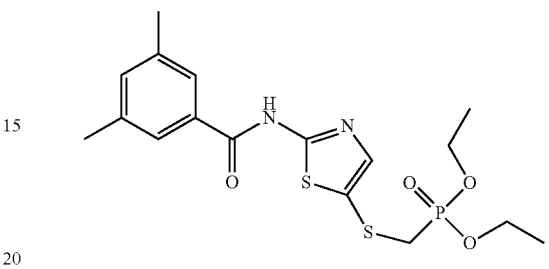

To a 0° C. solution of Part A compound (50 mg, 0.17 mmol) in absolute EtOH (2 mL) was added $NaBH_4$ (13 mg, 0.35 mmol), and the mixture was stirred for 1 h at 0° C. The excess $NaBH_4$ was quenched with acetone (0.5 mL), and the mixture was warmed to RT. The mixture was added to a flask charged with $ICH_2PO_3Et_2$ (62 mg, 0.22 mmol). The reaction was stirred at RT for 18 h, then was concentrated in vacuo. The residue was purified by preparative HPLC (Phenomenex Luna 5 μm C18 21.2×100 mm column; detection at 220 nm; flow rate=20 mL/min; continuous gradient from 70% A to 100% B over 8 min+7 min hold time at 100% B, where A=90:10:0.1 $H_2O$:MeOH:TFA and B=90:10:0.1 MeOH:$H_2O$:TFA) to provide the title compound (22.4 mg, 32% yield) as a white solid. $[M+H]^+$=415.1; $^1H$ NMR (400 MHz, DMSO-D6): δ 7.71 (s, 1H), 7.66 (s, 2H), 7.27 (s, 1H), 4.02 (m, 4H), 3.27 (s, 2H), 2.34 (s, 6H), 1.21 (m, 6H).

Example 25

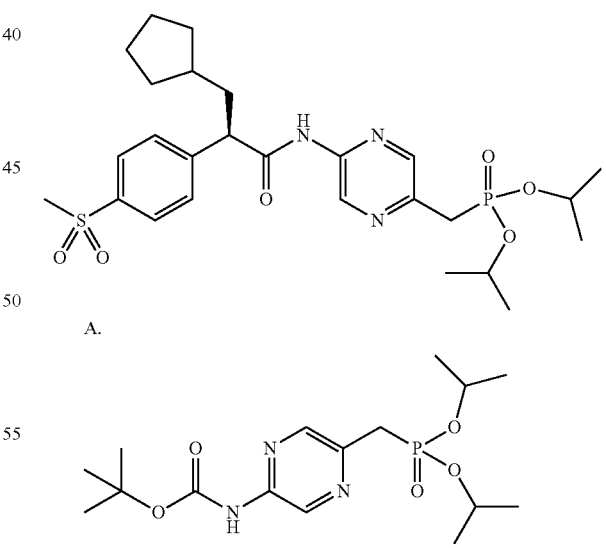

A.

A mixture of tert-butyl 5-(bromomethyl)pyrazin-2-ylcarbamate (399 mg, 1.23 mmol) and $(iPrO)_3P$ (2 mL) was heated at 100° C. overnight. The reaction mixture was cooled to RT, then was chromatographed (120 g $SiO_2$; continuous gradient from 0-50% EtOAc in DCM, followed by a continuous gradient from 0-10% MeOH in DCM) to give 399 mg (86% yield) of Part A compound as a light yellow solid (88% purity by HPLC). [M+H]⁺=374.3; ¹H-NMR (400 MHz, CDCl₃): δ 9.18 (s, 1H), 8.24 (s, 1H), 7.32 (s, 1H), 4.67 (m, 2H), 3.33 (d, 2H), 1.54 (s, 9H), 1.25-1.30 (m, 12H).

B.

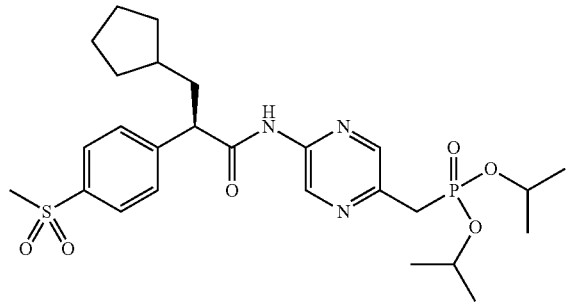

A 0° C. solution of Part A compound (200 mg, 0.535 mmol) in DCM (1 mL) was treated with 1 mL of 4N aqueous HCl in dioxane under Ar. The reaction mixture was allowed to warm to RT overnight, then was concentrated in vacuo. The residue was dissolved in water (5 mL) and extracted with Et₂O to remove an impurity. The aqueous solution was basified with 1 N aqueous NaOH and extracted with DCM (3×2 mL). The combined organic extracts were rinsed with brine, dried (MgSO₄), and concentrated in vacuo to provide 103 mg (71% yield) of diisopropyl (5-aminopyrazin-2-yl)methylphosphonate as a yellow, waxy solid. [M+H]⁺=274.3. This material was used directly in the next step without further purification.

Example 1D acid was converted to the corresponding acid chloride using oxalyl chloride (as described in Example 2 Part A). The acid chloride was transferred with two 0.3 mL portions of DCM into a 0° C. mixture of the above amine (45 mg, 0.165 mmol) and pyridine (53.4 μL, 0.66 mmol) in DCM (0.7 mL) under Ar. The reaction was allowed to warm to RT overnight, then was extracted with DCM (5 mL). The organic extract was washed with 2 mL each of 0.1N aqueous HCl, water, and brine, was dried (MgSO₄), and concentrated in vacuo to afford 142 mg of crude product. The crude material was chromatographed (40 g SiO₂; continuous gradient from 10-100% EtOAc in DCM) to give the title compound (25.6 mg, 28% yield) as a colorless oil. [M+H]⁺=552.4; ¹H-NMR (400 MHz, CDCl₃): δ 9.40 (s, 1H), 8.24 (s, 2H), 7.93 (d, 2H), 7.61 (d, 2H), 4.68 (m, 2H), 3.74 (m, 1H), 3.34 (d, 2H), 3.05 (s, 3H), 2.22 (m, 1H), 1.95 (m, 1H), 1.10-2.83 (m, 9H), 1.25-1.29 (m, 12H).

Example 26

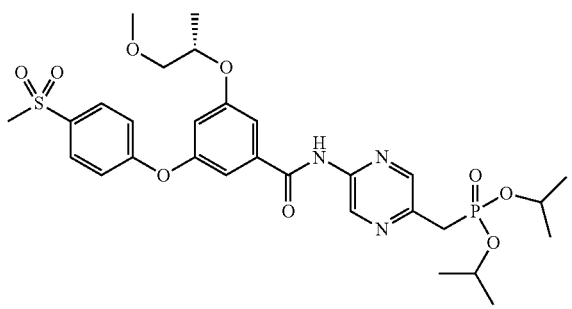

A.

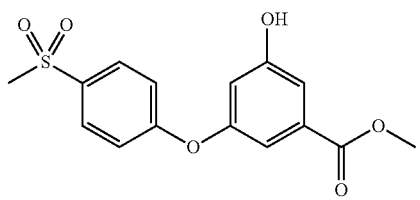

To a rapidly stirred mixture of methyl 3,5-dihydroxybenzoate (38 g, 0.226 mol) and K₂CO₃ (47.7 g, 0.345 mol) in DMF (150 mL) heated at 120° C. under Ar was added a solution of 1-fluoro-4-(methylsulfonyl)benzene (20 g, 0.115 mol) in DMF (50 mL) over 3 h. After heating at 120° C. overnight, the reaction mixture was cooled to RT, diluted with DMF (300 mL), and then treated with Celite® as a filter aid. The heterogeneous reaction mixture was filtered, and the filter cake was thoroughly rinsed with more DMF. The combined filtrates were concentrated in vacuo, and the residue was partitioned between 1N aqueous HCl (200 mL) and EtOAc (250 mL). A further 100 mL of water was added. The aqueous layer was extracted with EtOAc (200 mL), and the combined organic extracts were rinsed with water and brine (250 mL each), and dried (MgSO₄). Volatiles were removed in vacuo. The residue was chromatogaphed in 3 portions. Each portion was absorbed onto SiO₂ (~20 g) and chromatographed (330 g SiO₂; elution with a continuous gradient of 0-20% EtOAc in CH₂Cl₂ followed by isocratic 20% EtOAc:CH₂Cl₂) to give Part A compound (14.77 g; combined yield of 40%) as a white solid. [M+H]⁺=323.0; ¹H-NMR (400 MHz, CDCl₃): δ 7.89 (d, 2H), 7.33 (s, 1H), 7.22 (s, 1H), 7.11 (dd, 2H), 6.89 (d, 1H), 3.89 (s, 3H), 3.07 (s, 3H).

B.

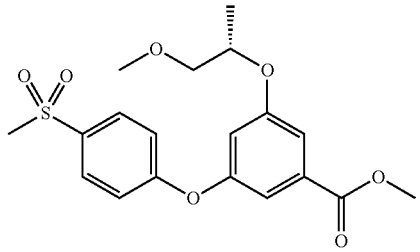

To a 5° C. mixture of Part A compound (5 g, 15.5 mmol), (R)-(-)-1-methoxy-2-propanol (2 mL, 20.4 mmol) and polymer-supported Ph₃P (13.4 g of 3 mmol/g, 40.2 mmol) in THF (175 mL) was added dropwise a solution of DIAD (4.5 mL, 23.2 mmol) in THF (25 mL) over 25 min under Ar (internal temperature maintained at 5° C.). The reaction mixture was allowed to warm to RT overnight, and was then filtered. The solids were thoroughly washed with THF and CH₂Cl₂. The combined filtrates were concentrated in vacuo, re-dissolved in CH₂Cl₂ and divided in 2 equal portions. The first portion was chromatographed (330 g SiO₂; elution with a continuous gradient of 0-10% EtOAc in CH₂Cl₂ over 40 min) to give 2.53 g of pure Part B compound as a colorless oil. Impure product fractions from this column were combined with the rest of the crude product and this mixture was chromatographed as above on 330 g SiO2, but with a continuous gradient from 0-8% EtOAc in CH₂Cl₂ to give Part B compound (3.02 g) as a colorless oil. The combined yield of Part B compound was 5.55 g (90%). [M+H]$^+$=395.0; $^1$H-NMR (400 MHz, CDCl$_3$): δ 7.90 (d, 2H), 7.48 (s, 1H), 7.30 (s, 1H), 7.11 (dd, 2H), 6.86 (d, 1H), 4.61 (m, 1H), 3.90 (s, 3H), 3.49-3.62 (m, 2H), 3.40 (s, 3H), 3.07 (s, 3H), 1.32 (d, 3H).

C.

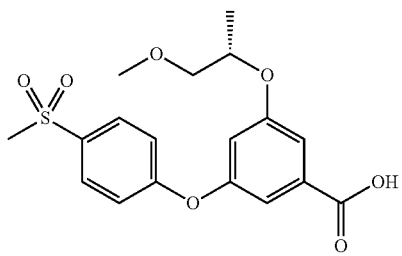

To a 0° C. solution of Part B compound (4.24 g, 10.75 mmol) in THF (50 mL) and water (15 mL) was added LiOH.H$_2$O (1.287 g, 53.7 mmol). The reaction mixture was allowed to warm to RT overnight (reaction complete by LC/MS). The reaction mixture was concentrated in vacuo and 50 mL of H$_2$O was added; the solution was acidified with 5N aqueous HCl. The mixture was extracted with EtOAc (2×100 mL). The combined EtOAc extracts were washed with brine (50 mL), dried (MgSO$_4$) and concentrated in vacuo to provide Part C compound (3.95 g, 96.5% yield) as a colorless glass. [M+H]$^+$=381.1; $^1$H-NMR (400 MHz, CDCl$_3$): δ 7.91 (d, 2H), 7.52 (s, 1H), 7.35 (s, 1H), 7.13 (dd, 2H), 6.90 (s, 1H), 4.61 (m, 1H), 3.52-3.64 (m, 2H), 3.42 (s, 3H), 3.07 (s, 3H), 1.33 (d, 3H).

D.

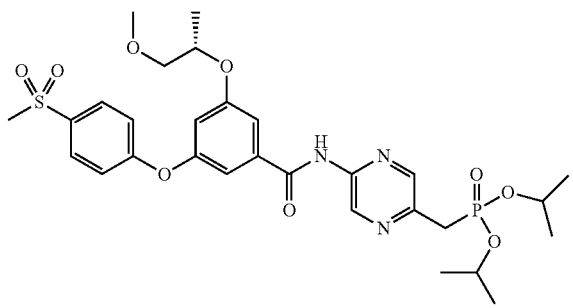

To a 0° C. solution of Example 25A compound (199 mg, 0.533 mmol) in DCM (1 mL) was added TFA (1 mL) under Ar. The reaction mixture was allowed to warm to RT. After 5.5 h, the reaction mixture was concentrated in vacuo and partitioned between 0.5N aqueous HCl and Et$_2$O (4 mL each). The aqueous layer was basified with solid K$_2$CO$_3$, then extracted with DCM (3×). The combined organic extracts were washed with brine, dried (MgSO$_4$), and concentrated in vacuo to provide 108 mg (74%) of diisopropyl (5-aminopyrazin-2-yl)methylphosphonate isolated as a yellow solid. [M+H]$^+$=274.3.

The Part C acid (32 mg, 0.0841 mmol) was converted to the corresponding acid chloride using oxalyl chloride (as described in Example 2 Part A). The crude acid chloride was transferred with two portions (0.2 mL each) of DCM to a mixture of diisopropyl (5-aminopyrazin-2-yl)methylphosphonate (25.3 mg, 0.0926 mmol) and pyridine (27.2 µL, 0.370 mmol) in DCM (0.4 mL) cooled to 0° C. under Ar. The reaction was allowed to warm to RT overnight. The reaction mixture was then extracted with DCM (4 mL), washed with 2 mL each of 0.5N aqueous HCl, water, sat. aqueous NaHCO$_3$ and brine, dried (MgSO$_4$) and concentrated in vacuo. The crude product (47 mg) was chromatographed (12 g SiO$_2$; elution with a continuous gradient from 15 to 100% EtOAc in DCM) to provide 17.6 mg (30%) of the title compound as a colorless oil. [M+H]$^+$=636.3; $^1$H-NMR (400 MHz, CDCl$_3$): δ 9.57 (s, 1H), 8.46 (s, 1H), 8.34 (s, 1H), 7.93 (d, 2H), 7.36 (s, 1H), 7.18 (s, 1H), 7.17 (d, 2H), 6.87 (s, 1H), 4.60-4.75 (m, 3H), 3.52-3.63 (m, 2H), 3.41 (s, 3H), 3.39 (d, 2H), 3.08 (s, 3H), 1.25-1.36 (m, 15H).

Example 27 (Isomer A) and Example 28 (Isomer B)

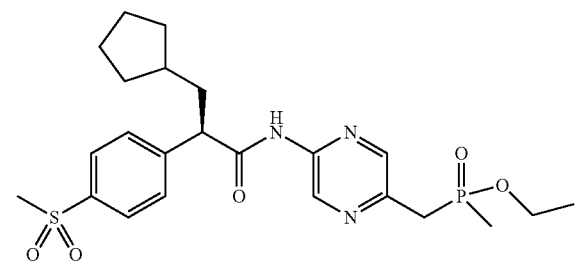

A.

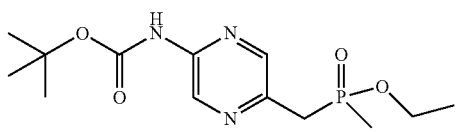

A mixture of tert-butyl 5-(bromomethyl)pyrazin-2-ylcarbamate (300 mg, 1.04 mmol) and diethyl methylphosphonite (0.2 mL) in THF (0.2 mL) was heated overnight at 100° C., then cooled to RT and dissolved in EtOAc (15 mL). The solution was washed with water (3×5 mL) and brine (5 mL), was dried (MgSO$_4$), and concentrated in vacuo. The crude product (279 mg) was chromatographed (SiO$_2$; 80 g; elution with a continuous gradient from 0-100% EtOAc in DCM) to give Part A compound (114 mg) as a waxy white solid, which still contained some by-product from the diethyl methylphosphonite reagent. [M+H]$^+$=316.3.

B.

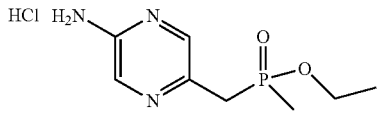

A 0° C. solution of Part A compound (114 mg, 0.361 mmol) in DCM (1 mL) was treated with 4N HCl in dioxane (1 mL). The reaction was allowed to warm to RT overnight, then was diluted with Et$_2$O to fully precipitate the desired product HCl salt and decanted. This process was repeated several times to yield Part B compound (82 mg; 90%) as a white solid. LC/MS showed the correct [M+H]$^+$=216.3 for the free amine.

C.

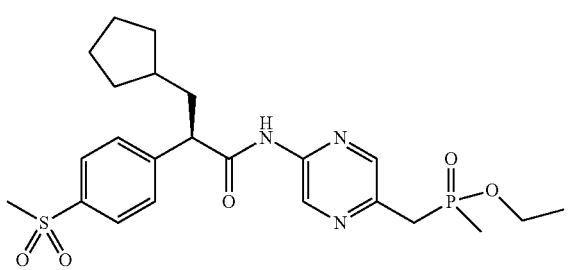

Example 1 Part D compound (91.9 mg, 0.310 mmol) was converted to the corresponding acid chloride using oxalyl chloride (as described in Example 2 Part A). The crude acid chloride was dissolved in a minimal volume of DCM and added to a 0° C. mixture of Part B compound (52 mg, 0.242 mmol) and pyridine (78.2 µL, 0.968 mmol) in DCM (1 mL) under Ar. The reaction was allowed to warm to RT overnight, then was diluted with DCM (7 mL) and washed with two 2 mL portions of 0.5N aqueous HCl, water, sat. aqueous NaHCO$_3$ and brine, dried (MgSO$_4$) and concentrated in vacuo. The crude material (150 mg) was chromatographed (40 g SiO$_2$; elution with a continuous gradient from 0 to 100% EtOAc in DCM, followed by a continuous gradient from 0-10% MeOH in DCM) to give the product diastereomers (43 mg) as a mixture. Preparative reverse phase HPLC on a YMC ODS-A 5µ30×100 mm column (elution with a continuous 40-100% gradient from 90:10:0.1 to 10:90:0.1, water:MeOH:TFA) gave 17.9 mg of a faster-eluting isomer A and 18.3 mg of the slower-eluting isomer B. Each of the above samples was dissolved in 6 mL of DCM and rinsed with 2 mL of sat. aqueous NaHCO$_3$ to remove TFA. The DCM solutions were rinsed with brine, dried (MgSO$_4$) and concentrated in vacuo to give the desired Isomers A and B.

Isomer A (Example 27) was obtained as 16.8 mg of a colorless glass. [M+H]$^+$=494.4; $^1$H-NMR (400 MHz, CD$_3$OD): δ 9.31 (s, 1H), 8.31 (s, 1H), 7.92 (m, 2H), 7.72 (m, 2H), 3.96-4.12 (m, 3H), 3.44 (d, 2H), 3.30 (s, 3H), 2.18-2.26 (m, 1H), 1.13-1.89 (m, 9H), 1.56 (d, 3H), 1.27 (m, 3H).

Isomer B (Example 28) was obtained as 15.6 mg of a colorless glass: [M+H]$^+$=494.4; $^1$H-NMR (400 MHz, CD$_3$OD): δ 9.31 (s, 1H), 8.31 (s, 1H), 7.91 (m, 2H), 7.70 (m, 2H), 3.97-4.12 (m, 3H), 3.44 (d, 2H), 3.30 (s, 3H), 2.16-2.26 (m, 1H), 1.13-1.88 (m, 9H), 1.54 (d, 3H), 1.28 (m, 3H).

Example 29

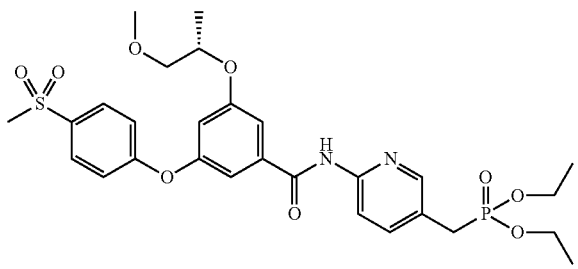 [SMILES: CCOP(=O)(Cc1ccc(NC(=O)c2cc(Oc3ccc(S(C)(=O)=O)cc3)cc(O[C@@H](C)COC)c2)nc1)OCC]

EDC (19.7 mg, 0.100 mmol) was added to a 0° C. mixture of the Example 26C acid (34.6 mg, 0.091 mmol), HOAT (14.8 mg, 0.109 mmol), diethyl (6-aminopyridin-3-yl)methylphosphonate (24.4 mg, 0.100 mmol) and Et$_3$N (12.6 µL, 0.091 mmol) in 0.7 mL of DCM under Ar. The reaction mixture was allowed to warm to RT overnight. An additional 12 mg of amine was added and stirring was continued for 4 days. The reaction was extracted with 3 mL of DCM and washed with 1 mL each of 0.5N aqueous HCl, water, sat. aqueous NaHCO$_3$ and brine, dried (MgSO$_4$) and concentrated in vacuo. The crude product (34 mg) was purified by preparative reverse phase HPLC on a 30×100 mm Phenomenex Axia Luna 5µ C18 column (continuous gradient from 30-100% 90:10:0.1 to 10:90:0.1, water:CH$_3$CN: TFA) to provide 29 mg of desired product. This material was dissolved in 3 mL of DCM and washed with two 1 mL portions of sat. aqueous NaHCO$_3$, brine and dried (MgSO$_4$). Concentration in vacuo provided 20.8 mg (38% yield) of the title compound as a colorless oil. [M+H]$^+$=607.3; $^1$H-NMR (400 MHz, CDCl$_3$): δ 8.54 (s, 1H), 8.30 (d, 1H), 8.20 (s, 1H), 7.91 (d, 2H), 7.72 (d, 1H), 7.34 (s, 1H), 7.12-7.17 (m, 3H), 6.85 (s, 1H), 4.62 (m, 1H), 4.06 (m, 4H), 3.50-3.62 (m, 2H), 3.41 (s, 3H), 3.11 (d, 2H), 3.08 (s, 3H), 1.23-1.35 (m, 9H).

Example 30

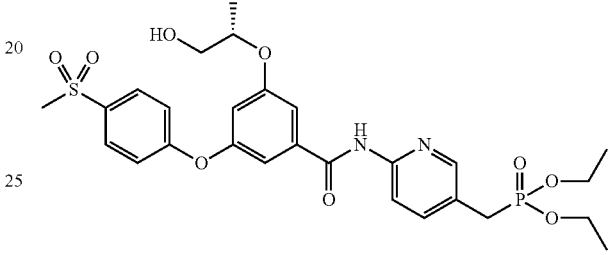

A.

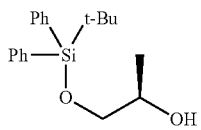

Imidazole (1.86 g, 27.4 mmol) was added to a mixture of (R)-propane-1,2-diol (1 mL, 13.7 mmol) and TBSCl (4.1 mL, 16.44 mmol) in DMF (13 mL) at RT. The reaction was stirred at RT overnight, then was concentrated in vacuo. The residue was extracted with DCM (25 mL) and washed with water (20 mL). The aqueous layer was re-extracted with DCM (25 mL), and the combined organic extracts were washed with brine (20 mL), dried (MgSO$_4$) and concentrated in vacuo. The crude oily product (6 g) was chromatographed (120 g SiO$_2$; continuous gradient from 0-20%, EtOAc in hexane) to afford Part A compound (3.69 g, 86% yield) as a colorless oil. [M+H]$^+$ not observed in LC/MS. $^1$H-NMR (400 MHz, CDCl$_3$): δ 7.67 (m, 4H), 7.41 (m, 6H), 3.91 (m, 1H), 3.61 (dd, 1H), 3.45 (dd, 1H), 2.58 (d, 1H), 1.10 (d, 3H), 1.07 (s, 9H).

B.

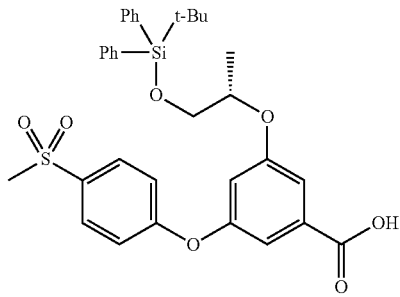

A solution of DIAD (0.216 mL, 1.12 mmol) in THF (0.5 mL) was added dropwise over 3 min to a 0° C. mixture of the Part A compound (304 mg, 0.967 mmol), methyl 3-hydroxy-5-(4-(methylsulfonyl)phenoxy)benzoate (240 mg, 0.744 mmol) and polymer-supported Ph₃P (1.6 mmol/g load, 1.2 g, 1.92 mmol) in 10 mL of THF under Ar. The reaction was allowed to warm to RT. After 3 hours at RT, the reaction was filtered and the resin thoroughly rinsed with THF and DCM. The combined filtrates were concentrated in vacuo. The residue was chromatographed (SiO₂; 40 g; continuous gradient from 0-40% EtOAc in hexane) to give partially purified product (contained some reduced DIAD by ¹H-NMR) which was used in the next step without further purification.

LiOH.H₂O (93 mg, 2.22 mmol) was added to a 0° C. mixture of the methyl ester from above (nominally 0.744 mmol) in 4 mL of THF and 1 mL of water. The reaction was allowed to warm to RT overnight. Analytical HPLC indicated that ~16% of the starting material remained, so more LiOH.H₂O (31 mg) was added. After an additional 4.5 h, the reaction mixture was concentrated in vacuo, then was partitioned between water and EtOAc (15 mL each). The aqueous layer was extracted with 15 mL of EtOAc. The combined organic extracts were washed with 10% aqueous KHSO₄ (10 mL), 10 mL each of water and brine, dried (MgSO₄) and concentrated in vacuo to give Part B compound (402 mg, 90% yield), which still contained some reduced DIAD. ¹H NMR (400 MHz, CDCl₃) partial assignments: δ 7.90 (d, 2H), 7.63 (d, 4H), 7.46 (s, 1H), 7.30-7.43 (m, 7H), 7.10 (d, 2H), 6.82 (s, 1H), 4.58 (m, 1H), 3.77 (dd, 2H), 3.06 (s, 3H), 1.01 (s, 9H).

C.

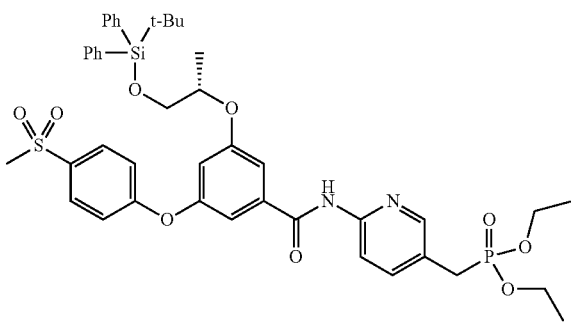

EDC (26.1 mg, 0.136 mmol) was added to a 0° C. mixture of Part B compound (75 mg, 0.124 mmol), HOAT (20.2 mg, 0.149 mmol), diethyl (6-aminopyridin-3-yl)methylphosphonate (39.3 mg, 0.161 mmol) and Et₃N (19 μL, 0.136 mmol) in 1.5 mL of DCM under Ar. After 5 days, LC/MS analysis showed a ca. 62:9 ratio of desired product to the HOAT ester of the Part B acid. After another 24 h, the reaction mixture was diluted with 7 mL of DCM and washed with 2 mL each of 0.5N aqueous HCl, water, sat. aqueous NaHCO₃ and brine, dried (MgSO₄) and concentrated in vacuo. The crude product (85 mg) was chromatographed (12 g SiO₂; elution with a continuous gradient from 0-5% MeOH to DCM) to provide Part C compound (46 mg; 45%) as a colorless oil. [M+H]⁺=831.4; ¹H-NMR (400 MHz, CDCl₃): δ 8.57 (s, 1H), 8.31 (d, 1H), 8.21 (s, 1H), 7.90 (d, 2H), 7.74 (d, 1H), 7.63 (m, 4H), 7.32-7.43 (m, 6H), 7.28 (s, 1H), 7.07-7.14 (m, 3H), 6.79 (s, 1H), 4.59 (m, 1H), 4.08 (m, 4H), 3.78 (dd, 2H), 3.12 (d, 2H), 3.07 (s, 3H), 1.33 (d, 3H), 1.25-1.30 (m, 6H), 1.02 (s, 9H).

D.

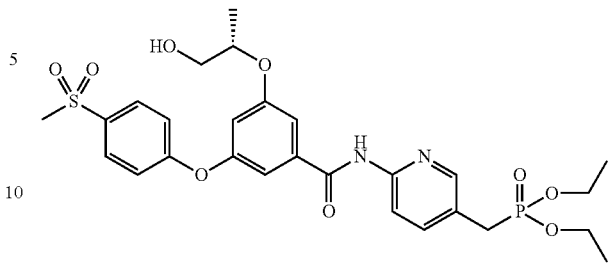

To a 0° C. solution of Part C compound (46 mg, 0.0553 mmol) in 1.5 mL of THF under Ar was added Bu₄NF (0.11 mL of a 1M solution in THF, 0.11 mmol). The reaction was allowed to warm to RT. After 4 hr, the reaction mixture was concentrated in vacuo and partitioned between 6 mL of EtOAc and 2 mL of water. The organic extract was washed with 2 mL each of water and brine, dried (MgSO₄) and concentrated in vacuo. The residue (44 mg) was purified by preparative reverse phase HPLC on a 30×100 mm Phenomenex Axia Luna 5μ C18 column (linear 20-100% gradient from 90:10:0.1 to 10:90:0.1, water:CH₃CN:TFA). The purified material was dissolved in DCM (6 mL) and washed with 2 mL each of sat. aqueous NaHCO₃ and brine, dried (MgSO₄) and concentrated in vacuo to yield the title compound (25 mg; 76%) as a colorless oil. [M+H]⁺=593.2; ¹H-NMR (400 MHz, CDCl₃): δ 8.85 (s, 1H), 8.31 (d, 1H), 8.17 (s, 1H), 7.92 (d, 2H), 7.72 (d, 1H), 7.34 (s, 1H), 7.16 (s, 1H), 7.12 (d, 2H), 6.81 (s, 1H), 4.58 (m, 1H), 4.07 (m, 4H), 3.77 (m, 2H), 3.08 (s, 3H), 1.27 (m, 6H).

Example 31

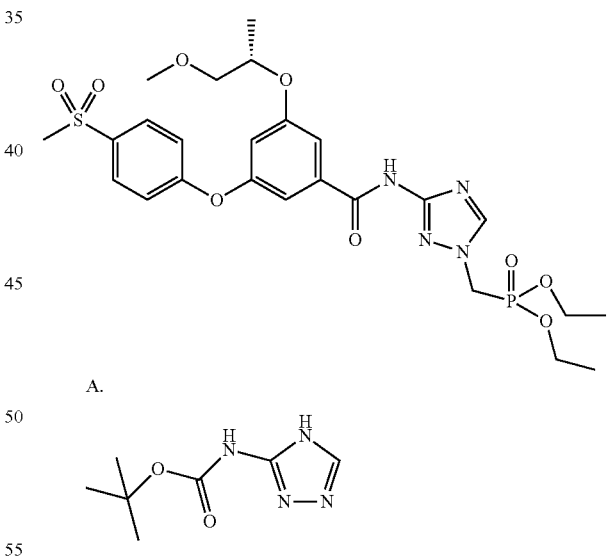

A.

To a RT slurry of 3-amino-1,2,4-triazole (1.0 g, 11.9 mmol) in hexanes (20 mL) was added TMEDA (0.07 g, 0.6 mmol) and di-tert-butyl dicarbonate (3.89 g, 17.8 mmol). The reaction mixture was stirred at RT for 24 h, poured into sat. aqueous NaHCO₃ (150 mL) and the product was extracted with EtOAc (2×25 mL). The organic extracts were combined, dried (MgSO₄) and concentrated in vacuo. The residue was chromatographed (SiO₂: continuous gradient from 0% EtOAc/Hexane to 100% EtOAc/Hex) to give the desired Part A compound (1.33 g, 61% yield) as a white solid. [M+H]⁺=185.0; ¹H NMR (400 MHz, CDCl₃): δ 7.48 (s, 1H), 1.66 (s, 9H)

B.

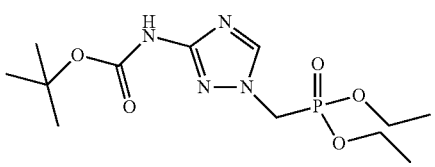

To a 0° C. solution of Part A compound (0.500 g, 2.71 mmol) in DMF (5 mL) was added 60% NaH in oil (0.119 g, 2.99 mmol), in 1 portion, and the resultant slurry was stirred at 0° C. for 1 h. ICH$_2$PO$_3$Et$_2$ (0.830 g, 2.99 mmol) was added, and the reaction mixture was stirred overnight at RT. The reaction mixture was poured into brine (35 mL); and extracted with EtOAc (4×25 mL); the combined organic extracts were dried (MgSO$_4$) and concentrated in vacuo. The residue was purified by preparative HPLC (Phenomenex Luna AXIA 30×100 mm column; detection at 220 nm; flow rate=40 mL/min.; continuous gradient from 100% A to 100% B over 15 min.+2 min. hold at 100% B, where A=90:10 H$_2$O:MeOH and B=90:10 MeOH:H$_2$O) to provide the Part B compound (0.059 g, 6.5% yield) as a white solid. [M+H]=335.1; $^1$H NMR (400 MHz, DMSO-d$_6$): δ 9.59 (s, 1H), 8.24 (d, J=1.76 Hz, 1H), 4.75 (d, J=11.87 Hz, 2H), 4.10-4.00 (m, 4H), 1.42 (s, 9H) 1.21 (t, J=7.03 Hz, 6H).

C.

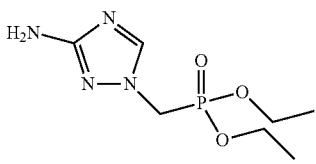

To a RT solution of Part B compound (0.059 g, 0.177 mmol) in CH$_2$Cl$_2$ (1 mL) was added TFA (2.04 mL, 3.13 mmol). The reaction mixture was stirred at RT for 2 h, then was concentrated in vacuo. The residue was purified by preparative HPLC (Phenomenex Luna 21.2×100 mm column; detection at 220 nm; flow rate=20 mL/min.; continuous gradient from 100% A to 100% B over 15 min.+2 min. hold at 100% B, where A=90:10:0.1 H$_2$O:MeOH:TFA and B=90:10: 0.1 MeOH:H$_2$O:TFA) to provide Part C compound (0.050 g, 81% yield) as a clear oil. $^1$H NMR (400 MHz, CDCl$_3$) δ 7.27 (s, 1H), 6.78 (s, 2H), 4.43 (d, J=13.62 Hz, 2H), 4.24-4.15 (m, 4H), 1.32-1.38 (m, 6H).

D.

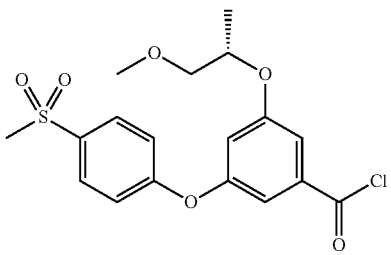

To a RT solution of Example 26 Part C compound (0.023 g, 0.060 mmol) in CH$_2$Cl$_2$ (1 mL) were added oxalyl chloride (10.6 μL, 0.121 mmol) and DMF (0.9 μL, 0.012 mmol) and the reaction mixture was stirred at RT for 1 h. Volatiles were removed in vacuo to provide crude Part D compound (0.060 g) as a yellow oil.

E.

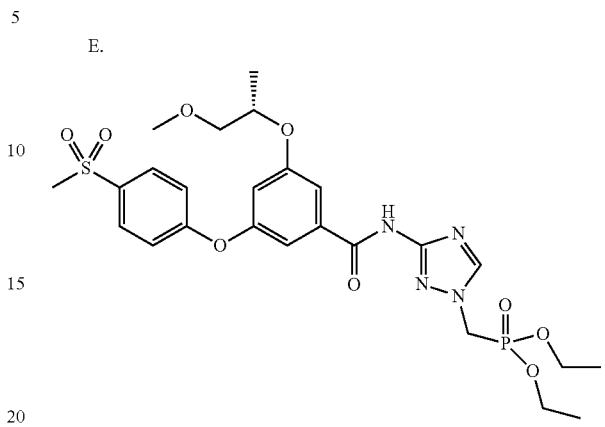

To a RT solution of crude Part D compound (0.060 g, 0.24 mmol) in CH$_2$Cl$_2$ (1 mL) were added a solution of Part C compound (0.031 g, 0.090 mmol) and pyridine (0.019 mL, 0.241 mmol) in CH$_2$Cl$_2$ (1 mL). The reaction mixture was stirred at RT overnight, then was partitioned between sat. aqueous NaHCO$_3$ (1 mL) and EtOAc (2 mL); the organic phase was washed with sat. aqueous NaHCO$_3$ (1 mL), dried (MgSO$_4$) and concentrated in vacuo. The residue was purified by preparative HPLC (Phenomenex Luna AXIA 21.2×100 mm column; detection at 220 nm; flow rate=40 mL/min.; continuous gradient from 100% A to 100% B over 15 min.+2 min. hold at 100% B, where A=90:10 H$_2$O:MeOH and B=90: 10 MeOH:H$_2$O) to provide the title compound (0.007 g, 19.0% yield) as a white solid. [M+H]$^+$=597.3; $^1$H NMR (400 MHz, CDCl$_3$): δ 9.65 (s, 1H), 8.42 (d, J=1.76 Hz 1H), 7.92 (t, J=1.76 Hz, 1H), 7.90 (t, J=1.76 Hz, 7.45 (t, J=1.75 Hz, 1H), 7.32 (t, J=1.76 Hz 1H), 7.15 (t, J=1.76 1H), 7.14 (t, J=1.76 Hz), 6.88 (t, J=2.19 Hz 1H), 4.80-4.75 (m, 1H), 4.70 (d, J=13.18 Hz, 2H), 4.29-4.19 (m, 4H), 3.64-3.54 (m, 2H), 3.42 (s, 3H), 3.07 (s, 3H), 1.35 (t, J=7.03, 9H).

Example 32

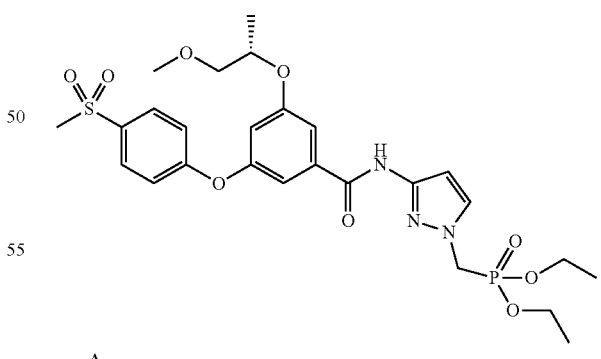

A.

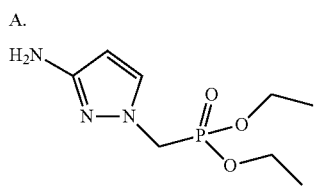

To a 0° C. solution of 1H-pyrazol-3-amine (1.00 g, 12.03 mmol) in DMF (25 mL) was added potassium tert-butoxide (2.70 g, 24.07 mmol) and the reaction mixture was stirred at 0° C. for 1 h. ICH$_2$PO$_3$Et$_2$ (3.35 g, 12.03 mmol) was added, and the reaction mixture was stirred at 0° C. for 1.5 h, then was allowed to warm to RT and stirred at RT overnight. Volatiles were removed in vacuo, and the residue was partitioned between brine (30 mL) and EtOAc (30 mL). The product was extracted with EtOAc (5×30 mL); the combined organic extracts were dried (MgSO$_4$), and concentrated in vacuo. The residue was purified by preparative HPLC (Phenomenex Luna AXIA 5 µm C18 30×100 mm column; detection at 220 nm; flow rate=40 mL/min.; continuous gradient from 100% A to 20% B over 25 min.+2 min. hold at 20% B, where A=90:10 H$_2$O:MeCN and B=90:10 MeCN:H$_2$O) to provide the Part A compound (0.470 g, 16.8% yield) as a pale yellow oil. [M+H]$^+$=233.9; $^1$H NMR (400 MHz, CDCl$_3$): δ 7.29 (s, 1H), 5.66 (d, J=2.20 Hz, 1H), 4.36 (d, J=11.55 Hz, 2H), 4.10 (m, 4H), 3.76 (s, 2H) 1.29 (t, J=7.15 Hz, 6H).

B.

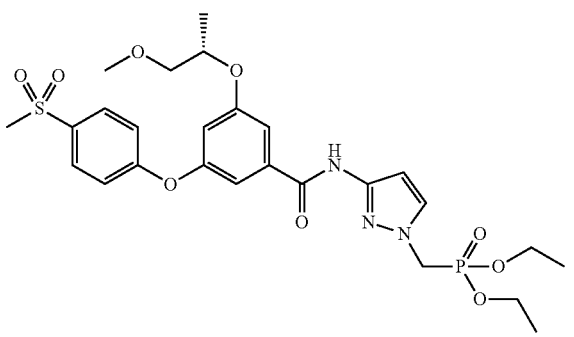

To a RT solution of Example 26 Part C compound (0.16 g, 0.421 mmol) in DMF (8 mL) were added EDAC (0.161 g, 0.841 mmol), HOAT (0.114 g, 0.841 mmol), and iPr$_2$NEt (0.185 mL, 1.05 mmol), and the reaction mixture was stirred at RT for 30 min. A solution of Part A compound (0.123 g, 0.526 mmol) in DMF (2 mL) was added and the reaction mixture was stirred at RT overnight, then poured into H$_2$O (40 mL). The mixture was extracted with EtOAc (2×15 mL); the combined organic extracts were dried (MgSO$_4$) and concentrated in vacuo. The residue was purified by preparative HPLC (Phenomenex Luna 5µ C18 30×100 mm column; detection at 220 nm; flow rate=40 mL/min.; continuous gradient from 100% A to 1000% B over 25 min.+10 min. hold at 100% B, where A=90:10 H$_2$O:MeCN and B=90:10 MeCN:H$_2$O) to provide the title compound (0.149 g, 59.4% yield) as a white solid. [M+H]$^+$=596.3; $^1$H NMR (400 MHz, CDCl$_3$): δ 8.98 (s, 1H), 7.92 (t, J=1.65 Hz, J=3.3 Hz 1H), 7.90 (t, J=2.70 Hz, j=2.2 Hz, 1H) 7.47 (d, J=2.2 Hz, 1H), 7.35 (t, J=1.65 Hz, 1H), 7.20 (t, J=2.2 Hz, 1H), 7.14 (t, J=2.75 Hz, J=2.2 Hz, 1H), 7.12 (t, J=2.75 Hz, J=2.20 Hz, 6.90 (d, J=2.20 Hz, 1H), 6.82 (t, J=2.20 Hz, 1H), 4.67-4.59 (m, 1H), 4.51 (d, J=12.09 Hz, 2H), 4.13-4.03 (m, 4H), 3.58 (dd, J=10.44 Hz, J=6.05 Hz, 1H), 3.51 (dd, J=10.44 Hz, J=3.85 Hz, 1H), 3.40 (s, 3H), 3.08 (s, 3H), 1.33 (d, J=6.05 Hz, 3H), 1.27 (t, J=7.14 Hz, 6H).

Example 33

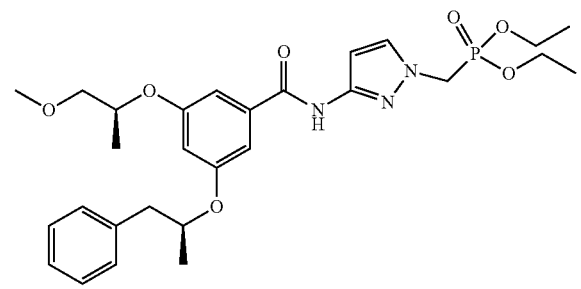

A.

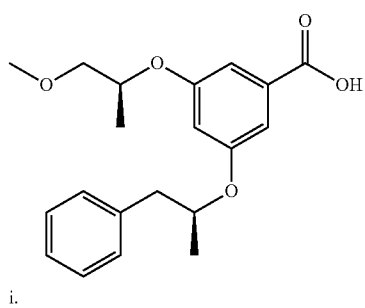

i.

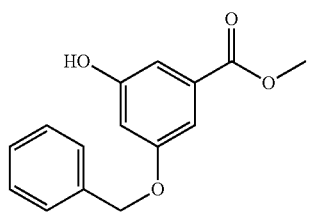

To a solution of methyl 3,5-dihydroxybenzoate (10.0 g, 59.5 mmol) in DMF (60.0 mL) under Ar was added K$_2$CO$_3$ (12.4 g, 89.7 mmol) at RT. Benzyl bromide (10.0 mL, 84.2 mmol; filtered through basic Al$_2$O$_3$ prior to use) was added slowly over 10 min. The reaction mixture was stirred for 12 h at RT and then carefully quenched with sat. aqueous NH$_4$Cl (50 mL), followed by H$_2$O (350 mL). The aqueous suspension was extracted with CH$_2$Cl$_2$ (1×30 mL, 2×50 mL). The combined organic extracts were washed with H$_2$O (100 mL) and brine, dried [MgSO$_4$] and concentrated in vacuo to give the crude product (27.0 g) as a golden-colored oil. The crude material was chromatographed (product eluted during the 30% EtOAc/hexane portion of a stepwise gradient (10-50% EtOAc/hexane) to yield Part A(i) compound (4.6 g, 30%) as a cream-colored powder.

ii.

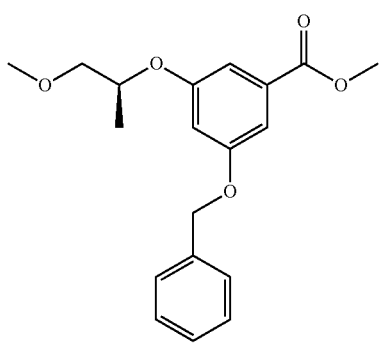

To a 0° C. solution of Part A(i) compound (1.0 g, 3.9 mmol) in THF (16.8 mL) were successively added (R)-(−)-1-methoxy-2-propanol (0.5 g, 5.8 mmol) and Ph₃P (1.5 g, 5.8 mmol), followed by slow addition of DIAD (1.1 mL, 5.8 mmol). The reaction mixture was warmed to RT and stirred at RT for 2 days. The reaction mixture was diluted with H₂O and extracted with Et₂O. The organic layer was dried [MgSO₄] and concentrated in vacuo to give a thick, pale, yellow oil. This crude material was chromatographed (product eluted during the 10% EtOAc/hexane portion of a stepwise gradient of 10-30% EtOAc/hexane) to give Part A(ii) compound (1.1 g, 85% yield) as a colorless oil.

iii.

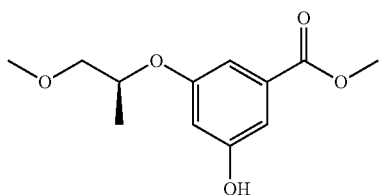

A flask containing Part A(ii) compound (1.2 g, 3.6 mmol) in MeOH (45.4 mL) was evacuated and flushed with Ar. In one portion, 10% Pd/C (0.38 g, 0.36 mmol) was added. The mixture was stirred under an atmosphere of H₂ for 12 h at RT, then was filtered through Celite®, which was washed with EtOAc. The combined filtrates were concentrated in vacuo to give Part A(iii) compound (0.81 g, 93% yield) as a yellow oil.

iv.

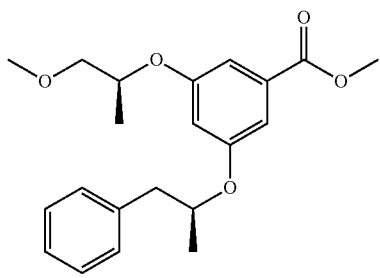

To a 0° C. solution of Part A(iii) compound (0.14 g, 0.59 mmol) in THF (2.9 mL) were added Ph₃P (0.4 g, 1.3 mmol) and (R)-1-phenylpropan-2-ol (0.2 g, 1.3 mmol) under Ar. The reaction mixture was stirred for 5 min at 0° C., then DIAD (0.3 mL, 1.3 mmol) was added dropwise. The reaction mixture was stirred at RT for 12 h, then was diluted with H₂O and extracted with EtOAc (2×). The combined organic extracts were washed with 1N aqueous NaOH and brine, dried [MgSO₄] and concentrated in vacuo to give a pale yellow oil (1.0 g). This crude material was chromatographed (product eluted during the 10% EtOAc/hexane portion of a stepwise gradient from 5-20% EtOAc/hexane) to give Part A(iv) compound (0.17 g, 81% yield) as a near-colorless oil.

v.

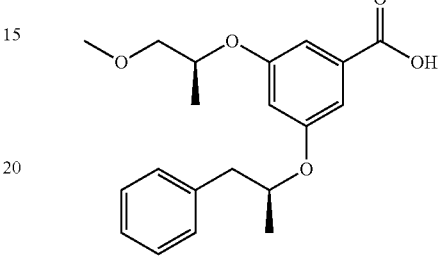

To a solution of Part A(iv) compound (0.17 g, 0.5 mmol) in THF (1.8 mL) and H₂O (0.6 mL) was added LiOH.H₂O (0.02 g, 0.52 mmol) at RT. The reaction mixture was stirred at 45° C. for 1 h; an additional portion of LiOH.H₂O was added, and stirring was continued at 45° C. The starting material was consumed after 6 h, and the reaction was cooled to RT. Volatiles were removed in vacuo, and the remaining aqueous layer was acidified to pH 2 with 0.5 N aqueous HCl, then was extracted with EtOAc (3×). The combined organic extracts were washed with brine, dried [MgSO₄] and concentrated in vacuo to give crude Part A(v) compound (0.16 g, 86%) as a pale-yellow oil.

B.

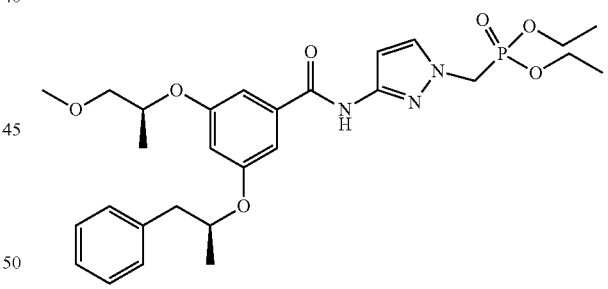

To a RT solution of Part A(v) compound (0.030 g, 0.087 mmol) in DMF (1.5 mL) was added EDAC (0.033 g, 0.174 mmol), HOAt (0.024 g, 0.174 mmol), and DIEA (0.038 mL, 0.218 mmol). The reaction mixture was stirred at RT for 30 min, after which a solution of Example 32 Part A compound (0.025 g, 0.109 mmol) in DMF (0.5 mL) was added. The reaction mixture was stirred at RT overnight, then was poured into water (7 mL); the mixture was extracted with EtOAC (2×10 mL). The combined organic extracts were dried (MgSO₄) and concentrated in vacuo. The residue was purified by preparative HPLC (Phenomenex Luna AXIA 100A 5μ C18 column; detection at 220 nm; flow rate=40 mL/min.; continuous gradient from 100% A to 100% B over 25 min.+2 min. hold at 100% B, where A=90:10 H₂O:MeCN and B=90:10 MeCN:H₂O) to provide the title compound (0.027 g, 56.3% yield) as a clear oil. [M+H]+=560.4; 1H NMR (400 MHz, CDCl3): δ 8.59 (s, 1H), 7.44-7.46 (m, 1H), 7.32-7.19 (m, 5H), 7.00 (t, J=1.65 Hz, 1H), 6.97 (t, J=2.2 Hz, 1H), 6.91 (d, J=2.2 Hz, 1H), 6.63 (t, J=2.2 Hz, 1H), 4.65-4.53 (m, 2H), 4.44 (d, J=11.54 Hz, 2H), 4.14-4.04 (m, 4H), 3.56 (dd, J=9.9 Hz, J=5.5 Hz, 1H), 3.49 (dd, J=9.89 Hz, J=3.84 Hz, 1H), 3.41 (s, 3H), 3.06 (dd, J=13.74 Hz, J=6.04 Hz, 1H), 2.85 (dd, J=13.74 Hz, J=6.04 Hz, 1H), 1.26 (m, 12H).

Example 34

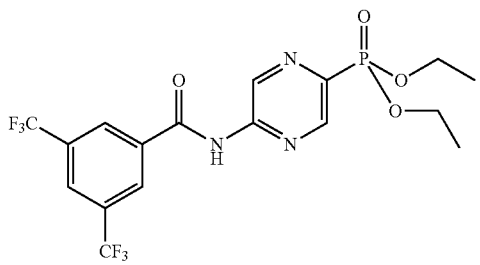

A.

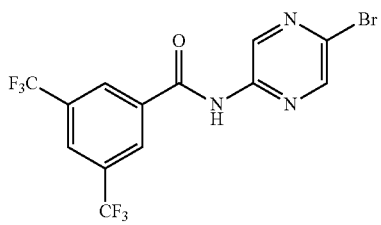

To a 0° C. solution of 3,5-bis(trifluoromethyl)benzoic acid (129 mg, 0.50 mmol) in CH2Cl2 (1 mL) was added oxalyl chloride (0.375 mL, 0.75 mmol, 2M in CH2Cl2) and DMF (1 drop). The reaction was stirred at 0° C. for 30 min and was then warmed to RT and was stirred for 4 h. The mixture was concentrated in vacuo. To a solution of the acid chloride residue in CH2Cl2 (3 mL) was added 5-bromopyrazin-2-amine (130 mg, 0.75 mmol) and pyridine (0.061 mL, 0.75 mmol). The reaction was stirred at RT for 18 h and was diluted with CH2Cl2 (6 mL), and was washed with 0.5 N aqueous HCl (1 mL, 2×), water (1 mL), sat. aqueous NaHCO3 (1 mL), and Brine. The organic layer was dried (MgSO4), filtered, and concentrated in vacuo. The residue was chromatographed (SiO2) to provide the Part A compound (40 mg, 19% yield) as a white solid.

B.

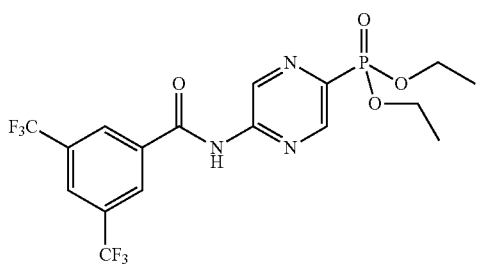

THF (degassed) (0.40 mL) was added to Part A compound (25.0 mg; 0.060 mmol) and (Ph3P)4Pd° (13.9 mg; 0.012 mmol). H(O)P(OEt)2 (9.33 µL; 0.072 mmol) was added followed by TEA (11.7 µL; 0.084 mmol). The reaction mixture was heated at 85° C. for 5 h, then was cooled to RT and partitioned between EtOAc (3 mL) and brine (3 mL). The organic phase was dried (MgSO4) and concentrated in vacuo. The crude product was purified by preparative HPLC (YMC reverse phase ODS-A-5 µm 30×100 mm column; flow rate=40 mL/min, 45 to 100% solvent B over 12 min, hold to 15 min, where solvent A=90:10:0.1 H2O:MeOH:TFA and solvent B=90:10:0.1 MeOH:H2O:TFA) to give the title compound (11.6 mg; 41%) as a light yellow solid. [M+H]+=472.2; 1H NMR (400 MHz, CDCl3): δ 1.37 (t, 6H), 4.27 (m, 4H), 8.12 (s, 1H), 8.53 (s, 2H), 8.82 (s, 1H), 9.53 (s, 1H), 9.80 (s, 1H).

Example 35

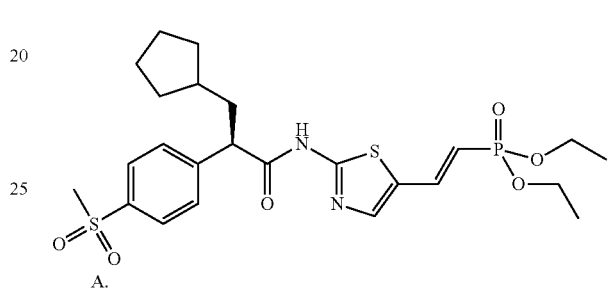

A.

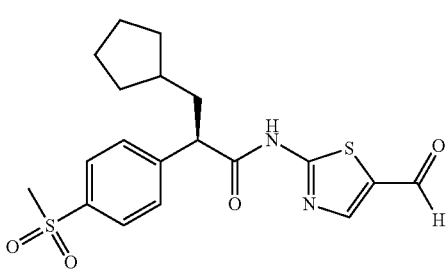

DIPEA (66 µL; 0.378 mmol) was added to a stirred solution of Example 1 Part D compound (80 mg; 0.270 mmol), 2-amino-5-formylthiazole (43.3 mg; 0.338 mmol) and HOAt (44.0 mg; 0.324 mmol) in DMF (1.0 mL). EDAC (62.0 mg; 0.324 mmol) was added. After 3 h at RT, the reaction mixture was partitioned between EtOAc (8 mL) and H2O (8 mL). The organic phase was washed with 1N aqueous HCl (5 mL), sat. aqueous NaHCO3 (5 mL) and brine (5 mL), dried (MgSO4) and concentrated in vacuo. The crude product was chromatographed (SiO2; continuous gradient from 0 to 100% EtOAc in hexanes over 11 min, hold at 100% EtOAc for 4 min) to give Part A compound (81 mg; 74%) as a foam.

B.

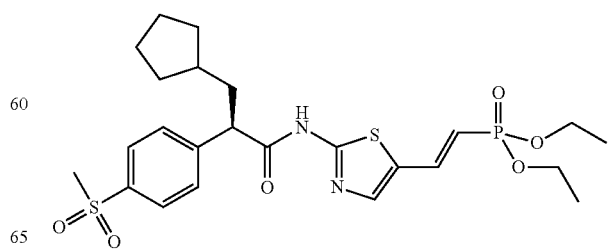

CH$_2$(PO$_3$Et)$_2$ (59.4 µL; 0.239 mmol) was added to a mixture of powdered LiCl (10.13 mg; 0.239 mmol) in CH$_3$CN (1.0 mL). DBU (35.7 µL; 0.239 mmol) was added followed by a solution of Part A compound (81.0 mg; 0.199 mmol) in CH$_3$CN (1.0 mL). After 24 h at RT more CH$_2$(PO$_3$Et)$_2$ (9.92 µL; 0.040 mmol), DBU (5.96 µL; 0.040 mmol) and LiCl (1.7 mg; 0.040 mmol) were added. After 72 h the reaction mixture was concentrated in vacuo. The residue was partitioned between EtOAc (8 mL) and 0.2 N aqueous HCl (8 mL). The organic phase was washed with brine (6 mL), dried (MgSO$_4$) and concentrated in vacuo. The crude product was chromatographed (SiO$_2$; continuous gradient from 0% to 100% EtOAc in hexanes over 6 min, switched to 2% MeOH in EtOAC and held for 8 min) to give the title compound (67 mg; 62%) as a colorless solid. [M+H]$^+$=541.1; $^1$H NMR (400 MHz, CDCl$_3$) (19:1, E/Z): δ 1.15 (m, 2H), 1.37 (m, 6H), 1.48 (m, 2H), 1.66 (m, 3H), 1.78 (m, 2H), 1.92 (m, 1H), 2.27 (m, 1H), 3.03 (s, 3H), 4.12 (m, 5H), 5.88 (dd, J=17.3 Hz, 1H), 7.58 (s, 1H), 7.66 (d, 2H), 7.89 (d, 2H), 8.14 (dd, J=17.1 Hz, 1H).

Example 36

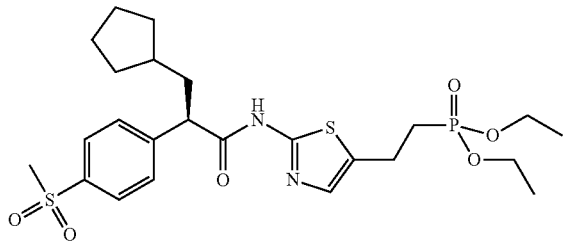 [SMILES: CCOP(=O)(CCc1cnc(NC(=O)[C@H](CC2CCCC2)c2ccc(S(C)(=O)=O)cc2)s1)OCC]

20% Pd(OH)$_2$ (16 mg) was added to a solution of Example 35 compound (35 mg; 0.065 mmol) in MeOH (0.40 mL). A H$_2$ (g) atmosphere was introduced via balloon. After 48 h of stirring, the reaction mixture was filtered. The catalyst was rinsed with MeOH (1.5 mL), EtOAc (1.5 mL) and CHCl$_3$ (1.5 mL) and the combined filtrates were concentrated in vacuo. The crude product was purified by preparative HPLC (YMC reverse phase ODS-A-5u 20×100 mm column; flow rate=20 mL/min, 15 to 100% solvent B over 10 min, hold to 12 min, where solvent A=90:10:0.1 H$_2$O:MeOH:TFA and solvent B=90:10:0.1 MeOH:H$_2$O:TFA) to provide the title compound (18 mg; 51%). [M+H]$^+$=543.2; $^1$H NMR (400 MHz, CD$_3$OD): δ19 (m, 2H), 1.29 (t, 6H), 1.51 (m, 2H), 1.64 (m, 3H), 1.80 (m, 3H), 2.17 (m, 3H), 3.05 (m, 2H), 3.09 (s, 3H), 3.96 (t, 1H), 4.07 (m, 4H), 7.20 (s, 1H), 7.67 (d, 2H), 7.92 (d, 2H).

Example 37

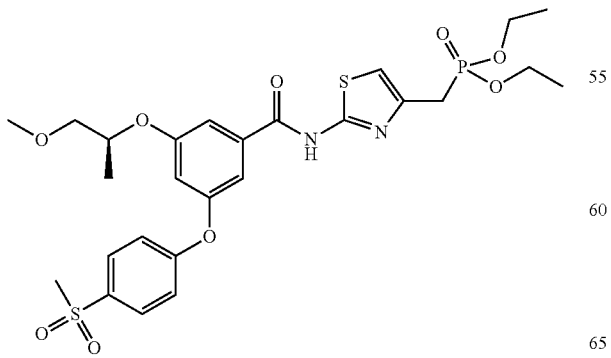

DIPEA (387 µL; 2.22 mmol) was added to a cold (0° C.) solution of Example 26 Part C compound (704 mg; 1.85 mmol), Example 13 Part E compound (556 mg; 2.22 mmol) and HOAt (302 mg; 2.22 mmol) in DMF (7.4 mL). EDAC (426 mg; 2.22 mmol) was added. After 24 h at RT, the reaction mixture was partitioned between EtOAc (100 mL) and H$_2$O (75 mL). The organic phase was washed with 0.5 N aqueous HCl (50 mL), sat. aqueous NaHCO$_3$ (50 mL) and brine (50 mL), dried (MgSO$_4$) and concentrated in vacuo. The crude product was purified by preparative HPLC (YMC reverse phase ODS-A-5u 30×250 mm column; flow rate=30 mL/min, 15 to 100% solvent B over 25 min, hold to 30 min, where solvent A=90:10:0.1 H$_2$O:CH$_3$CN:TFA and solvent B=90:10:0.1 CH$_3$CN:H$_2$O:TFA). The product was purified by preparative HPLC a second time using the same conditions but using MeOH instead of CH$_3$CN to give the title compound (778 mg; 69%) as a white foam. [M+H]$^+$=613.2; $^1$H NMR (400 MHz, CDCl$_3$): δ 1.26 (t, 6H), 1.35 (d, 3H), 3.08 (s, 3H), 3.34 (d, 2H), 3.41 (s, 3H), 3.55 (m, 2H), 4.08 (m, 4H), 4.69 (m, 1H), 6.88 (s, 2H), 7.14 (d, 2H), 7.30 (s, 1H), 7.48 (s, 1H), 7.92 (d, 2H).

Example 38

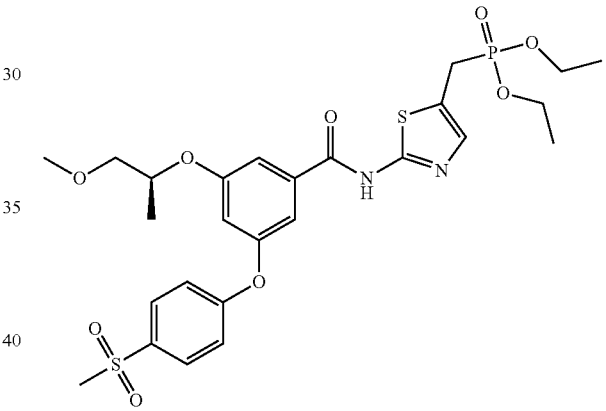

The title compound (39 mg; 78%; yellow solid) was synthesized from Example 15 Part D compound employing the procedure described for Example 37. [M+H]$^+$=613.3; $^1$H NMR (400 MHz, CDCl$_3$): δ 1.34 (m, 9H), 3.08 (s, 3H), 3.28 (d, 2H), 3.41 (s, 3H), 3.59 (m, 2H), 4.15 (m, 4H), 4.84 (m, 1H), 6.93 (s, 1H), 7.15 (d, 2H), 7.34 (d, 1H), 7.40 (s, 1H), 7.63 (s, 1H), 7.92 (d, 2H).

Example 39

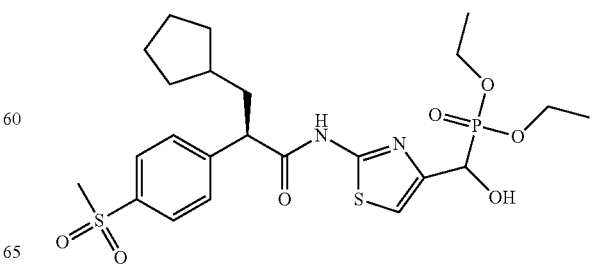

-continued

A.

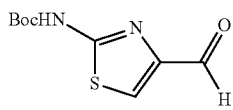

A solution of Example 13 Part B compound (0.94 g; 4.08 mmol) in DCM (8 mL) was added dropwise to a 0° C. solution of Dess-Martin periodinane (1.82 g; 4.28 mmol) in DCM (8 mL). After 20 h at RT, the reaction was diluted with DCM (4 mL) and 1.0 N aqueous NaOH (6 mL). After stirring for 10 min, the mixture was filtered through Celite®. The organic phase was washed with brine (10 mL), dried (MgSO$_4$) and concentrated in vacuo. The residue was chromatographed (SiO$_2$; continuous gradient from 0 to 50% EtOAc in hexanes over 12 min, hold at 50% EtOAc in hexanes for 8 min) to give Part A compound (0.65 g; 70%) as a white solid.

B.

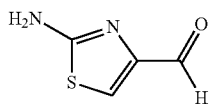

TFA (2.0 mL) was added to a 0° C. solution of Part A compound (0.64 g; 2.80 mmol) in DCM (4.0 mL). After 20 h at RT the reaction mixture was concentrated in vacuo. The residue was partitioned between EtOAc (10 mL) and sat. aqueous NaHCO$_3$ (8 mL). The aqueous phase was isolated and extracted with EtOAc (5×8 mL). The combined organic extracts were dried (MgSO$_4$) and concentrated in vacuo to give Part B compound (0.30 g; 83%) as a yellow solid.

C.

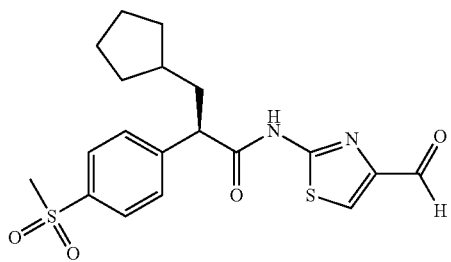

DIPEA (88.7 µL; 0.509 mmol) was added to a stirred solution of Example 1 Part D compound (130 mg; 0.439 mmol), Part B compound (67.4 mg; 0.526 mmol) and HOAt (69.3 mg; 0.509 mmol) in DMF (1.5 mL). EDAC (97.6 mg; 0.509 mmol) was added. After 20 h stirring at RT the reaction mixture was partitioned between EtOAc (12 mL) and H$_2$O (12 mL). The organic phase was washed with 0.5 N aqueous HCl (8 mL), sat. aqueous NaHCO$_3$ (8 mL) and brine (8 mL), dried (MgSO$_4$) and concentrated in vacuo. The crude product was chromatographed (SiO$_2$; continuous gradient from 0 to 80% EtOAc in hexanes over 13 min, hold at 80% EtOAC in hexanes for 3 min) to give Part C compound (100 mg; 56%) as a yellow foam.

D.

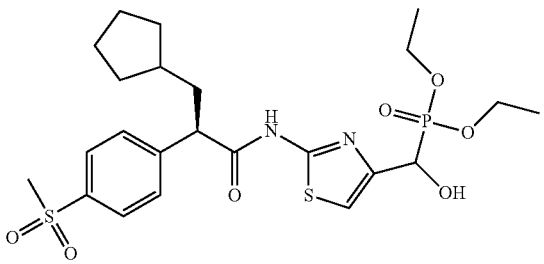

H(O)P(OEt)$_2$ (10.0 µL; 0.078 mmol) was added to Part C compound (30.0 mg; 0.074 mmol) followed by pyridine (6.6 µL; 0.081 mmol). The reaction mixture was heated at 70° C. for 5 h, then cooled to RT. After 48 h more H(O)P(OEt)$_2$ (10.0 µL; 0.078 mmol) and pyridine (10.0 mL; 0.123 mmol) were added and heating at 70° C. was continued. After 7 h the reaction was cooled to RT and diluted with EtOAc (3 mL), washed with 1.0 N aqueous HCl (1.5 mL) and brine (1.5 mL), dried (MgSO$_4$) and concentrated in vacuo. The crude product was chromatographed (SiO$_2$; continuous gradient from 0 to 100% EtOAc in hexanes over 3 min, switch to 3% MeOH in EtOAc and hold for 8 min) The product was then purified by preparative HPLC (YMC reverse phase ODS-A-5u 20×100 mm column; flow rate=20 mL/min, 10 to 100% solvent B over 10 min, hold to 12 min, where solvent A=90:10:0.1 H$_2$O:MeOH:TFA and solvent B=90:10:0.1 MeOH:H$_2$O: TFA) to give the title compound (14 mg; 35%) as a light yellow solid (diastereomeric mixture). [M+H]$^+$=545.2; $^1$H NMR (400 MHz, CDCl$_3$): δ1.13 (m, 2H), 1.28 (m, 6H), 1.49 (m, 2H), 1.60 (m, 3H), 1.76 (m, 2H), 1.96 (m, 1H), 2.23 (m, 1H), 3.04 (s, 3H), 4.01 (t, 1H), 4.16 (m, 4H), 5.18 (dd, 1H), 7.03 (d, 1H), 7.65 (d, 2H), 7.90 (d, 2H).

Example 40

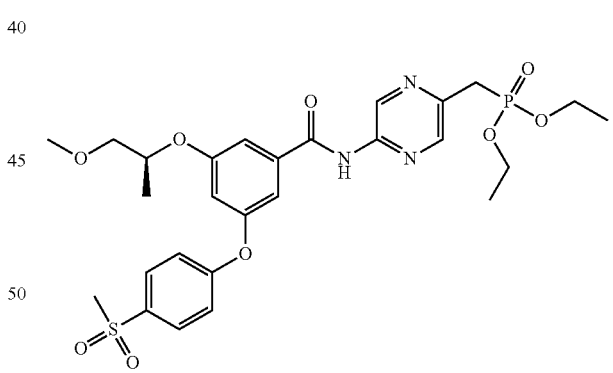

Oxalyl chloride (2.0 M in DCM) (45.0 µL; 0.091 mmol) was added to a solution of Oxalyl chloride (2.0 M in DCM) (45.0 µL; 0.091 mmol) was added to a solution of Example 26 Part C compound (23.0 mg; 0.060 mmol) in DCM (0.20 mL). DMF (5 µL) was added. Gas evolution occurred. The reaction mixture was stirred at RT for 1 h, then was concentrated in vacuo. The residue was stripped from DCM (2×1 mL). The crude acid chloride was dissolved in DCM (0.25 mL). Example 7 Part B compound (16.2 mg; 0.066 mmol) was added followed by pyridine (14.6 µL; 0.180 mmol). After 20 h at RT the reaction was concentrated in vacuo. The residue was partitioned between EtOAc (4 mL) and 0.5 N aqueous HCl (3 mL). The organic phase was washed with sat. aqueous NaHCO₃ (3 mL) and brine (3 mL), dried (MgSO₄) and concentrated in vacuo. The crude product was purified by preparative HPLC (YMC reverse phase ODS-A-5u 30×100 mm column; flow rate=40 mL/min, 15 to 100% solvent B over 12 min, hold to 14 min, where solvent A=90:10:0.1 H₂O:MeOH: TFA and solvent B=90:10:0.1 MeOH:H₂O:TFA) to give the title compound (13 mg; 36%) as a white solid. [M+H]⁺=608.2; ¹H NMR (400 MHz, CDCl₃): δ 1.32 (m, 9H), 3.07 (s, 3H), 3.40 (s, 3H), 3.44 (d, 2H), 3.57 (q, 2H), 4.13 (m, 4H), 4.63 (m, 1H), 6.88 (s, 1H), 7.16 (d, 2H), 7.19 (s, 1H), 7.35 (s, 1H), 7.93 (d, 2H), 8.32 (s, 1H), 8.53 (s, 1H), 9.59 (s, 1H).

Example 41

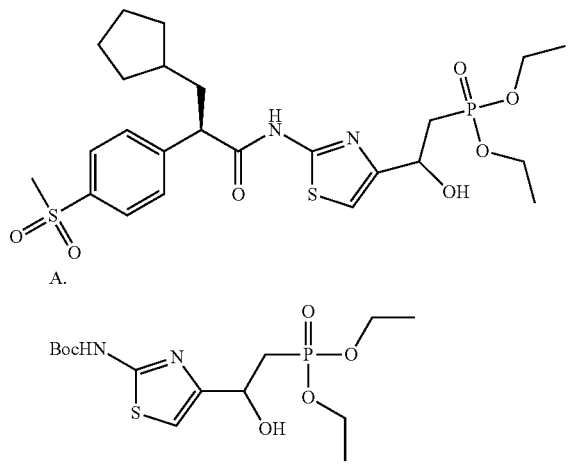

A.

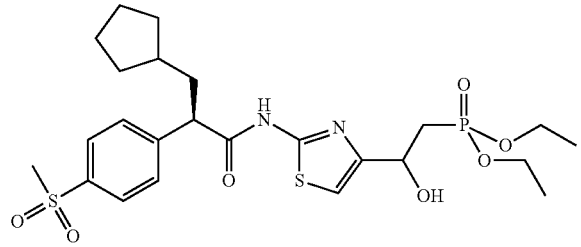

nBuLi (575 μL of a 1.6 M solution in hexanes; 0.920 mmol) was added dropwise to a cold (−78° C.) solution of Me(O)P(OEt)₂ (134 μL; 0.920 mmol) in THF (0.30 mL). After 20 min a solution of Example 39 Part A compound (100 mg; 0.438 mmol) in THF (0.70 mL) was added dropwise. After 1 h at −78° C., the reaction was quenched by addition of AcOH (63 μL; 1.10 mmol). The reaction was warmed to RT and concentrated using a stream of Ar. The residue was partitioned between EtOAc (5 mL) and brine (4 mL). The organic phase was dried (MgSO₄) and concentrated in vacuo. The crude product was chromatographed (SiO₂; continuous gradient from 0 to 100% EtOAc in hexanes over 8 min, switch to 4% MeOH in EtOAc and hold for 6 min) to give Part A compound (104 mg; 62%) as a syrup.

B.

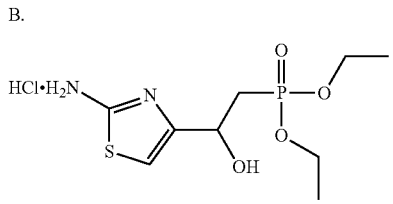

HCl (100 μL of a 4.0 N solution in 1,4 dioxane) was added to Part A compound (104 mg; 0.273 mmol). After 20 h, the reaction mixture was concentrated in vacuo to give Part B compound (64 mg; 75%) as an oil, which was used in the next step without further purification.

C.

DIPEA (56.0 μL; 0.324 mmol) was added to a stirred solution of Example 1 Part D compound (32.0 mg; 0.108 mmol), Part B compound (48.0 mg; 0.151 mmol) and HOAt (16.9 mg; 0.124 mmol) in DMF (0.42 mL). EDAC (23.8 mg; 0.124 mmol) was added. After 2 h at RT the reaction mixture was partitioned between EtOAc (4 mL) and 0.5 N aqueous HCl (3 mL). The organic phase was washed with sat. aqueous NaHCO₃ (3 mL) and brine (3 mL), dried (MgSO₄) and concentrated in vacuo. The crude product was purified by preparative HPLC (YMC reverse phase ODS-A-5u 20×100 mm column; flow rate=20 mL/min, 15 to 100% solvent B over 12 min, hold to 14 min, where solvent A=90:10:0.1 H₂O:MeOH: TFA and solvent B=90:10:0.1 MeOH:H₂O:TFA) to give the title compound (27 mg; 45%) as a white solid. [M+H]⁺=559.3; ¹H NMR (400 MHz, CDCl₃): δ 1.15 (m, 2H), 1.27 (m, 3H), 1.35 (t, 3H), 1.49 (m, 2H), 1.62 (m, 3H), 1.78 (m, 2H), 1.95 (m, 1H), 2.25 (m, 1H), 2.41 (m, 2H), 3.04 (s, 3H), 4.03 (t, 1H), 4.16 (m, 4H), 5.19 (t, 1H), 6.93 (s, 1H), 7.65 (d, 2H), 7.90 (d, 2H).

Example 42

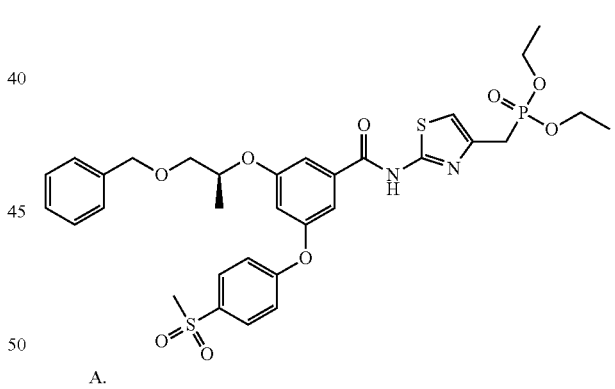

A.

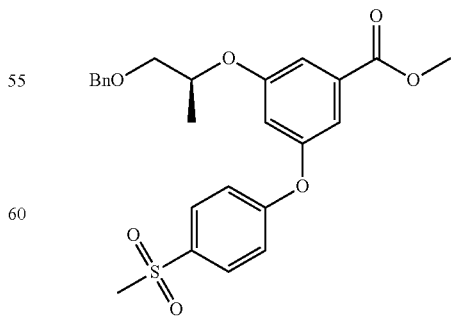

To a cold (internal temperature maintained at 5° C.) solution of Example 26A (3.7 g, 11.5 mmol), (R)-(−)-1-benzyloxy-2-propanol (2.5 g, 15 mmol), and polymer-supported Ph₃P (30 g of 1 mmol/g, 30 mmol) in THF (150 mL) under N₂ (g) was added dropwise over 15 min a solution of DIAD (3.4 mL, 17.3 mmol). The reaction mixture was warmed to RT and was stirred for 18 h, then filtered. The solids were thoroughly washed with THF and CH₂Cl₂. The combined filtrates were concentrated in vacuo. The mixture was chromatographed (SiO₂; EtOAc/Hexane 1:1) to give Part A compound (6.0 g, 110%) as a colorless oil. [M+H]=471.2; ¹H NMR (400 MHz, CDCl₃) δ 7.90 (2H, d, J=8.79 Hz), 7.48 (1H, s), 7.27-7.37 (6H, m), 7.09 (2H, d, J=8.79 Hz), 6.83-6.89 (1H, m), 4.60-4.69 (1H, m), 4.58 (2H, s), 3.90 (3H, s), 3.54-3.70 (2H, m), 3.06 (3H, s), 1.34 (3H, d, J=6.15 Hz).

B.

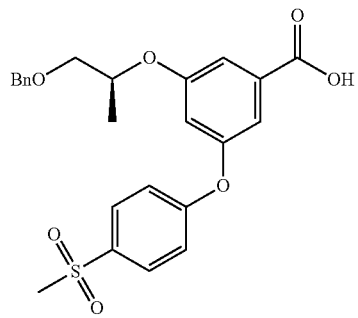

A solution of Part A (6 g, 13 mmol), LiOH (1.6 g, 39 mmol), and H₂O (50 mL) in THF (20 mL) was stirred at RT for 3 h, then was concentrated in vacuo. The aqueous solution was washed with Et₂O (15 mL×4), acidified to pH 4 with concentrated HCl, and was extracted with EtOAc (50 mL). The organic layer was washed with H₂O, dried (MgSO₄), filtered, and concentrated in vacuo to give Part B compound (5 g, 95%) as a white solid. [M+H]=457.2; ¹H NMR (400 MHz, CDCl₃) δ 7.91 (2H, d, J=8.79 Hz), 7.52 (1H, s), 7.27-7.38 (6H, m), 7.11 (2H, d, J=8.79 Hz), 6.90 (1H, t, J=2.20 Hz), 4.61-4.70 (1H, m), 4.59 (2H, s), 3.56-3.70 (2H, m), 3.07 (3H, s), 1.35 (3H, d, J=6.59 Hz).

C.

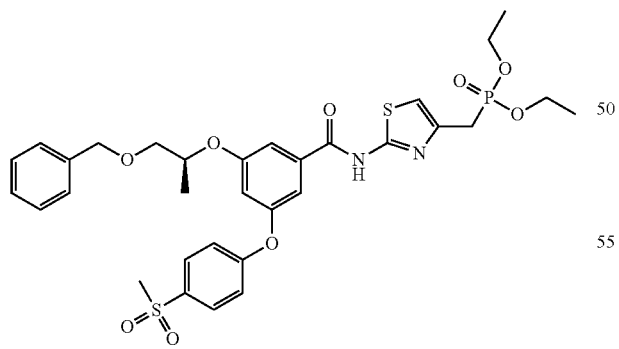

DIPEA (22.0 μL; 0.127 mmol) was added to a 0° C. solution of Part C compound (50 mg; 0.110 mmol), Example 13 Part E compound (33.0 mg; 0.131 mmol) and HOAt (17.0 mg; 0.127 mmol) in DMF (0.44 mL), followed by EDAC (24.0 mg; 0.127 mmol). After 24 h at RT the reaction mixture was partitioned between EtOAc (7 mL) and 0.5 N aqueous HCl (5 mL). The organic phase was washed with sat. aqueous NaHCO₃ (5 mL) and brine (5 mL), dried (MgSO₄) and concentrated in vacuo. The crude product was chromatographed (SiO₂; continuous gradient from 0 to 100% EtOAc in hexanes over 12 min, hold at 100% EtOAc for 4 min). The product was further purified by dissolving in MeOH (1 mL) and loading onto a 0.5 g SAX (strong anion exchange) column. The column was eluted with MeOH (4 mL). The filtrate was concentrated to give the title compound (50 mg; 67%) as a light yellow residue. [M+H]⁺=689.3; ¹H NMR (400 MHz, CDCl₃): δ 1.26 (t, 6H), 1.34 (m, 3H), 3.08 (s, 3H), 3.34 (d, 2H), 3.62 (m, 2H), 4.06 (m, 4H), 4.58 (s, 2H), 4.68 (m, 1H), 6.85 (s, 1H), 6.88 (s, 1H), 7.14 (d, 2H), 7.20 (s, 1H), 7.27 (m, 5H), 7.39 (s, 1H), 7.92 (d, 2H).

Example 43

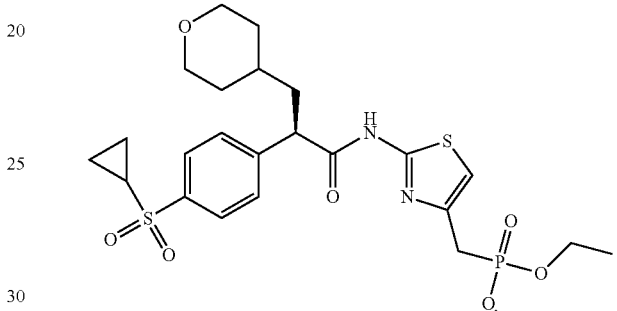

A.

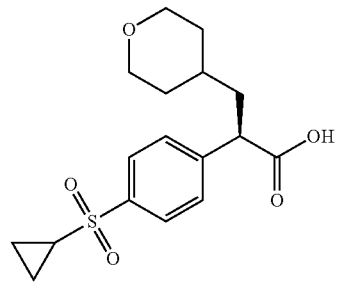

Note: The following procedure was adapted from WO 2006/016178 and WO 2006/016174.

i.

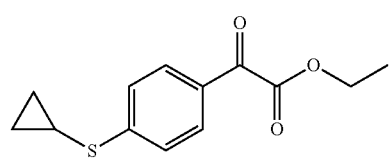

To a 0° C. suspension of NH₄Cl (8.44 g, 63.3 mmol) in DCM (40 mL) was added ethyl 2-chloro-2-oxoacetate (5.53 mL, 49.7 mmol) over 10 min. The reaction was stirred at 0° C. for 30 min. Cyclopropyl phenyl sulfide (6.5 mL, 45.2 mmol) was then added over a period of 45 min, keeping the temperature at 0° C. [Note: when sulfide was added, reaction immediately turned deep purple/red in color]. The reaction was allowed to warm to RT and was stirred at RT for 18 h. Ice water (100 mL) was slowly added to the mixture at 0° C. The organic phase was washed with H₂O (2×), sat. aqueous NaHCO$_3$ (2×), and again with H$_2$O. The organic layer was dried [MgSO$_4$] and concentrated in vacuo to give crude Part A(i) compound (6.1 g, 54%) as a yellow oil.

ii.

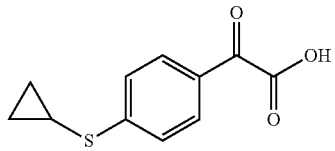

A solution of Part A(i) compound (6.1 g, 24.37 mmol) in toluene (50 mL) was heated to 50° C. with stirring. 3N aqueous NaOH (9.75 mL, 29.2 mmol) was added dropwise while keeping the temperature at 60° C. After the addition was complete, the reaction was stirred at 50° C. for 4 h, then was cooled to RT and neutralized by cautious addition of conc HCl (0.821 mL, 26.8 mmol). The reaction was stirred at RT for 18 h. The organic phase was concentrated in vacuo to give crude Part A(ii) compound (6.0 g, 111%) as a yellow solid.

iii.

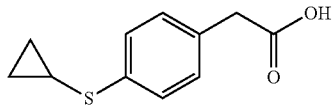

To NH$_2$NH$_2$.H$_2$O (5.89 mL, 121 mmol) at −78° C. was added Part A(ii) compound (5.4 g, 24.30 mmol) in one portion, and the reaction was heated to 80° C. with stirring, then was cooled to RT. KOH (0.818 g, 14.58 mmol) was added; the reaction was stirred at RT for several minutes, and then a second portion of KOH (0.818 g, 14.58 mmol) was added. The reaction was stirred at RT for several minutes, and then a third portion of KOH (0.818 g, 14.58 mmol) was added. The reaction again was stirred at RT for several minutes, and a fourth portion of KOH (0.818 g, 14.58 mmol) was added. The reaction was then heated at 100° C. with stirring for 18 h. The reaction was cooled to RT and diluted with H$_2$O. The reaction mixture was partitioned between Et$_2$O and H$_2$O. The layers were separated, and the aqueous layer was transferred to a round bottom flask. The organic layer was washed with H$_2$O, and the combined aqueous layers were treated with heptane (~50 mL), and the mixture was stirred vigorously. The stirred solution was treated dropwise with concentrated HCl (11.66 mL, 384 mmol) over 30 min at 0° C. The suspension was warmed to RT and was stirred at RT for several hours. A yellow precipitate formed and was filtered off; this material was washed with 1N aqueous HCl and heptane, then was dried in vacuo for $\overline{48}$ h. Part A(iii) compound (3.7 g, 73% yield) was thus isolated as a pale yellow solid.

iv.

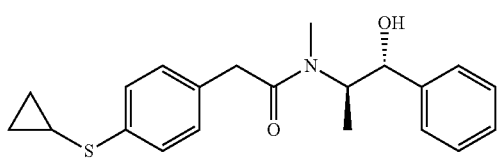

Part A(iii) compound was stripped from toluene (2×). To a −10° C. mixture of Part A(iii) compound (3.7 g, 17.76 mmol) and K$_2$CO$_3$ (7.37 g, 53.3 mmol) in anhydrous acetone (50 mL) was added dropwise trimethylacetyl chloride (2.297 mL, 18.65 mmol) while maintaining the temperature at −10° C. The reaction was stirred at −10° C. for 30 min, then warmed to 0° C. for 1 h and finally warmed to RT for 30 min. The mixture was recooled to −10° C. and was treated with (1R, 2R)-(−)-pseudoephedrine (4.40 g, 26.6 mmol). The reaction was stirred at −10° C. for 1 h, then was warmed to 25° C. and stirred for 18 h at 25° C. The reaction was quenched with H$_2$O (25 mL) and extracted with EtOAc. The organic phase was washed with 1N aqueous HCl, dried (MgSO$_4$) and concentrated in vacuo to give crude Part D compound. Crude Part D compound was dissolved in CH$_2$Cl$_2$ and chromatographed (SiO$_2$; 120 g; gradient from 30% EtOAc/Hexane to 100% EtOAc). The combined fractions were concentrated in vacuo to give Part A(iv) compound (1.16 g, 18.4% yield) as a white solid.

v.

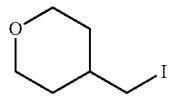

a.

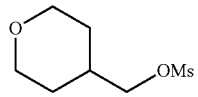

To a solution of tetrahydropyran-4-MeOH (5.0 g, 43 mmol) in CH$_2$Cl$_2$ (30 mL) was added Et$_3$N (7.2 mL, 51.6 mmol). The mixture was cooled to 0° C., and methanesulfonyl chloride (4.0 mL, 51.6 mmol) was added. The mixture was stirred at 0° C. for several hours, then was slowly warmed to RT. The reaction was stirred at RT for 18 h, then was concentrated in vacuo. The residue was taken up in EtOAc and was washed with sat. NaHCO$_3$. The organic layer was dried [MgSO$_4$] and concentrated in vacuo to give the mesylate Part A(v)(a) compound (8.3 g, quantitative yield) as a white, needle-like solid.

b.

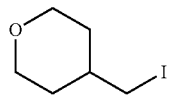

A mixture of the mesylate Part A(v)(a) compound (8.3 g, 43.0 mmol) and NaI (12.8 g, 85.5 mmol) was refluxed at 65° C. in acetone (100 mL) for 18 h, then was cooled to RT and filtered. The filter cake was washed with acetone. The combined filtrates were concentrated in vacuo, and the residue was partitioned between Et$_2$O and water. The aqueous layer was extracted with Et$_2$O (3×). The combined organic extracts were washed with 10% aqueous Na$_2$S$_2$O$_3$ and water, dried [MgSO$_4$] and concentrated in vacuo to give Part A(v)(b) compound (7.1 g, 74% yield) as a yellow oil.

vi.

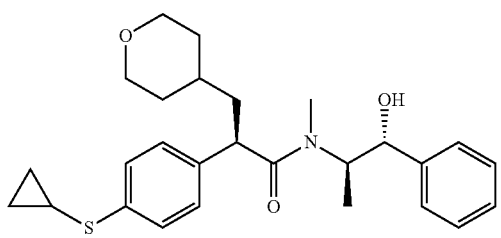

All starting materials were evaporated with toluene several times and all glassware was dried in an oven overnight. To a −78° C. solution of LiHMDS (5.91 mL, 5.91 mmol) in THF (15 mL) was added dropwise a solution of Part A(iv) compound (1.0 g, 2.81 mmol) in THF (15 mL) over 15 min. The reaction was stirred at −78° C. for 15 min, then was warmed to 0° C. for 45 min and recooled to −78° C. Distilled DMPU (0.714 mL, 5.91 mmol) was added and the reaction was stirred at −78° C. for ~15 min, after which Part A(v) iodide (0.954 g, 4.22 mmol) was added. The reaction was stirred at −78° C. for 1 h, then was slowly warmed to RT and stirred for 18 h. The reaction was quenched with sat. aqueous NH$_4$Cl (~10 mL) and diluted with EtOAc. The mixture was washed with H$_2$O. The aqueous layer was extracted with EtOAc, and the combined organic extracts were washed with brine, dried [MgSO$_4$] and concentrated in vacuo to give Part A(vi) compound (1.3 g, 100%) as a yellow oil.

vii.

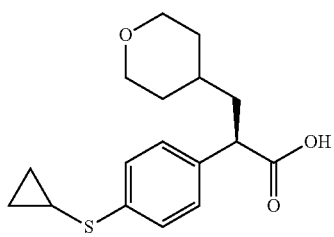

A solution of Part A(vi) compound (1.3 g, 2.87 mmol) and 9N concentrated H$_2$SO$_4$ (10.4 mL, 94 mmol) in dioxane (20 mL) was refluxed at 110° C. for 18 h, then was cooled to RT. The solution was diluted with EtOAc (50 mL) and washed with H$_2$O (40 mL×2) and brine (20 mL). The organic layer was dried [MgSO$_4$] and concentrated in vacuo to give Part A(vii) compound (1.17 g, 133% yield) as a yellow, sticky oil.

viii.

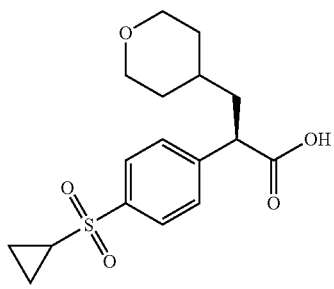

To a solution of Part A(vii) compound (0.9 g, 2.94 mmol) in isopropanol (20 mL) and water (10 mL) was added oxone (4.15 g, 6.76 mmol). The reaction was stirred at RT for 18 h, then was filtered, and the filtrate was concentrated in vacuo. The residue was taken up in EtOAc and was washed with H$_2$O and brine. The organic layer was dried [MgSO$_4$] and concentrated in vacuo to give Part A(viii) compound (0.9 g, 91% yield) as a pale yellow foam.

B.

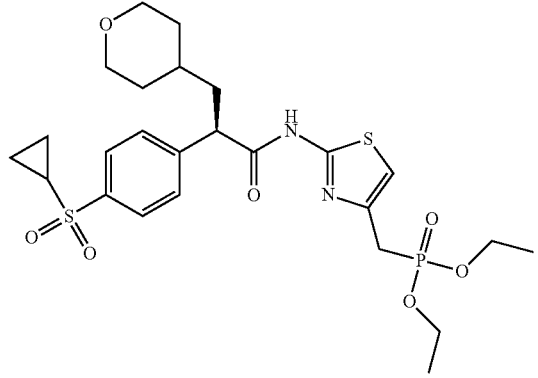

Oxalyl chloride (58.0 μL of a 2.0 M solution in DCM; 0.116 mmol) was added to a solution of Part A compound (26.0 mg; 0.077 mmol) in DCM (0.25 mL). DMF (5 μL) was added. Gas evolution occurred. The reaction mixture was stirred at RT for 1 h, then was concentrated in vacuo. The residue was stripped from DCM (2×1 mL). The crude acid chloride was dissolved in DCM (0.32 mL). Example 13 Part E compound (23.0 mg; 0.092 mmol) was added followed by pyridine (18.7 μL; 0.231 mmol). After 20 h at RT the reaction was concentrated in vacuo. The residue was partitioned between EtOAc (4 mL) and 0.5 N aqueous HCl (3 mL). The organic phase was washed with sat. aqueous NaHCO$_3$ (3 mL) and brine (3 mL), dried (MgSO$_4$) and concentrated in vacuo. The crude product was purified by preparative HPLC (YMC reverse phase ODS-A-5 μm 30×100 mm column; flow rate=40 mL/min, 15 to 100% solvent B over 16 min, hold to 20 min, where solvent A=90:10:0.1 H$_2$O:MeOH:TFA and solvent B=90:10:0.1 MeOH:H$_2$O:TFA) to give the title compound (17 mg; 39%) as a light yellow solid. [M+H]$^+$=571.4; $^1$H NMR (400 MHz, CDCl$_3$): δ 1.04 (m, 2H), 1.33 (m, 11H), 1.63 (m, 2H), 1.87 (m, 1H), 2.21 (m, 1H), 2.46 (m, 1H), 3.28 (m, 4H), 3.92 (m, 2H), 4.02 (t, 1H), 4.11 (m, 4H), 6.88 (d, 1H), 7.61 (d, 2H), 7.88 (d, 2H).

Example 44

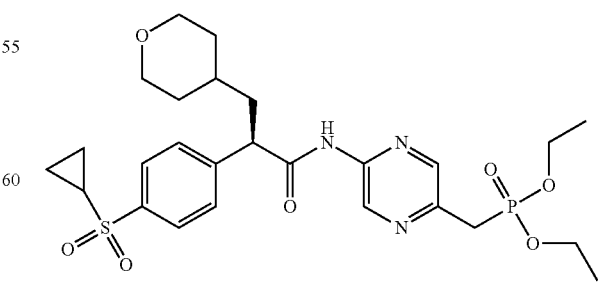

The title compound (22 mg; 51%; light yellow solid) was synthesized from Example 7 Part B compound and Example 43 Part A(viii) compound employing the procedure for the synthesis of Example 43 compound. [M+H]⁺=566.4; ¹H NMR (400 MHz, CDCl₃): δ 1.05 (m, 2H), 1.34 (m, 10H), 1.48 (m, 1H), 1.67 (m, 2H), 1.79 (m, 1H), 2.22 (m, 1H), 2.46 (m, 1H), 3.35 (m, 4H), 3.92 (d, 2H), 4.04 (t, 1H), 4.14 (m, 4H), 7.62 (d, 2H), 7.85 (d, 2H), 8.20 (s, 1H), 9.34 (s, 1H), 9.36 (s, 1H).

Example 45

A.

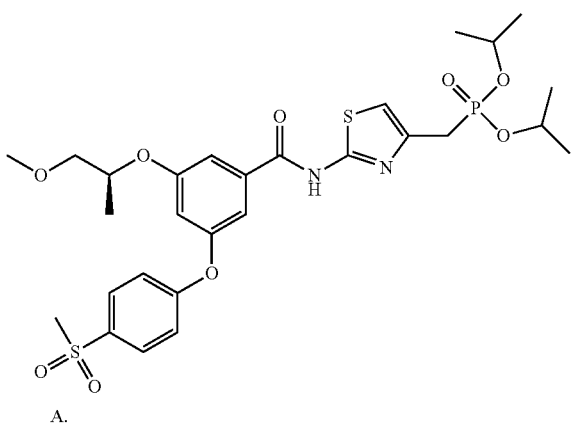

(iPrO)₃P (2.02 mL; 8.20 mmol) was added to a vessel containing Example 13 Part C compound (600 mg; 2.05 mmol). The reaction vessel was capped and the mixture was heated at 85° C. for 16 h, then cooled to RT. The solution was directly chromatographed (SiO₂; continuous gradient from 0 to 100% EtOAc in hexanes over 7 min, switched to 4% MeOH in EtOAc and held for 12 min) to give Part A compound (607 mg; 78%) as a viscous solid.

B.

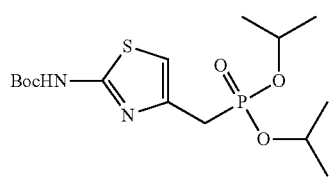

TFA (2.0 mL) was added to a 0° C. solution of Part A compound (559 mg; 1.48 mmol) in DCM (4 mL). The reaction mixture was allowed to warm to RT and stirred at RT for 2 h, then was concentrated in vacuo. The residue was partitioned between EtOAc (15 mL) and sat. aqueous NaHCO₃ (10 mL). The aqueous phase was extracted with EtOAc (10 mL). The combined organic extracts were washed with brine (10 mL), dried (MgSO₄) and concentrated in vacuo to give Part B compound (0.41 g; 100%) as a yellow solid.

C.

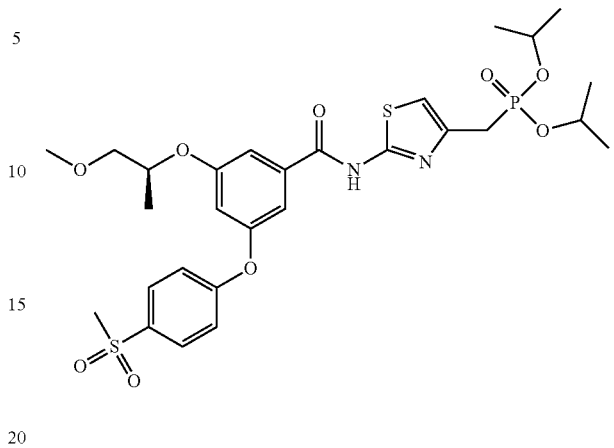

DIPEA (81.3 µL; 0.467 mmol) was added to a solution of Part B compound (135.6 mg; 0.487 mmol), Example 26 Part C compound (154.5 mg; 0.406 mmol) and HOAt (63.6 mg; 0.467 mmol) in DMF (1.5 mL). EDAC (89.5 mg; 0.467 mmol) was added. After 48 h at RT the reaction mixture was partitioned between EtOAc (15 mL) and H₂O (12 mL). The organic phase was washed with 0.5 N aqueous HCl (10 mL), sat. aqueous NaHCO₃ (10 mL) and brine (10 mL), dried (MgSO₄) and concentrated in vacuo. The crude product was purified by preparative HPLC (YMC reverse phase ODS-A-5u 30×250 mm column; flow rate=30 mL/min, 20 to 100% solvent B over 18 min, held to 25 min, where solvent A=90:10:0.1 H₂O:MeOH:TFA and solvent B=90:10:0.1 MeOH:H₂O:TFA) to give the title compound (0.24 g; 92%) as a light yellow solid. [M+H]⁺=641.3; ¹H NMR (400 MHz, CDCl₃): δ1.25 (m, 6H), 1.31 (m, 9H), 3.08 (s, 3H), 3.27 (d, 2H), 3.41 (s, 3H), 3.58 (m, 2H), 4.71 (m, 2H), 4.80 (m, 1H), 6.92 (s, 1H), 6.99 (s, 1H), 7.15 (d, 2H), 7.37 (s, 1H), 7.58 (s, 1H), 7.92 (d, 2H).

Example 46

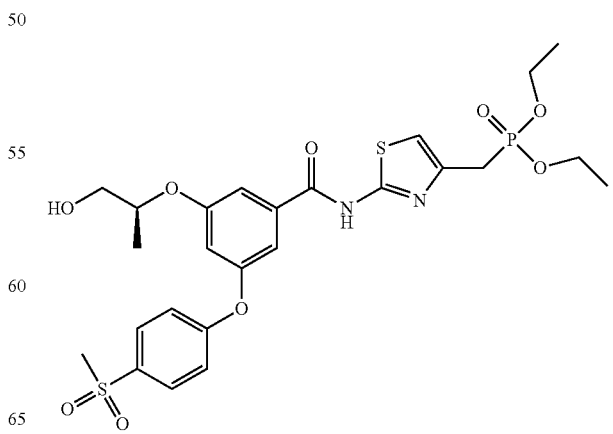

A.

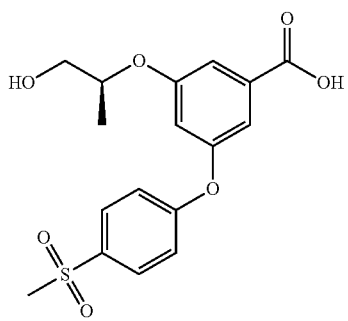

A mixture of 10% Pd/C (100 mg) and Example 42 Part B compound (1.03 g; 2.26 mmol) in EtOAc (6 mL) was stirred under an $H_2$ atmosphere for 8 h, after which the reaction mixture was filtered. The catalyst was rinsed with MeOH (10 mL) and the combined filtrates were concentrated in vacuo to give Part A compound (0.82 g; 99%).

B.

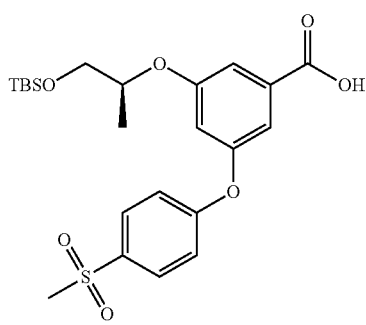

A solution of TBSCl (1.01 g; 6.71 mmol) in DMF (6 mL) was added to Part A compound (0.82 g; 2.24 mmol), followed by imidazole (0.91 g; 13.43 mmol). After 20 h the reaction mixture was partitioned between EtOAc (50 mL) and sat. aqueous $NH_4Cl$ (50 mL). The organic phase was washed with sat. aqueous $NH_4Cl$ (25 mL) and brine (25 mL), dried ($MgSO_4$) and concentrated in vacuo. The crude product was chromatographed ($SiO_2$; continuous gradient from 0 to 100% EtOAc in hexanes over 14 min, hold at 100% EtOAc for 4 min) to give Part B compound (725 mg; 68%) as a white foam.

C.

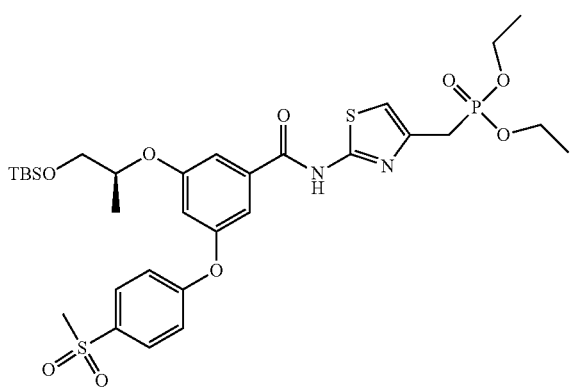

DIPEA (14.5 μL; 0.083 mmol) was added to a RT solution of Part B compound (30.8 mg; 0.064 mmol), Example 13 Part E compound (21.6 mg; 0.086 mmol) and HOAt (10.9 mg; 0.080 mmol) in DMF (0.33 mL). EDAC (15.3 mg; 0.080 mmol) was then added. After 48 h at RT the reaction mixture was partitioned between EtOAc (3 mL) and $H_2O$ (3 mL). The organic phase was washed with brine (30 mL), dried ($MgSO_4$) and concentrated in vacuo to give Part C compound (53 mg; 100%) as a syrup. The crude product was used in the next step without further purification.

D.

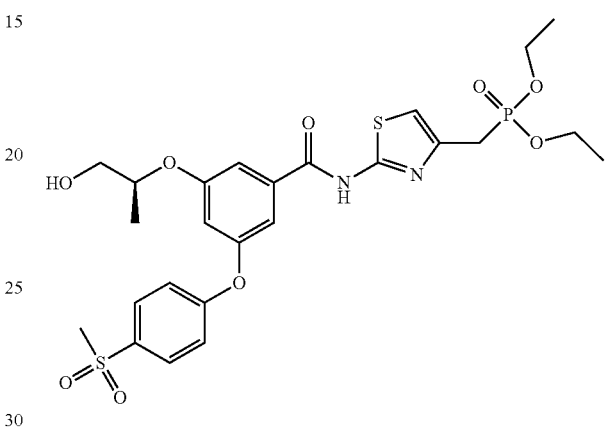

TBAF (1.0 M in THF) (152 μL; 0.152 mmol) was added to a 0° C. solution of Part C compound (54 mg; 0.76 mmol) in THF (0.22 mL). The reaction was allowed to warm to RT and stirred for 2 h at RT, then was concentrated in vacuo. The residue was partitioned between EtOAc (2.5 mL) and brine (2.5 mL). The organic phase was dried ($MgSO_4$) and concentrated in vacuo. The crude product was purified by preparative HPLC (YMC reverse phase ODS-A-5u 30×100 mm column; flow rate=40 mL/min, 10 to 100% solvent B over 10 min, hold to 13 min, where solvent A=90:10:0.1 $H_2O$:MeOH:TFA and solvent B=90:10:0.1 MeOH:$H_2O$:TFA) to give the title compound (23 mg; 51%) as a colorless syrup. $[M+H]^+=599.3$; $^1H$ NMR (400 MHz, $CDCl_3$): δ 1.33 (m, 9H), 3.07 (s, 3H), 3.33 (d, 2H), 3.79 (q, 2H), 4.15 (m, 4H), 4.82 (m, 1H), 6.93 (s, 1H), 7.05 (d, 1H), 7.15 (d, 2H), 7.44 (s, 1H), 7.70 (s, 1H), 7.92 (d, 1H).

Example 47

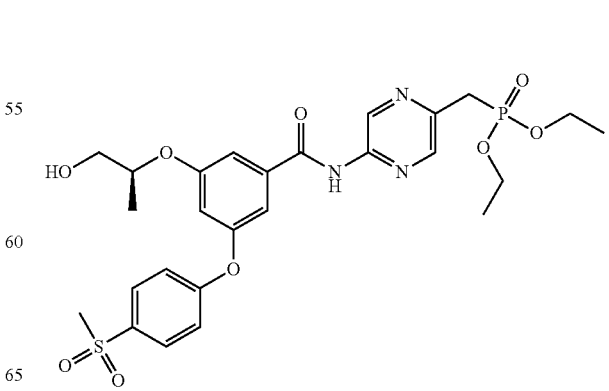

A.

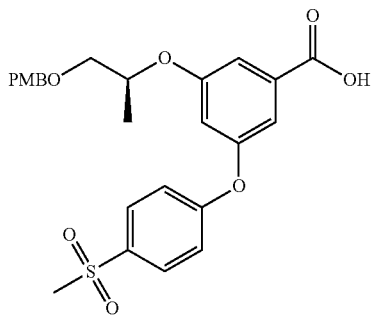

Powdered KOH (141 mg; 2.51 mmol) was added to a solution of Example 46 Part B compound (0.41 g; 1.12 mmol) in DMSO-D6 (2.5 mL). A solution of 4-methoxybenzyl bromide (0.47 g; 2.35 mmol) in DMSO-D6 (1 mL) was added. After 2 h H$_2$O (0.5 mL) was added. After 30 min the solution was partitioned between EtOAc (20 mL) and H$_2$O (20 mL). The organic phase was dried (MgSO$_4$) and concentrated in vacuo. The crude product was chromatographed (SiO$_2$; continuous gradient from 0 to 70% EtOAc in hexanes over 13 min, held at 70% EtOAc for 4 min) to give Part A compound (195 mg; 33%).

B.

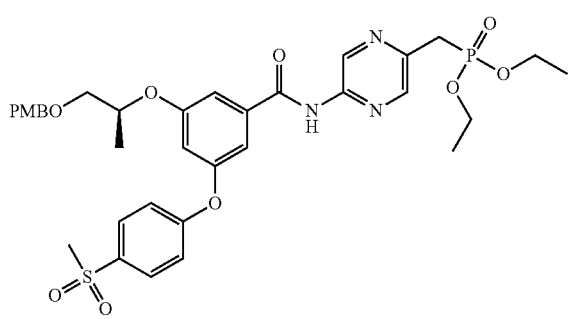

Oxalyl chloride (2.0 M in DCM) (72 µL; 0.144 mmol) was added to a 0° C. solution of Part A compound (43.9 mg; 0.096 mmol) in DCM (0.33 mL). DMF (5 µL) was added. Gas evolution occurred. After stirring for 1.5 h at RT the solution was concentrated in vacuo. The residue was stripped from CHCl$_3$ (2 mL). The crude acid chloride was dissolved in DCM (0.40 mL). Example 7 Part B compound (29.4 mg; 0.120 mmol) was added followed by pyridine (23.3 uL; 0.288 mmol). After 14 h at RT the reaction was concentrated in vacuo. The residue was partitioned between EtOAc (3 mL) and 0.5 N aqueous HCl (2 mL). The organic phase was washed with sat. aqueous NaHCO$_3$ (2 mL) and brine (2 mL), dried (MgSO$_4$) and concentrated in vacuo. The crude product was chromatographed (SiO$_2$; continuous gradient from 0 to 100% EtOAc in hexanes over 13 min, switched to 3% MeOH in EtOAc and held for 7 min) to give Part B compound (28 mg; 40%).

C.

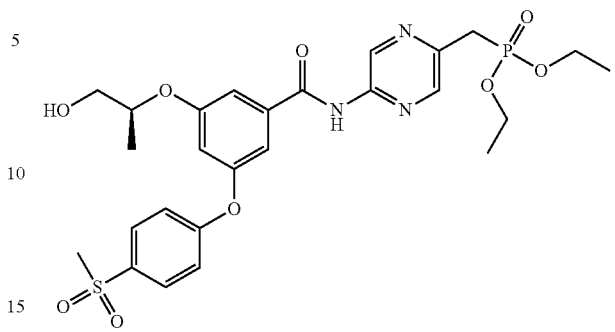

DDQ (9.4 mg; 0.041 mmol) was added to a solution of Part B compound (28 mg; 0.039 mmol) in DCM (400 µL) and H$_2$O (25 mL). After stirring for 1 h at RT the mixture was concentrated in vacuo. The residue was partitioned between EtOAc (3 mL) and sat. aqueous NaHCO$_3$ (2 mL). The organic phase was washed with sat. aqueous NaHCO$_3$ (2 mL) and brine (2 mL), dried (MgSO$_4$) and concentrated in vacuo. The crude product was purified by preparative HPLC (YMC reverse phase ODS-A-5u 30×100 mm column; flow rate=40 mL/min, 10 to 100% solvent B over 10 min, hold to 14 min, where solvent A=90:10:0.1 H$_2$O:ACN:TFA and solvent B=90:10: 0.1 ACN:H$_2$O:TFA) to give 20 mg of a syrup. The material was further chromatographed to remove aldehyde contaminant (SiO$_2$; elute with 100% EtOAc to remove aldehyde, then switch to 5% MeOH in EtOAc to elute product) to give the title compound (12 mg; 52%) as a colorless syrup. [M+H]$^+$=594.3; $^1$H NMR (400 MHz, CDCl$_3$): δ1.29 (m, 9H), 2.29 (s, 1H), 3.08 (s, 3H), 3.42 (d, 2H), 3.77 (m, 2H), 4.11 (m, 4H), 4.59 (m, 1H), 6.86 (s, 1H), 7.14 (d, 2H), 7.19 (s, 1H), 7.37 (s, 1H), 7.93 (d, 2H), 8.30 (s, 1H), 8.68 (s, 1H), 9.57 (s, 1H).

Example 48

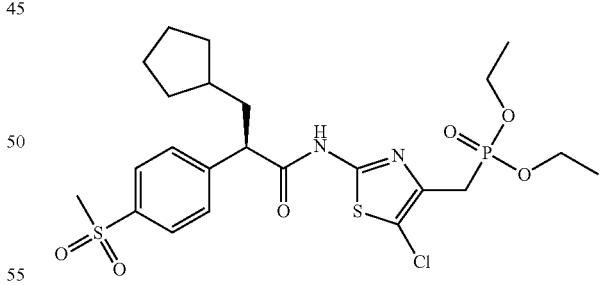

NCS (13.1 mg; 0.098 mmol) was added to a solution of Example 13 compound (52.0 mg; 0.098 mmol) in MeOH (0.5 mL) at RT and stirred at RT for 48 h. Volatiles were removed in vacuo. The residue was purified by preparative HPLC (YMC reverse phase ODS-A-5u 30×100 mm column; flow rate=40 mL/min, 20 to 100% solvent B over 12 min, hold to 18 min, where solvent A=90:10:0.1 H$_2$O:MeOH:TFA and solvent B=90:10:0.1 MeOH:H$_2$O:TFA) to give the title compound (42 mg; 76%) as a white solid. [M+H]$^+$=563.3; $^1$H NMR (400 MHz, CDCl$_3$): δ1.13 (m, 2H), 1.29 (m, 6H), 1.48

(m, 2H), 1.60 (m, 3H), 1.74 (m, 2H), 1.92 (m, 1H), 2.20 (m, 1H), 3.06 (s, 3H), 3.33 (d, 2H), 3.84 (t, 1H), 4.11 (m, 4H), 7.59 (d, 2H), 7.89 (d, 2H).

Example 49

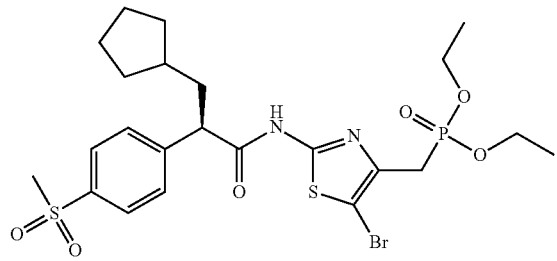 [SMILES: CCOP(=O)(Cc1nc(NC(=O)[C@H](CC2CCCC2)c2ccc(S(C)(=O)=O)cc2)sc1Br)OCC]

The title compound (23 mg; 69%; white solid) was synthesized employing the same procedure as for the synthesis of Example 48, except that NBS was used instead of NCS. The bromination reaction was complete within 1 h. [M+H]$^+$=607.3; $^1$H NMR (400 MHz, CDCl$_3$): δ1.13 (m, 2H), 1.28 (m, 6H), 1.48 (m, 2H), 1.59 (m, 3H), 1.76 (m, 2H), 1.92 (m, 1H), 2.20 (m, 1H), 3.06 (s, 3H), 3.31 (d, 2H), 3.83 (t, 1H), 4.09 (m, 4H), 7.59 (d, 2H), 7.89 (d, 2H).

Example 50

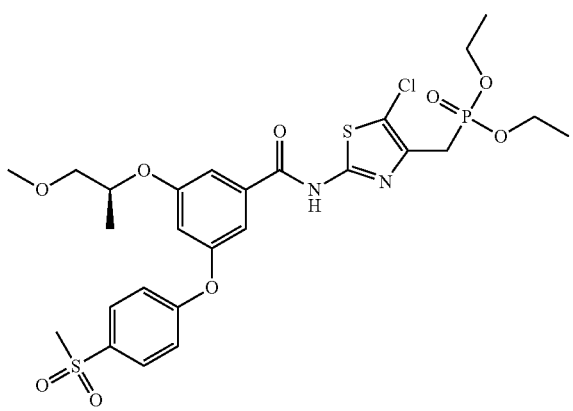 [SMILES: CCOP(=O)(Cc1nc(NC(=O)c2cc(Oc3ccc(S(C)(=O)=O)cc3)cc(O[C@@H](C)COC)c2)sc1Cl)OCC]

NCS (8.55 mg; 0.064 mmol) was added to a solution of Example 37 compound (39.0 mg; 0.064 mmol) in MeOH (0.4 mL). After 48 h at RT the reaction mixture was concentrated in vacuo. The crude product was purified by preparative HPLC (YMC reverse phase ODS-A-5u 30×100 mm column; flow rate=40 mL/min, 25 to 100% solvent B over 10 min, hold to 13 min, where solvent A=90:10:0.1 H$_2$O:MeOH:TFA and solvent B=90:10:0.1 MeOH:H$_2$O:TFA) to give the title compound (27 mg; 66%) as a white solid. [M+H]$^+$=647.2; $^1$H NMR (400 MHz, CDCl$_3$): δ 1.29 (t, 6H), 1.35 (d, 3H), 3.09 (s, 3H), 3.29 (d, 2H), 3.41 (s, 3H), 3.56 (q, 2H), 4.10 (m, 4H), 4.65 (m, 1H), 6.89 (s, 1H), 7.15 (d, 2H), 7.19 (s, 1H), 7.36 (s, 1H), 7.94 (d, 2H).

Example 51

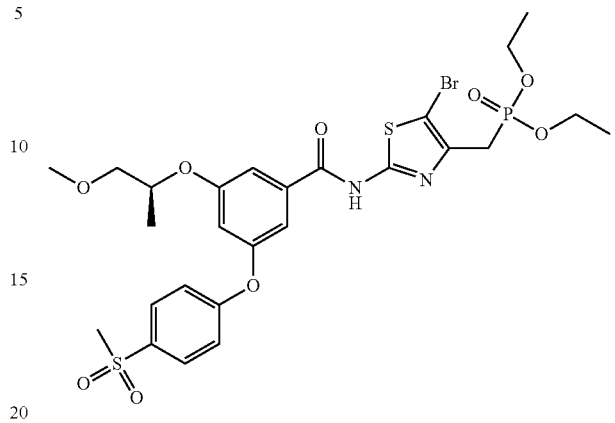

The title compound (32 mg; 78%; white solid) was synthesized employing the same procedure as described for the synthesis of Example 50, except that NBS was used instead of NCS. The bromination reaction was complete within 1 h. [M+H]$^+$=691.3; $^1$H NMR (400 MHz, CDCl$_3$): δ 1.29 (t, 6H), 1.34 (d, 3H), 3.09 (s, 3H), 3.33 (d, 2H), 3.41 (s, 3H), 3.55 (q, 2H), 4.09 (m, 4H), 4.65 (m, 1H), 6.89 (s, 1H), 7.14 (d, 2H), 7.21 (s, 1H), 7.38 (s, 1H), 7.94 (d, 2H).

Example 52

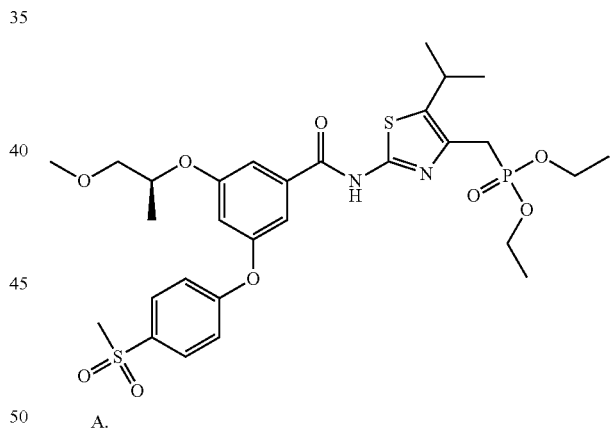

A.

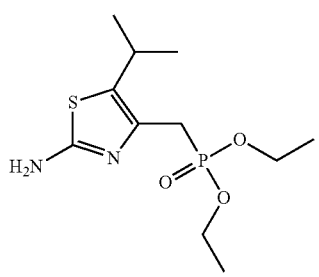

Compound A (120 mg; 16% for 5 steps; soft white solid) was synthesized from methyl 2-amino-5-isopropyl-1,3-thiazole-4-carboxylate employing the same procedure used to prepare Example 13 Part E compound.

B.

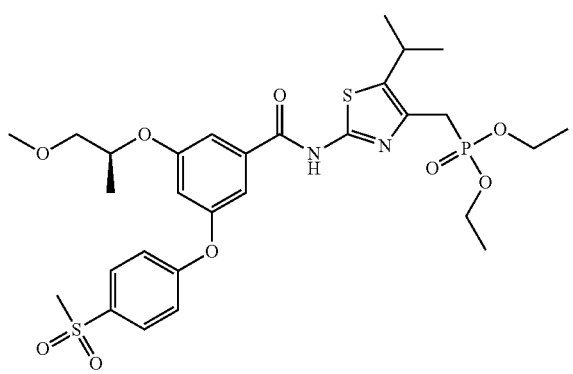

DIPEA (19.2 μL; 0.110 mmol) was added to a solution of Part A compound (33.6 mg; 0.115 mmol), Example 26 Part C compound (36.4 mg; 0.096 mmol) and HOAt (15.0 mg; 0.110 mmol) in DMF (0.35 mL), followed by EDAC (21.1 mg; 0.110 mmol). After 24 h at RT the reaction mixture was partitioned between EtOAc (15 mL) and 0.5 N aqueous HCl (10 mL). The organic phase was washed with sat. aqueous NaHCO₃ (10 mL) and brine (10 mL), dried (MgSO₄) and concentrated in vacuo. The crude product was purified by preparative HPLC (YMC reverse phase ODS-A-5u 30×100 mm column; flow rate=40 mL/min, 15 to 100% solvent B over 10 min, hold to 12 min, where solvent A=90:10:0.1 H₂O:ACN:TFA and solvent B=90:10:0.1 ACN:H₂O:TFA) to give the title compound (49 mg; 75%) as a colorless residue. [M+H]$^+$=655.3; $^1$H NMR (400 MHz, CDCl₃): δ 1.29 (t, 6H), 1.35 (m, 9H), 3.07 (s, 3H), 3.28 (d, 2H), 3.31 (m, 1H), 3.41 (s, 3H), 3.57 (m, 2H), 4.13 (m, 4H), 4.84 (m, 1H), 6.92 (s, 1H), 7.15 (d, 2H), 7.38 (s, 1H), 7.62 (s, 1H), 7.92 (d, 2H).

Example 53

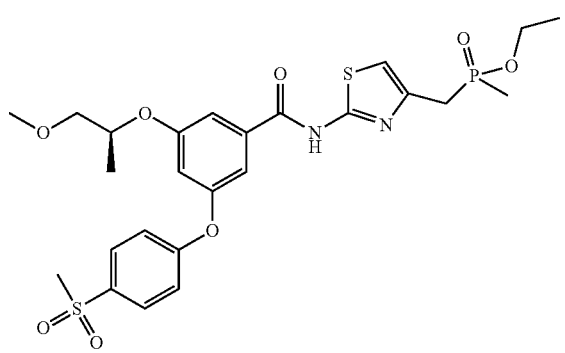

A.

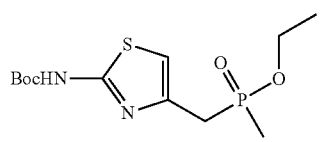

Diethyl methylphosphonite (690 mg; 5.07 mmol) was added to a solution of Example 13 Part C compound (496 mg; 1.69 mmol) in THF (0.5 mL). The reaction mixture was heated at 75° C. for 16 h, then was cooled to RT. The solution was directly loaded onto a 12 g SiO₂ column and the crude product was chromatographed (continuous gradient from 0 to 100% EtOAc in hexanes over 4 min, switched to 5% MeOH in EtOAc and held for 10 min) to give Part A compound (493 mg; 91%) as a light yellow solid.

B.

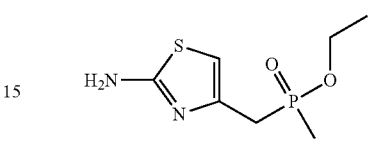

TFA (2.0 mL) was added to a 0° C. solution of Part A compound (768 mg; 2.40 mmol) in DCM (6 mL). The reaction mixture was stirred at RT for 3 h, then was concentrated in vacuo. The residue was partitioned between EtOAc (15 mL) and sat. aqueous NaHCO₃ (10 mL). The aqueous phase was extracted with EtOAc (2×10 mL). The combined organic extracts were dried (MgSO₄) and concentrated in vacuo to give Part B compound (203 mg; 38%).

C.

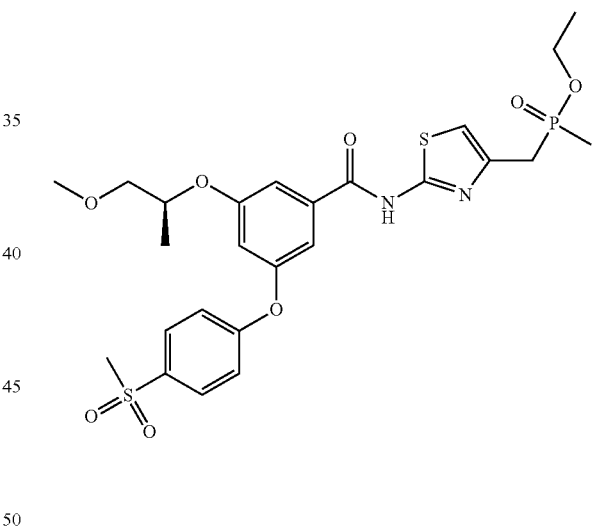

DIPEA (228 μL; 1.31 mmol) was added to a solution of Part B compound (369 mg; 1.67 mmol), Example 26 Part C compound (415 mg; 1.09 mmol) and HOAt (178 mg; 1.31 mmol) in DMF (4.0 mL). EDAC (251 mg; 1.31 mmol) was added. After 48 h at RT the reaction mixture was partitioned between EtOAc (15 mL) and H₂O (12 mL). The organic phase was washed with 0.5 N aqueous HCl (10 mL), sat. aqueous NaHCO₃ (10 mL) and brine (10 mL), dried (MgSO₄) and concentrated in vacuo. The crude product was chromatographed (SiO₂; continuous gradient from 0 to 100% EtOAc in hexanes over 6 min, switch to 1% MeOH in EtOAc and hold for 4 min, then switched to 4% MeOH in EtOAc and hold for 10 min) to give title compound (354 mg; 56%) as a white solid (diastereomeric mixture). [M+H]$^+$=583.3; $^1$H NMR (400 MHz, CDCl₃): δ 1.34 (m, 6H), 1.50 (d, 3H), 3.08 (s, 3H), 3.32

(m, 1H), 3.41 (s, 3H), 3.57 (m, 3H), 4.06 (m, 2H), 4.76 (m, 1H), 6.89 (s, 2H), 7.15 (d, 2H), 7.44 (s, 1H), 7.61 (s, 1H), 7.92 (d, 2H).

Example 54

A.

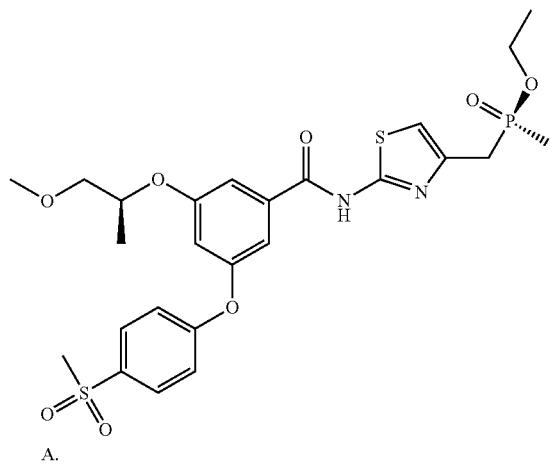

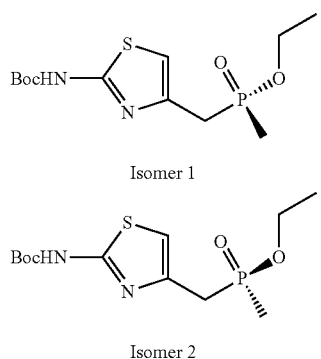

The two isomers of Example 53 Part A compound (2.6 g; 8.12 mmol) were separated by chiral preparative HPLC (ChiralPak AD, 5×50 cm column, 20µ, isocratic at 15% of 50/50 MeOH:EtOH; 85% heptane, 50 mL/min for 2 h). The material was purified in three runs. Isomer 1 had a retention time of 38 min and isomer 2 had a retention time of 52 min. Fractions containing isomer 1 were concentrated in vacuo to give 1.07 g (82%) of a glassy solid. Fractions containing isomer 2 were concentrated in vacuo to give 1.09 g (84%) of a glassy solid.

B.

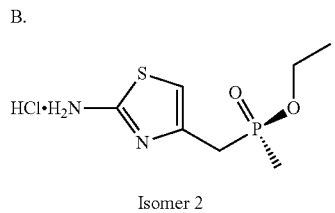

Isomer 2

HCl (6.0 mL of a 4.0 N solution in 1,4 dioxane) was added to Part A compound isomer 2 (1.05 g; 3.28 mmol). After stirring at RT for 5 h, the reaction mixture was concentrated in vacuo. The residue was dissolved in H₂O (20 mL), frozen and lyophilized. The lyophilate was dissolved in MeOH (25 mL) and concentrated in vacuo to give Part B compound (0.85 g; 100%) as a white foam.

C.

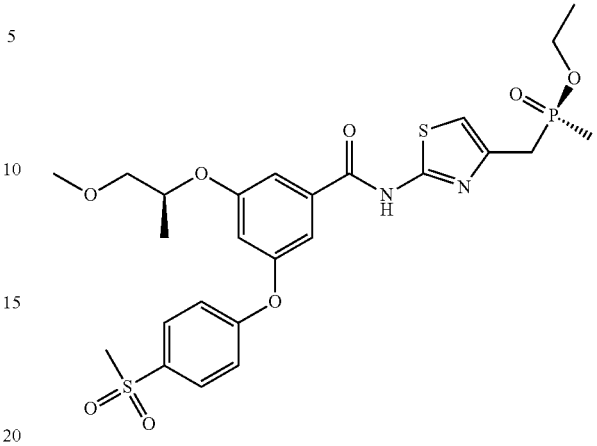

DIPEA (1.45 mL; 8.28 mmol) was added to a solution of Part B compound (0.85 g; 3.31 mmol), Example 26 Part C compound (1.05 g; 2.76 mmol) and HOAt (526 mg; 3.86 mmol) in DMF (10.0 mL). EDAC (741 mg; 3.86 mmol) was added. After 72 h at RT the reaction mixture was partitioned between EtOAc (140 mL) and H₂O (120 mL). The organic phase was washed with 0.5 N aqueous HCl (100 mL), sat. aqueous NaHCO₃ (100 mL) and brine (80 mL), dried (MgSO₄) and concentrated in vacuo. The crude product was divided into 4 portions and purified by preparative HPLC (YMC reverse phase ODS-A-5u 30×250 mm column; flow rate=30 mL/min, 20 to 100% solvent B over 20 min, hold to 25 min, where solvent A=90:10:0.1 H₂O:MeOH:TFA and solvent B=90:10:0.1 MeOH:H₂O:TFA). The product was purified by preparative HPLC a second time using same conditions but using CH₃CN instead of MeOH to give the title compound (920 mg; 57%) as a white solid. [M+H]⁺=583.0; ¹H NMR (400 MHz, CDCl₃): δ 1.33 (m, 6H), 1.45 (d, 3H), 3.07 (s, 3H), 3.34 (m, 1H), 3.40 (s, 3H), 3.55 (q, 2H), 3.86 (m, 1H), 4.05 (m, 2H), 4.70 (m, 1H), 6.77 (d, 1H), 6.86 (s, 1H), 7.14 (d, 2H), 7.49 (s, 1H), 7.62 (s, 1H), 7.91 (d, 2H).

Example 55

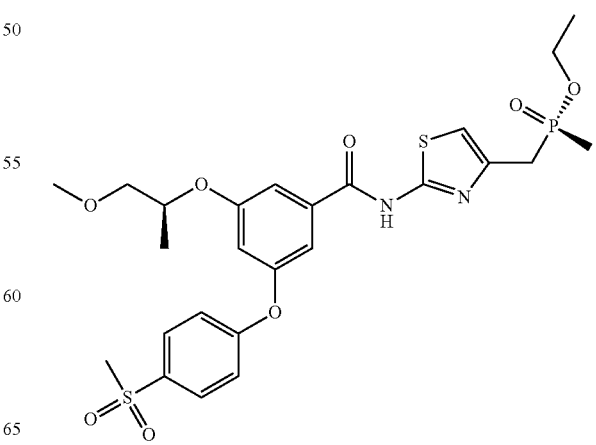

The title compound (133 mg, 44% crude yield, white solid) was prepared from Example 54 Part A Isomer 1 employing the procedure set forth in Example 54. [M+H]$^+$=583.2; $^1$H NMR (400 MHz, CDCl$_3$): δ 1.33 (m, 6H), 1.45 (d, 3H), 3.07 (s, 3H), 3.32 (m, 1H), 3.40 (s, 3H), 3.55 (q, 2H), 3.77 (m, 1H), 4.06 (m, 2H), 4.70 (m, 1H), 6.77 (d, 1H), 6.86 (s, 1H), 7.14 (d, 2H), 7.47 (s, 1H), 7.59 (s, 1H), 7.91 (d, 2H).

Example 56

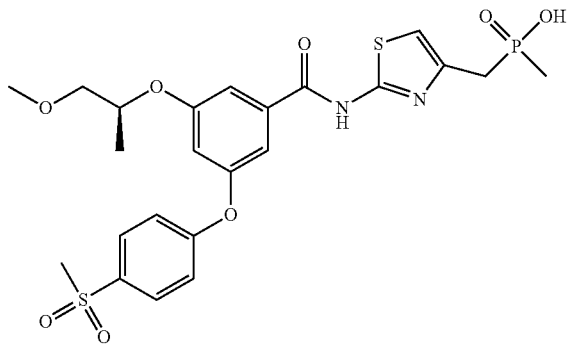

2.0 N aqueous NaOH (81 μL; 0.162 mmol) was added to a mixture of Example 55 compound (31.5 mg; 0.054 mmol) in EtOH (70 μL) and THF (70 μL). After 16 h the mixture was partitioned between EtOAc (2 mL) and 0.5 N aqueous HCl (1 mL). The organic phase was washed with brine (1 mL), dried (MgSO$_4$) and concentrated in vacuo to give title compound (27.4 mg; 91%) as a white solid. [M+H]$^+$=555.0; $^1$H NMR (400 MHz, CDCl$_3$): δ 1.28 (d, 3H), 1.37 (d, 3H), 3.10 (s, 3H), 3.21 (d, 2H), 3.43 (s, 3H), 3.59 (q, 2H), 4.77 (m, 1H), 6.74 (s, 1H), 6.92 (s, 1H), 7.20 (d, 2H), 7.70 (s, 1H), 7.77 (s, 1H), 7.93 (d, 2H).

Example 57

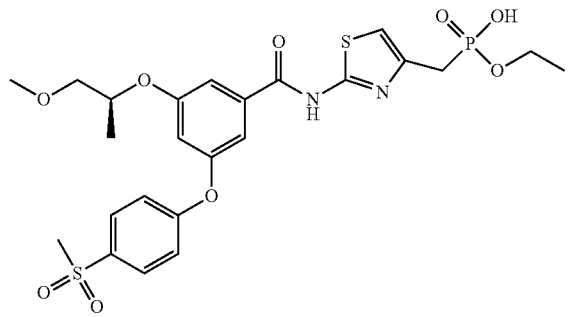 [SMILES: CCOP(=O)(O)Cc1csc(NC(=O)c2cc(Oc3ccc(S(C)(=O)=O)cc3)cc(O[C@@H](C)COC)c2)n1]

2.5 N aqueous NaOH (131 μL; 0.328 mmol) was added to a solution of Example 37 compound (67 mg; 0.109 mmol) in MeOH (130 μL) and THF (130 μL). The solution was heated at 50° C. for 20 h, then was cooled to RT and partitioned between EtOAc (4 mL) and 1.0 N aqueous HCl (2 mL). The organic phase was washed with brine (2 mL), dried (MgSO$_4$) and concentrated in vacuo. The crude product was purified by preparative HPLC (YMC reverse phase ODS-A-5 μm 30×100 mm column; flow rate=40 mL/min, 15 to 100% solvent B over 10 min, hold to 12 min, where solvent A=90:10: 0.1 H$_2$O:ACN:TFA and solvent B=90:10:0.1 ACN:H$_2$O:

TFA) to give a white solid. The material was purified by preparative HPLC a second time (same conditions as above but using MeOH in place of ACN) to give title compound (30 mg; 47%) as a white solid. [M+H]$^+$=585.0; $^1$H NMR (400 MHz, CD$_3$OD): δ 1.30 (m, 6H), 3.12 (s, 3H), 3.28 (d, 2H), 3.37 (s, 3H), 3.56 (m, 2H), 4.05 (m, 2H), 4.71 (m, 1H), 6.96 (m, 2H), 7.24 (d, 2H), 7.31 (s, 1H), 7.48 (s, 1H), 7.97 (d, 2H).

Examples 58 and 59

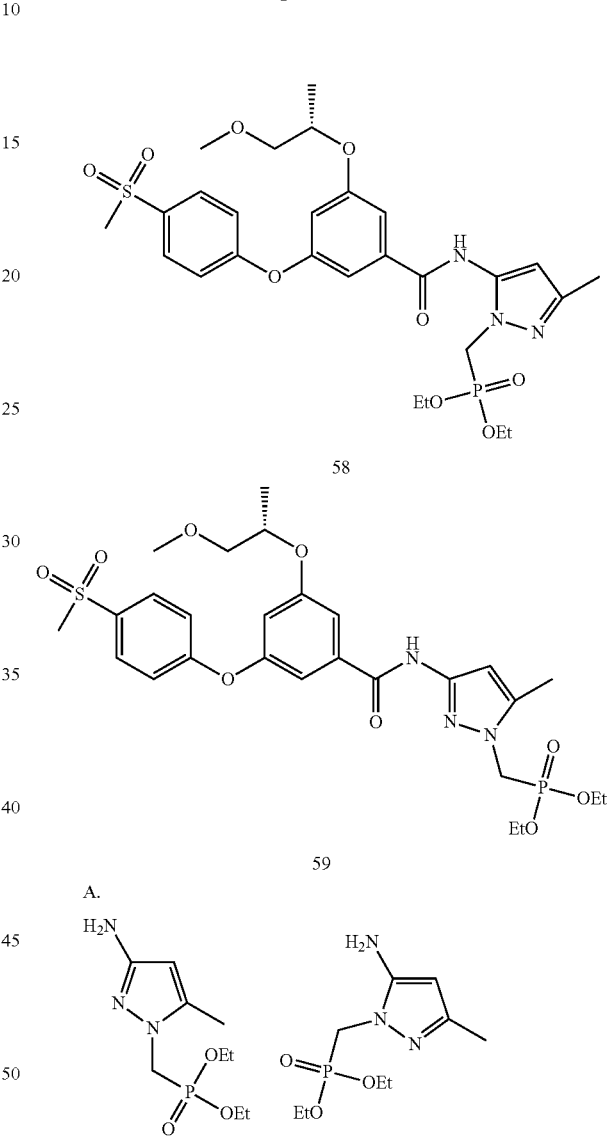

A.

To a stirred 0° C. solution of 5-methyl-1H-pyrazol-3-amine (260 mg, 2.68 mmol) in DMF (4 mL) was added KOtBu (601 mg, 5.35 mmol). The reaction was stirred at 0° C. for 30 min, and then ICH$_2$PO$_3$Et$_2$ (1116 mg, 4.02 mmol) was added dropwise. The reaction was stirred at 0° C. for 1 h, then was warmed to RT and stirred at RT for 18 h. Volatiles were removed in vacuo at 50° C. The residue was partitioned between EtOAc and brine. The aqueous layer was extracted with EtOAc (4×), and the combined organic extracts were dried (MgSO$_4$) and concentrated in vacuo to give a brown oil. The crude residue was purified by preparative HPLC (Luna 5u 21.2×100 mm column; flow rate=20 mL/min, 0 to 100% solvent B over 12 min, hold to 15 min, where solvent A=90:

10:0.1 H₂O:MeOH:TFA and solvent B=90:10:0.1 MeOH:H₂O:TFA) to afford the Part A compounds (1:1 mixture, 80 mg, 12%) as a white solid.

B.

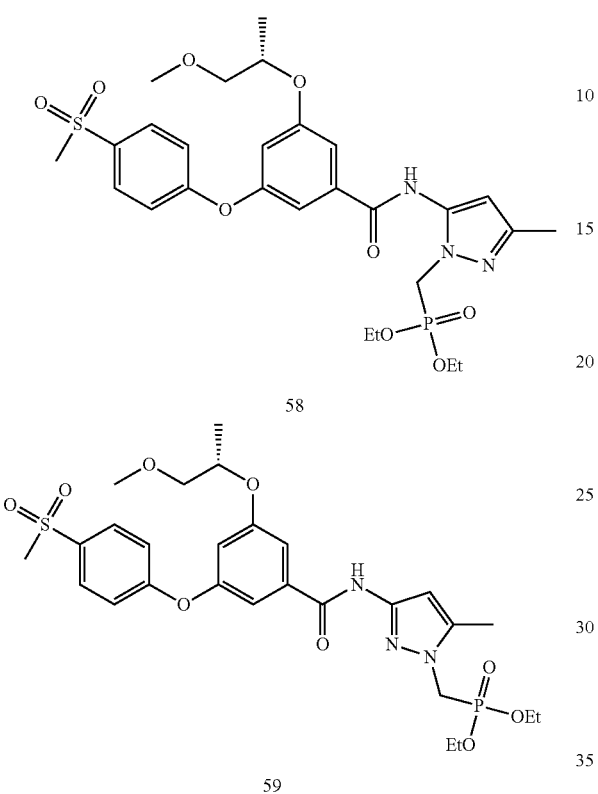

58

59

To a RT solution of Example 26C acid (0.110 g, 0.288 mmol) in DMF (4.5 mL), was added EDC (0.110 g, 0.576 mmol), HOAT (0.078 g, 0.576 mmol), and DIEA (0.088 mL, 0.5004 mmol). The homogeneous yellow solution was stirred at 25° C. for 30 min. A solution of Part A compound (0.100 g, 288 mmol) in DIEA (0.088 mL, 0.5004 mmol) and DMF (1.5 mL) was added, and the homogeneous yellow reaction mixture was stirred at 25° C. for 2 h, then was poured into water (15 mL). The mixture was extracted with EtOAc (10 mL); the organic phase was dried (MgSO₄) and concentrated in vacuo. The residue was purified by preparative HPLC (Phenomenex Luna 5μ C18 30×250 mm column; detection at 220 nm; flow rate=20 mL/min.; continuous gradient from 100% A to 100% B over 30 min.+7 min. hold at 100% B, where A=90:10 H₂O:MeOH and B=90:10 MeOH:H₂O) to provide a yellow foam (a mixture of the two regioismers).

The regioisomers were separated by chiral preparative HPLC (5 cm×50 cm AD column, detection at 220 nm, isocratic 50:50 EtOH:MeOH mobile phase, 50 mL/min. flow) to provide the title compound 58 (27 mg, 15.2% yield) as a tan solid and the title compound 59 (64 mg, 36.3% yield) as an off-white solid.

Example 58

[M+H]⁺=610.4; ¹H NMR (400 MHz, CDCl₃) δ10.56 (s, 1H), 7.91 (d, J=8.79 Hz, 2H), 7.52 (t, J=1.75, 1.76 Hz, 1H), 7.37 (t, J=1.75, 1.32 Hz, 1H), 7.15 (d, J=8.79 Hz, 2H), 6.83 (t, J=2.20 Hz, 1H), 6.44 (s, 1H), 4.64-4.74 (m, 1H), 4.50 (d, J=10.55 Hz, 2H), 3.97-4.17 (m, 4H), 3.49-3.64 (m, 2H), 3.42 (s, 3H), 3.07 (s, 3H), 2.26 (s, 3H), 1.36 (d, J=6.15 Hz, 3H), 1.27 (t, J=7.03 Hz, 6H).

Example 59

[M+H]⁺=610.4; ¹H NMR (400 MHz, CDCl₃) δ 8.6 (s, 1H), 7.92 (d, J=8.79 Hz, 2H), 7.31 (t, J=1.76 Hz, 1H), 7.12-7.17 (m, 3H), 6.83 (t, J=2.19, 1.76 Hz, 1H), 6.66 (s, 1H), 4.57-4.69 (m, 1H), 4.37 (d, J=11.42 Hz, 2H), 4.01-4.15 (m, 4H), 3.48-3.63 (m, 2H), 3.42 (s, 3H), 3.09 (s, 3H), 2.34 (s, 3H), 1.34 (d, J=6.59 Hz, 3H), 1.29 (t, J=7.03 Hz, 6H).

Example 60

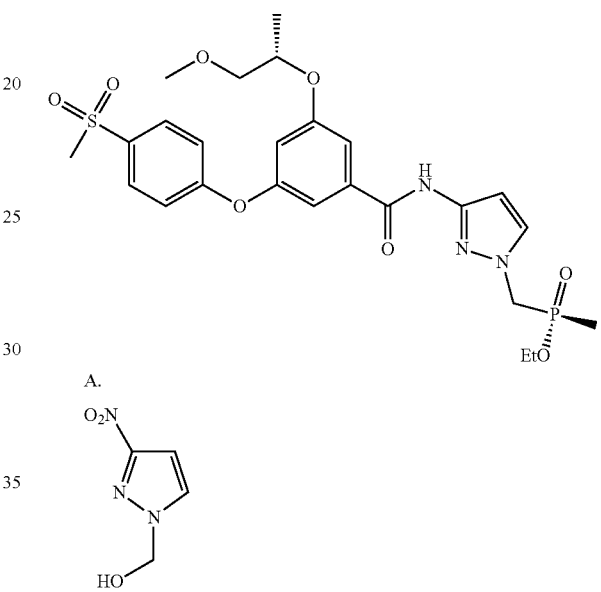

A.

O₂N

HO

To a suspension of 3-nitro-1H-pyrazole (1.00 g, 8.84 mmol) in water (31 mL) was added formaldehyde (37 wt % in water, 1.317 mL, 17.69 mmol). The reaction mixture was stirred at RT for 48 h (after 2 h the reaction mixture became a homogeneous pale yellow solution). The reaction mixture was diluted with sat. aqueous NaHCO₃ (20 mL) and extracted with CH₂Cl₂ (4×40 mL) and EtOAc (3×50 mL). The combined organic extracts were dried (MgSO₄) and concentrated in vacuo to provide Part A compound (1.26 g, 99% yield) as a white solid. ¹H NMR (400 MHz, CD₃OD) δ 7.69 (d, J=2.20 Hz, 1H), 6.95 (d, J=2.75 Hz, 1H), 5.62 (d, J=7.70 Hz, 2H), 4.40 (t, J=7.70, 7.69 Hz, 1H).

B.

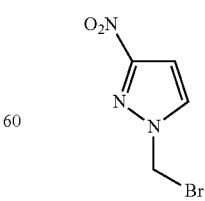

To a 75° C. solution of Part A compound (1.809 g, 12.64 mmol) in MeCN (54 mL) was added PBr₃ (1.788 mL, 18.96 mmol) dropwise over 10 min. The reaction mixture was stirred at 75° C. for 15 min, then was cooled to RT and filtered. The filter cake was washed with CH$_3$CN (2×2 mL), and the combined filtrates were concentrated in vacuo. The residue was partitioned between EtOAc (50 mL) and sat. aqueous NaHCO$_3$ (30 mL). The organic phase was washed with brine (20 mL), dried (MgSO$_4$), and concentrated in-vacuo. The residue was chromatographed (SiO$_2$: continuous gradient 0% EtOAc/Hexane to 70% EtOAc/Hex) to provide Part B compound (1.693 g, 65% yield) as a pale yellow oil. $^1$H NMR (400 MHz, CDCl$_3$) δ 7.80 (d, J=2.20 Hz, 1H), 7.01 (d, J=2.75 Hz, 1H), 5.98 (s, 2H).

C.

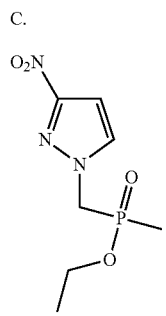

To a solution of Part B compound (1.7366 g, 8.43 mmol) in THF (4 mL) was added CH$_3$P(OEt)$_2$ (1.377 g, 10.12 mmol). The reaction mixture was stirred at 75° C. for 15 h. Additional CH$_3$P(OEt)$_2$ (0.53 g, 3.89 mmol) was added, and the reaction mixture was stirred at 75° C. for 24 h, then was cooled to RT. Volatiles were removed in vacuo, and the residue was chromatographed (SiO$_2$: continuous gradient from 0% MeOH/CH$_2$Cl$_2$ to 15% MeOH/CH$_2$Cl$_2$) to provide Part C compound (1.56 g, 80% yield) as an orange oil. [M+H]$^+$=234.1; $^1$H NMR (400 MHz, CDCl$_3$) δ 7.71 (d, J=3.30 Hz, 1H), 6.96 (d, J=2.75 Hz, 1H), 4.63 (d, J=9.34 Hz, 2H), 4.03-4.20 (m, 4H), 1.57 (d, J=14.85 Hz, 3H), 1.30-1.37 (m, 6H).

D.

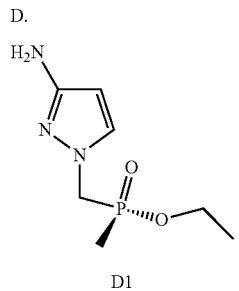

D1

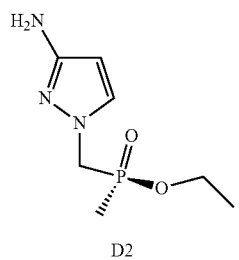

D2

To a solution of Part C compound (1.60 g, 6.86 mmol) in MeOH (190 mL) was added 10% Pd/C (0.730 g, 0.686 mmol). The reaction mixture was stirred under an H$_2$(g) atmosphere for 3 h. The reaction mixture was filtered through Celite®, and the filtrate was concentrated in vacuo. The individual stereoisomers were separated on a Chiralcel OJ column (5 cm×50 cm, isocratic conditions: 40% IPA in heptane, detection at 220 nm, 50 mL/min. flow) to provide isomer D1 (0.59 g, 42.3% yield) as an off-white solid and isomer D2 (0.56 g, 40% yield) as a tan solid.

Isomer D1: [M+H]$^+$=204.1; $^1$H NMR (400 MHz, CDCl$_3$) δ 7.24 (d, J=2.19 Hz, 1H), 5.66 (d, J=2.20 Hz, 1H), 4.32 (d, J=8.79 Hz, 2H), 4.02-4.17 (m, 2H), 3.59-3.81 (s, 2H), 1.48 (d, J=14.50 Hz, 3H), 1.33 (t, J=7.03 Hz, 3H), specific rotation=48.5°.

Isomer D2: [M+H]$^+$=204.1; $^1$H NMR (400 MHz, CDCl$_3$) δ 7.21-7.27 (m, 1H), 5.62-5.70 (m, 1H), 4.32 (d, J=8.79 Hz, 2H), 4.01-4.19 (m, 2H), 3.55-3.81 (s, 2H), 1.48 (d, J=14.50 Hz, 3H), 1.33 (t, J=7.03 Hz, 3H), specific rotation=−49.6°.

E.

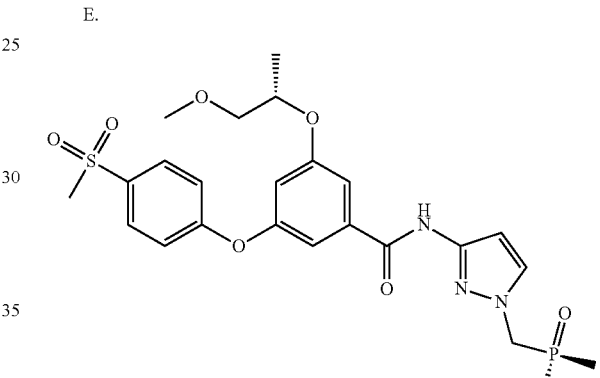

To a RT solution of Example 26 Part C compound (0.120 g, 0.315 mmol) in DMF (6 mL) was added EDAC (0.121 g, 0.631 mmol), HOAT (0.086 g, 0.631 mmol), and DIEA (0.165 mL, 0.946 mmol). The reaction mixture was stirred at RT for 30 min and Part D1 compound (0.064 g, 0.315 mmol) was added. The reaction mixture was stirred at RT for 18 h. The reaction mixture was poured into water (40 mL) and the mixture was extracted with EtOAc (3×15 mL). The combined organic extracts were concentrated in vacuo. The residue was purified by preparative HPLC (Phenomenex Luna 5 µm C18 30×100 mm column; detection at 220 nm; flow rate=40 mL/min; continuous gradient from 100% A to 100% B over 20 min.+2 min. hold at 100% B, where A=90:10:0.1 H$_2$O:MeOH:TFA and B=90:10:0.1 MeOH:H$_2$O:TFA) to provide the title compound (0.121 g, 68.1% yield) as a white solid. [M+H]$^+$=566.3; $^1$H NMR (400 MHz, CDCl$_3$): δ 9.24 (s, 1H), 7.91 (d, J=8.78 Hz 2H), 7.46 (d, J=1.76 Hz, 1H), 7.38 (t, J=1.76 Hz, 1H), 7.23 (t, J=1.76 Hz, 1H), 7.13 (d, J=8.79 Hz, 2H), 6.96 (d, J=2.19 Hz, 1H), 6.84 (t, J=2.20 Hz, 1H), 4.73-4.63 (m, 1H), 4.56 (dd, J=16.25, 8.35 Hz, 1H), 4.46 (dd, J=15.82, 8.35, 9.67 Hz, 1H), 4.20-4.05 (m, 2H), 3.63-3.50 (m, 2H), 3.42 (s, 3H), 3.08 (s, 3H), 1.51 (d, J=14.5 Hz, 3H), 1.39-1.29 (m, 6H).

Example 61

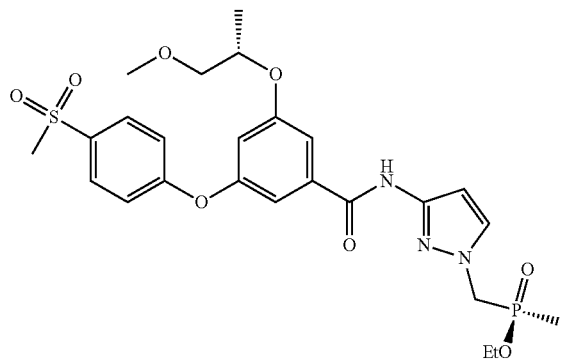 [SMILES: CCO[P@](C)(=O)Cn1ccc(NC(=O)c2cc(Oc3ccc(S(C)(=O)=O)cc3)cc(O[C@@H](C)COC)c2)n1]

To a RT solution of Example 26C acid (0.120 g, 0.315 mmol) in DMF (6 mL) was added EDAC (0.121 g, 0.631 mmol), HOAT (0.086 g, 0.631 mmol), and DIEA (0.165 mL, 0.946 mmol). The reaction mixture was stirred at RT for 30 min and Example 60 Part D2 compound (0.064 g, 0.315 mmol) was added. The reaction mixture was stirred at RT for 18 h, then was poured into water (40 mL). The mixture was extracted with EtOAc (3×15 mL); the combined organic extracts were concentrated in vacuo. The residue was purified by preparative HPLC (Phenomenex Luna 5 μm C18 30×100 mm column; detection at 220 nm; flow rate=40 mL/min.; continuous gradient from 100% A to 100% B over 20 min.+2 min. hold at 100% B, where A=90:10:0.1 H$_2$O:MeOH:TFA and B=90:10:0.1 MeOH:H$_2$O:TFA) to provide the title compound (0.117 g, 65.4% yield) as a white solid. [M+H]$^+$=566.3; $^1$H NMR (400 MHz, CDCl$_3$): δ 9.19 (s, 1H), 7.92 (d, J=9.22 Hz 2H), 7.46 (d, J=1.76 Hz, 1H), 7.37 (t, J=1.76 Hz, 1H), 7.22 (t, J=1.76 Hz, 1H), 7.13 (d, J=8.78 Hz, 2H), 6.96 (d, J=2.63 Hz, 1H), 6.85 (t, J=2.20 Hz, 1H), 4.72-4.62 (m, 1H), 4.56 (dd, J=16.25, 8.35 Hz, 1H), 4.46 (dd, J=15.82, 8.35, 9.67 Hz, 1H), 4.19-4.05 (m, 2H), 3.63-3.50 (m, 2H), 3.42 (s, 3H), 3.08 (s, 3H), 1.51 (d, J=14.5 Hz, 3H), 1.38-1.29 (m, 6H).

Example 62

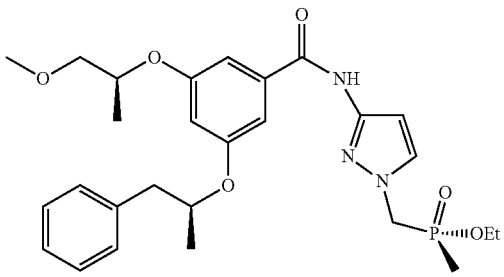 [SMILES: CCO[P@@](C)(=O)Cn1ccc(NC(=O)c2cc(O[C@@H](C)COC)cc(O[C@@H](C)Cc3ccccc3)c2)n1]

To a RT solution of Example 33 Part A acid ((0.030 g, 0.087 mmol) in DMF (2.0 mL) was added EDAC (0.033 g, 0.174 mmol), HOAt (0.024 g, 0.174 mmol) and DIEA (0.046 mL, 0.261 mmol). The reaction mixture was stirred at RT for 30 min, after which Example 60 Part D1 compound (0.018 g, 0.087 mmol) was added. The reaction mixture was stirred at RT for 18 h, then was poured into water (20 mL). The mixture was extracted with EtOAc (2×10 mL); the combined organic extracts were dried (MgSO$_4$) and concentrated in vacuo. The residue was purified by preparative HPLC (Phenomenex Luna 5μ C18 21.2×100 mm column; detection at 220 nm; flow rate=40 mL/min.; continuous gradient from 100% A to 100% B over 15 min.+2 min. hold at 100% B, where A=90:10:0.1 H$_2$O:MeOH:TFA and B=90:10:0.1 MeOH:H$_2$O:TFA) to provide the title compound (0.034 g, g, 74.8% yield) as a tacky off-white solid. [M+H]$^+$=530.4; $^1$H NMR (400 MHz, CDCl$_3$): δ 9.16 (s, 1H), 7.45 (d, J=1.65 Hz, 1H), 7.32-7.18 (m, 5H), 7.06 (t, J=1.65 Hz, 1H), 7.03 (t, J=1.65 Hz, 1H), 6.98 (d, J=2.19 Hz, 1H), 6.64 (t, J=2.2 Hz, 1H), 4.69-4.56 (m, 2H), 4.55-4.40 (m, 2H), 4.18-4.04 (m, 2H), 3.57 (dd, J=10.45 Hz, J=6.04 Hz, 1H), 3.50 (dd, J=9.89 Hz, J=3.85 Hz, 1H), 3.41 (s, 3H), 3.06 (dd, J=13.74 Hz, J=6.04 Hz, 1H), 2.86 (dd, J=13.75 Hz, J=6.05 Hz, 1H), 1.53 (d, J=14.84 Hz, 3H), 1.35-1.27 (m, 9H).

Example 63

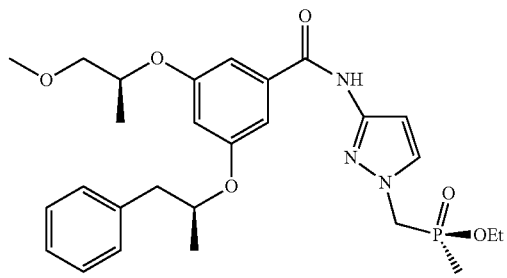 [SMILES: CCO[P@](C)(=O)Cn1ccc(NC(=O)c2cc(O[C@@H](C)COC)cc(O[C@@H](C)Cc3ccccc3)c2)n1]

To a RT solution of Example 33 Part A acid ((0.030 g, 0.087 mmol) in DMF (2.0 mL) was added EDAC (0.033 g, 0.174 mmol), HOAt (0.024 g, 0.174 mmol) and DIEA (0.046 mL, 0.261 mmol). The reaction mixture was stirred at RT for 30 min, after which Example 60 Part D2 compound (0.018 g, 0.087 mmol) was added. The reaction was stirred at RT for 18 h, then was poured into water (20 mL). The mixture was extracted with EtOAc (2×10 mL) and the combined organic extracts were dried (MgSO$_4$) and concentrated in vacuo. The residue was purified by preparative HPLC (Phenomenex Luna 5μ C18 21.2×100 mm column; detection at 220 nm; flow rate=40 mL/min.; continuous gradient from 100% A to 100% B over 15 min.+2 min. hold at 100% B, where A=90:10:0.1 H$_2$O:MeOH:TFA and B=90:10:0.1 MeOH:H$_2$O:TFA) to provide the title compound (0.03626 g, 79% yield) as a tacky white solid. [M+H]$^+$=530.4; $^1$H NMR (400 MHz, CDCl$_3$): δ 9.17 (s, 1H), 7.45 (d, J=2.20 Hz, 1H), 7.32-7.17 (m, 5H), 7.06 (t, J=2.2 Hz, 1H), 7.03 (t, J=2.2 Hz, 1H), 6.98 (d, J=2.19 Hz, 1H), 6.64 (t, J=2.2 Hz, 1H), 4.70-4.57 (m, 2H), 4.54-4.40 (m, 2H), 4.17-4.03 (m, 2H), 3.57 (dd, J=9.90 Hz, J=6.04 Hz, 1H), 3.50 (dd, J=10.44 Hz, J=3.38 Hz, 1H), 3.41 (s, 3H), 3.06 (dd, J=13.74 Hz, J=6.59 Hz, 1H), 2.85 (dd, J=13.75 Hz, J=6.05 Hz, 1H), 1.52 (d, J=14.29 Hz, 3H), 1.36-1.26 (m, 9H).

Example 64

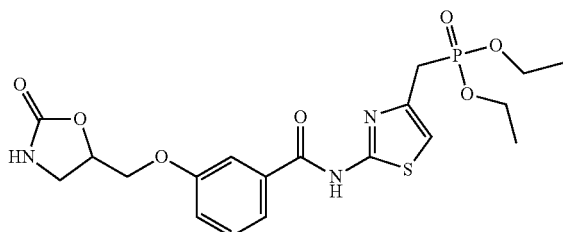

A.

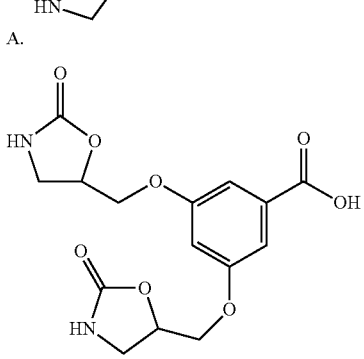

A mixture of methyl 3,5-dihydroxybenzoate (350 mg, 2.082 mmol), 5-(chloromethyl)oxazolidin-2-one (1.0 g, 7.38 mmol), and K$_2$CO$_3$ (5.75 g, 41.6 mmol) in DMF (10 mL) was stirred at 80° C. for 18 h, then was cooled to RT and filtered. The filter cake was washed with EtOAc, and the combined filtrates were concentrated in vacuo to give a brown oil. The crude methyl bis-alkylated benzoate was dissolved in THF (1 mL), and aqueous 1N NaOH (1 mL, 1.00 mmol) was added. The mixture was stirred at RT for 18 h, then concentrated in vacuo. The residue was acidified with TFA and then purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give Part A compound (83 mg, 9% yield) as a red solid. [M+H]$^+$=353.1; $^1$H NMR (400 MHz, MeOH-d$_4$) δ 3.56 (dd, J=8.79, 6.60 Hz, 2H) 3.75 (t, J=9.07 Hz, 2H) 4.10-4.30 (m, 4H) 4.96-5.07 (m, 2H) 6.77-6.85 (m, 0H) 7.22 (d, J=2.75 Hz, 2H).

B.

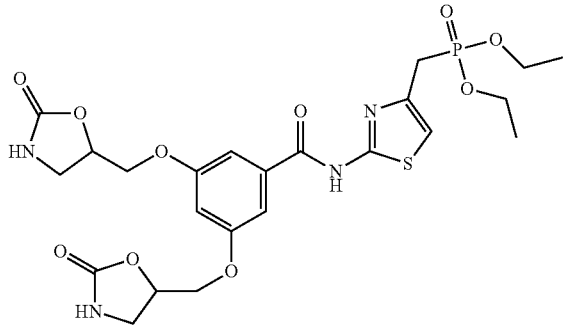

A mixture of Part A compound (13 mg, 0.037 mmol), Example 13 Part E compound (23 mg, 0.037 mmol), HOAt (10 mg, 0.072 mmol), EDCI (20 mg, 0.500 mmol) and DIPEA (0.2 mL, 1.148 mmol) in DMF (0.5 mL) was stirred at 21° C. for 18 h. The reaction mixture was diluted with EtOAc (1 mL) and washed with 1N aqueous HCl (1 mL). The organic layer was dried (MgSO$_4$) and concentrated in vacuo. The residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give the title compound (12.5 mg, 58.0% yield) as a white solid. [M+H]$^+$=585.3; $^1$H NMR (400 MHz, CDCl$_3$) δ 1.33 (t, J=7.15 Hz, 6H) 3.35 (d, J=21.44 Hz, 2H) 3.63 (dd, J=8.25, 6.60 Hz, 2H) 3.79 (t, J=8.79 Hz, 2H) 4.11-4.20 (m, 4H) 4.21-4.37 (m, 4H) 4.96-5.04 (m, 2H) 5.76 (br. s., 2H) 6.80 (br. s., 1H) 7.04 (d, J=3.85 Hz, 1H) 7.44 (s, 2H).

Example 65

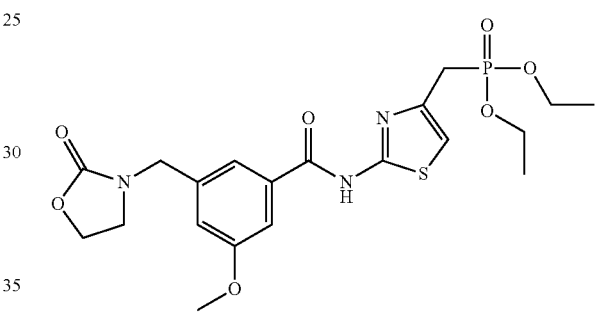

A.

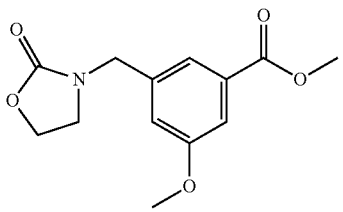

A suspension of NaH (70 mg of a 60% suspension in oil, 1.750 mmol) in THF (3 mL) was stirred at 0° C. under N$_2$ (g) for 15 min. The reaction was cooled to −30° C. and oxazolidin-2-one (125 mg, 1.436 mmol) was added. The mixture was stirred at −30° C. for 30 min, then was warmed to RT and stirred for 30 min. The mixture was cooled to −30° C. again and a solution of methyl 3-(bromomethyl)-5-methoxybenzoate (200 mg, 0.772 mmol) in THF (2 mL) was added. The mixture was stirred at RT for 5 days, then was cooled to −30° C. and sat. aqueous NH$_4$Cl (1 mL) was added. The aqueous layer was back-extracted with EtOAc (2×5 mL), and the combined organic extracts were dried (Na$_2$SO$_4$) and concentrated in vacuo. The residue was chromatographed [SiO$_2$; EtOAc/Hexane (1:1)] to give Part A compound 184 mg, 90% yield) as a clear oil. [M+H]$^+$=266.01; $^1$H NMR (500 MHz, CDCl$_3$) δ 3.46 (t, J=7.70 Hz, 2H) 3.85 (s, 3H) 3.92 (s, 3H) 4.33 (t, J=7.70 Hz, 2H) 4.44 (s, 2H) 7.05 (s, 1H) 7.50 (s, 1H) 7.54 (s, 1H).

B.

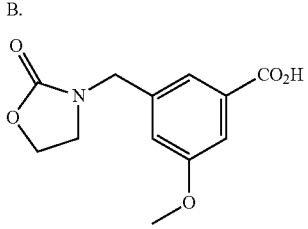

A mixture of Part A compound (50 mg, 0.188 mmol), and NaOH (1 mL, 1.00 mmol) in THF (2 mL) was stirred at RT for 2 h, then was acidified with 1N aqueous HCl (0.5 mL). The mixture was filtered and concentrated in vacuo; the residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 $H_2O$:MeOH:TFA and B=90:10:0.1 MeOH:$H_2O$:TFA) to give Part B compound as a white solid (42 mg, 0.167 mmol, 89%). [M+H]$^+$=251.98; $^1$H NMR (400 MHz, $CD_3OD$) δ 3.53 (t, J=8.24 Hz, 2H), 3.84 (s, 3H), 4.34 (t, J=8.24 Hz, 2H), 4.44 (s, 2H), 7.09 (t, J=1.65 Hz, 1H), 7.49 (dd, J=2.75, 1.10 Hz, 1H), 7.55 (s, 1H).

C.

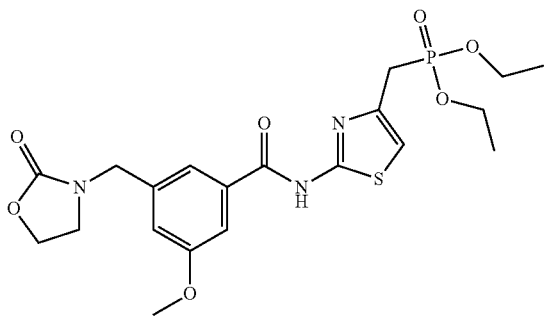

A mixture of Part B compound (12 mg, 0.048 mmol), Example 13 Part E compound (11.95 mg, 0.048 mmol), HOAt (10 mg, 0.072 mmol), DIPEA (0.2 mL, 1.148 mmol) and EDCI (20 mg, 0.500 mmol) in DMF (0.5 mL) was stirred at RT in for 18 h, then was diluted with EtOAc (1 mL) and washed with 1N aqueous HCl (1 mL). Volatiles were removed in vacuo. The crude residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 $H_2O$:MeOH:TFA and B=90:10:0.1 MeOH:$H_2O$:TFA) to give the title compound as a clear oil (20 mg, 87% yield). [M+H]$^+$=483.99; $^1$H NMR (400 MHz, $CDCl_3$) δ 1.33 (t, J=7.15 Hz, 6H), 3.36 (d, J=21.44 Hz, 2H), 3.52 (s, J=8.24, 8.24 Hz, 2H), 3.91 (s, 3H), 4.12-4.22 (m, J=7.35, 7.35, 7.28, 7.15 Hz, 4H) 4.33 (t, J=8.25 Hz, 2H), 4.46 (s, 2H), 7.05 (d, J=3.30 Hz, 1H), 7.17 (s, 1H), 7.66 (s, 1H), 7.68 (d, J=2.20 Hz, 1H).

Example 66

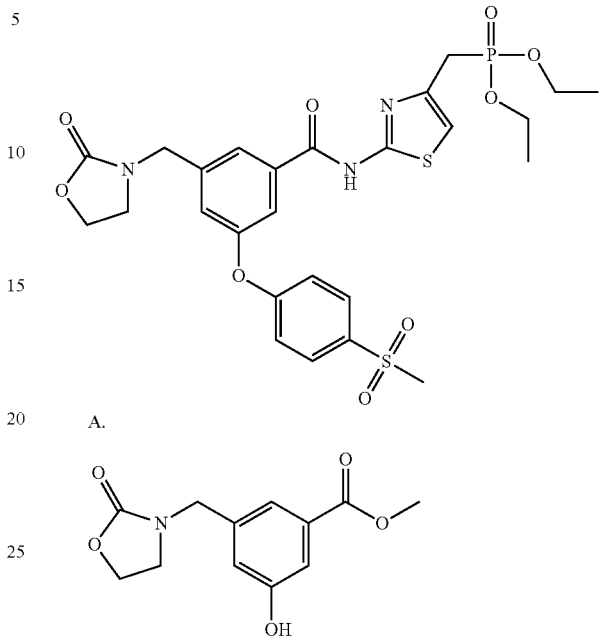

A.

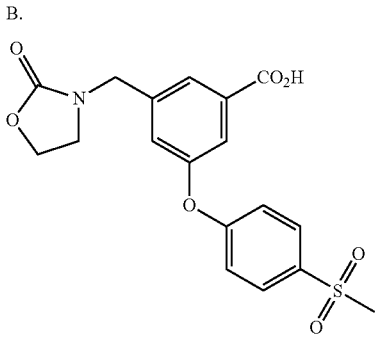

To a 0° C. solution of Example 64 Part B compound (177 mg, 0.667 mmol) in DCM (1 mL) was added $BBr_3$ (1 mL, 1.000 mmol). The reaction was stirred at 0° C. for 24 h, after which volatiles were removed in vacuo. The residue was dissolved in MeOH (3 mL), and the pH was adjusted to pH ~4 with sat. aqueous $NaHCO_3$. Solids were removed by filtration, and the filtrate was concentrated in vacuo. The residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 $H_2O$:MeOH:TFA and B=90:10:0.1 MeOH:$H_2O$:TFA) to give the Part A compound (67 mg, 40% yield) as a white solid. [M+H]$^+$=252.19; $^1$H NMR (400 MHz, $CD_3OD$) δ 3.52 (t, J=8.24 Hz, 2H), 3.88 (s, 3H), 4.34 (t, J=8.24 Hz, 2H), 4.40 (s, 2H), 6.97 (s, 1H), 7.36 (s, 1H), 7.42 (s, 1H).

B.

A solution of Part A compound (67 mg, 0.267 mmol), 1-fluoro-4-(methylsulfonyl)benzene (50 mg, 0.287 mmol), and $K_2CO_3$ (300 mg, 2.171 mmol) in DMF (3 mL) was stirred at 100° C. in a sealed tube for 18 h, then was cooled to RT. Solids were filtered off, and the filtrate was concentrated in vacuo. The residue was acidified with TFA and then purified by preparative HPLC (Phenomenex AXIA 5 μm C18 30×100 mm column; detection at 220 nm; flow rate=40 mL/min;

continuous gradient from 30% A to 100% B over 10 min+1 min hold time at 100% B, where A=90:10:0.1 H₂O:MeOH:TFA and B=90:10:0.1 MeOH:H₂O:TFA) to give Part B compound (73 mg, 69.9% yield) as a white solid. [M+H]⁺=392.01; ¹H NMR (400 MHz, CD₃OD) δ 3.12 (s, 3H), 3.57 (t, J=8.24 Hz, 2H), 4.36 (t, J=8.24 Hz, 2H), 4.50 (s, 2H), 7.20 (d, J=8.79 Hz, 2H), 7.32 (s, 1H), 7.63 (s, 1H), 7.84 (s, 1H), 7.96 (d, J=8.79 Hz, 2H).

C.

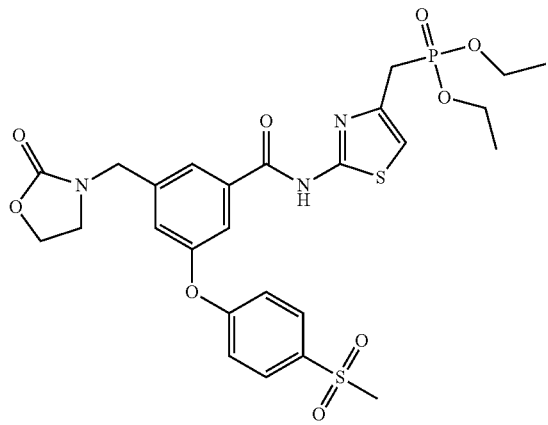

A mixture of Part B compound (15 mg, 0.038 mmol), Example 13 Part E compound (9.59 mg, 0.038 mmol), HOAt (10 mg, 0.072 mmol), EDCI (20 mg, 0.500 mmol), and DIPEA (0.2 mL, 1.148 mmol) in DMF (0.5 mL) was stirred at 25° C. for 18 h. The mixture was diluted with EtOAc (1 mL) and washed with 1N aqueous HCl (1 mL). The organic phase was dried (MgSO₄) and concentrated in vacuo. The residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10:0.1 MeOH:H₂O:TFA) to give the title compound (17 mg, 70% yield) as a white solid. [M+H]⁺=624.2; ¹H NMR (400 MHz, CDCl₃) (1.32 (t, J=7.15 Hz, 6H), 3.07 (s, 3H), 3.33 (d, J=21.44 Hz, 2H), 3.64 (t, J=7.70 Hz, 2H), 4.15 (dd, J=8.25, 7.15 Hz, 4H), 4.35 (t, J=8.24 Hz, 2H), 4.51 (s, 2H), 7.05 (d, J=3.85 Hz, 1H), 7.14 (d, J=8.79 Hz, 2H), 7.40 (s, 1H), 7.76 (t, J=1.65 Hz, 1H), 7.89-7.96 (m, 3H).

Example 67

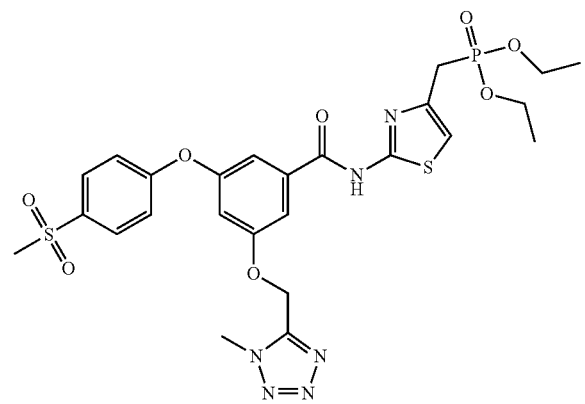

A.

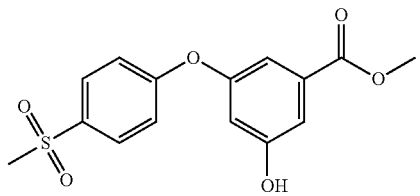

A mixture of methyl 3,5-dihydroxybenzoate (10 g, 59.5 mmol) and K₂CO₃ (13 g, 94 mmol) in DMF (50 mL) was stirred at 120° C. for 2 h. A solution of 1-fluoro-4-(methylsulfonyl)benzene (5 g, 28.7 mmol) in DMF (10 mL) was added, and the reaction was stirred at 120° C. for another 24 h. The reaction mixture was filtered, and the resulting filter cake was rinsed with DMF (50 mL). The combined filtrates were concentrated in vacuo. The residue was partitioned between EtOAc (100 mL) and 1N aqueous HCl (100 mL). The aqueous layer was extracted with EtOAc (50 mL×3), and the combined organic extracts were washed with water, dried (Na₂SO₄), filtered, and concentrated in vacuo. The crude residue was chromatographed (SiO₂; EtOAc/Hexane 1:3) to give Part A compound (4 g, 43% yield) as yellow solid. [M+H]⁺=323.0; ¹H NMR (400 MHz, CDCl₃) δ 3.08 (s, 3H), 3.91 (s, 3H), 6.13 (s, 1H), 6.80 (t, J=2.20 Hz, 1H), 7.11 (d, J=8.79 Hz, 2H), 7.27-7.28 (m, 1H), 7.41-7.44 (m, 1H), 7.91 (d, J=8.79 Hz, 2H).

B.

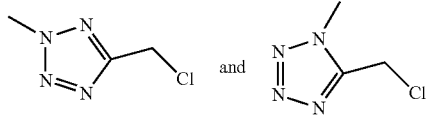

To a stirred solution of 5-(chloromethyl)-2H-tetrazole (0.5 g, 4.22 mmol) in Et₂O (5 mL) was added dropwise a solution of CH₂N₂ in Et₂O (5 mL) prepared from 1-methyl-3-nitro-1-nitrosoguanidine (700 mg, 4.76 mmol) and 40% aqueous KOH (4 g, 28.5 mmol, 10 mL water) at 0° C. The reaction solution was maintained at 0° C. during the addition, and the reaction was stirred at RT for 1 h and was then concentrated using a stream of air. Residual solvent was removed in vacuo to give the Part B isomeric compounds as yellow oils (400 mg, 71.5% yield).

C.

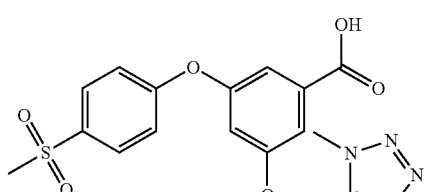

149

-continued

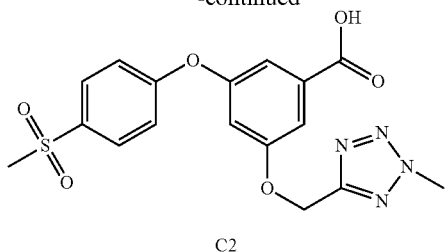

C2

A mixture of Part A compound (100 mg, 0.310 mmol), Part B compound (41.1 mg, 0.310 mmol), and K₂CO₃ (300 mg, 2.17 mmol) was stirred at 100° C. in a sealed tube for 18 h, then was cooled to RT. The reaction mixture was diluted with EtOAc (5 mL) and washed with H₂O (5 mL×2); the organic layer was dried (Na₂SO₄) and concentrated in vacuo to give a yellow oil. This crude methyl ester was stirred in 1N aqueous NaOH (0.5 mL, 0.500 mmol) and THF (1 mL) for 2 h. The reaction was concentrated in vacuo and was acidified with TFA. The two isomers were separated by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10:0.1 MeOH:H₂O:TFA) to give Part C1 compound (40 mg, 31% yield) as a white solid and Part C2 compound (72 mg, 57% yield) as a white solid.

Part C1 Compound: [M+H]⁺=405.1; ¹H NMR (400 MHz, DMSO-d6) δ 3.22 (s, 3H), 4.13 (s, 3H), 5.63 (s, 2H), 7.20-7.28 (m, 4H), 7.49 (s, 1H), 7.95 (d, J=8.79 Hz, 2H), 13.35 (s, 1H).

Part C2 Compound: [M+H]⁺=405.1; ¹H NMR (400 MHz, DMSO-d6) δ 3.21 (s, 3H), 4.38 (s, 3H), 5.47 (s, 2H), 7.18 (d, J=5.50 Hz, 2H), 7.24 (d, J=8.79 Hz, 2H), 7.44 (s, 1H), 7.94 (d, J=8.79 Hz, 2H), 13.30 (s, 1H).

D.

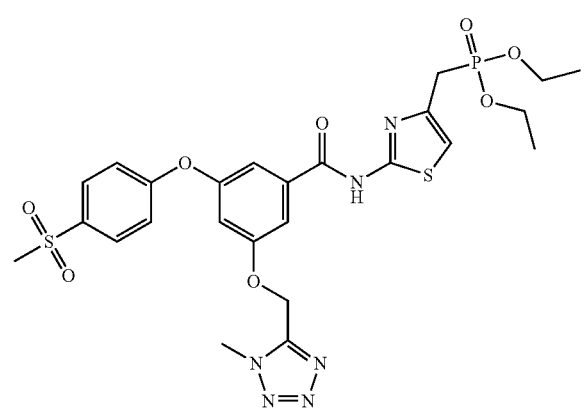

A mixture of Part C1 compound (12 mg, 0.030 mmol), Example 13 Part E compound (7.43 mg, 0.030 mmol), HOAt (10 mg, 0.072 mmol), EDCI (20 mg, 0.500 mmol), and DIPEA (0.2 mL, 1.148 mmol) in DMF (0.5 mL) was stirred at 25° C. for 18 h. The reaction mixture was diluted with EtOAc (1 mL) and washed with 1N aqueous HCl (1 mL). The organic layer was dried (Na₂SO₄) and concentrated in vacuo. The residue was purified by preparative HPLC (Phenomenex AXIA 5 µm C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10:0.1 MeOH:H₂O:TFA) to give the title compound (12 mg, 64% yield) as a white solid. [M+H]⁺=636.99; ¹H NMR (400 MHz, CDCl₃) δ 1.30 (t, J=6.87 Hz, 6H), 3.08 (s, 3H), 3.29 (d, J=21.44 Hz, 2H), 4.08-4.17 (m, J=7.56, 7.56, 7.42, 7.15 Hz, 4H), 4.18 (s, 3H), 5.56 (s, 2H), 6.98 (s, 1H), 7.03 (d, J=3.30 Hz, 1H), 7.15 (d, J=8.79 Hz, 2H), 7.50 (s, 1H), 7.80 (s, 1H), 7.94 (d, J=8.79 Hz, 2H).

Example 68

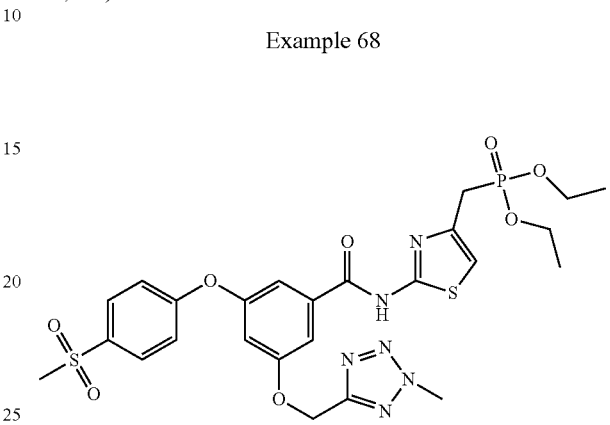

A mixture of Example 67 Part C2 Compound (12 mg, 0.030 mmol), Example 13 Part E compound (7.43 mg, 0.030 mmol), HOAt (10 mg, 0.072 mmol), DIPEA (0.2 mL, 1.148 mmol), and EDCI (0.500 mL, 0.500 mmol) in DMF (0.5 mL) was stirred at 25° C. for 18 h. The reaction mixture was diluted with EtOAc (1 mL) and washed with 1N aqueous HCl (1 mL). The organic layer was dried (Na₂SO₄) and concentrated in vacuo. The residue was purified by preparative HPLC (Phenomenex AXIA 5 µm C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10:0.1 MeOH:H₂O:TFA) to give the title compound (10 mg, 53% yield) as a white solid. [M+H]⁺=637.00; ¹H NMR (400 MHz, CDCl₃) δ 1.30 (t, J=7.15 Hz, 6H), 3.07 (s, 3H), 3.32 (d, J=21.44 Hz, 2H), 4.07-4.17 (m, J=7.35, 7.35, 7.28, 7.15 Hz, 4H), 4.39 (s, 3H), 5.48 (s, 2H), 6.97-7.02 (m, 2H), 7.15 (d, J=8.79 Hz, 2H), 7.49 (s, 1H), 7.78 (s, 1H), 7.93 (d, J=8.79 Hz, 2H).

Example 69

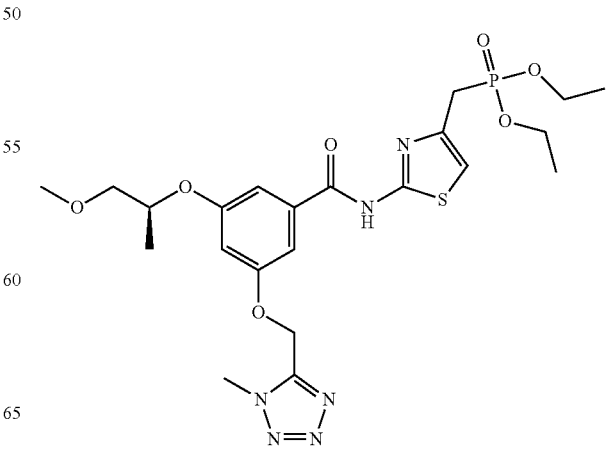

-continued

A.

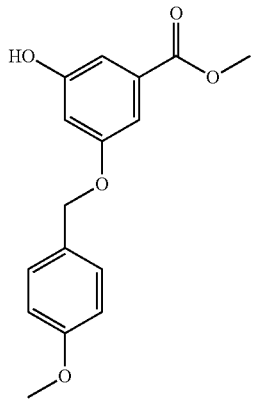

C.

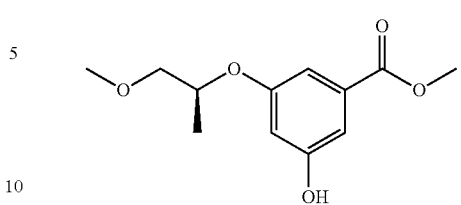

A solution of crude Part B compound (1.75 g, 4.86 mmol) and TFA (3 mL, 38.9 mmol) in dry DCM (5 mL) was stirred at RT for 2 h. Volatiles were removed in vacuo, and the residue was chromatographed (SiO$_2$; EtOAc/Hexane 1:5) to give Part C compound (407 mg, 35%) as a clear oil. [M+H]$^+$=241.27; $^1$H NMR (400 MHz, CDCl$_3$) δ 1.29 (d, J=6.05 Hz, 3H), 3.41 (s, 3H), 3.47-3.62 (m, 2H), 3.88 (s, 3H), 4.51-4.62 (m, 1H), 4.95 (br. s., 1H), 6.65 (s, 1H), 7.13 (dd, J=5.22, 1.37 Hz, 2H).

A mixture of 1-(bromomethyl)-4-methoxybenzene (2.151 mL, 14.92 mmol), methyl 3,5-dihydroxybenzoate (5 g, 29.7 mmol), and K$_2$CO$_3$ (12.33 g, 89 mmol) in MeCN (100 mL) was stirred at 80° C. for 3 days. The reaction was diluted with water (50 mL), acidified with 12N HCl (30 mL) to pH ~2, and extracted with EtOAc (20 mL×3). The combined organic extracts were washed with water, dried (Na$_2$SO$_4$) and concentrated in vacuo. The residue was chromatographed (SiO$_2$: EtOAc/Hexane 1:3) to give Part A compound (3.0 g, 35% yield) as a white solid. $^1$H NMR (400 MHz, CDCl$_3$) δ 3.82 (s, 3H), 3.90 (s, 3H), 5.00 (s, 2H), 5.14 (s, 1H), 6.66 (t, J=2.20 Hz, 1H), 6.92 (d, J=8.35 Hz, 2H), 7.10-7.16 (m, 1H), 7.22-7.29 (m, 1H), 7.35 (d, J=8.35 Hz, 2H).

D.

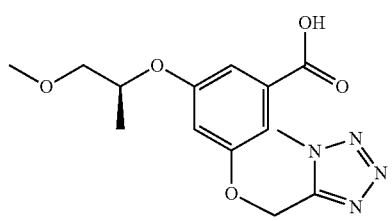

D1

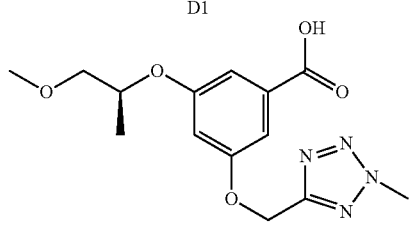

D2

B.

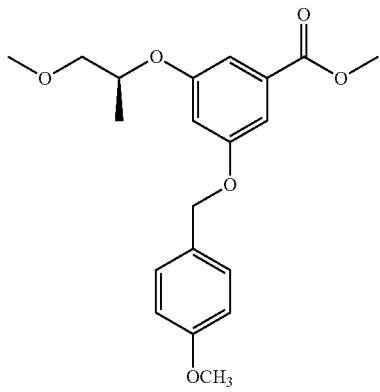

A mixture of Part C compound (300 mg, 1.249 mmol), Example 67 Part B compound (166 mg, 1.249 mmol), and K$_2$CO$_3$ (300 mg, 2.171 mmol) in DMF (3 mL) was stirred at 100° C. in a sealed tube for 18 h, then was cooled to RT. Solids were filtered off, and the filtrate was concentrated in vacuo. The residue was acidified with TFA and the two isomers were separated by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O: MeOH:TFA and B=90:10:0.1 MeOH:H$_2$O:TFA) to give Part D1 compound (160 mg, 40% yield) as a white solid and Part D2 compound (33 mg, 8.2% yield) as a white solid.

Part D1 compound: [M+H]$^+$=323.15; $^1$H NMR (400 MHz, CDCl$_3$) δ 1.31 (d, J=6.05 Hz, 3H), 3.43 (s, 3H), 3.50-3.64 (m, 2H), 4.18 (s, 3H), 4.57-4.67 (m, 1H), 5.47 (s, 2H), 6.82 (t, J=2.47 Hz, 1H), 7.30 (dd, J=2.20, 1.10 Hz, 1H), 7.35 (s, 1H).

To a 0° C. solution of Ph$_3$P (1.820 g, 6.94 mmol), Part A compound (1 g, 3.47 mmol), and (R)-1-methoxypropan-2-ol (0.365 mL, 4.16 mmol) in dry THF (5 mL) was added DIAD (1.012 mL, 5.20 mmol). The reaction was stirred at RT for 18 h. Volatiles were removed in vacuo, and the residue was chromatographed (SiO$_2$; EtOAc/Hexane, 1:5) to give crude Part B compound (1.7 g, 136%), which was used in the next step without further purification.

Part D2 compound: [M+H]$^+$=323.18; $^1$H NMR (400 MHz, CDCl$_3$) δ 1.32 (d, J=6.05 Hz, 3H), 3.42 (s, 3H), 3.48-3.62 (m, 2H), 4.39 (s, 3H), 4.55-4.64 (m, 1H), 5.35 (s, 2H), 6.86 (t, J=2.47 Hz, 1H), 7.34 (s, 1H), 7.37 (dd, J=2.20, 1.10 Hz, 1H).

E.

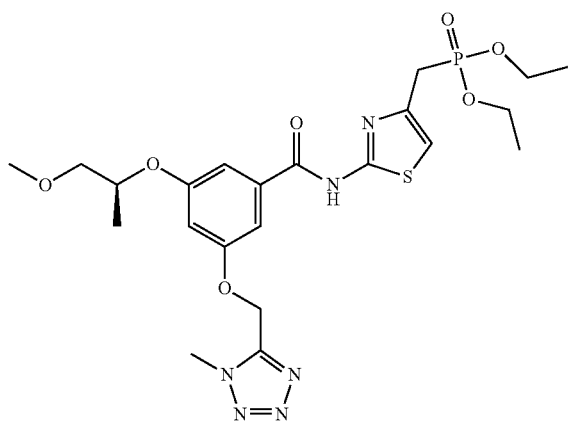

A mixture of Part D1 compound (15 mg, 0.047 mmol), Example 13 Part E compound (11.65 mg, 0.047 mmol), HOAt (10 mg, 0.072 mmol), EDCI (20 mg, 0.500 mmol), and DIPEA (0.2 mL, 1.148 mmol) in DMF (0.5 mL) was stirred at 25° C. for 18 h. The reaction mixture was diluted with EtOAc (1 mL) and washed with 1N aqueous HCl (1 mL). The organic phase was dried (Na$_2$SO$_4$) and concentrated in vacuo. The residue was purified by preparative HPLC(Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give the title compound (13 mg, 50% yield) as a white solid. [M+H]$^+$=555.3; $^1$H NMR (400 MHz, CDCl$_3$) δ 1.28-1.35 (m, 9H), 3.29-3.36 (m, 2H), 3.40 (s, 3H), 3.49-3.61 (m, 2H), 4.09-4.19 (m, 7H), 4.74 (td, J=6.19, 3.79 Hz, 1H), 5.49 (s, 2H), 6.84 (t, J=2.15 Hz, 1H), 7.03 (d, J=3.54 Hz, 1H), 7.47 (t, J=1.77 Hz, 1H), 7.49 (dd, J=2.02, 1.52 Hz, 1H).

Example 70

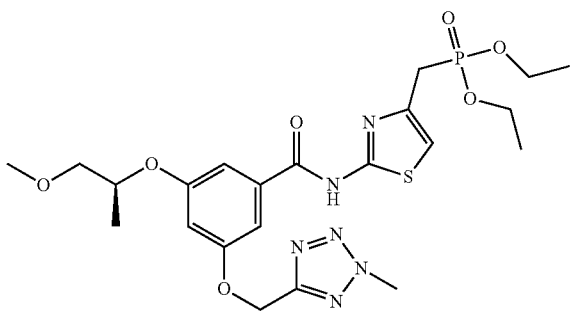 [SMILES: CCOP(=O)(Cc1csc(NC(=O)c2cc(OCc3nnn(C)n3)cc(O[C@@H](C)COC)c2)n1)OCC]

The title compound (10 mg; 58% yield; colorless oil) was synthesized employing the procedure described in Example 69 Part E, except that Example 69 Part D2 was used in the sequence instead of Example 69 Part D1. [M+H]$^+$=555.3; $^1$H NMR (400 MHz, CDCl$_3$) δ 1.25-1.37 (m, 9H), 3.26-3.37 (m, 2H), 3.40 (s, 3H), 3.47-3.62 (m, 2H), 4.06-4.19 (m, 4H), 4.38 (s, 3H), 4.71 (td, J=6.19, 4.04 Hz, 1H), 5.40 (s, 2H), 6.86 (t, J=2.27 Hz, 1H), 6.98 (d, J=3.54 Hz, 1H), 7.40 (d, J=1.52 Hz, 1H), 7.45 (d, J=1.52 Hz, 1H).

Example 71

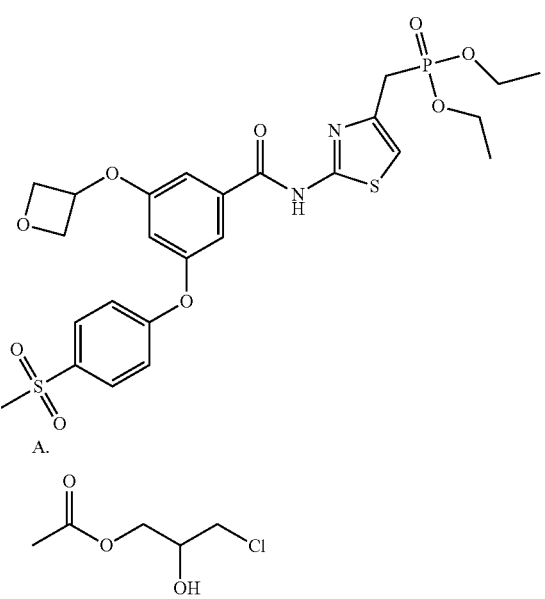

A.

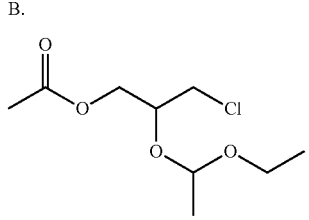

To a solution of FeCl$_3$ (100 mg, 0.62 mmol) in HOAc (68.8 mL, 1202 mmol) was added 2-(chloromethyl)oxirane (111.2 g, 1202 mmol) with stirring, over a 10-min period. The mixture was heated at 70° C. with stirring for 24 h, then was cooled to RT and filtered to give Part A compound (183 g, 100% yield) as a yellow oil. $^1$H NMR (400 MHz, CDCl$_3$) (2.11 (s, 3H), 3.57-3.66 (m, 2H), 4.05-4.12 (m, 1H), 4.21 (t, J=4.83 Hz, 2H).

B.

To crude Part A compound (183 g, 1202 mmol) was added pTsOH (1 g, 5.26 mmol), followed by dropwise addition of ethyl vinyl ether (118 mL, 1232 mmol) over a period of 2 h. The flask was cooled to maintain a reaction temperature of 35-37° C. After the addition was complete, the mixture was heated at 40-45° C. for 18 h, then cooled to RT to give crude Part B compound (270 g, 100%) as a red liquid.

C.

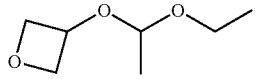

To a 110° C. solution of NaOH (110 g, 2750 mmol) in water (110 mL) was added Part B compound (270 g, 1202 mmol) over a 1.5 h period. The reaction mixture was refluxed for another 4 h, then was cooled to RT and washed with water (110 mL). The aqueous layer was extracted with DCM (110 mL), and the combined organic extracts were concentrated in vacuo to give a brown oil. Distillation (bp=45-50° C. @ 0.5 mm Hg) gave Part C compound (15 g, 8.5%) as a clear oil. $^1$H NMR (400 MHz, CDCl$_3$) δ 1.15 (t, J=7.15 Hz, 3H), 1.25 (d, J=5.50 Hz, 3H), 3.44 (dd, J=9.34, 7.15 Hz, 1H), 3.56 (q, J=7.15 Hz, 1H), 4.55-4.84 (m, 4H).

D.

A solution of Part C compound (15 g, 103 mmol) in MeOH (5.26 mL, 125 mmol) was cooled to 15-18° C., and p-TsOH (100 mg, 0.581 mmol) was added with stirring. The reaction mixture was stirred for 45 min, after which NaHCO$_3$ (50 mg, 0.595 mmol) was added. Distillation at 35-40° C. (0.1 mmHg) gave crude Part D compound (7.0 g, 95%) as a clear oil.

E.

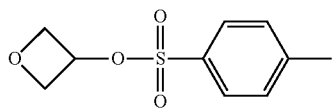

To a well-stirred 50° C. solution of Part D compound (7 g, 94 mmol) and p-TsCl (12.8 g, 67.1 mmol) in water (15 mL) was added dropwise a solution of NaOH (2.69 g, 67.1 mmol) in water (15 mL). The reaction was heated for 1 h at 50° C., then cooled to RT and toluene (10 mL) was added. The aqueous layer was extracted with toluene (5 mL×2). The combined organic extracts were washed with conc NH$_4$OH (3×) and water (2×), then concentrated in vacuo. Hexane (50 mL) was added to the residue and a solid was formed, which was collected by filtration and then was dried in vacuo for 1 h to give Part E compound (10 g, 65% yield) as a white solid. [M+H]$^+$=229.1; $^1$H NMR (400 MHz, CDCl$_3$) δ ppm 2.46 (s, 3H), 4.64-4.75 (m, 4H), 5.27-5.34 (m, 1H), 7.37 (d, J=8.25 Hz, 2H), 7.78 (d, J=8.25 Hz, 2H).

F.

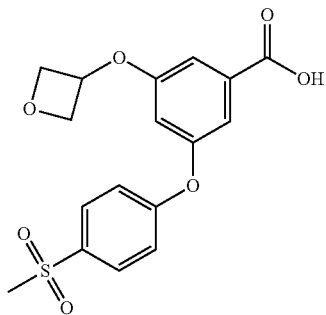

A mixture of Example 67 Part A compound (450 mg, 1.396 mmol), Part E compound (500 mg, 2.190 mmol), and K$_2$CO$_3$ (2.7 g, 19.54 mmol) in DMF (5 mL) was stirred in a sealed tube at 110° C. for 18 h, then was cooled to RT. The reaction was filtered, the solids were washed with DMF, and the combined filtrates were concentrated in vacuo. The residue was neutralized with TFA and purified by preparative HPLC(Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give the Part F compound (220 mg, 42% yield) as a white solid. [M+H]$^+$=365.2; $^1$H NMR (400 MHz, CDCl$_3$) δ 3.08 (s, 3H), 4.78 (dd, J=7.15, 4.95 Hz, 2H), 5.02 (t, J=6.87 Hz, 2H), 5.23-5.31 (m, 1H), 6.75 (t, J=1.92 Hz, 1H), 7.13 (d, J=8.79 Hz, 2H), 7.18 (s, 1H), 7.39 (s, 1H), 7.93 (d, J=8.24 Hz, 2H).

G.

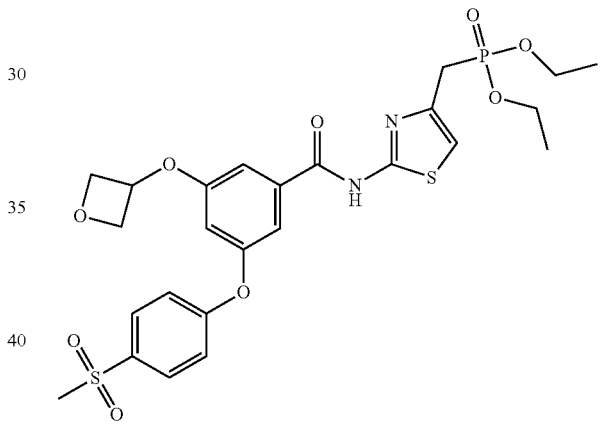

A mixture of Part F compound (14 mg, 0.038 mmol), Example 13 Part E compound (9.62 mg, 0.038 mmol), HOAt (10 mg, 0.072 mmol), EDCI (20 mg, 0.500 mmol) and DIPEA (0.2 mL, 1.148 mmol) in DMF (0.5 mL) was stirred at 40° C. for 18 h, then was cooled to RT. The reaction mixture was partitioned between EtOAc (1 mL) and 1N aqueous HCl (1 mL). The organic layer was dried (Na$_2$SO$_4$) and concentrated in vacuo. The residue was purified by preparative HPLC (Phenomenex AXIA 5 μm C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give the title compound (13 mg, 55.6% yield) as a white solid. [M+H]$^+$=597.2; $^1$H NMR (400 MHz, CDCl$_3$) δ 1.28 (t, J=7.03 Hz, 6H), 3.08 (s, 3H), 3.34 (d, J=21.09 Hz, 2H), 4.04-4.16 (m, 4H), 4.75 (dd, J=7.47, 4.83 Hz, 2H), 5.05 (t, J=6.81 Hz, 2H), 5.36-5.45 (m, J=5.49, 5.38, 5.33, 5.33 Hz, 1H), 6.82 (t, J=2.20 Hz, 1H), 6.96 (d, J=3.52

Hz, 1H), 7.15 (d, J=8.79 Hz, 2H), 7.24 (s, 1H), 7.42 (s, J=1.76, 1.76 Hz, 1H), 7.94 (d, J=9.23 Hz, 2H).

Example 72

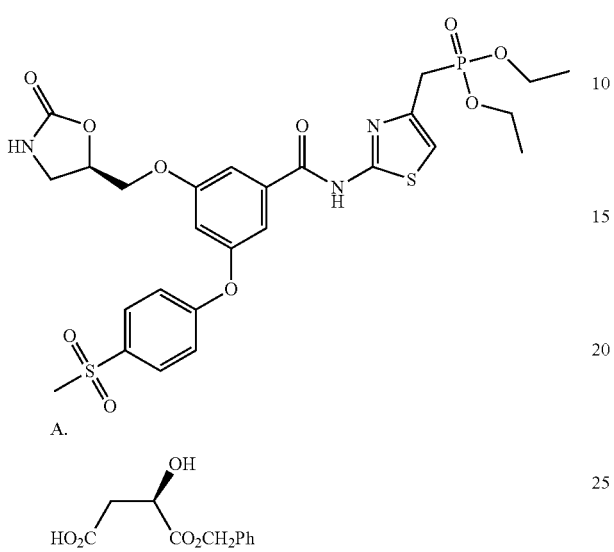

A.

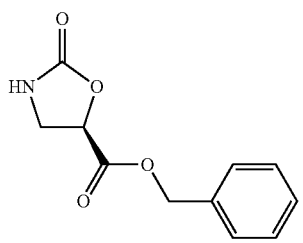

Pre-cooled TFAA (25 mL, 177 mmol) at 0° C. was added to D-malic acid (5 g, 37.3 mmol) with stirring. The suspension was stirred for 2 h at RT, then was concentrated in vacuo. Dry benzyl alcohol (25 mL, 240 mmol) was added and the solution was stirred overnight at RT. Volatiles (benzyl alcohol and TFAA) were removed in vacuo. The residue was chromatographed [SiO$_2$; EtOAc/Hexane (1:1+0.5% TFA)] to give Part A compound (7.9 g, 94% yield) as a colorless oil. $^1$H NMR (400 MHz, CDCl$_3$) δ 2.80-2.96 (m, 2H), 4.55 (dd, J=6.19, 4.42 Hz, 1H), 5.24 (s, 2H), 7.30-7.38 (m, 5H); [a]=+12.19 @ 1.4% w/v in DMF at 589 nm.

B.

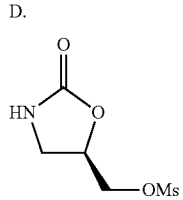

To a solution of the Part A compound (7.9 g, 35.2 mmol) and Et$_3$N (5.6 mL, 40.2 mmol) in Toluene (120 mL) was slowly added Ph$_2$PON$_3$ (8.64 mL, 40.0 mmol) over ~30 min. The reaction mixture was refluxed for 2 h, stirred at 70° C. for 2 h, then cooled to RT and stirred at RT for 3 days. Volatiles were removed in vacuo; the residue was dissolved in water and extracted with EtOAc (20 mL×3). The combined organic extracts were washed with sat. aqueous NaHCO$_3$, dried (Na$_2$SO$_4$) and concentrated in vacuo. The residue was chromatographed [SiO$_2$; EtOAc/Hexane (1:1)] to give Part B compound (2.28 g, 27.5% yield) as a pale solid. [M+H]$^+$=222.16; $^1$H NMR (400 MHz, CDCl$_3$) δ 3.58-3.73 (m, 1H), 3.86 (t, J=9.35 Hz, 1H), 5.02 (dd, J=9.60, 5.56 Hz, 1H), 5.24 (d, J=1.77 Hz, 2H), 6.40 (br. s., 1H), 7.36 (s, 5H); [a]=−4.56 @ 1.2% w/v in DMF at 589 nm.

C.

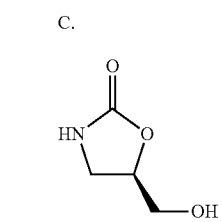

To a 0° C. suspension of Part B compound (2.28 g, 10.31 mmol) in EtOH (50 mL) was slowly added NaBH$_4$ (0.390 g, 10.31 mmol). The mixture was stirred for 3 h at 0° C., then was warmed to RT and sat. aqueous NH$_4$Cl (2 mL) was added. The reaction was stirred for 30 min, then the solids were filtered off, and the filtrate was concentrated in vacuo. The residue was chromatographed (SiO$_2$; EtOAc/MeOH, 5:1) to give Part C compound (0.966 g, 80% yield) as a white solid. $^1$H NMR (400 MHz, DMSO-d6) δ 3.20 (t, J=7.70 Hz, 1H), 3.41-3.57 (m, 3H), 4.52 (dt, J=15.39, 4.67 Hz, 1H), 5.06 (t, J=5.77 Hz, 1H), 7.39 (br. s., 1H); [a]=−33.11 @ 1.1% w/v in EtOH at 589 nm.

D.

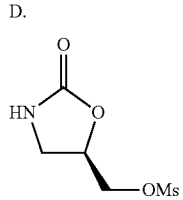

To a −5° C. solution of Part C compound (966 mg, 8.25 mmol) and pyridine (10 mL, 124 mmol) in DCM (15 mL) was slowly added MsCl (0.8 mL, 10.27 mmol) over 1 h. After 3 h, the volatiles were removed in vacuo at a minimal temperature. The residue was chromatographed (SiO$_2$; CH$_2$Cl$_2$/MeOH 95:5 v/v) to give Part D compound (1.5 g, 93% yield) as a colorless solid. $^1$H NMR (400 MHz, DMSO-d6) δ 3.21-3.27 (m, 4H), 3.58 (t, J=9.34 Hz, 1H), 4.28-4.35 (m, 1H), 4.36-4.43 (m, 1H), 4.80-4.88 (m, 1H), 7.63 (br. s., 1H); [a]=−33.93 @ 0.55% w/v in EtOH at 589 nm.

E.

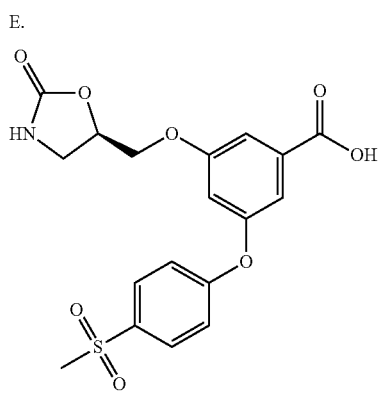

A mixture of Example 26 Part A compound (400 mg, 1.241 mmol), Part D compound (242 mg, 1.241 mmol), and K₂CO₃ (2.7 g, 19.54 mmol) in DMF (5 mL) was stirred in a sealed tube at 110° C. for 18 h, then was cooled to RT and filtered. The filtrate was concentrated in vacuo. The residue was neutralized with TFA and then purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10:0.1 MeOH:H₂O:TFA) to give the Part E compound (260 mg, 51.4% yield) as a white solid. [M+H]⁺=408.1; ¹H NMR (400 MHz, CD₃OD) δ 3.12 (s, 3H), 3.55 (dd, J=9.01, 6.37 Hz, 1H), 3.75 (t, J=9.23 Hz, 1H), 4.17-4.24 (m, 1H), 4.26-4.33 (m, 1H), 4.97-5.05 (m, 1H), 6.98 (t, J=2.20 Hz, 1H), 7.19 (d, J=8.79 Hz, 2H), 7.30 (s, 1H), 7.47 (s, 1H), 7.95 (d, J=9.23 Hz, 2H); [a]=−23.97 @ 1.4% w/v in MeOH at 589 nm.

F.

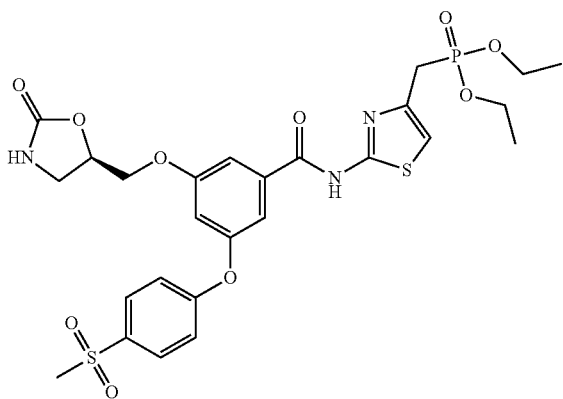

A mixture of Part E compound (20 mg, 0.049 mmol), Example 13 Part E compound (12.29 mg, 0.049 mmol), HOAt (10 mg, 0.072 mmol), EDCI (20 mg, 0.500 mmol), and DIPEA (0.2 mL, 1.148 mmol) in DMF (0.5 mL) was stirred at 25° C. for 18 h. Volatiles were removed in vacuo and the residue was purified by preparative HPLC (Phenomenex AXIA 5 μm C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10:0.1 MeOH: H₂O:TFA) to give the title compound (17 mg, 51.4% yield) as a white solid. [M+H]⁺=640.3; ¹H NMR (400 MHz, CDCl₃) δ 1.31 (td, J=7.07, 5.05 Hz, 6H), 3.07 (s, 3H), 3.32 (d, J=21.22 Hz, 2H), 3.64 (dd, J=8.84, 6.32 Hz, 1H), 3.82 (t, J=8.97 Hz, 1H), 4.07-4.18 (m, 4H), 4.38 (d, J=4.55 Hz, 2H), 4.96-5.06 (m, 1H), 6.12 (br. s., 1H), 6.93 (t, J=2.27 Hz, 1H), 6.99 (d, J=3.79 Hz, 1H), 7.15 (d, J=8.84 Hz, 2H), 7.50 (dd, J=2.15, 1.39 Hz, 1H), 7.71 (t, J=1.77 Hz, 1H), 7.92 (d, J=8.84 Hz, 2H); e.e.=98.2% (Chiralpak AS, 250×4.6 mm ID; 10 nm, RT, 60% (50/50 MeOH-EtOH): 40% Heptane, 1 mL/min).

Example 73

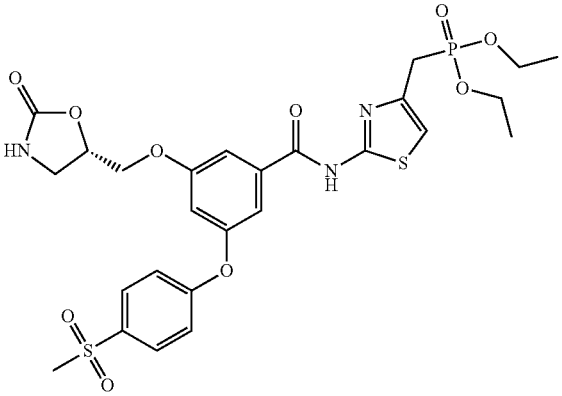 [SMILES: CCOP(=O)(Cc1csc(NC(=O)c2cc(OC[C@@H]3CNC(=O)O3)cc(Oc3ccc(S(C)(=O)=O)cc3)c2)n1)OCC]

The title compound (22 mg; 58% yield; white solid) was synthesized from L-malic acid employing the same procedure as described in Example 72. [M+H]⁺=640.3; ¹H NMR (400 MHz, CDCl₃) δ 1.33 (t, J=7.07 Hz, 6H), 3.07 (s, 3H), 3.38 (d, J=21.47 Hz, 2H), 3.64 (dd, J=8.84, 6.57 Hz, 1H), 3.81 (t, J=8.97 Hz, 1H), 4.17 (dd, J=8.21, 7.20 Hz, 3H), 4.29-4.37 (m, 1H), 4.40-4.48 (m, 1H), 4.99-5.08 (m, 1H), 5.91 (br. s., 1H), 6.96 (t, J=2.15 Hz, 1H), 7.06 (d, J=3.79 Hz, 1H), 7.15 (dq, J=8.84, 4.80 Hz, 1H), 7.51 (dd, 1H), 7.71 (t, J=1.52 Hz, 1H), 7.93 (dq, J=8.84, 4.80 Hz, 1H); e.e.=99.9% (Chiralpak AS, 250×4.6 mm ID; 10 μm, RT, 60% (50/50 MeOH-EtOH): 40% Heptane, 1 mL/min)

Example 74

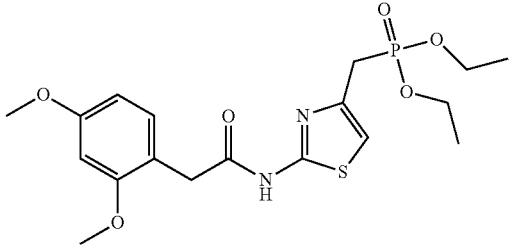 [SMILES: CCOP(=O)(Cc1csc(NC(=O)Cc2ccc(OC)cc2OC)n1)OCC]

A mixture of 2-(2,4-dimethoxyphenyl)acetic acid (20 mg, 0.12 mmol), Example 13 Part E compound (25 mg, 0.1 mmol), HOAt (20 mg, 0.015 mmol), EDCI (25 mg, 0.500 mmol), and DIPEA (0.2 mL, 1.148 mmol) in DMF (0.5 mL) was stirred at 25° C. for 18 h. The reaction mixture was concentrated in vacuo, and the residue was purified by preparative HPLC (Phenomenex AXIA 5 μm C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10:0.1 MeOH:H₂O:TFA) to give the title compound (2.6 mg, 6% yield) as a yellow oil. [M+H]⁺=429.4; ¹H NMR (400 MHz, CDCl₃) δ 1.31 (t, J=7.03 Hz, 6H), 3.25-3.34 (d, J=21.53 Hz, 2H), 3.79 (s, 3H), 3.80 (s, 3H), 3.83 (s, 2H), 4.09-4.18 (m, 4H), 6.46-6.50 (m, 2H), 6.91 (d, J=3.52 Hz, 1H), 7.15 (d, 1H);

Examples 75 to 77

The following examples were prepared in the same manner as Example 74:

| Example # | Structure | [M + H]+ | 1H NMR (400 MHz, CDCl3) | Yield and Description |
|---|---|---|---|---|
| 75 | 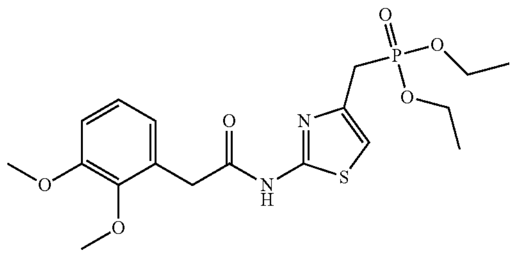 [SMILES: CCOP(=O)(Cc1csc(NC(=O)Cc2cccc(OC)c2OC)n1)OCC] | 429.4 | δ 1.29 (t, J = 7.03 Hz, 6 H), 3.27 (d, J = 21.09 Hz, 2 H), 3.83-3.91 (m, 8 H), 4.04-4.17 (m, 4 H), 6.83-6.93 (m, 3 H), 7.01-7.08 (m, 1H) | 8.3 mg (19% yield); yellow oil |
| 76 | 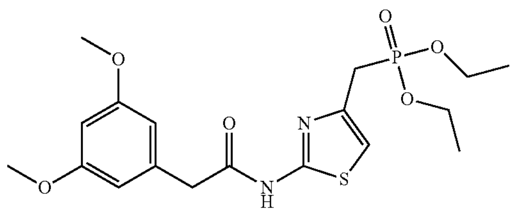 [SMILES: CCOP(=O)(Cc1csc(NC(=O)Cc2cc(OC)cc(OC)c2)n1)OCC] | 429.4 | (1.27 (t, J = 7.03 Hz, 6 H), 3.25 (d, J = 21.09 Hz, 2 H), 3.75-3.78 (m, 2 H), 3.79 (s, 6 H), 4.02-4.12 (m, 4 H), 6.40-6.43 (m, 1 H), 6.47 (d, J = 2.20 Hz, 2 H), 6.82 (none, 1H) | 8.6 mg (20% yield); yellow oil |
| 77 | 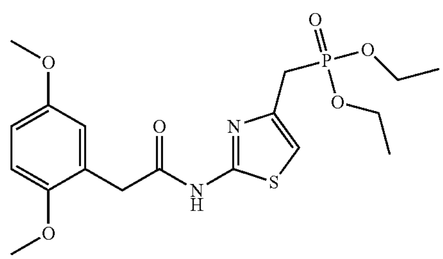 [SMILES: CCOP(=O)(Cc1csc(NC(=O)Cc2cc(OC)ccc2OC)n1)OCC] | 429.4 | δ 1.29 (t, J = 7.03 Hz, 6 H), 3.23-3.31 (m, 2 H), 3.77 (s, 3 H), 3.82 (s, 5 H), 4.06-4.14 (m, 4 H), 6.82-6.87 (m, 4 H) | 8.3 mg (19% yield); yellow oil |

Example 78

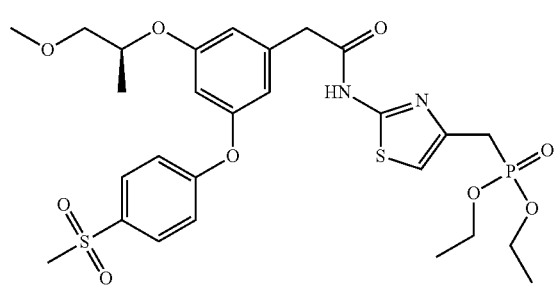

A.

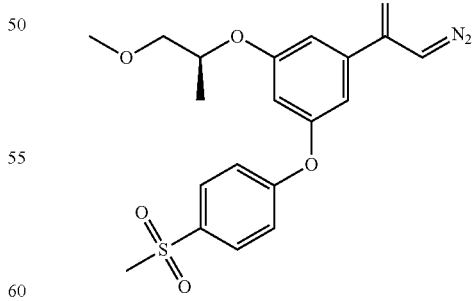

A solution of Example 26C acid (146 mg, 0.384 mmol) and (COCl)₂ (2 mL of a 2M solution in DCM, 4 mmol) in DCM (2 mL) was stirred at RT for 18 h, then was concentrated in vacuo. The crude acid chloride was taken up in Et₂O (5 mL) and was added dropwise to a 0° C. solution of CH₂N₂ in Et₂O (5 mL) prepared from 1-methyl-3-nitro-1-nitrosoguanidine (735 mg, 5 mmol) and 40% aqueous KOH (0.8 g, 15 mmol, 2 mL water) at 0° C. The reaction mixture was stirred at RT for 1 h and was concentrated under a stream of air; residual solvent were removed in vacuo. The residue was chromatographed (SiO$_2$; EtOAc/Hexane 5:1) to give Part A compound (130 mg, 84% yield) as a yellow oil. [M+H]$^+$=405.2; $^1$H NMR (400 MHz, CDCl$_3$) δ 1.28 (d, J=6.15 Hz, 3H), 3.03 (s, 3H), 3.36 (s, 3H), 3.43-3.57 (m, 2H), 4.51-4.62 (m, 1H), 5.86 (s, 1H), 6.79 (t, J=2.20 Hz, 1H), 6.99 (s, 1H), 7.08 (d, J=8.79 Hz, 2H), 7.15 (s, 1H), 7.87 (d, 2H).

B.

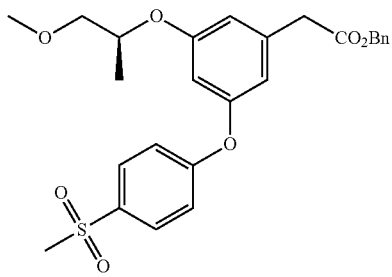

To a −25° C. solution of Part A compound (130 mg, 0.321 mmol) and BnOH (0.5 mL, 5 mmol) in dry THF (2 mL) was added over 15 min a solution of PhCO$_2$Ag (206.1 mg, 0.9 mmol) in Et$_3$N (1.67 mL, 12 mmol). The reaction mixture was stirred at RT for 5 h in the dark. The reaction was filtered through Celite®; the filtrate was concentrated in vacuo, and the residue was chromatographed [SiO$_2$; EtOAc/Hexane(2:1)] to give Part B compound (130 mg, 83.6%) as a clear oil. [M+H]$^+$=485.2; $^1$H NMR (400 MHz, CDCl$_3$) δ 1.28 (d, J=6.15 Hz, 3H), 3.05 (s, 3H), 3.39 (s, 3H), 3.44-3.50 (m, 1H), 3.52-3.58 (m, 1H), 3.62 (s, 2H), 4.45-4.54 (m, 1H), 5.14 (s, 2H), 6.56 (t, J=2.20 Hz, 1H), 6.59 (t, J=1.76 Hz, 1H), 6.73 (d, J=1.76 Hz, 1H), 7.08 (d, J=9.23 Hz, 2H), 7.28-7.38 (m, 5H), 7.86 (d, J=8.79 Hz, 2H).

C.

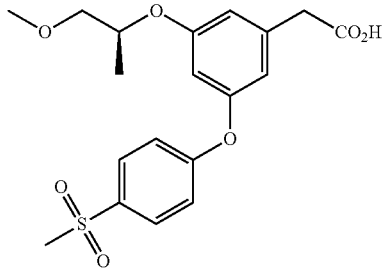

A solution of Part B compound (130 mg, 0.268 mmol) and 10% Pd—C (20 mg) in EtOAc (10 mL) was stirred under H$_2$ (g; 60 psi) for 18 h. The catalyst was removed by filtration and the filtrate was concentrated in vacuo to give Part C compound (86 mg, 81.4%) as a clear oil. [M+H]$^+$=395.1; $^1$H NMR (400 MHz, CDCl$_3$) δ 1.28 (d, J=6.15 Hz, 3H), 3.05 (s, 3H), 3.38 (s, 3H), 3.44-3.51 (m, 1H), 3.51-3.57 (m, 1H), 3.58 (s, 2H), 4.46-4.56 (m, 1H), 6.55 (t, J=2.20 Hz, 1H), 6.58 (s, 1H), 6.72 (s, 1H), 7.09 (d, J=8.79 Hz, 2H), 7.87 (d, 2H).

D.

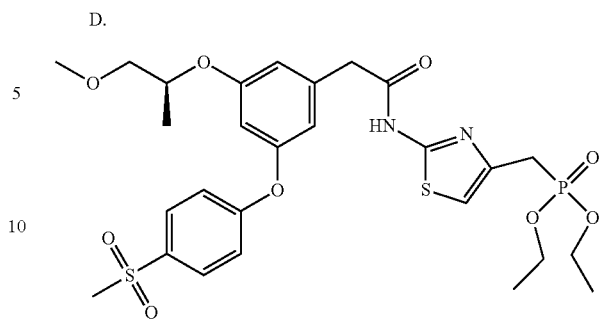

A solution of Part C compound (43 mg, 0.109 mmol) and (COCl)$_2$ (3.0 mL of a 2M solution in DCM, 6 mmol) in DCM (3 mL) was stirred at RT for 18 h, then was concentrated in vacuo. The crude acid chloride was taken up in DCM (2 mL) and was added over 15 min to a 0° C. solution of Example 13 Part E compound (37 mg, 0.148 mmol) and pyridine (0.2 mL, 2.5 mmol) in DCM (3 mL). The reaction was stirred at 0° C. for 30 min, then was concentrated in vacuo. The residue was purified by preparative HPLC (Phenomenex AXIA 5 µm C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give the title compound (20 mg, 29% yield) as a yellow oil. [M+H]$^+$=627.3; $^1$H NMR (400 MHz, CDCl$_3$) δ 1.21-1.34 (m, 6H), 3.06 (s, 3H), 3.23-3.34 (m, 2H), 3.38 (s, 3H), 3.44-3.51 (m, 1H), 3.51-3.59 (m, 1H), 3.77 (s, 2H), 4.03-4.15 (m, 4H), 4.46-4.58 (m, 1H), 6.58 (t, J=2.20 Hz, 1H), 6.64 (s, 1H), 6.79 (s, 1H), 6.85 (d, J=3.52 Hz, 1H), 7.11 (d, J=8.79 Hz, 2H), 7.88 (d, 2H).

Example 79

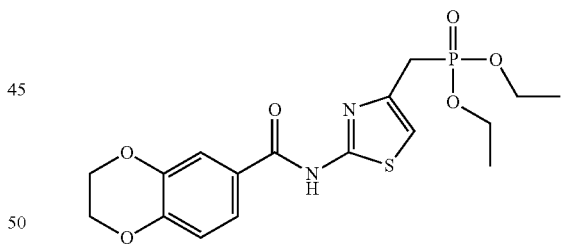

A solution of 2,3-dihydrobenzo[b][1,4]dioxine-6-carboxylic acid (20 mg, 0.11 mmol), Example 13 Part E compound (20 mg, 0.083 mmol), HOAt (20 mg, 0.147 mmol), EDCI (40 mg, 0.21 mmol), and DIPEA (40 mg, 0.31 mmol) in DMF (1 mL) was stirred at 25° C. for 18 h. The reaction mixture was concentrated in vacuo, and the residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give the title compound (8.2 mg, 24% yield) as a white solid. [M+H]$^+$=413.3; $^1$H NMR (400 MHz, CDCl$_3$) δ 1.29 (t, J=7.03 Hz, 6H), 3.27-3.36 (d, J=21.09 Hz, 2H), 4.06-4.16 (m, 4H), 4.28-4.37 (m, 4H), 6.94 (d, J=3.52 Hz, 1H), 6.99 (d, J=8.35 Hz, 1H), 7.64-7.71 (m, 2H).

Example 80

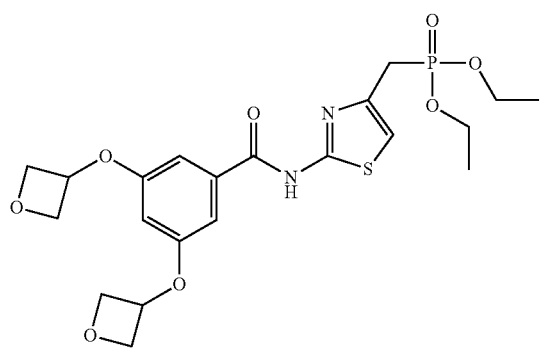

A.

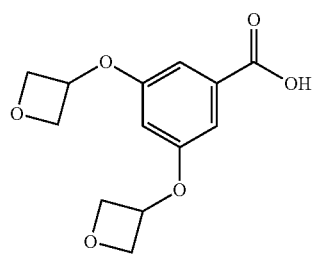

A mixture of methyl 3,5-dihydroxybenzoate (200 mg, 1.189 mmol), Example 71 Part E compound (600 mg, 2.63 mmol), and K$_2$CO$_3$ (2 g, 14.47 mmol) in DMF (10 mL) was stirred in a sealed tube at 115° C. for 18 h, then was cooled to RT. Solids were removed by filtration and were washed with DMF. The combined filtrates were concentrated in vacuo. The residue was neutralized with TFA and was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10:0.1 MeOH:H$_2$O:TFA) to give Part A compound (60 mg, 19.0%) as a white solid. [M+H]$^+$=267.2; $^1$H NMR (400 MHz, CD$_3$OD) δ 4.68 (dd, J=7.15, 4.95 Hz, 4H), 5.02 (t, J=6.60 Hz, 4H), 5.26-5.35 (m, 2H), 6.46 (t, J=2.20 Hz, 1H), 6.98 (d, J=2.20 Hz, 2H).

B.

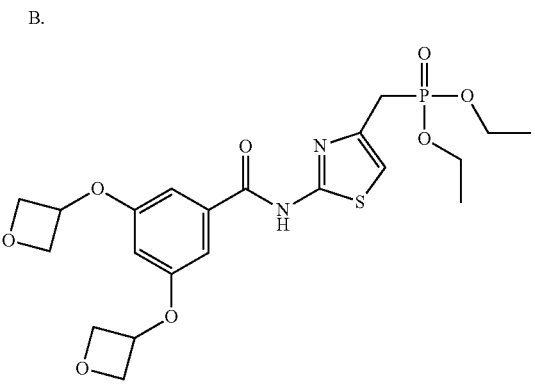

A mixture of Part A compound (21 mg, 0.079 mmol), Example 13 Part E compound (19.74 mg, 0.079 mmol), HOAt (20 mg, 0.145 mmol), EDCI (20 mg, 0.500 mmol), and DIPEA (0.2 mL, 1.148 mmol) in DMF (0.5 mL) was stirred at 25° C. for 18 h, then was concentrated in vacuo. The residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H$_2$O: MeOH:TFA and B=90:10:0.1 MeOH:H$_2$O:TFA) to give the title compound (25 mg, 63.6% yield) as a white solid. [M+H]$^+$=499.3; $^1$H NMR (400 MHz, CDCl$_3$) (7.09 (2H, d), 7.03 (1H, d, J=3.30 Hz), 6.54 (1H, t, J=2.20 Hz), 5.31-5.39 (2H, m), 5.04 (4H, t, J=6.60 Hz), 4.74 (4H, dd, J=7.70, 4.95 Hz), 4.10-4.19 (4H, m), 3.36 (1H, s), 3.31 (1H, s), 1.32 (6H, t, J=6.87 Hz).

Example 81

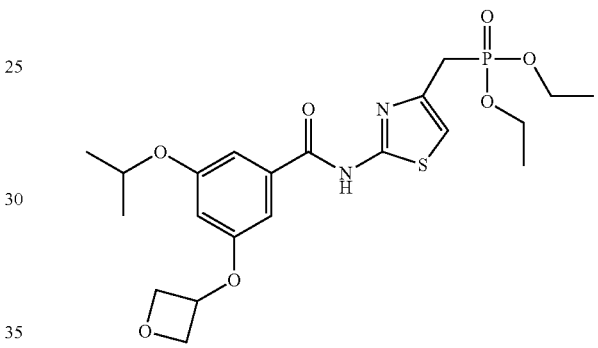

A.

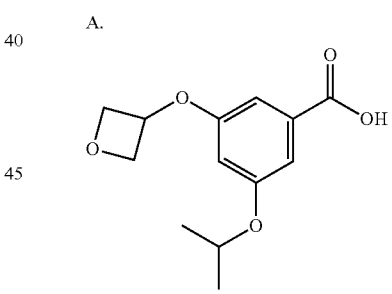

A mixture of methyl 3-hydroxy-5-isopropoxybenzoate (100 mg, 0.476 mmol), Example 71 Part E compound (180 mg, 0.789 mmol), and K$_2$CO$_3$ (1 g, 7.24 mmol) in DMF (5 mL) was stirred in a sealed tube at 115° C. for 18 h, then was cooled to RT. Solids were filtered off and washed with DMF. The combined filtrates were concentrated in vacuo. The residue was neutralized with TFA and purified by preparative HPLC (Phenomenex AXIA 5 μm C18 30×100 mm column; detection at 220 nm; flow rate=40 mL/min; continuous gradient from 30% A to 100% B over 10 min+1 min hold time at 100% B, where A=90:10:0.1 H$_2$O:MeOH:TFA and B=90:10: 0.1 MeOH:H$_2$O:TFA) to give Part A compound (100 mg, 83% yield) as a white solid. $^1$H NMR (400 MHz, CDCl$_3$) δ 1.35 (d, J=6.05 Hz, 6H), 4.59 (dt, J=12.09, 6.05 Hz, 1H), 4.77 (dd, J=7.42, 5.22 Hz, 2H), 5.01 (t, J=6.60 Hz, 2H), 5.19-5.27 (m, 1H), 6.52 (t, J=2.47 Hz, 1H), 6.94 (s, 1H), 7.27 (s, 1H).

B.

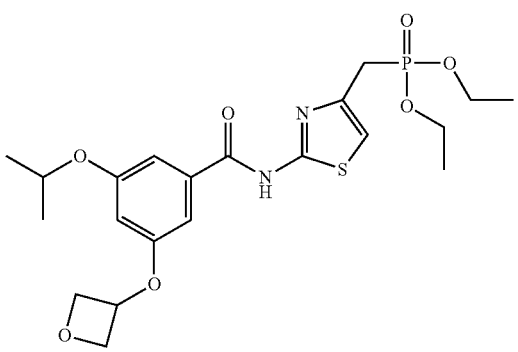

A mixture of Part A compound (21 mg, 0.083 mmol), Example 13 Part E compound (20.83 mg, 0.083 mmol), HOAt (20 mg, 0.145 mmol), EDCI (20 mg, 0.500 mmol), and DIPEA (0.2 mL, 1.148 mmol) in DMF (0.5 mL) was stirred at 25° C. for 18 h, then was concentrated in vacuo. The residue was neutralized with TFA and was purified by preparative HPLC (Phenomenex AXIA 5 μm C18 30×100 mm column; detection at 220 nm; flow rate=40 mL/min; continuous gradient from 30% A to 100% B over 10 min+1 min hold time at 100% B, where A=90:10:0.1 $H_2O$:MeOH:TFA and B=90:10:0.1 MeOH:$H_2O$:TFA) to give the title compound (28 mg, 0.058 mmol, 69.4% yield) as a clear wax. $[M+H]^+$=485.3; $^1H$ NMR (400 MHz, $CDCl_3$) δ 7.31 (1H, t, J=1.52 Hz), 6.96-7.01 (2H, m), 6.56 (1H, t, J=2.27 Hz), 5.28-5.35 (1H, m, J=5.53, 5.53, 5.49, 5.43 Hz), 5.03 (2H, t, J=6.95 Hz), 4.64-4.78 (3H, m), 4.13 (4H, dd, J=8.21, 7.20 Hz), 3.36 (1H, s), 3.30 (1H, s), 1.35 (6H, d, J=6.06 Hz), 1.30 (6H, t, J=7.07 Hz).

Example 82

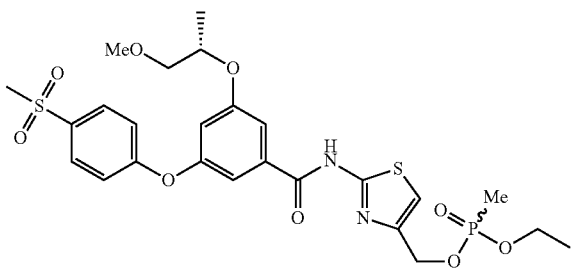

A.

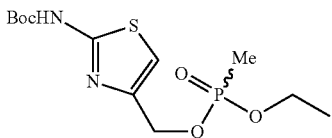

To a solution of tert-butyl 4-(chloromethyl)thiazol-2-yl-carbamate (249 mg, 1.00 mmol) and $CH_3P(OEt)_2$ (124.2 mg, 1.00 mmol) in MeCN (4.0 mL) under Ar at RT was added 18-crown-6 (52.9 mg, 0.2 mmol), $K_2CO_3$ (138.2 mg, 1.00 mmol), and (n-Bu)$_4$NI (74.0 mg, 0.20 mmol). The reaction mixture was heated at 55° C. for 2 h, then cooled to RT and quenched with saturated aqueous $NaHCO_3$. The mixture was extracted with EtOAc (2×). The combined organic extracts were washed with brine, dried ($MgSO_4$) and concentrated in vacuo. The residual oil was chromatographed ($SiO_2$; continuous gradient from 0% EtOAc/Hexane to 100% EtOAc/Hexane) to provide Part A compound (171 mg, 51% material balance, 90% purity by HPLC) as a colorless oil.

B.

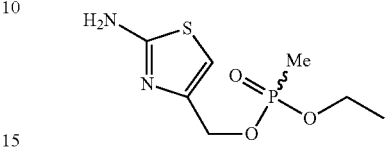

To a RT solution of Example 82 Part A compound (171 mg, ~0.51 mmol) in $CH_2Cl_2$ (1.5 mL) [Note: the flask was fitted with a $CaCl_2$-filled drying tube to protect from atmospheric moisture] was added TFA (0.5 mL). The reaction was stirred at RT for 14 h, then was concentrated in vacuo and then stripped from $CH_2Cl_2$. The oily residue was used without further purification or characterization for Part C.

C.

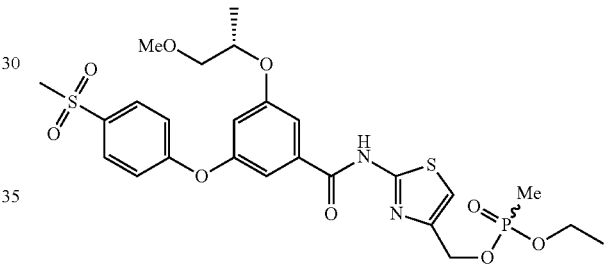

A RT solution of Example 26 Part C acid (193.4 mg, 0.51 mmol) in $CH_2Cl_2$ (2.0 mL) [Note: the flask was fitted with a $CaCl_2$-filled drying tube to protect from atmospheric moisture] was treated with oxalyl chloride (0.305 mL of a 2 M solution in $CH_2Cl_2$, 0.61 mmol) and DMF (0.020 mL). The reaction mixture was stirred at RT for 2 h, then was concentrated in vacuo, and re-dissolved in $CH_2Cl_2$ (2 mL). To this RT solution under Ar was added a solution of Part B compound in $CH_2Cl_2$ (2 mL), followed by $Et_3N$ (0.213 mL, 1.53 mmol). After 15 h at RT, the reaction mixture was diluted with $CH_2Cl_2$ and washed with sat. aqueous $NaHCO_3$. The organic extract was dried ($Na_2SO_4$) and concentrated in vacuo. The residue was purified by preparative HPLC (Phenomenex Luna 5u C18 30×250 mm column; detection at 220 nm; flow rate=30 mL/min; continuous gradient from 20% B to 100% B over 20 min+5 min hold time at 100% B, where A=90:10:0.1 $H_2O$:$CH_3CN$:TFA and B=10:90:0.1 $H_2O$:$CH_3CN$:TFA) to provide the title compound (33 mg, 11%) as a colorless thick oil. $[M+H]^+$=599.2; $^1H$ NMR (400 MHz, $CDCl_3$): δ 11.23 (br s, 1H), 7.92 (d, J=8.8 Hz, 2H), 7.57 (t, J=1.6 Hz, 1H), 7.47 (t, J=1.6 Hz, 1H), 7.13 (d, J=8.8 Hz, 2H), 6.95 (s, 1H), 6.87 (t, J=2.2 Hz, 1H), 5.22 (m, 2H), 4.68 (m, 1H), 4.05 (m, 2H), 3.56

(ddd, J=6.6, 10.5, 30.3 Hz, 2H), 3.39 (s, 1H), 3.09 (s, 1H), 1.51 (dd, J=13.7, 17.6 Hz, 3H), 1.34 (d, J=6.6 Hz, 3H), 1.27 (dt, J=2.2, 7.2 Hz, 3H).

Example 83

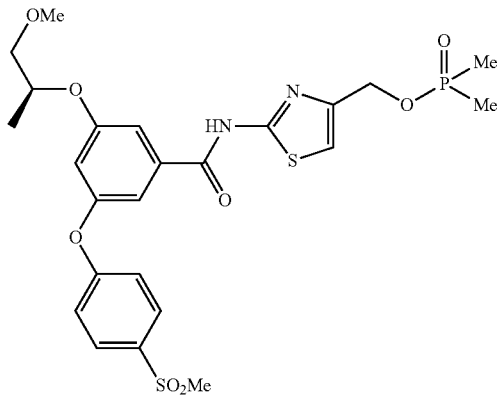

A.

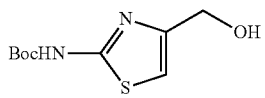

To a stirred solution of ethyl 2-(tert-butoxycarbonylamino) thiazole-4-carboxylate (2.24 g, 8.23 mmol) in $CH_2Cl_2$ (25 mL) under Ar at −78° C. was added a solution of DiBALH (25.5 mL, 1.0 M in $CH_2Cl_2$, 25.5 mmol) at such a rate as to keep the temperature≤−65° C. The reaction was stirred for 20 min at −65° C., then was allowed to warm to −30° C. After 30 min, the reaction mixture was quenched with 1 M sodium potassium tartrate solution (30 mL), warmed to RT and stirred for 2 h at RT. The mixture was filtered through Celite®, which was washed with $CH_2Cl_2$. The combined filtrates were dried ($Na_2SO_4$), and concentrated in vacuo. The resulting oil was chromatographed ($SiO_2$; continuous gradient from 0% EtOAc/Hexane to 100% EtOAc/Hexane) to provide Part A compound (1.66 g, 88% yield) as an amorphous white solid.

B.

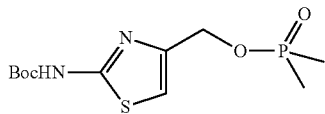

To a 0° C. solution of Part A compound (310 mg, 1.35 mmol) in $CH_2Cl_2$ (5 mL) under Ar was added dimethylphosphinic chloride (182 mg, 1.62 mmol), and then $Et_3N$ (0.244 mL, 1.75 mmol) over 2 min. The reaction was allowed to warm to RT and stirred at RT for 14 h, then was diluted with EtOAc. The mixture was washed with 1% aqueous HCl and brine. The organic phase was dried ($MgSO_4$) and concentrated in vacuo to give Part B compound as a colorless oil (413 mg, 100% crude). This material was used in the next step without further purification.

C.

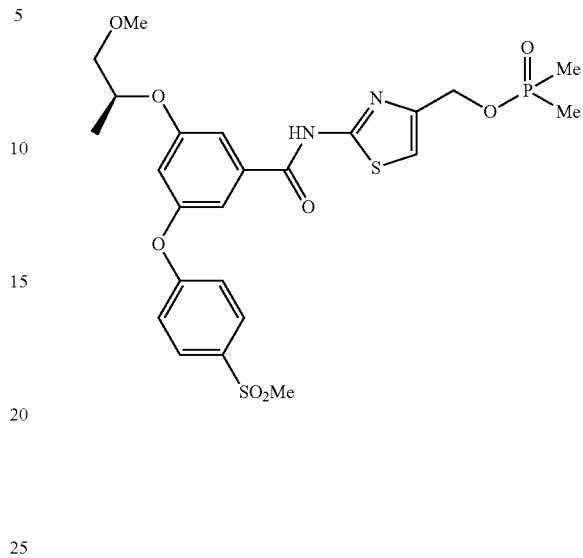

C1: To a stirred solution of Part B compound (410 mg, 1.34 mmol) in $CH_2Cl_2$ (3 mL) at RT [Note: the flask was fitted with a $CaCl_2$-filled drying tube to protect from atmospheric moisture] was added TFA (1 mL). The reaction was stirred for 14 h at RT, and the reaction mixture was concentrated in vacuo and re-dissolved in MeOH (5 mL). The solution was passed through 2 StratroSpheres™ PL-$HCO_3$ MP SPE cartridges (0.9 meq capacity), and the eluant was evaporated in vacuo to provide Part C1 compound. The resulting colorless oil (225 mg) was re-dissolved in $CH_2Cl_2$ (2 mL). One half (by weight) of this solution was used without further characterization for Part C2.

C2: To a stirred slurry of Example 26 Part C compound (152 mg, 0.40 mmol) and HOAt (54.5 mg, 0.40 mmol) in $CH_2Cl_2$ (2.4 mL) at RT under Ar was added EDC (76.3 mg, 0.40 mmol). A clear solution soon formed. After 30 min, the solution of Part C1 compound in $CH_2Cl_2$ from C1 was added, followed by $iPr_2NEt$ (0.028 mL, 0.20 mmol) and DMAP (5 mg, 0.04 mmol). The reaction was stirred for 16 h at RT, then was quenched with sat. aqueous $NH_4Cl$ and extracted twice with EtOAc. The combined organic extracts were dried ($Na_2SO_4$) and evaporated in vacuo to give an orange oil. The residue was purified by preparative HPLC (Phenomenex AXIA Luna 5u 30×75 mm column; detection at 220 nm; flow rate=40 mL/min; continuous gradient from 0% B to 100% B over 10 min+10 min hold time at 60% B, where A=90:10:0.1 $H_2O$: $CH_3CN$:TFA and B=10:90:0.1 $H_2O$:$CH_3CN$:TFA) to provide the title compound (28.9 mg, 13% yield) as a waxy white solid. $[M+H]^+$=569.0; $^1H$ NMR (400 MHz, $CDCl_3$) δ 11.75 (br s, 1H), 7.92 (d, J=8.8 Hz, 2H), 7.63 (t, J=2.2 Hz, 1H), 7.49 (t, J=1.9 Hz, 1H), 7.14 (d, J=8.8 Hz, 2H), 6.94 (s, 1H), 6.87 (t, J=2.2 Hz, 1H), 5.20 (d, J=7.7 Hz, 2H), 4.70 (m, 1H), 3.55 (ddd, J=6.0, 9.9, 30.2 Hz, 2H), 3.40 (s, 1H), 3.08 (s, 1H), 1.53 (dd, J=2.8, 14.3 Hz, 6H), 1.33 (d, J=6.6 Hz, 3H).

Example 84

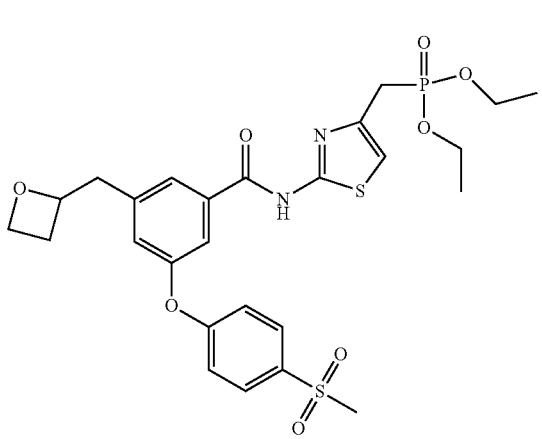

B.

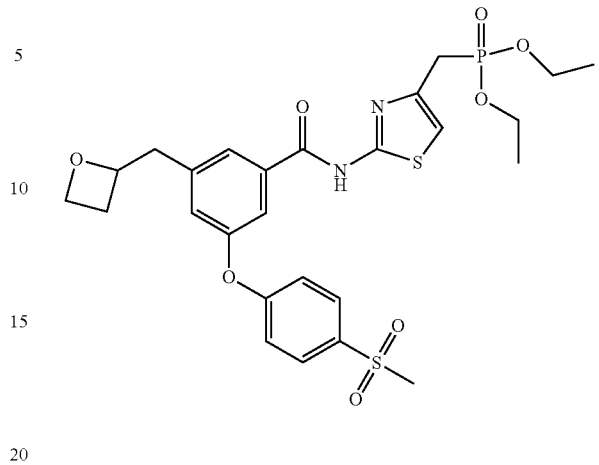

A.

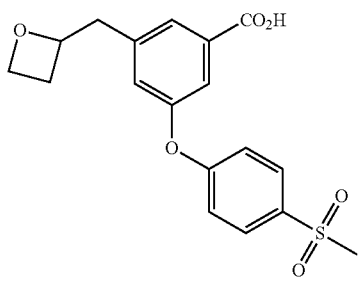

To a 0° C. solution of Example 26 Part A compound (100 mg, 0.310 mmol), Ph₃P (150 mg, 0.572 mmol), and oxetan-2-ylmethanol (40 mg, 0.454 mmol) in THF (5 mL) was added DIAD (0.2 mL, 1.029 mmol). The reaction was stirred at RT for 18 h, and volatiles were removed in vacuo. The residue was chromatographed (EtOAc/Hexane, 1:1) to give the crude methyl ester. To a solution of this material in MeOH (1 mL) was added 1N aqueous NaOH (1 mL). The reaction was stirred at RT for 2 h and then acidified with TFA and concentrated in vacuo. The residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10: 0.1 MeOH:H₂O:TFA) to give Part A compound (40 mg, 34.1% yield) as a white solid. [M+H]⁺=377.2; ¹H NMR (400 MHz, CDCl₃) δ 2.66-2.88 (m, 2H), 3.08 (s, 3H), 4.20 (d, J=3.85 Hz, 2H), 4.66-4.81 (m, 2H), 5.16-5.25 (m, 1H), 6.92 (t, J=2.47 Hz, 1H), 7.11 (d, J=8.79 Hz, 2H), 7.36 (d, J=2.20 Hz, 1H), 7.52 (dd, J=2.20, 1.10 Hz, 1H), 7.92 (d, J=8.79 Hz, 2H).

A mixture of Part A compound (15 mg, 0.040 mmol), Example 13 Part E compound (20 mg, 0.080 mmol), HOAt (20 mg, 0.145 mmol), EDCI (40 mg, 1.000 mmol) and DIPEA (0.2 mL, 1.148 mmol) in DMF (0.5 mL) was stirred at 25° C. for 18 h. The reaction mixture was concentrated in vacuo, and the crude residue was purified by preparative HPLC (Phenomenex AXIA 5u C18 30×100 mm column; detection at 220 nm; flow rate=40 mL/min; continuous gradient from 30% A to 100% B over 10 min+1 min hold time at 100% B, where A=90:10:0.1 H₂O:MeOH:TFA and B=90:10: 0.1 MeOH:H₂O:TFA) to provide the title compound (9.8 mg, 0.016 mmol, 39.7% yield) as a white solid. [M+H]⁺=611.3; ¹H NMR (400 MHz, CDCl₃) δ 7.93 (2H, d, J=8.79 Hz), 7.59 (1H, s), 7.39 (1H, s), 7.15 (2H, d, J=8.79 Hz), 6.94-6.98 (2H, m), 5.12-5.20 (1H, m), 4.62-4.78 (2H, m), 4.22-4.32 (2H, m), 4.06-4.17 (4H, m, J=7.35, 7.35, 7.28, 7.15 Hz), 3.32 (2H, d, J=20.89 Hz), 3.08 (3H, s), 2.64-2.86 (2H, m), 1.30 (6H, t, J=6.87 Hz).

Example 85

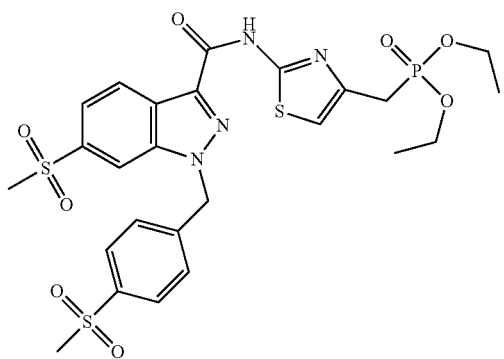

-continued

A.

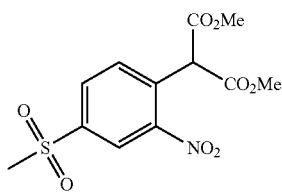

To a solution of KOtBu (17.1 mL, 17.1 mmol) in t-BuOH (10 mL) was added dropwise dimethyl malonate (2.0 mL, 17.1 mmol). To the resulting mixture was added a warm solution of 1-chloro-4-(methylsulfonyl) 2-nitrobenzene (2.0 g, 8.6 mmol) in t-BuOH (10 mL). The reaction mixture was heated at reflux for 15 h, then was cooled to RT and diluted with EtOAc (50 mL), washed with water and brine (30 mL each), dried (MgSO$_4$) and concentrated in vacuo to provide Part A compound (2.8 g, 100%).

B.

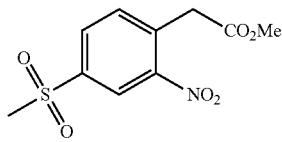

To a solution of Part A compound (2.8 g, 8.6 mmol) in DMSO (10 mL) was added NaCl (1.0 g, 17.1 mmol) and water (2 mL, 111 mmol). The mixture was heated at 120° C. for 5 h, then was cooled to RT and diluted with EtOAc (50 mL). The organic layer was washed with water and brine (35 mL each), dried (MgSO$_4$) and concentrated in vacuo. The residue was chromatographed (SiO$_2$; 30 min gradient from 100% to 0% hexane/EtOAc) to provide Part B compound (863 mg, 37% yield over 2 steps).

C.

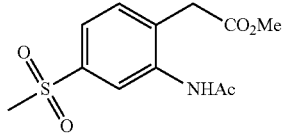

To a solution of Part B compound (830 mg, 3.0 mmol) and Ac$_2$O (2.0 mL, 21.6 mmol) in toluene (10 mL) was slowly added 10% Pd/C (200 mg, 1.7 mmol). The reaction was stirred under an atmosphere of H$_2$ (g) (1 atm) at RT for 4 h. The catalyst was filtered off and washed with toluene (2×). The combined filtrates were concentrated in vacuo to provide crude Part C compound (398 mg, 46%).

D.

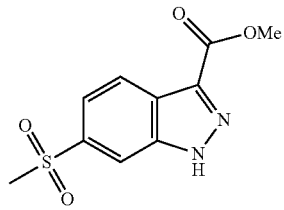

To a 90-95° C. solution of Part C compound (398 mg, 1.4 mmol) in AcOH (6 mL) was added dropwise t-butyl nitrite (0.18 mL, 1.5 mmol). The reaction was stirred at 95° C. for 30 min. The reaction was cooled to RT and was diluted with EtOAc (30 mL). The organic layer was washed with water (15 mL) and brine (15 mL), dried (MgSO$_4$), and concentrated in vacuo until a solid precipitated. This solid precipitate was collected by filtration and washed with toluene to give Part D compound (280 mg, 79% yield), which was used in the next step without further purification.

E.

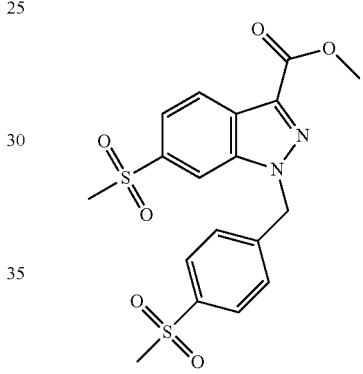

1

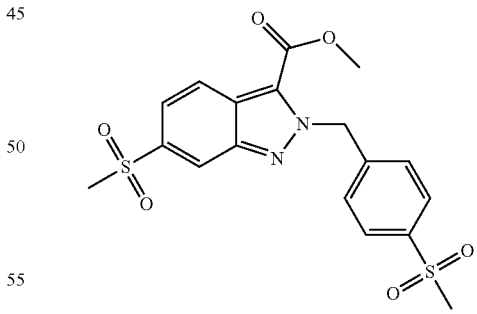

2

To a solution of Part D compound (30 mg, 0.12 mmol) in CH$_3$CN (1.5 mL) was added 1-(chloromethyl)-4-(methylsulfonyl)benzene (72.4 mg, 0.35 mmol), K$_2$CO$_3$ (48.9 mg, 0.35 mmol), and (n-Bu)$_4$NI (3.5 mg, 9.4 μmol). The reaction was stirred at 80° C. for 3 h, then cooled to RT. Solids were filtered off and washed with acetone. The combined filtrates were concentrated in vacuo to afford a mixture of the Part E compounds.

F.

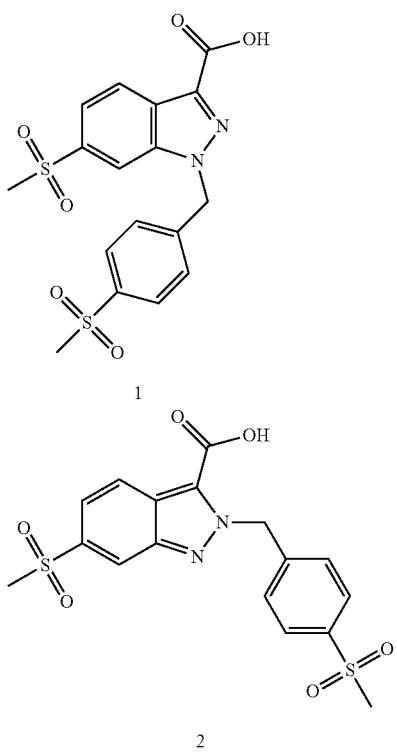

To a solution of Part E compounds (0.12 mmol theoretical yield) in THF (1 mL) was added 1N aqueous NaOH (0.4 mL, 0.40 mmol). The reaction was stirred at RT for 15 h., then was diluted with EtOAc (4 mL) and acidified with 1N aqueous HCl (0.45 mL). The organic layer was washed with brine, dried (MgSO$_4$) and concentrated in vacuo. The crude mixture was purified by preparative HPLC (Phenomenex Luna AXIA 30×100 mm column; detection at 220 nm; flow rate=25 mL/min; continuous gradient from 60% A to 100% B over 10 min, where A=90:10:0.1 H$_2$O:MeOH:TFA and B=90:10:0.1 MeOH:H$_2$O:TFA) to provide Part F1 compound (15.2 mg, 32% yield over 2 steps) and Part F2 compound (9.0 mg, 19% yield over 2 steps).

G.

To a solution of Part F1 compound (7 mg, 0.02 mmol) in CH$_2$Cl$_2$ (0.8 mL) was added oxalyl chloride (0.03 mL of a 2M solution in DCM, 0.05 mmol) and DMF (1.3 μL, 0.02 mmol). The reaction was stirred at RT for 1 h, then was concentrated in vacuo. The residue was taken up in THF (0.4 mL) and added to a solution of Example 13 Part E compound (17.2 mg, 0.07 mmol) and NaHCO$_3$ (7.2 mg, 0.09 mmol) in THF/H$_2$O (1:1, 0.8 mL). The reaction was stirred at RT for 2 h, then was diluted with EtOAc (4 mL) and water (1 mL). The organic layer was concentrated in vacuo. The residue was purified by preparative HPLC (Phenomenex Luna AXIA 30×100 mm column; detection at 220 nm; flow rate=40 mL/min; continuous gradient from 70% A to 100% B over 10 min, where A=90:10:0.1 H$_2$O:MeOH:TFA and B=90:10:0.1 MeOH:H$_2$O:TFA) to provide the title compound (0.63 mg, 5.7% yield) as a white solid. [M+H]$^+$=641.2; $^1$H NMR (400 MHz, CDCl$_3$) δ 8.63 (1H, d, J=8.35 Hz), 8.21 (1H, s), 7.96 (2H, d, J=8.35 Hz), 7.90 (1H, d, J=8.35 Hz), 7.63 (2H, d, J=8.35 Hz), 6.94-7.04 (1H, m), 5.81 (2H, s), 4.05-4.21 (4H, m), 3.35 (2H, d, J=21.09 Hz), 3.16 (3H, s), 3.05 (3H, s), 1.33 (6H, t, J=7.03 Hz).

Examples 86 to 92

The following Examples were synthesized from Example 85 Part D compound by employing the general synthetic route described for the preparation of Example 85 compound from Example 85 Part D compound.

| Example # | Structure | [M + H]$^+$ | $^1$H NMR | Yield and Description |
| --- | --- | --- | --- | --- |
| 86 | 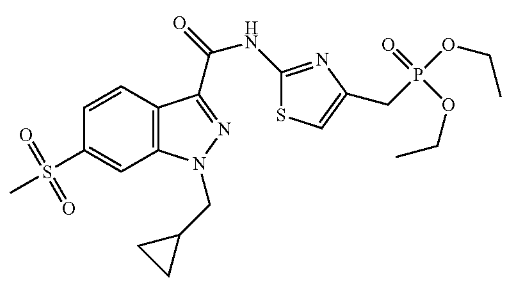 [SMILES: CCOP(=O)(Cc1csc(NC(=O)c2nn(CC3CC3)c3cc(S(C)(=O)=O)ccc23)n1)OCC] | 527.0 | (400 MHz, CDCl$_3$) δ 8.62 (1 H, d, J = 8.79 Hz), 8.24 (1 H, s), 7.86 (1 H, d, J = 8.35 Hz), 6.94 (1 H, d, J = 3.95 Hz), 4.41 (2 H, d, J = 7.03 Hz), 4.04-4.21 (4 H, m), 3.35 (2 H, d, J = 21.09 Hz), 3.16 (3 H, s), 1.41-1.52 (1 H, m), 1.32 (6 H, t, J = 7.03 Hz), 0.66-0.75 (2 H, m), 0.50-0.58 (2 H, m) | 4.0 mg (24% yield), white solid |

-continued

| Example # | Structure | [M + H]+ | 1H NMR | Yield and Description |
|---|---|---|---|---|
| 87 | 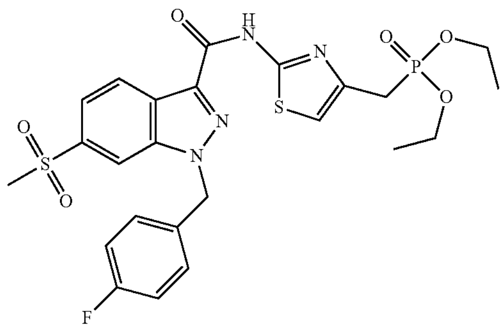 [SMILES: CCOP(=O)(Cc1csc(NC(=O)c2nn(Cc3ccc(F)cc3)c3cc(S(C)(=O)=O)ccc23)n1)OCC] | 581.1 | (400 MHz, CDCl3) δ 8.62 (1 H, d, J = 7.91 Hz), 8.18 (1 H, s), 7.79-7.89 (1 H, m), 7.34 (2 H, dd, J = 8.57, 5.05 Hz), 7.06 (2 H, t, J = 8.57 Hz), 6.92 (1 H, d, J = 3.52 Hz), 5.67 (2 H, s), 4.02-4.20 (4 H, m), 3.34 (2 H, d, J = 21.09 Hz), 3.13 (3 H, s), 1.31 (6 H, t, J = 7.03 Hz) | 8.5 mg (37% yield), grey solid |
| 88 | 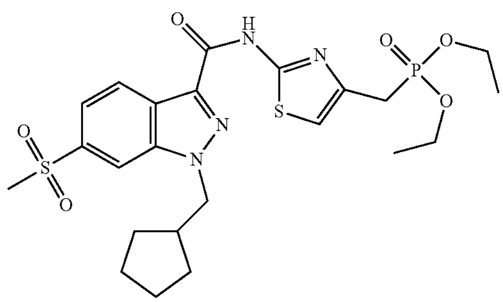 [SMILES: CCOP(=O)(Cc1csc(NC(=O)c2nn(CC3CCCC3)c3cc(S(C)(=O)=O)ccc23)n1)OCC] | 555.1 | (500 MHz, CDCl3) δ 8.60 (1 H, d, J = 7.70 Hz), 8.22 (1 H, s), 7.85 (1 H, d, J = 7.15 Hz), 6.96 (1 H, d, J = 3.85 Hz), 4.46 (2 H, d, J = 7.15 Hz), 4.06-4.21 (4 H, m), 3.35 (2 H, d, J = 20.89 Hz), 3.17 (3 H, s), 2.62-2.75 (1 H, m), 1.68-1.81 (4 H, m), 1.57-1.68 (2 H, m), 1.34-1.43 (2 H, m), 1.32 (6 H, t, J = 7.15 Hz) | 8.5 mg (40% yield), white solid |
| 89 | 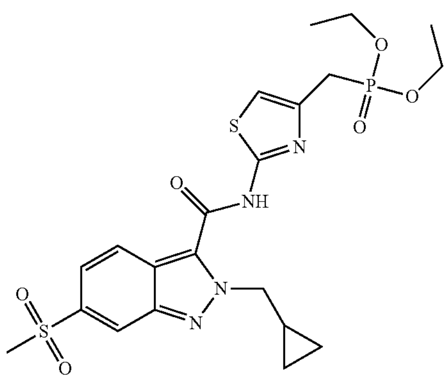 [SMILES: CCOP(=O)(Cc1csc(NC(=O)c2c3ccc(S(C)(=O)=O)cc3nn2CC2CC2)n1)OCC] | 527.0 | (500 MHz, CDCl3) δ ppm 8.56 (1 H, s), 8.05 (1 H, d, J = 8.80 Hz), 7.75 (1 H, d, J = 9.35 Hz), 7.07 (1 H, d, J = 3.30 Hz), 4.77 (2 H, d, J = 7.15 Hz), 4.08-4.24 (4 H, m), 3.38 (2 H, d, J = 21.44 Hz), 3.12 (3 H, s), 1.46-1.63 (1 H, m), 1.26-1.37 (6 H, m), 0.51-0.65 (4 H, m) | 3.0 mg (21% yield), oil |
| 90 | 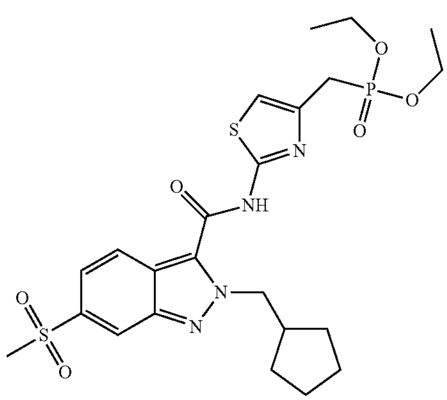 [SMILES: CCOP(=O)(Cc1csc(NC(=O)c2c3ccc(S(C)(=O)=O)cc3nn2CC2CCCC2)n1)OCC] | 555.1 | (500 MHz, CDCl3) δ 8.54 (1 H, s), 8.06 (1 H, d, J = 8.80 Hz), 7.74 (1 H, d, J = 9.35 Hz), 7.05 (1 H, d, J = 3.30 Hz), 4.87 (2 H, d, J = 7.70 Hz), 4.09-4.21 (4 H, m), 3.36 (2 H, d, J = 21.44 Hz), 3.12 (3 H, s), 2.56-2.71 (1 H, m), 1.64-1.76 (4 H, m), 1.51-1.63 (2 H, m), 1.35-1.43 (2 H, m), 1.32 (6 H, t, J = 7.15 Hz) | 3.5 mg (29% yield), oil |

| Example # | Structure | [M + H]+ | 1H NMR | Yield and Description |
|---|---|---|---|---|
| 91 | 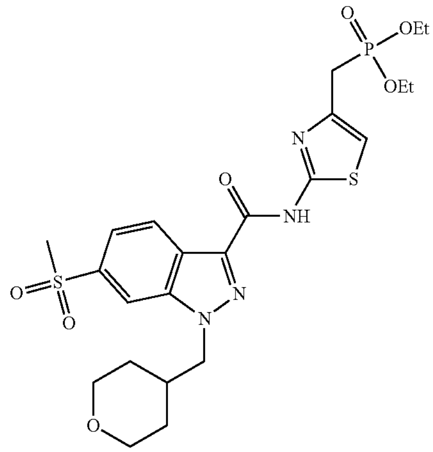 [SMILES: CCOP(=O)(Cc1csc(NC(=O)c2nn(CC3CCOCC3)c3cc(S(C)(=O)=O)ccc23)n1)OCC] | 571.3 | (500 MHz, CDCl3) δ 8.57 (1 H, d, J = 8.25 Hz), 8.22 (1 H, s), 7.88 (1 H, d, J = 9.90 Hz), 7.04 (1 H, d, J = 3.85 Hz), 4.43 (2 H, d, J = 7.15 Hz), 4.12-4.24 (4 H, m), 4.01 (2 H, dd, J = 11.55, 2.75 Hz), 3.43-3.49 (2 H, m), 3.40 (2 H, d, J = 21.44 Hz), 3.18 (3 H, s), 2.51-2.68 (1 H, m), 1.43-1.64 (4 H, m), 1.34 (6 H, t, J = 7.15 Hz) | 10.5 mg (37% yield), grey solid |
| 92 | 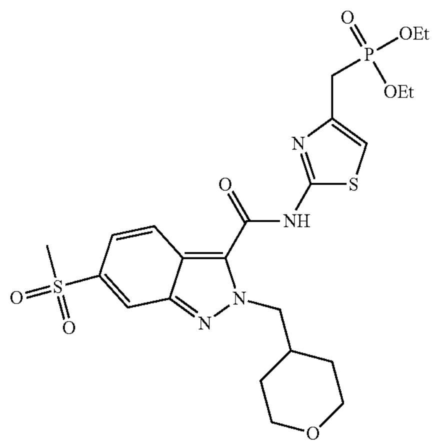 [SMILES: CCOP(=O)(Cc1csc(NC(=O)c2c3ccc(S(C)(=O)=O)cc3nn2CC2CCOCC2)n1)OCC] | 571.3 | (500 MHz, CDCl3) δ 8.55 (1 H, s), 8.04 (1 H, d, J = 8.80 Hz), 7.76 (1 H, d, J = 10.45 Hz), 7.12 (1 H, d, J = 3.85 Hz), 4.81 (2 H, d, J = 7.15 Hz), 4.13-4.28 (4 H, m), 3.99-4.08 (2 H, m), 3.33-3.48 (4 H, m), 3.13 (3 H, s), 2.32-2.53 (1 H, m), 1.48-1.65 (4 H, m), 1.36 (6 H, t, J = 6.87 Hz) | 4.8 mg (24% yield), yellow oil |

Example 93

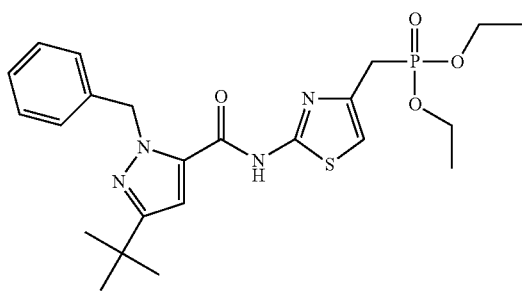 [SMILES: CCOP(=O)(Cc1csc(NC(=O)c2cc(C(C)(C)C)nn2Cc2ccccc2)n1)OCC]

To a solution of Example 13 Part E compound (50 mg, 0.20 mmol) in DCM (1 mL) was added 1-benzyl-3-tert-butyl-1H-pyrazole-5-carbonyl chloride (71.9 mg, 0.26 mmol) and pyridine (0.02 mL, 0.26 mmol). The reaction was stirred at RT for 16 h, then was concentrated in vacuo. The residue was purified by preparative HPLC (Phenomenex Luna AXIA 30×100 mm column; detection at 220 nm; flow rate=40 mL/min; continuous gradient from 50% A to 100% B over 10 min, where A=90:10:0.1 H2O:MeOH:TFA and B=90:10:0.1 MeOH:H2O:TFA) to give the title compound (64 mg, 65% yield) as an oil. [M+H]+=491.1; 1H NMR (400 MHz, CDCl3) δ 7.31 (1H, s), 7.17-7.30 (5H, m), 6.96 (1H, d, J=3.52 Hz), 5.81 (2H, s), 4.05-4.19 (4H, m), 3.31 (2H, d, J=21.09 Hz), 1.36 (9H, s), 1.29 (6H, t, J=7.03 Hz).

Example 94

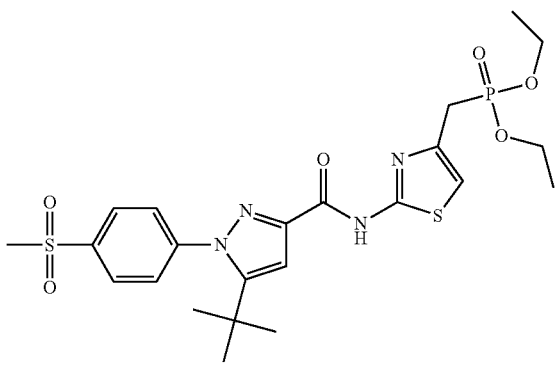

A.

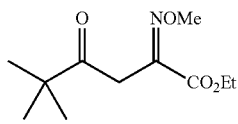

To a solution of ethyl trimethylacetopyruvate (205 mg, 1.02 mmol) in dry EtOH (1 mL) was added O-methylhydroxylamine hydrochloride (90 mg, 1.07 mmol) and 3 Å mol. sieves. The reaction was stirred at RT for 15 h, then was filtered and washed with EtOH. The filtrated was concentrated in vacuo, and the residue was partitioned between $Et_2O$ and sat. aqueous $NaHCO_3$. The $Et_2O$ layer was washed with water and brine, dried ($MgSO_4$) and concentrated in vacuo to give Part A compound (176 mg, 75%) as a red-orange oil.

B.

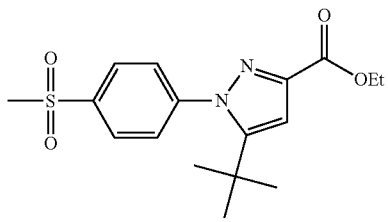

1

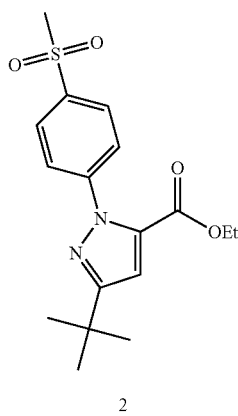

2

To a solution of Part A compound (176 mg, 0.77 mmol) in AcOH:EtOH (1.5 mL) was added (4-(methylsulfonyl)phenyl)hydrazine (286 mg, 1.54 mmol). The reaction was stirred at 90° C. for 10 h, then was cooled to RT. The reaction mixture was concentrated in vacuo, and the residue was partitioned between EtOAc and 0.2 N aqueous HCl. The organic layer was washed with water and brine, dried ($MgSO_4$) and concentrated in vacuo. The residue was chromatographed ($SiO_2$; 15 min gradient from 0% EtOAc/Hexanes to 100% EtOAc/Hexanes) to provide Part B1 compound (214 mg, 80%) and Part B2 compound (20 mg, 7%).

C.

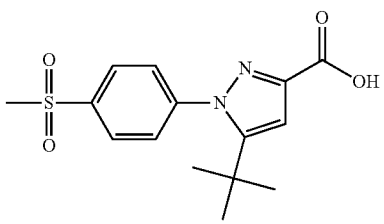

To a solution of the Part B1 compound (23 mg, 0.07 mmol) in THF (1 mL) was added 1N aqueous NaOH. The mixture was stirred at RT for 15 h, then was diluted with EtOAc (4 mL) and acidified with 1N aqueous HCl (0.5 mL). The organic layer was washed with brine, dried ($MgSO_4$) and concentrated in vacuo to give crude Part C compound (23 mg, 109% recovery).

D.

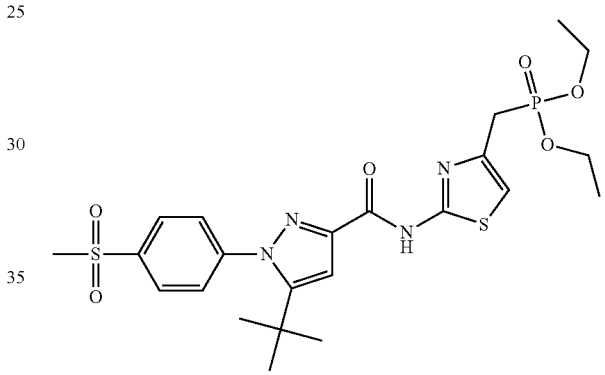

To a solution of Part C compound (21.3 mg, 0.07 mmol) in DMF (1 mL) was added Example 13 Part E compound (33.0 mg, 0.13 mmol), EDCI (25.3 mg, 0.13 mmol), HOBT (20.2 mg, 0.13 mmol), and Hunig's Base (0.034 mL, 0.20 mmol). The reaction mixture was stirred at RT for 4 days and was purified directly by preparative HPLC (Phenomenex Luna AXIA 30×100 mm column; detection at 220 nm; flow rate=40 mL/min; continuous gradient from 50% A to 100% B over 10 min, where A=90:10:0.1 $H_2O$:MeOH:TFA and B=90:10:0.1 MeOH:$H_2O$:TFA) to provide the title compound (14 mg, 38% yield) as a yellow oil. $[M+H]^+=555.1$; $^1H$ NMR (500 MHz, $CDCl_3$) δ 8.11 (2H, d), 7.71 (2H, d, J=8.25 Hz), 6.99

(1H, s), 6.98 (1H, d, J=3.85 Hz), 4.10-4.18 (4H, m), 3.98 (1H, s), 3.35 (2H, d, J=21.44 Hz), 3.13 (3H, s), 1.30 (6H, t, J=7.15 Hz), 1.27 (9H, s).

Example 95

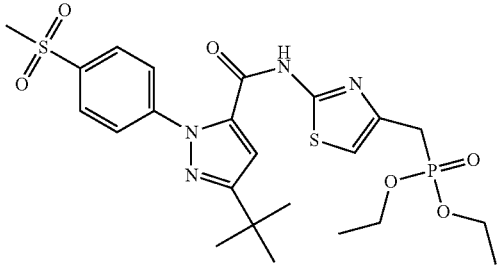 [SMILES: CCOP(=O)(Cc1csc(NC(=O)c2cc(C(C)(C)C)nn2-c2ccc(S(C)(=O)=O)cc2)n1)OCC]

The title compound (10 mg, 32% yield, brown solid) was synthesized from Example 94 Part B2 compound using the procedure employed in Example 94. [M+H]⁺=555.1; ¹H NMR (500 MHz, CDCl₃) δ 8.04 (2H, d, J=8.80 Hz), 7.68 (2H, d, J=8.80 Hz), 7.49 (1H, s), 7.01 (1H, d, J=3.85 Hz), 4.15-4.22 (4H, m), 3.37 (2H, d, J=21.44 Hz), 3.11 (3H, s), 1.40 (9H, s), 1.34 (6H, t, J=6.87 Hz).

Example 96

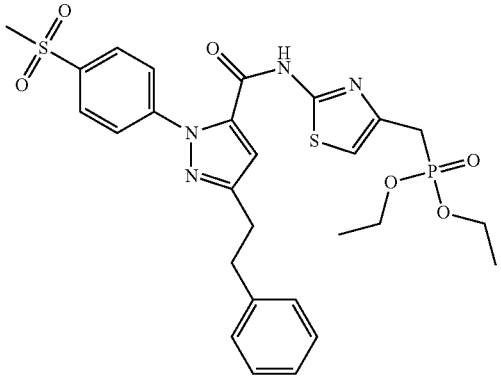

A.

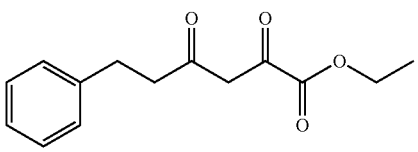

To a 0° C. solution of benzylacetone (0.54 mL, 3.6 mmol) and diethyl oxalate (0.53 mL, 3.9 mmol) in dry EtOH (6 mL) was added NaOEt (0.31 mL, 3.9 mmol). The reaction was slowly warmed to RT and stirred for 15 h at RT, then was diluted with EtOAc (20 mL) and washed with brine. The organic layer was dried (MgSO₄) and concentrated in vacuo to provide Part A compound (0.65 g, 73% yield) as a yellow oil.

B.

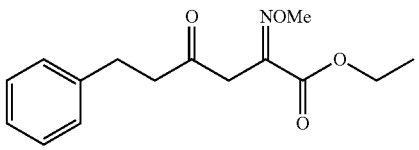

To a solution of the Part A compound (0.65 g, 2.6 mmol) in dry EtOH (5 mL) was added O-methylhydroxylamine hydrochloride (0.31 g, 3.7 mmol) and 3 A mol.sieves (2 g). The reaction was stirred at RT for 15 h, then was filtered and washed with EtOH. The combined filtrates were concentrated in vacuo, and the residue was partitioned between Et₂O and sat. aqueous NaHCO₃. The Et₂O layer was washed with water and brine, dried (MgSO₄) and concentrated in vacuo. The residue was chromatographed (SiO₂; 16 min gradient from 0% EtOAc/Hexanes to 100% EtOAc/Hexanes) to provide Part B compound (117 mg, 16%).

C.

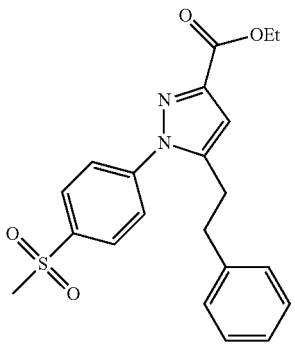

1

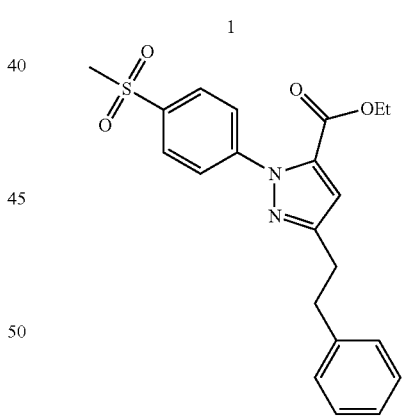

2

To a solution of Part B compound (117 mg, 0.42 mmol) in AcOH:EtOH (1.5 mL) was added (4-(methylsulfonyl)phenyl)hydrazine (157 mg, 0.84 mmol). The reaction was stirred at 100° C. for 10 h, then was cooled to RT and concentrated in vacuo. The residue was partitioned between EtOAc and 0.2N aqueous HCl. The organic layer was washed with water and brine, dried (MgSO₄), filtered, and concentrated in vacuo. The residue was chromatographed (SiO₂; 22 min continuous gradient from 0% EtOAc/Hexanes to 100% EtOAc/Hexanes) to give Part C1 compound (20 mg, 12%) and Part C2 compound (95 mg, 57%).

D.

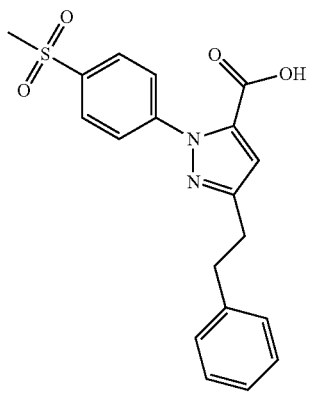

To a solution of Part C2 compound (28 mg, 0.07 mmol) in THF (1 mL) was added aqueous NaOH (0.3 mL of a 1 M solution, 0.30 mmol). The reaction was stirred at RT for 15 h, then was diluted with EtOAc (4 mL) and acidified with 1N aqueous HCl (0.5 mL). The organic layer was washed with brine, dried (MgSO$_4$) and concentrated in vacuo to give Part D compound (29 mg, 111% crude).

E.

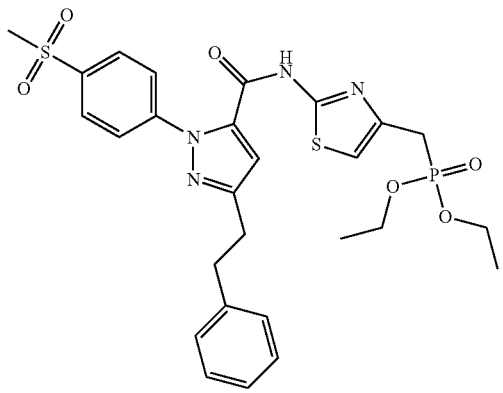

To a solution of the Part D compound (25.9 mg, 0.07 mmol) in DMF (1 mL) was added Example 13 Part E compound (35.0 mg, 0.14 mmol), EDCI (26.8 mg, 0.14 mmol), HOBT (21.4 mg, 0.14 mmol) and Hunig's Base (0.037 mL, 0.21 mmol). The reaction was stirred at RT for 2 days, then was concentrated in vacuo. The residue was purified directly by preparative HPLC (Phenomenex Luna AXIA 30×100 mm column; detection at 220 nm; flow rate=40 mL/min; continuous gradient from 50% A to 100% B over 10 min, where A=90:10:0.1 H$_2$O:MeOH:TFA and B=90:10:0.1 MeOH:H$_2$O:TFA) to provide the title compound (7 mg, 17% yield) as a grey solid. [M+H]$^+$=603.0; $^1$H NMR (500 MHz, CDCl$_3$) δ 8.04 (2H, d, J=8.80 Hz), 7.67 (2H, d, J=8.25 Hz), 7.18-7.36 (5H, m), 7.14 (1H, br. s.), 6.90 (1H, s), 4.01-4.17 (4H, m), 3.32 (2H, d, J=21.44 Hz), 3.00-3.15 (7H, m), 1.22-1.35 (6H, m).

Example 97

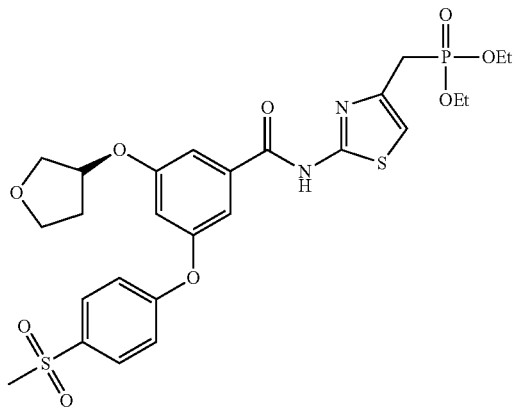

A.

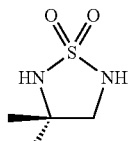

To a refluxing solution of sulfamide (6.09 mL; 102.0 mmol) in anhydrous pyridine (109.0 mL) was added dropwise 2-methylpropane-1,2-diamine (10.7 mL; 102.0 mmol) over 30 min via syringe pump. The reaction mixture was refluxed for 16 h, then was cooled to RT and concentrated in vacuo. The residue was triturated with hexanes until the filtrate was nearly colorless. The resulting solid was dried in vacuo to give Part A compound (14.89 g, 97%) as a beige solid.

B.

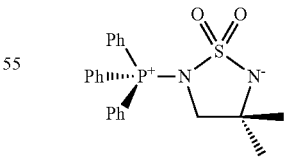

To a stirred solution of Ph$_3$P (26.0 g; 99.0 mmol) and Part A compound (14.89 g; 99.0 mmol) in anhydrous THF (300 mL) was added DIAD (19.3 mL; 99.0 mmol) dropwise over 5 min under Ar. The reaction mixture was stirred at RT for 16 h. The resulting off-white solid was filtered off, washed with anhydrous THF and anhydrous Et$_2$O, then dried in vacuo to give Part B compound (36.68 g, 90%) as an off-white solid.

C.

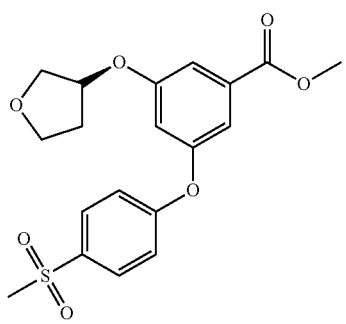

To a suspension of Part B compound (1.4 g, 3.5 mmol) in DCM (6 mL) was added a solution of Example 26A compound (141 mg, 0.44 mmol) and (R)-(−)-3-hydroxytetrahydrofuran (0.08 mL, 1.0 mmol) in toluene (2 mL). The reaction was stirred at RT for 15 h, then was diluted with EtOAc, and washed with water and brine. The organic layer was dried (MgSO$_4$), filtered, and concentrated in vacuo. The residue was chromatographed (SiO$_2$; 19 min gradient from 0% EtOAc/Hexanes to 100% EtOAc/0% Hexanes) to provide Part C compound (254 mg, 148% yield).

D.

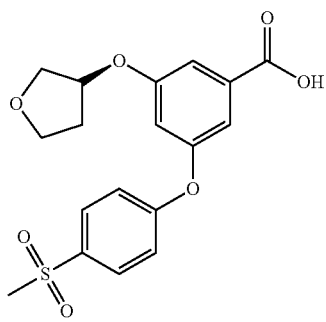

To a mixture of the Part C compound (254 mg, 0.65 mmol) in THF (2 mL) was added 1N aqueous NaOH (1 mL, 1.0 mmol). The reaction was stirred at RT for 15 h, then was diluted with EtOAc (6 mL) and acidified with 1N aqueous HCl (0.5 mL). The organic layer was washed with brine, dried (MgSO$_4$) and concentrated in vacuo. The residue was purified by preparative HPLC (Phenomenex Luna AXIA 30×100 mm column; detection at 220 nm; flow rate=40 mL/min; continuous gradient from 70% A to 100% B over 10 min, where A=90:10:0.1 H$_2$O:MeOH:TFA and B=90:10:0.1 MeOH:H$_2$O:TFA) to give the Part D compound (90 mg, 54% yield over 2 steps) as a colorless oil.

E.

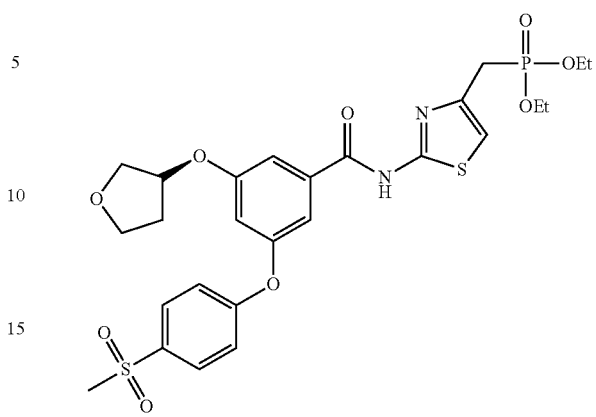

To a solution of Part D compound (43.0 mg, 0.11 mmol) in DMF (1 mL) was added Example 13 Part E compound (56.9 mg, 0.23 mmol), EDCI (43.6 mg, 0.23 mmol), HOBT (34.8 mg, 0.23 mmol), and Hunig's Base (0.059 mL, 0.34 mmol). The reaction was stirred at RT for 24 h and was purified directly by preparative HPLC (Phenomenex Luna AXIA 30×100 mm column; detection at 220 nm; flow rate=40 mL/min; continuous gradient from 70% A to 100% B over 10 min, where A=90:10:0.1 H$_2$O:MeOH:TFA and B=90:10:0.1 MeOH:H$_2$O:TFA) to provide the title compound (36 mg, 52% yield) as a white solid. [M+H]$^+$=611.3; $^1$H NMR (500 MHz, CDCl$_3$) δ 7.94 (2H, d, J=8.80 Hz), 7.63 (1H, s), 7.49 (1H, s), 7.16 (2H, d, J=8.80 Hz), 7.07 (1H, d, J=3.85 Hz), 6.91 (1H, s), 5.22-5.33 (1H, m), 4.12-4.24 (4H, m), 3.85-4.08 (4H, m), 3.37 (2H, d, J=20.89 Hz), 3.08 (3H, s), 2.08-2.41 (2H, m), 1.34 (6H, t, J=7.15 Hz).

Example 98

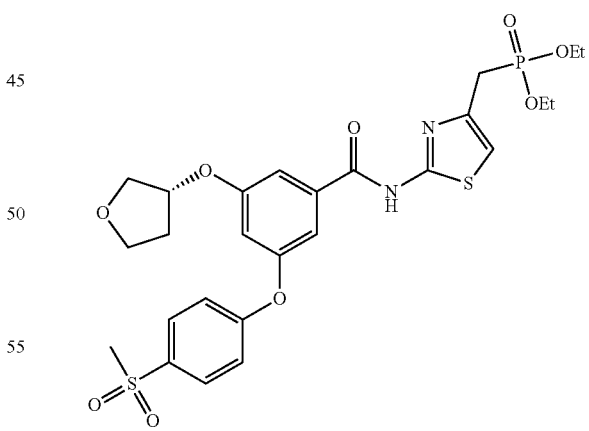

The title compound (10 mg, 16% yield, white solid) was prepared from (S)-(+)-3-hydroxytetrahydrofuran employing the same procedure as described for the synthesis of Example 97 compound. [M+H]$^+$=611.3; $^1$H NMR (500 MHz, CDCl$_3$) δ 7.94 (2H, d, J=8.80 Hz), 7.57 (1H, s), 7.44 (1H, s), 7.16 (2H, d, J=8.80 Hz), 7.00 (1H, d, J=3.30 Hz), 6.89 (1H, s), 5.15-5.26

(1H, m), 4.06-4.19 (4H, m), 3.86-4.06 (4H, m), 3.32 (2H, d, J=20.89 Hz), 3.08 (3H, s), 2.06-2.39 (2H, m), 1.30 (6H, t, J=7.15 Hz).

Example 99

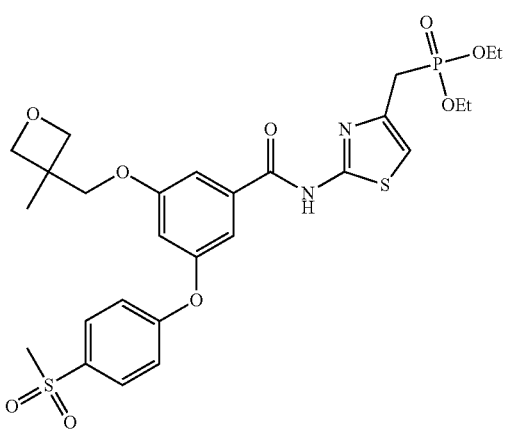 [SMILES: CCOP(=O)(Cc1csc(NC(=O)c2cc(OCC3(C)COC3)cc(Oc3ccc(S(C)(=O)=O)cc3)c2)n1)OCC]

The title compound (24 mg, 42% yield, white solid) was prepared from 3-Methyl-3-Oxetane-methanol employing the same procedure as described for the synthesis of Example 97 compound. [M+H]+=625.3; 1H NMR (500 MHz, CDCl3) δ 7.94 (2H, d, J=8.80 Hz), 7.70 (1H, s), 7.51 (1H, s), 7.13-7.20 (2H, m), 7.07 (1H, d, J=3.30 Hz), 6.97 (1H, s), 4.70 (2H, d, J=6.05 Hz), 4.51 (2H, d, J=6.05 Hz), 4.13-4.26 (6H, m), 3.98 (1H, s), 3.38 (2H, d, J=21.44 Hz), 3.08 (3H, s), 1.47 (3H, s), 1.34 (6H, t, J=7.15 Hz).

Example 100

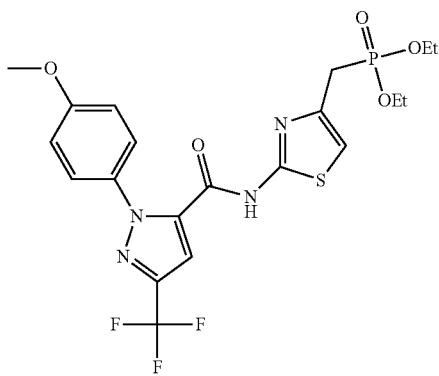 [SMILES: CCOP(=O)(Cc1csc(NC(=O)c2cc(C(F)(F)F)nn2-c2ccc(OC)cc2)n1)OCC]

To a solution of 1-(4-methoxyphenyl)-3-(trifluoromethyl)-1H-pyrazole-5-carboxylic acid (61 mg, 0.213 mmol) [see WO 1998/57937] in DMF (1 ml), was added Example 13 Part E compound (107 mg, 0.426 mmol), EDC (82 mg, 0.426 mmol), HOBT (65.3 mg, 0.426 mmol), and DIPEA (0.111 ml, 0.639 mmol). The reaction mixture was stirred at RT for 4 days. The reaction mixture was purified directly by preparative HPLC (Phenomenex Luna AXIA 30×100 mm column; detection at 220 nm; flow rate=40 mL/min; continuous gradient from 50% B to 100% B over 10 min, where A=90:10:0.1 H2O:MeOH:TFA and B=90:10:0.1 MeOH:H2O:TFA) to provide the title compound (13 mg, 12% yield) as a grey solid.

[M+H]+=519.0; 1H NMR (400 MHz, CDCl3) δ 7.59 (1H, s), 7.33-7.46 (2H, m), 6.91-7.02 (2H, m), 6.80 (1H, d, J=3.52 Hz), 3.99-4.15 (4H, m), 3.86 (3H, s), 3.51 (2H, d, J=21.53 Hz), 1.26 (6H, t, J=7.03 Hz).

Example 101

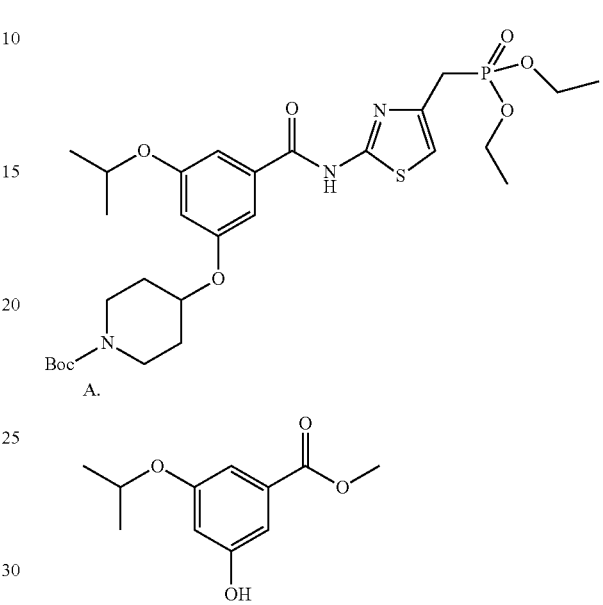

A.

To a solution of methyl 3,5-dihydroxybenzoate (2.7 g, 16.06 mmol) in CH3CN (35 mL) was added K2CO3 (2.70 g, 19.54 mmol), followed by slow addition of 2-bromopropane (1.975 g, 16.06 mmol). The reaction mixture was heated to 80° C. for 3 days. The reaction mixture was diluted with water and extracted with EtOAc (3×). The combined organic layer was washed H2O and brine, dried (MgSO4), filtered, and concentrated in vacuo. The residue was purified by column chromatography (SiO2; continuous gradient 15% EtOAc/Hex to 60% EtOAc/Hexane) to give Part A compound (1.22 g, 36% yield) as yellow solid. [M+H]+=211.0; 1H NMR (400 MHz, CDCl3) δ 1.33 (d, J=6.15 Hz, 6H), 3.89 (s, 3H), 4.51-4.62 (m, 1H), 5.21 (s, 1H), 6.59 (t, J=2.42 Hz, 1H), 7.08-7.12 (m, 1H), 7.13-7.17 (m, 1H).

B.

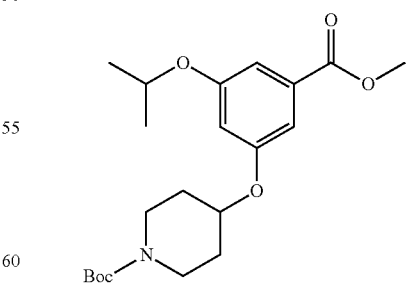

To a solution of Part A compound (300 mg, 1.427 mmol) and tert-butyl 4-hydroxypiperidine-1-carboxylate (1.15 g, 5.7 mmol) in toluene (2 mL) was added a suspension of Example 97B compound (2.34 g, 5.7 mmol) in DCM (2 mL). The reaction mixture was stirred at RT for 3 h, then was concentrated in vacuo. The residue was chromatographed (SiO₂; continuous gradient from 10% EtOAc/Hex to 60% EtOAc/Hexane) to give Part B compound (490 mg, 87%) as a light yellow solid. [M+H]⁺=294.0; ¹H NMR (500 MHz, CDCl₃) δ 1.32 (d, J=6.05 Hz, 6H), 1.45 (s, 9H), 1.66-1.78 (m, 2H), 1.85-1.96 (m, 2H), 3.26-3.38 (m, 3H), 3.62-3.72 (m, 3H), 3.86-3.90 (m, 3H), 4.44-4.51 (m, 1H), 4.52-4.62 (m, 1H), 6.61 (t, J=2.20 Hz, 1H), 7.10-7.19 (m, 2H).

C.

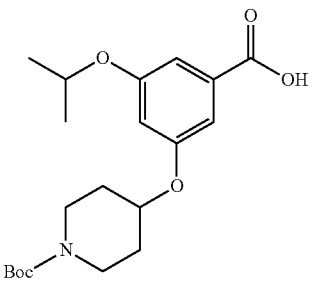

To a 0° C. solution of Part B compound (490 mg, 1.245 mmol) in THF/water (1/1, 4 mL) was added LiOH.H₂O (209 mg, 4.98 mmol). The mixture was stirred at RT for 18 h, then was diluted with EtOAc and acidified with 1N aqueous HCl to pH ~4-5. The aqueous layer was extracted with EtOAc (2×). The combined organic extracts were washed with 1N aqueous HCl, H₂O, and brine, dried (MgSO₄) and concentrated in vacuo to provide Part C compound (440 mg, 93% yield) as a white solid. [M+H]⁺=561.1.

D.

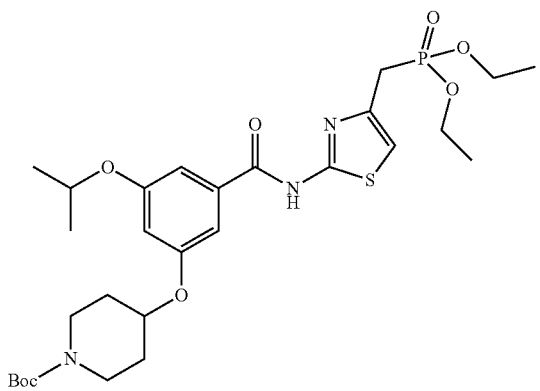

To a solution of Part C compound (200 mg, 0.527 mmol) and Example 13 Part E compound (132 mg, 0.527 mmol) (buffered with DIEA) in DCM/DMF (1/1) were successively added HOAT (201 mg, 1.476 mmol), EDCI (202 mg, 1.054 mmol), and DIEA (641 µL, 3.69 mmol). The reaction mixture was stirred at RT for 18 h, then was diluted with DCM. The organic layer was washed with water (2×) and brine, dried (MgSO₄) and concentrated in vacuo. The residue was chromatographed (SiO₂; continuous gradient 0% DCM/MeOH to 5% DCM/MeOH) to give the title compound (140 mg, 43% yield) as a white solid. [M+H]⁺=612; ¹H NMR (500 MHz, CDCl₃) δ 1.26 (t, J=7.15 Hz, 6H), 1.33 (d, J=6.05 Hz, 6H), 1.45 (s, 9H), 1.63 (s, 2H), 1.67-1.80 (m, 2H), 1.92 (dd, J=12.65, 3.85 Hz, 2H), 3.21-3.39 (m, 4H), 3.63-3.76 (m, 2H), 4.00-4.14 (m, 4H), 4.44-4.53 (m, 1H), 4.53-4.62 (m, 1H), 6.63 (t, J=2.20 Hz, 1H), 6.84 (d, J=3.85 Hz, 1H), 8.00 (s, 1H).

Example 102

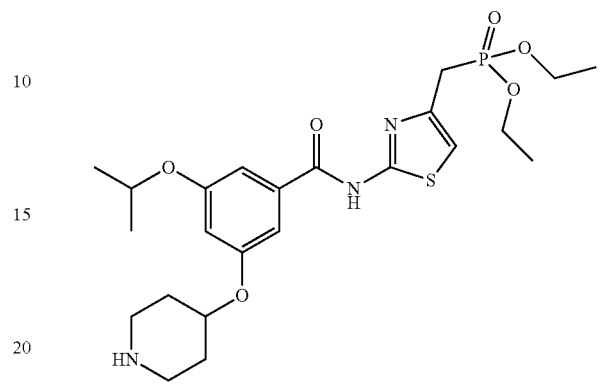

To a solution of Example 101 compound (15 mg, 0.025 mmol) in DCM (0.5 mL) was added TFA (0.15 mL). The reaction mixture was stirred at RT for 2 h, then was concentrated in vacuo. The residue was purified by preparative HPLC (Phenomenex AXIA 5u C18 30×100 mm column; detection at 220 nm; flow rate=40 mL/min; continuous gradient from 35% B to 100% B over 10 min, where A=90:10:0.1 H₂O:MeOH:TFA and B=90:10:0.1 MeOH:H₂O:TFA) give the title compound (11 mg, 85% yield) as a white solid. [M+H]⁺=512; ¹H NMR (500 MHz, CDCl₃) δ 1.29 (t, J=7.15 Hz, 6H), 1.33 (d, J=5.50 Hz, 6H), 2.08-2.16 (m, 2H), 2.16-2.26 (m, 2H), 3.22 (d, J=9.90 Hz, 2H), 3.30 (d, J=21.44 Hz, 2H), 3.35 (d, J=7.70 Hz, 2H), 4.02-4.17 (m, 4H), 4.60-4.73 (m, 1H), 4.82 (s, 1H), 6.69 (t, J=2.20 Hz, 1H), 6.96 (d, J=3.30 Hz, 1H), 7.36 (d, J=8.80 Hz, 2H), 9.37 (s, 1H), 9.47 (s, 1H).

Example 103

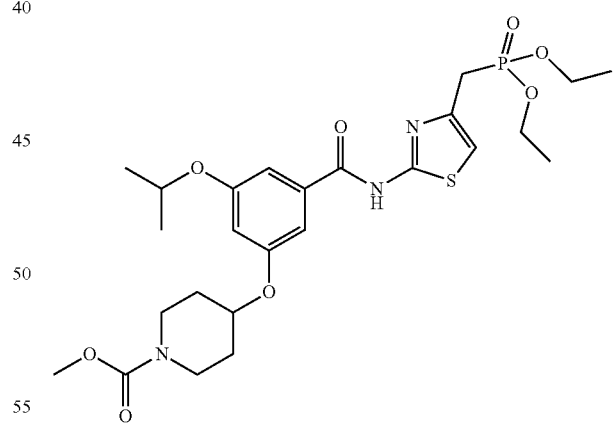

To a solution of Example 102 compound (30 mg, 0.059 mmol) in THF (1 mL) and sat. aqueous NaHCO₃ (1 mL) was added methyl chloroformate (6.77 µL, 0.088 mmol). The reaction mixture was stirred at RT for 18 h, then was diluted with EtOAc. The aqueous layer was extracted with EtOAc (2×), and the combined organic extracts were concentrated in vacuo. The residue was purified by preparative HPLC (Phenomenex AXIA 5u C18 30×100 mm column; detection at 220 nm; flow rate=40 mL/min; continuous gradient from 35% B to 100% B over 10 min, where A=90:10:0.1 H₂O:MeOH:TFA and B=90:10:0.1 MeOH:H₂O:TFA) to give the title compound (16 mg, 48% yield) as a white solid. [M+H]⁺=570.3; ¹H NMR (500 MHz, CDCl₃) δ 1.30 (t, J=7.15 Hz, 6H), 1.33 (d, J=6.05 Hz, 6H), 1.76 (s, 2H), 1.91 (s, 2H), 3.31 (d, J=20.89 Hz, 2H), 3.31 (d, J=20.89 Hz, 2H), 3.44 (s, 2H), 3.66 (d, J=5.50 Hz, 2H), 3.69 (s, 3H), 4.10-4.17 (m, 4H), 4.64-4.75 (m, 2H), 6.69 (t, J=2.20 Hz, 1H), 7.01 (d, J=3.30 Hz, 1H), 7.33 (dd, J=4.67, 1.92 Hz, 2H).

Example 104

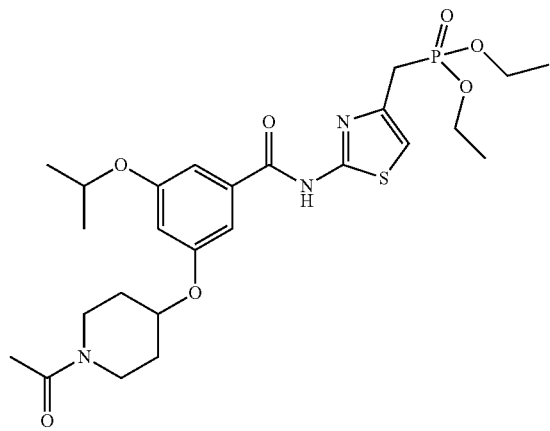 [SMILES: CCOP(=O)(Cc1csc(NC(=O)c2cc(OC(C)C)cc(OC3CCN(C(C)=O)CC3)c2)n1)OCC]

To a solution of Example 102 compound (30 mg, 0.059 mmol) in DCM (1 mL) was added pyridine (0.1 mL) and acetyl chloride (6.90 mg, 0.088 mmol). The reaction was stirred at RT for 18 h, then was diluted with EtOAc. The aqueous layer was extracted with EtOAc (2×), and the combined organic extracts were concentrated in vacuo. The residue was purified by preparative HPLC (Phenomenex AXIA 5u C18 30×100 mm column; detection at 220 nm; flow rate=40 mL/min; continuous gradient from 35% B to 100% B over 10 min, where A=90:10:0.1 H₂O:MeOH:TFA and B=90:10:0.1 MeOH:H₂O:TFA) to give the title compound (22 mg, 68% yield) as a white solid. [M+H]⁺=554.4; ¹H NMR (500 MHz, CDCl₃) δ 1.34 (t, J=7.15 Hz, 6H), 1.36 (d, J=6.05 Hz, 6H), 1.79-2.04 (m, 4H), 2.17 (s, 3H), 3.36 (d, J=21.44 Hz, 2H), 3.43-3.54 (m, 1H), 3.63-3.86 (m, 3H), 4.12-4.24 (m, 4H), 4.68-4.86 (m, 2H), 6.73 (s, 1H), 7.06 (d, J=3.30 Hz, 2H), 7.39 (s, 2H).

Example 105

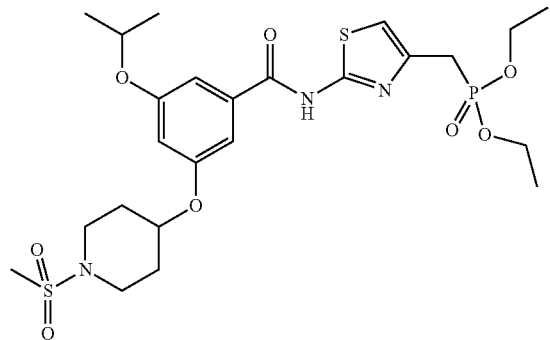 [SMILES: CCOP(=O)(Cc1csc(NC(=O)c2cc(OC(C)C)cc(OC3CCN(S(C)(=O)=O)CC3)c2)n1)OCC]

A solution of Example 102 compound (50 mg, 0.098 mmol) and Et₃N (10 mg, 0.098 mmol) in DCM (0.5 mL) was added to a solution of methanesulfonyl chloride (11.20 mg, 0.098 mmol) in DCM (0.5 mL). The reaction was stirred at RT for 18 h, then was diluted with EtOAc. The aqueous layer was extracted with EtOAc (2×), and the combined organic extracts were concentrated in vacuo. The residue was purified by preparative HPLC (Phenomenex AXIA 5 μm C18 30×100 mm column; detection at 220 nm; flow rate=40 mL/min; continuous gradient from 35% B to 100% B over 10 min, where A=90:10:0.1 H₂O:MeOH:TFA and B=90:10:0.1 MeOH:H₂O:TFA) to give the title compound (19.5 mg, 34% yield) as a colorless oil. [M+H]⁺=590.3; ¹H NMR (500 MHz, CDCl₃) δ 1.28-1.38 (m, 12H), 1.93-2.10 (m, 4H), 2.97 (s, 3H), 3.29-3.40 (m, 6H), 4.12-4.22 (m, 4H), 4.68-4.75 (m, 2H), 6.70 (t, J=2.20 Hz, 1H), 7.03 (d, J=3.85 Hz, 1H), 7.337 (d, 1.10 Hz, 2H).

Example 106

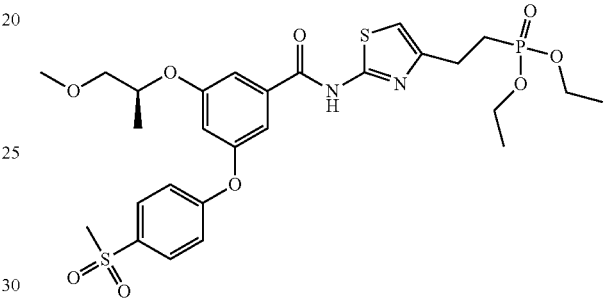

To a solution of Example 26 Part C compound (25.0 mg; 0.066 mmol), Example 18 Part D compound (20.9 mg; 0.079 mmol), and HOAt (10.3 mg; 0.076 mmol) in DMF (0.25 mL) were successively added DIPEA (13.2 μL; 0.076 mmol) and EDAC (14.6 mg; 0.076 mmol). The reaction was stirred at RT for 20 h, then was partitioned between EtOAc (4 mL) and H₂O (3 mL). The organic layer was washed with 0.5 N aqueous HCl (3 mL), sat. aqueous NaHCO₃ (3 mL), and brine (3 mL), dried (MgSO₄) and concentrated in vacuo. The residue was purified by preparative HPLC (YMC reverse phase ODS-A-5 μm 20×100 mm column; flow rate=20 mL/min, 15 to 100% solvent B over 10 min, hold to 14 min, where solvent A=90:10:0.1 H₂O:MeOH:TFA and solvent B=90:10:0.1 MeOH:H₂O:TFA) to give the title compound (22.0 mg; 54%) as a light yellow solid. [M+H]⁺=627.1; ¹H NMR (400 MHz, CDCl₃): δ 1.34 (m, 9H), 2.19 (m, 2H), 3.07 (m, 5H), 3.41 (s, 3H), 3.57 (m, 2H), 4.12 (m, 4H), 4.89 (m, 1H), 6.81 (s, 1H), 6.94 (s, 1H), 7.15 (d, 2H), 7.44 (s, 1H), 7.69 (s, 1H), 7.92 (d, 2H).

Example 107

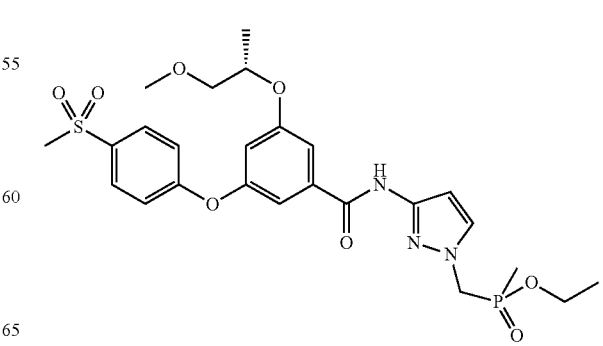

The title compound (20 mg, 65% yield, white solid) was prepared from racemic-ethyl (3-amino-1H-pyrazol-1-yl)methyl(methyl) phosphinate employing the same general sequence as used to prepare Example 58. [M+H]+=566.3; 1H NMR (400 MHz, CD3OD): δ 1.33 (d, J=6.6 Hz, 3H), 1.34 (t, J=6.6 Hz, 3H), 1.57 (d, J=14.3 Hz, 3H), 3.01 (s, 3H), 3.42 (s, 3H), 3.53-3.63 (m, 2H), 4.08-4.21 (m, 2H), 4.52 (dd, J=2.4, 6.0 Hz, 2H), 4.71 (m, 1H), 6.86 (d, J=2.2 Hz, 1H), 7.03 (s, 1H), 7.14 (d, J=8.8 Hz, 2H), 7.24 (s, 1H), 7.39 (s, 1H), 7.52 (d, J=2.2 Hz, 1H), 7.91 (d, J=8.8 Hz, 2H).

Example 108

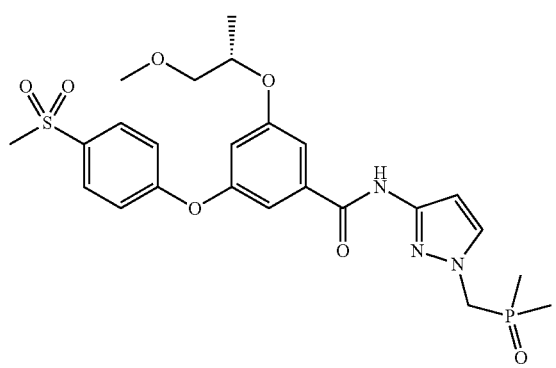

A.

To a stirred 10° C. solution of chloromethyl(methyl)phosphinic chloride (2 g, 13.61 mmol) in Et2O (10 mL) was added dropwise MeMgBr (4.54 mL of a 3 M solution in Et2O, 13.61 mmol). The reaction turned cloudy and gummy, then was slowly warmed to RT for 1 h. Volatiles were removed in vacuo and the residue was carefully quenched with sat. aqueous NaHCO3 and extracted with CHCl3 (4×). The combined organic extracts were dried (MgSO4) and concentrated in vacuo. To the resulting clear oil was added hexanes (50 mL); a white precipitate formed. The precipitated was filtered to collect the white solid (crystalline, fine needles) as Part A compound (360 mg, 21%).

B.

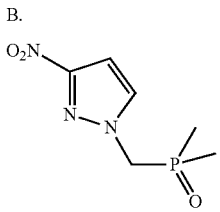

To a stirred solution of 3-nitro-1H-pyrazole (45 mg, 0.398 mmol) in DMF (2 mL) was added K2CO3 (70 mg, 0.506 mmol) and Part A compound (70 mg, 0.553 mmol). The reaction was stirred at 75° C. for 16 h, then was cooled to RT and partitioned between EtOAc and saturated aqueous NH4Cl. The aqueous layer was extracted with CHCl3 (10×), and the combined organic extracts were dried (MgSO4) and concentrated in vacuo to give Part B compound (50 mg, 62% yield) as a white solid.

C.

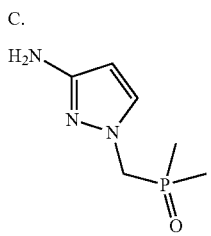

To a stirred solution of Part B compound (50 mg, 0.246 mmol) in MeOH (3 mL) was added Pd/C (26.2 mg, 0.025 mmol). The reaction was stirred under an atmosphere of H2 (balloon) for 1 h, then was filtered through Celite® and concentrated in vacuo to give Part C compound (35 mg, 82%) as a light yellow oil.

D.

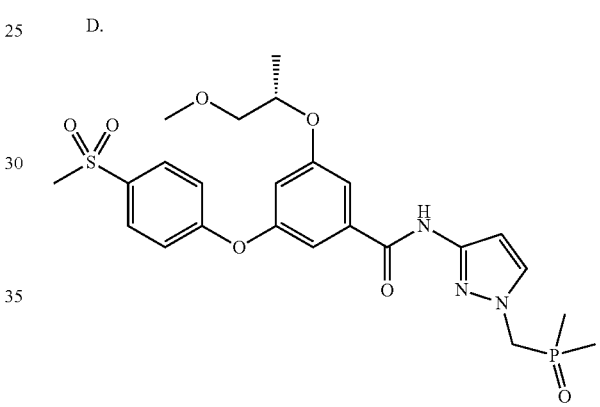

To a stirred solution of Example 26 Part C acid (77 mg, 0.202 mmol) in DMF (2 mL) was added HOBT (55.0 mg, 0.404 mmol), EDC (77 mg, 0.404 mmol), and Hunig's Base (0.106 mL, 0.606 mmol). The reaction was stirred at RT for 30 min, after which Part C compound (35 mg, 0.202 mmol) was added. The reaction was stirred at RT for 20 h, then was partitioned between 1N aqueous HCl and CH2Cl2. The organic phase was washed with sat. aqueous NH4Cl and brine, dried (MgSO4) and concentrated in vacuo. The residue was purified by preparative HPLC (Luna 5 μm 21.2×100 mm column; flow rate=20 mL/min, 0 to 100% solvent B over 12 min, hold to 15 min, where solvent A=90:10:0.1 H2O:MeOH:TFA and solvent B=90:10:0.1 MeOH:H2O:TFA) to give the title compound (59 mg, 55% yield) as a white solid. [M+H]+=536.3; 1H NMR (400 MHz, CD3OD): δ 1.31 (d, J=6.9 Hz, 3H), 1.64 (d, J=13.2 Hz, 6H), 2.99 (s, 3H), 3.40 (s, 3H), 3.48-3.61 (m, 2H), 4.60 (d, J=6.6 Hz, 2H), 4.68 (m, 1H), 6.84 (s, 1H), 6.96 (d, J=2.2 Hz, 1H), 7.11 (d, J=8.8 Hz, 2H), 7.21 (s, 1H), 7.34 (s, 1H), 7.52 (d, J=2.2 Hz, 1H), 7.88 (d, J=8.8 Hz, 2H).

Example 109

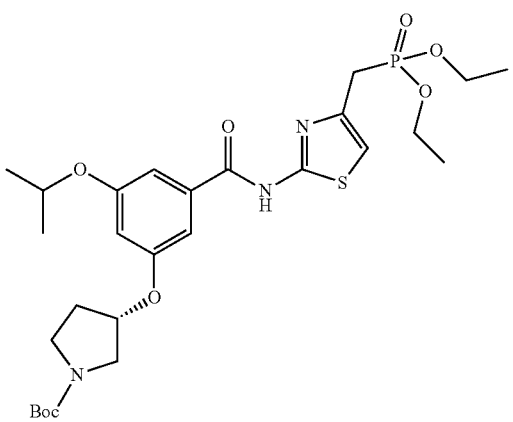 [SMILES: CCOP(=O)(Cc1csc(NC(=O)c2cc(OC(C)C)cc(O[C@H]3CCN(C(=O)OC(C)(C)C)C3)c2)n1)OCC]

A.

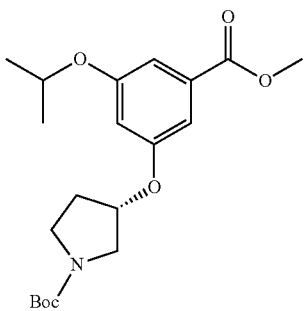

To a solution of Example 101 Part A compound (300 mg, 1.427 mmol) and (R) tert-butyl-3-hydroxypyrrolidine-carboxylate (534 mg, 2.85 mmol) in toluene (2 mL) was added a suspension of Example 97 Part B compound (1.17 g, 2.85 mmol) in DCM (2 mL). The reaction mixture was stirred at RT for 3 h, then was concentrated in vacuo. The residue was chromatographed (SiO$_2$; continuous gradient 10% EtOAc/Hex to 60% EtOAc/Hexane) to give Part A compound (500 mg, 92%) as a white solid. [M+H]$^+$=402; $^1$H NMR (400 MHz, CDCl$_3$) δ 1.25 (d, J=6.15 Hz, 6H), 1.39 (d, J=7.47 Hz, 9H), 1.95-2.22 (m, 2H), 3.25-3.46 (m, 4H), 3.47-3.58 (m, 1H), 3.82 (s, 3H), 4.61-4.73 (m, 1H), 5.07 (s, 1H), 6.76 (t, J=2.42 Hz, 1H), 7.00 (s, 1H), 7.03 (s, 1H).

B.

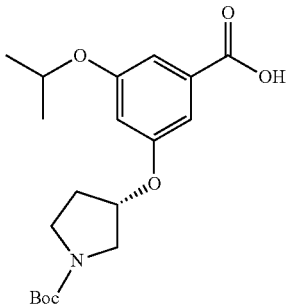

To a 0° C. solution of Part A compound (500 mg, 1.318 mmol) in THF/water (1/1, 4 mL) was added LiOH.H$_2$O (270 mg, 6.59 mmol). The mixture was stirred at RT for 18 h, then was diluted with EtOAc and acidified with 1N aqueous HCl to pH ~4-5. The aqueous layer was extracted with EtOAc (2×). The combined organic extracts were washed with 1N aqueous HCl, H$_2$O, and brine, dried (MgSO$_4$) and concentrated in vacuo to provide Part B compound (480 mg, 100% yield) as a white solid. MS [M−H]$^-$=364.4.

C.

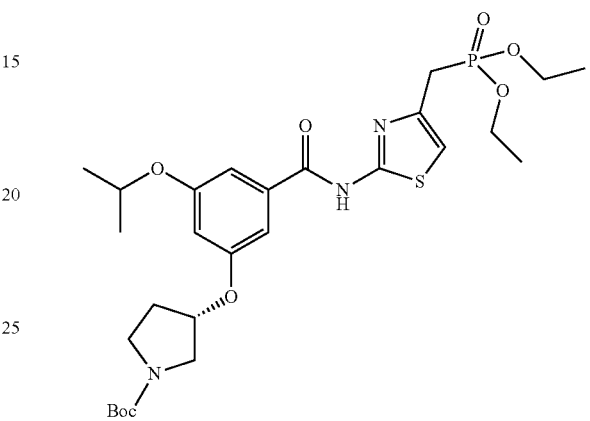

To a solution of Part B compound (200 mg, 0.547 mmol) and Example 13 Part E compound (137 mg, 0.547 mmol) in DCM/DMF (1/1; buffered with DIEA) were successively added HOAT (208 mg, 1.53 mmol), EDCI (210 mg, 1.094 mmol), and DIPEA (665 µL, 3.83 mmol). The reaction mixture was stirred at RT for 18 h, then was diluted with DCM. The organic phase was washed with water (2×) and brine, dried (MgSO$_4$), and concentrated in vacuo. The residue was chromatographed (SiO$_2$; continuous gradient from 0% DCM/MeOH to 5% DCM/MeOH) to give the title compound (160 mg, 49% yield) as a white solid. [M+H]$^+$=598.3; $^1$H NMR (500 MHz, CDCl$_3$) δ 1.26 (t, J=7.15 Hz, 6H), 1.33 (d, J=6.05 Hz, 6H,) 1.45 (s, 9H), 1.64 (s, 2H), 2.02-2.24 (m, 2H), 3.28 (d, J=21.44 Hz, 2H), 3.41-3.70 (m, 4H), 4.01-4.16 (m, 4H), 4.51-4.63 (m, 1H), 6.98 (s, 1H), 7.03 (s, 1H), 9.71 (s, 1H).

Example 110

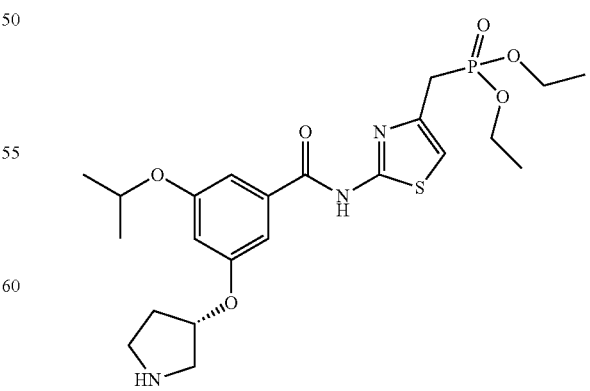

The title compound (10.4 mg, 71% yield, white solid) was prepared from Example 109 compound employing the same general sequence as used to prepare Example 102. [M+H]⁺=498.0; ¹H NMR (500 MHz, CDCl₃) δ 1.24-1.29 (m, 6H), 1.32 (d, J=6.05 Hz, 6H), 2.22-2.44 (m, 2H), 3.26 (d, J=21.44 Hz, 2H), 4.01-4.16 (m, 4H), 4.58-4.70 (m, 1H), 5.24 (s, 1H), 6.66 (s, 1H), 6.93 (d, J=3.30 Hz, 1H), 7.29 (s, 1H), 7.33 (s, 1H), 9.81 (s, 1H), 10.30 (s, 1H).

Example 111

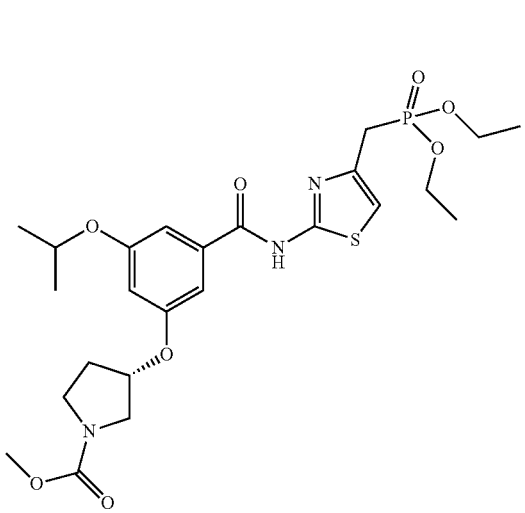 [SMILES: CCOP(=O)(Cc1csc(NC(=O)c2cc(OC(C)C)cc(O[C@H]3CCN(C(=O)OC)C3)c2)n1)OCC]

The title compound (22.5 mg, 68% yield, colorless oil) was prepared from Example 110 compound employing the same general sequence as used to prepare Example 103. [M+H]⁺=556.3; ¹H NMR (500 MHz, CDCl₃) δ 1.29-1.35 (m, 12H), 2.13 (s, 1H), 2.20 (s, 1H), 3.35 (d, J=21.44 Hz, 2H), 3.48-3.65 (m, J=28.04 Hz, 4H), 3.70 (d, J=11.55 Hz, 4H), 4.13-4.20 (m, 4H), 4.64-4.74 (m, 1H), 5.14 (s, 1H), 6.66 (t, J=1.92 Hz, 1H), 7.03 (d, J=3.30 Hz, 1H), 7.31-7.41 (m, 2H).

Example 112

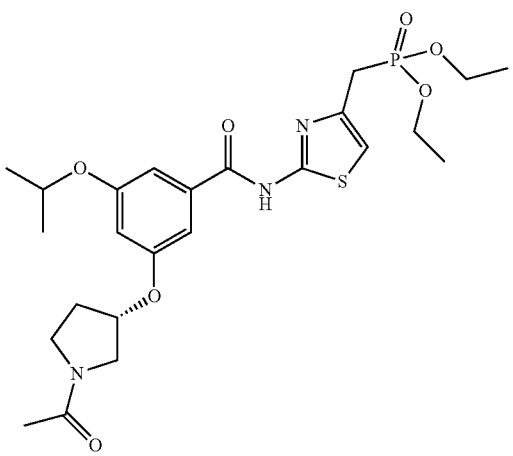 [SMILES: CCOP(=O)(Cc1csc(NC(=O)c2cc(OC(C)C)cc(O[C@H]3CCN(C(C)=O)C3)c2)n1)OCC]

The title compound (24 mg, 74% yield, light yellow oil) was prepared from Example 110 compound employing the same general sequence as used to prepare Example 104. [M+H]⁺=540.4; ¹H NMR (500 MHz, CDCl₃) δ 1.32-1.35 (m, 6H), 1.35-1.39 (m, 6H), 2.09-2.20 (m, J=23.09 Hz, 3H), 2.21-2.43 (m, 2H), 3.37 (d, J=21.44 Hz, 2H), 3.55-3.92 (m, 4H), 4.13-4.24 (m, 4H), 4.66-4.76 (m, 1H), 5.19-5.30 (m, 1H), 6.67-6.72 (m, 1H), 7.07 (d, J=3.85 Hz, 1H), 7.39 (s, 1H), 7.40-7.44 (m, 1H).

Example 113

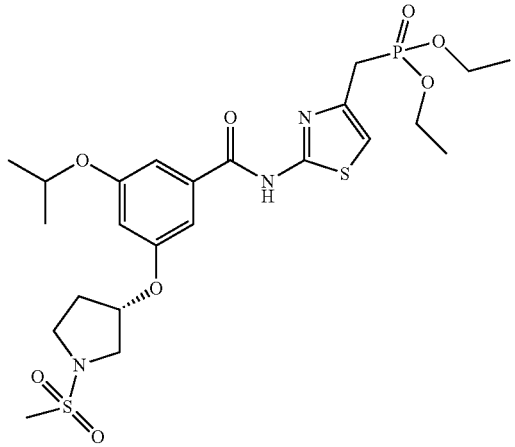 [SMILES: CCOP(=O)(Cc1csc(NC(=O)c2cc(OC(C)C)cc(O[C@H]3CCN(S(C)(=O)=O)C3)c2)n1)OCC]

The title compound (28 mg, 43% yield, white solid) was prepared from Example 110 compound employing the same general sequence as used to prepare Example 105. [M+H]⁺=576.3; ¹H NMR (500 MHz, CDCl₃) δ 1.32 (t, J=7.15 Hz, 6H), 1.35 (dd, J=6.05, 1.10 Hz, 6H), 2.17-2.37 (m, 2H), 2.83 (s, 3H), 3.34 (d, J=20.89 Hz, 2H), 3.42-3.52 (m, 1H), 3.54-3.71 (m, 3H), 4.11-4.23 (m, 4H), 4.65-4.77 (m, 1H), 5.16 (s, 1H), 6.64 (t, J=2.20 Hz, 1H), 7.35 (s, 1H), 7.41 (d, J=3.30 Hz, 1H).

Example 114

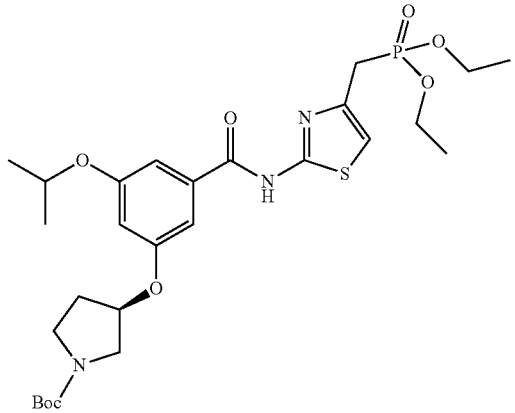 [SMILES: CCOP(=O)(Cc1csc(NC(=O)c2cc(OC(C)C)cc(O[C@@H]3CCN(C(=O)OC(C)(C)C)C3)c2)n1)OCC]

The title compound (176 mg, 32% yield, white solid) was prepared from (S) tert-butyl-3-hydroxypyrrolidine-carboxylate employing the same general sequence as used to prepare Example 109. [M+H]⁺=598.4; ¹H NMR (500 MHz, CDCl₃) δ 1.26 (t, J=7.15 Hz, 6H), 1.34 (d, J=5.50 Hz, 6H), 1.45 (s, 9H), 1.63 (s, 2H), 2.00-2.27 (m, 2H), 3.28 (d, J=20.89 Hz, 2H), 3.39-3.70 (m, 4H), 3.99-4.18 (m, 4H), 4.50-4.66 (m, 1H), 4.91 (s, 1H), 6.59 (s, 1H), 6.84 (s, 1H), 6.96-7.10 (m, 2H).

4.65-4.74 (m, 1H), 5.14 (s, 1H), 6.66 (t, J=1.92 Hz, 1H), 7.03 (d, J=3.30 Hz, 1H), 7.33 (s, 1H), 7.38 (s, 1H).

Example 115

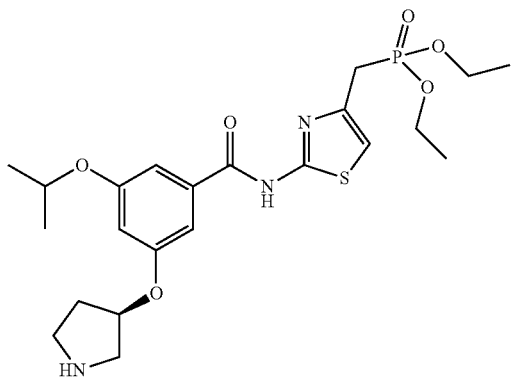 [SMILES: CCOP(=O)(Cc1csc(NC(=O)c2cc(OC(C)C)cc(O[C@@H]3CCNC3)c2)n1)OCC]

The title compound (13.4 mg, 67% yield, white solid) was prepared from Example 114 compound employing the same general sequence as used to prepare Example 110. [M+H]$^+$=498.3; $^1$H NMR (500 MHz, CDCl$_3$) δ 1.22-1.28 (m, 6H), 1.32 (d, J=6.05 Hz, 6H), 2.24-2.40 (m, 2H), 3.24 (d, J=21.44 Hz, 2H), 3.41-3.69 (m, 4H), 3.97-4.13 (m, 4H), 4.56-4.69 (m, 1H), 5.22 (s, 1H), 6.64 (t, J=2.20 Hz, 1H), 6.89 (d, J=3.85 Hz, 1H), 7.28 (s, 1H), 7.32 (s, 1H).

Example 116

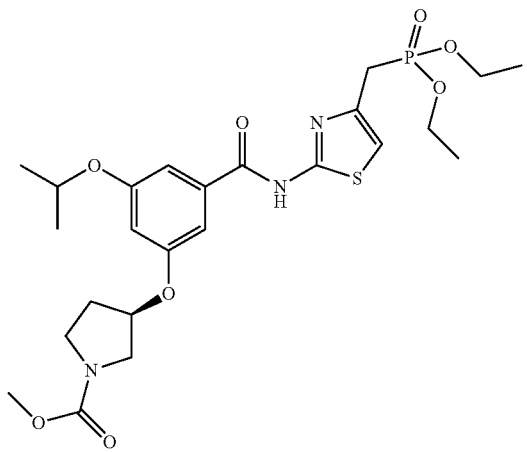 [SMILES: CCOP(=O)(Cc1csc(NC(=O)c2cc(OC(C)C)cc(O[C@@H]3CCN(C(=O)OC)C3)c2)n1)OCC]

The title compound (32.5 mg, 83% yield, colorless oil) was prepared from Example 115 compound employing the same general sequence as used to prepare Example 111. [M+H]$^+$=554; $^1$H NMR (500 MHz, CDCl$_3$) δ 1.29-1.32 (m, 6H), 1.33 (d, J=5.50 Hz, 6H), 2.05-2.28 (m, 2H), 3.35 (d, J=21.44 Hz, 2H), 3.45-3.74 (m, 7H), 4.11-4.22 (m, 4H), Example 117

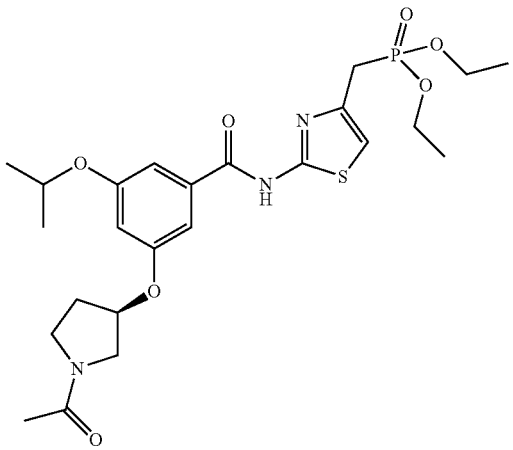 [SMILES: CCOP(=O)(Cc1csc(NC(=O)c2cc(OC(C)C)cc(O[C@@H]3CCN(C(C)=O)C3)c2)n1)OCC]

The title compound (28.5 mg, 75% yield, light yellow oil) was prepared from Example 115 compound employing the same general sequence as used to prepare Example 112. [M+H]$^+$=540.2; $^1$H NMR (500 MHz, CDCl$_3$) δ 1.29-1.32 (m, 6H), 1.32-1.36 (m, 6H), 2.12 (d, J=23.09 Hz, 3H), 2.19-2.39 (m, 2H), 3.34 (d, J=21.44 Hz, 2H), 3.55-3.88 (m, 4H), 4.11-4.21 (m, 4H), 4.64-4.73 (m, 1H), 5.17-5.28 (m, 1H), 6.64-6.69 (m, 1H), 7.04 (d, J=2.75 Hz, 1H), 7.35 (d, J=1.10 Hz, 1H), 7.39 (d, J=9.35 Hz, 1H).

Example 118

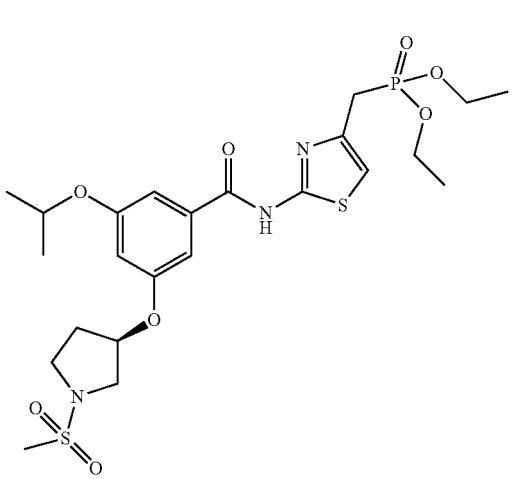 [SMILES: CCOP(=O)(Cc1csc(NC(=O)c2cc(OC(C)C)cc(O[C@@H]3CCN(S(C)(=O)=O)C3)c2)n1)OCC]

The title compound (12 mg, 30% yield, light yellow oil) was prepared from Example 115 compound employing the same general sequence as used to prepare Example 113. [M+H]$^+$=576.2; $^1$H NMR (500 MHz, CDCl$_3$) δ 1.31-1.34 (m, 6H), 1.36 (d, J=6.05 Hz, 6H), 2.08-2.39 (m, 2H), 2.85 (s, 3H), 3.37 (d, J=21.44 Hz, 2H), 3.44-3.54 (m, 1H), 3.56-3.72 (m, 3H), 4.13-4.25 (m, 4H), 4.68-4.80 (m, 1H), 5.18 (s, 1H), 6.66 (s, 1H), 7.07 (d, J=3.30 Hz, 1H), 7.37 (s, 1H), 7.43 (s, 1H).

Example 119

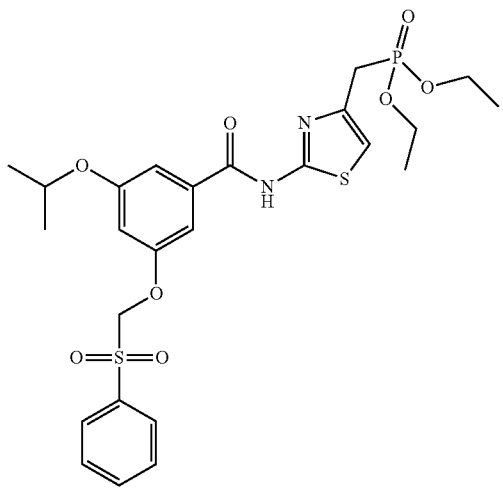 [SMILES: CCOP(=O)(Cc1csc(NC(=O)c2cc(OCS(=O)(=O)c3ccccc3)cc(OC(C)C)c2)n1)OCC]

A.

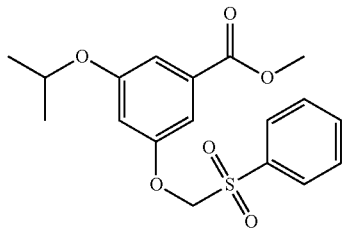

To a RT solution of Example 101 Part A ester (94.7 mg, 0.450 mmol) in MeCN (2.2 mL) under Ar was added 1,4,7,10,13,16-hexaoxacyclooctadecane (16 mg, 0.061 mmol), $K_2CO_3$ (178 mg, 1.288 mmol), and bromomethyl phenyl sulfone (120 mg, 0.510 mmol). The mixture was heated at 70° C. for 6 h, then at 90° C. for 4 h. DMF (1 mL) was added, and the reaction was heated at 115° C. for 24 h. After 24 hours, more bromomethyl phenyl sulphone (90 mg, 0.382 mmol) was added, and the reaction was stirred at 115° C. for 3 days, then cooled to RT and stirred at RT for 2 days. The dark brown mixture was partitioned between EtOAc and saturated aqueous $NaHCO_3$. The organic layer was washed with saturated aqueous $NaHCO_3$, water, and brine, dried ($Na_2SO_4$), and concentrated in vacuo. The residue was chromatographed ($SiO_2$, 12 g, eluting from 0-10%, then 35% EtOAc:hexanes, finally flushing with 100% EtOAc) to give impure Part A compound (70 mg) as an oil. The residue was further purified by preparative HPLC (Phenomenex AXIA Luna 5µ, 75×30 mm, detection at 220 nm; flow rate=40 mL/min; continuous gradient from 40% A to 100% B over 15 min+3 min hold time at 100% B, where A=90:10:0.1 $H_2O:CH_3CN:TFA$ and B=90:10:0.1 $CH_3CN:H_2O:TFA$) to give Part A compound (9.2 mg, 5.5%) as an oily solid.

B.

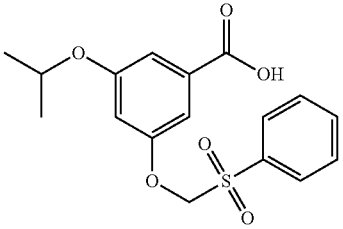

To a RT solution of Part A compound (9 mg, 0.025 mmol) in THF (0.2 mL) and MeOH (0.1 mL) under Ar was added 4N aqueous LiOH (0.062 mL, 0.247 mmol). The reaction was stirred at RT for 8 h, then was stored at −20° C. for 18 h. After warming to RT and diluting with EtOAc, volatiles were removed in vacuo to give a colorless solid. The residue was suspended in water, brought to pH 1 with 1N aqueous HCl (0.3 mL), and the aqueous layer was extracted with EtOAc (2×). The combined organic extracts were washed with brine, dried ($Na_2SO_4$) and concentrated in vacuo to give Part B compound (10.6 mg, >100% recovery) as a colorless solid.

C.

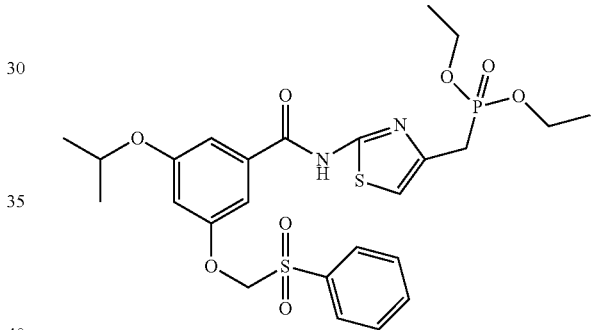

To Part B acid (8.76 mg, 0.025 mmol) was added a RT solution of Example 13 Part E amine (21 mg, 0.084 mmol) in $CH_2Cl_2$ (0.800 mL) under Ar. To the resulting mixture was added $iPr_2NEt$ (0.030 mL, 0.175 mmol) followed by addition of HATU (14.2 mg, 0.037 mmol). The solution was stirred at RT for 18 h, after which another portion of Example 13 Part E amine (15 mg, 0.06 mmol) was added, and stirring was continued at RT for 18 h. The reaction was partitioned between EtOAc and saturated aqueous $NaHCO_3$ after stirring for 15 min. The organic layer was washed with saturated aqueous $NaHCO_3$ and brine, dried ($Na_2SO_4$), and concentrated in vacuo. The residue was purified by preparative HPLC (Phenomenex Luna 5 µm 21.2×100 mm column, detection at 220 nm; flow rate=20 mL/min; continuous gradient from 60% A to 100% B over 10 min+2 min hold time at 100% B, where A=90:10:0.1 $H_2O:MeOH:TFA$ and B=90:10:0.1 $MeOH:H_2O:TFA$). This material was further purified by preparative HPLC (Phenomenex Luna, 5 micron 21.2×100 mm, detection at 220 nm; flow rate=20 mL/min; continuous gradient from 35% A to 100% B over 10 min+2 min hold time at 100% B, where A=90:10:0.1 $H_2O:MeOH:TFA$ and B=90:10:0.1 $MeOH:H_2O:TFA$). The material was finally purified by passing through a MeOH-treated cartridge of Polymer Lab StratoSpheres TM SPE PL-HCO3 MP SPE resin (500 mg), washing well with MeOH. The filtrate was concentrated in vacuo and the resulting solid dissolved in $CH_2Cl_2$/MeOH, filtered, and concentrated in vacuo to give the title compound (5 mg, 34%) as a tan solid. $[M+H]^+$=583.3; $^1H$ NMR (400 MHz, $CDCl_3$) δ 1.27 (t, J=6.87 Hz, 6H), 1.33 (d, J=6.05 Hz, 6H), 3.33 (d, J=20.89 Hz, 2H), 4.07 (td, J=7.15, 4.40 Hz, 4H), 4.55-4.58 (m, 1H), 5.11 (s, 2H), 6.67 (s, 1H), 6.83 (d, J=3.30 Hz, 1H), 7.08 (s, 1H), 7.16 (s, 1H), 7.59 (t, J=7.70 Hz, 2H), 7.69 (t, J=7.15 Hz, 1H), 7.97 (d, J=7.15 Hz, 2H).

Example 120

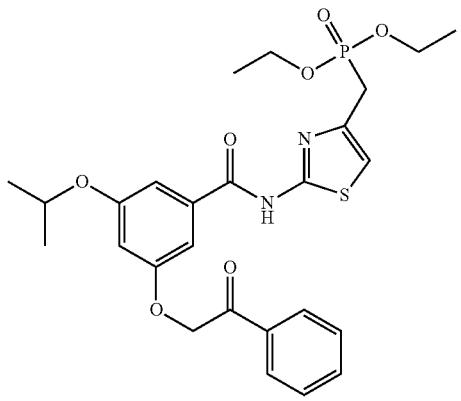

A.

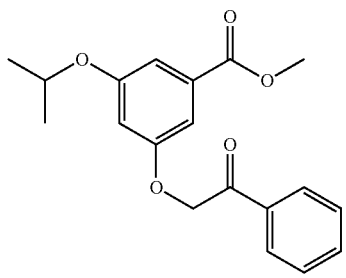

To a 0° C. solution of Example 101 Part A compound (183.9 mg, 0.875 mmol) in DMPU (4.5 mL) under Ar was added NaH (35.0 mg of a 60% dispersion in oil, 0.875 mmol). To the resulting solution was added 2-bromoacetophenone (174 mg, 0.875 mmol). The reaction was stirred at 0° C. for several min and then warmed to RT and stirred at RT for 1.5 h. More 2-bromoacetophenone (39 mg, 0.19 mmol) was added, and the reaction was stirred at RT for 1 h. The reaction was quenched with water and EtOAc was added. The organic layer was washed with water (2×) and brine (1×), dried (Na$_2$SO$_4$), and concentrated in vacuo. The residue was chromatographed (SiO$_2$, 12 g, eluting from 0-5% EtOAc:CH$_2$Cl$_2$, then flushing with 90% EtOAc) to give Part A compound (274 mg, 95%) as a yellow oil.

B.

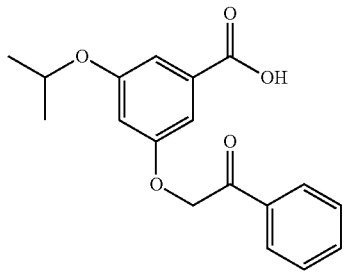

To a RT solution of Part A compound (101.4 mg, 0.309 mmol) in TF (2.4 mL) under Ar was added water (0.6 mL), followed by LiOH.H$_2$O (54.7 mg, 1.304 mmol). The reaction was stirred at RT for 18 h, and aqueous LiOH (0.2 mL of a 4 M solution, 0.8 mmol) was added. After stirring for 5.5 h, MeOH (0.5 mL) was added; stirring was continued at RT for 2.5 h and the reaction was stored at −20° C. for 18 h. After warming to RT, the reaction was stirred for another 4.5 h. Volatiles were removed in vacuo to give an orange aqueous mixture, which was acidified with 1N aqueous HCl (1.9 mL), then was partitioned between EtOAc and water. The organic layer was washed with water and brine, dried (Na$_2$SO$_4$) and concentrated in vacuo to give crude Part B compound (88 mg, 49%) as a yellow oil.

C.

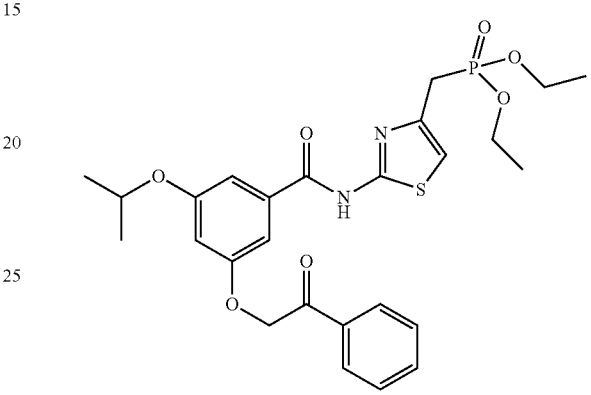

To a RT solution of Part B acid (≤88 mg, ≤0.280 mmol) in CH$_2$Cl$_2$ (1.4 mL) under Ar were successively added HATU (166 mg, 0.437 mmol), DIPEA (0.34 mL, 1.952 mmol) and a solution of Example 13 Part E compound (162 mg, 0.445 mmol) in CH$_2$Cl$_2$ (0.6 mL). The reaction was stirred at RT for 65 h, then was partitioned between EtOAc and sat. aqueous NaHCO$_3$. The organic layer was washed with saturated aqueous NaHCO$_3$ and brine, dried (Na$_2$SO$_4$) and concentrated in vacuo. The residue was purified by preparative HPLC (YMC ODS S5 30×250 mm column, detection at 220 nm; flow rate=25 mL/min; continuous gradient from 50% A to 100% B over 20 min+5 min hold time at 100% B, where A=90:10:0.1 H$_2$O:CH$_3$CN:TFA and B=90:10:0.1 CH$_3$CN:H$_2$O:TFA) to give the title compound (33 mg, 22%) as a gummy, yellow solid. [M+H]$^+$=545.3; $^1$H NMR (400 MHz, CD$_3$OD): δ 1.28 (t, J=7.15 Hz, 6H), 1.34 (d, J=6.05 Hz, 6H), 3.36 (d, J=16.49 Hz, 2H), 4.04-4.14 (m, 4H), 4.64-4.86 (m, 1H), 5.55 (s, 2H), 6.78-6.80 (m, 1H), 6.95-6.97 (m, 1H), 7.18-7.21 (m, 2H), 7.50-7.58 (t, J=7.97 Hz 2H), 7.65-7.70 (m, 1H), 8.07 (d, J=7.15 Hz, 2H).

Example 121

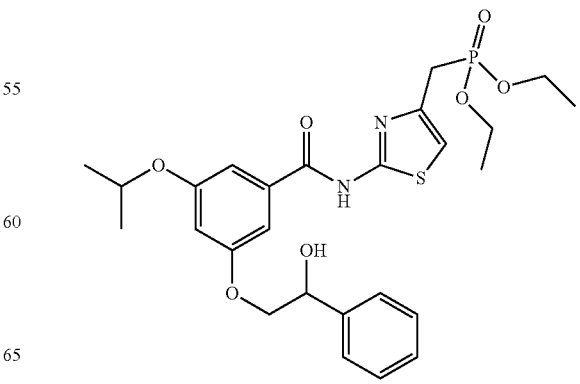

To a 0° C. solution of Example 120 ketone (28 mg, 0.051 mmol) in MeOH (1 mL) under Ar was added NaBH₄ (10 mg, 0.264 mmol). After 15 minutes, the reaction was allowed to warm to RT and stirred at RT for 4 h. The mixture was stored at −20° C. for 18 h, then was treated with pH 3 aqueous phosphate buffer, allowed to warm to RT and stirred at RT for 40 min. Volatiles were removed in vacuo, and the resulting aqueous mixture was partitioned between water, phosphate buffer and EtOAc. The organic layer was washed with water and brine, dried (Na₂SO₄) and concentrated in vacuo. The residue was purified by preparative HPLC (Phenomenex AXIA Luna 5 μm 75×30 mm, detection at 220 nm; flow rate=40 mL/min; continuous gradient from 40% A to 100% B over 15 min+3 min hold time at 100% B, where A=90:10:0.1 H₂O:CH₃CN:TFA and B=90:10:0.1 CH₃CN:H₂O:TFA) to give two fractions containing the desired title compound. Both fractions were passed through a MeOH-treated cartridge of Polymer Lab StratoSpheres TM SPE PL-HCO3 MP SPE resin (500 mg), washing well with MeOH. The filtrates were concentrated in vacuo, and the resulting solids were dissolved in CH₂Cl₂/MeOH, and concentrated in vacuo to give the title compound (17 mg, 60%) as a tan solid. [M+H]⁺=549.2; [M−H]⁺=547.2; ¹H NMR (400 MHz, CD₃OD): δ 1.28 (t, J=6.87 Hz, 6H), 1.33 (d, J=6.05 Hz, 6H), 3.35 (d, J=20.89 Hz, 2H), 4.05-4.17 (m, 6H), 4.63-4.69 (m, 1H), 5.02-5.07 (m, 1H), 6.71-6.73 (m, 1H), 6.95 (d, J=3.85 Hz, 1H), 7.13-7.15 (m, 2H), 7.27-7.30 (m, 1H), 7.37 (t, J=7.42 Hz, 2H), 7.48 (d, J=7.15 Hz, 2H).

Example 122

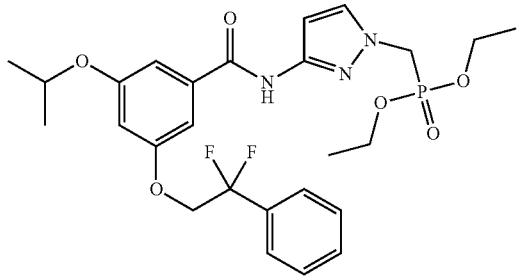

A.

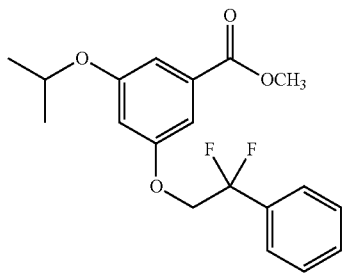

To a RT solution of Example 120 Part A compound (53.7 mg, 0.164 mmol) in CH₂Cl₂ (0.5 mL) under Ar was added bis-(2-methoxyethyl)aminosulfur trifluoride (0.3 mL, 1.627 mmol). The orange solution was stirred at RT under Ar for 18 h, then was diluted with CH₂Cl₂ and added carefully to a stirred mixture of ice and sat. aqueous NaHCO₃. The mixture was stirred for 1 h, then was partitioned between CH₂Cl₂ and sat. aqueous NaHCO₃. The aqueous layer was extracted CH₂Cl₂ (2×), and the combined organic extracts were washed with brine, dried (Na₂SO₄) and concentrated in vacuo to give crude Part A ester (54.4 mg, 95% recovered) as a yellow oil.

B.

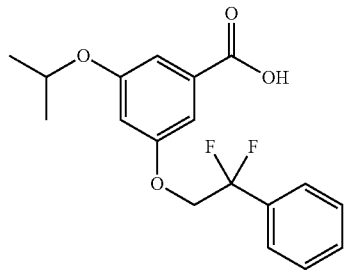

To a RT solution of Part A ester (54.4 mg, 0.155 mmol) in THF (0.8 mL) and MeOH (0.4 mL) under Ar was added 4N aqueous LiOH (0.35 mL, 1.4 mmol). The reaction was stirred at RT for 6 h, and the volatiles were removed in vacuo. The orange aqueous mixture was acidified with 1N aqueous HCl (1.5 mL). The resulting mixture was partitioned between water and EtOAc. The organic layer was washed with water and brine, dried (Na₂SO₄) and concentrated in vacuo to give Part B compound (46.7 mg, 89% recovered) as a yellow oily solid.

C.

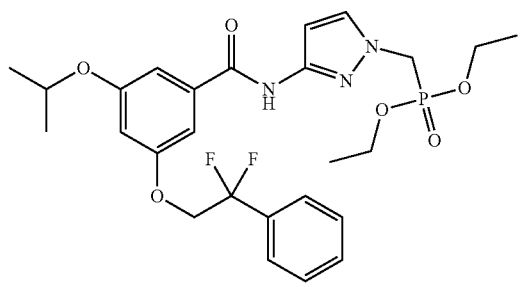

To a RT solution of Part B compound (21.2 mg, 0.063 mmol) in CH₂Cl₂ (0.6 mL) under Ar were successively added HATU (34 mg, 0.089 mmol), iPr₂NEt (35 μL, 0.201 mmol), and a solution of Example 32 Part A amine (20.6 mg, 0.088 mmol) in CH₂Cl₂ (0.3 mL). The reaction was stirred for 41 h at RT, then was diluted with CH₂Cl₂, saturated aqueous NaHCO₃, and EtOAc, then stirred for 15 min and partitioned between EtOAc and aqueous NaHCO₃. The aqueous layer was extracted with EtOAc (2×), and the combined organic extracts were washed with brine, dried (Na₂SO₄), and concentrated in vacuo. The residue was purified by preparative HPLC (YMC ODS 30×250 mm column, detection at 220 nm; flow rate=25 mL/min; continuous gradient from 50% A to 100% B over 25 min+7 min hold time at 100% B, where A=90:10:0.1 H₂O:CH₃CN:TFA and B=90:10:0.1 CH₃CN:H₂O:TFA) to give slightly impure title compound (34.3 mg) as a colorless oil. The residue was purified further by preparative HPLC (Phenomenex AXIA 5 micron C18 30×100 mm column, detection at 220 nm; flow rate=40 mL/min; continuous gradient from 60% A to 100% B over 10 min+5 min hold time at 100% B, where A=90:10:0.1 H₂O:MeOH:TFA and B=90:10:0.1 MeOH:H₂O:TFA) to give the title compound (25 mg, 59%, TFA salt) as a colorless oil. [M+H]⁺=552.2; [M−H]⁺=550.3; ¹H NMR (400 MHz, CDCl₃): δ 1.28 (t, J=7.15 Hz, 6H), 1.32 (d, J=6.05 Hz, 6H), 4.04-4.14 (m, 4H), 4.37-4.48 (m, 4H), 4.59 (dt, J=12.09, 6.05 Hz, 1H), 6.60 (s, 1H), 6.94 (s, 1H), 7.01 (s, 1H), 7.08 (s, 1H), 7.43-7.49 (m, 4H), 7.55-7.61 (m, 2H), 9.10 (s, 1H), $^{19}$F NMR (400 MHz, CDCl$_3$): δ −75.98, −103.82, −103.86.

Example 123

A.

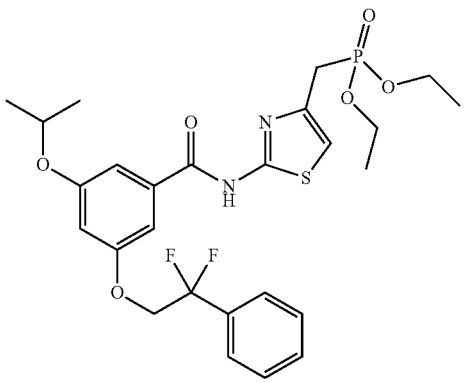

B.

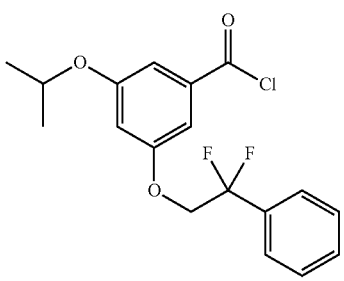

To a 0° C. solution of Example 122 Part B acid (46.7 mg, 0.139 mmol) in CH$_2$Cl$_2$ (1.5 mL) under Ar were successively added dropwise oxalyl chloride (250 µL of a 2M solution in 2 M in CH$_2$Cl$_2$, 0.5 mmol,) and DMF (15 µL). After 15 min, the reaction was allowed to warm to RT and the yellow reaction was stirred at RT for 3 h. Volatiles were removed in vacuo to give Part A compound (68.8 mg, >100% recovery) as an orange oily solid.

To a 0° C. solution of Example 13 Part E amine (36.7 mg, 0.147 mmol) in THF (0.4 mL) under Ar were successively added iPr$_2$NEt (120 µL, 0.689 mmol), a solution of Part A compound (24.7 mg, 0.0695 mmol) in CH$_2$Cl$_2$ (0.4 mL) and finally DMAP (1.7 mg, 0.014 mmol). The reaction was allowed to warm to RT and stirred for 20 h at RT, then was diluted with water and combined with the crude reaction mixture from a similar experiment using Part A acid chloride (24.7 mg, 0.0695 mmol) and Example 13 Part E amine (36.7 mg, 0.147 mmol). The combined reaction mixtures were partitioned between dilute aqueous NaHCO$_3$ and CH$_2$Cl$_2$. The aqueous layer was extracted with CH$_2$Cl$_2$ (2×), and the combined organic layers were dried (Na$_2$SO$_4$) and concentrated in vacuo. The residue was initially purified by preparative HPLC (YMC ODS 30×250 mm column, detection at 220 nm; flow rate=25 mL/min; continuous gradient from 50% A to 100% B over 30 min+7 min hold time at 100% B, where A=90:10:0.1 H$_2$O:CH$_3$CN:TFA and B=90:10:0.1 CH$_3$CN:H$_2$O:TFA). The residue was dissolved in MeOH and passed through a MeOH treated cartridge of Polymer Lab Strato-Spheres TM SPE PL-HCO$_3$ MP SPE (500 mg) resin, washing well with MeOH. The filtrate was concentrated in vacuo. The residue was dissolved in CH$_2$Cl$_2$/MeOH, filtered, and concentrated in vacuo to give the title compound (5.6 mg, 7%) as a tan gummy solid. [M+H]$^+$=569.3; [M−H]$^-$=567.3; $^1$H NMR (400 MHz, CDCl$_3$): δ 1.24 (t, J=7.15 Hz, 6H), 1.30 (d, J=6.05 Hz, 6H), 3.28 (d, J=20.89 Hz, 2H), 3.98-4.09 (m, 4H), 4.36 (t, J=12.37 Hz, 2H), 4.53 (dt, J=12.09, 6.05 Hz, 1H), 6.57 (s, 1H), 6.77 (d, J=3.30 Hz, 1H), 7.02 (s, 1H), 7.09 (s, 1H), 7.41-7.49 (m, 3H), 7.51-7.59 (m, 2H), 8.01 (d, J=7.15 Hz, 1H); $^{19}$F NMR (400 MHz, CDCl$_3$): δ −103.73, −103.76, −103.80.

Example 124

A.

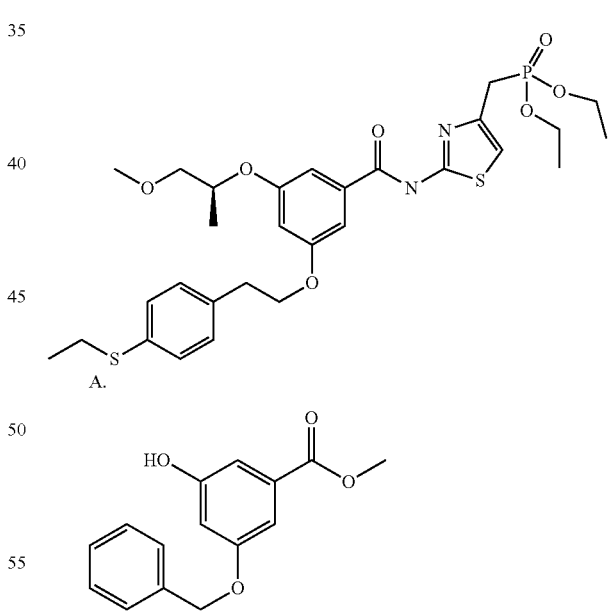

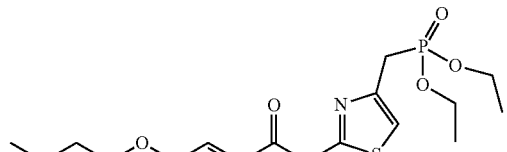

To a solution of methyl-3,5-dihydroxy benzoate (10.00 g; 59.5 mmol) in DMF (60.0 mL) under Ar was added K$_2$CO$_3$ (12.4 g; 89.7 mmol), followed by the slow addition of benzyl bromide (10.0 mL; 84.2 mmol) over 10 min. The reaction mixture was stirred at 25° C. for 16 h, then was quenched with sat. aqueous NH$_4$Cl (50 mL) and water (350 mL). The aqueous suspension was extracted with CH$_2$Cl$_2$ (3×50 mL). The combined organic extracts were washed with water and brine, dried (MgSO$_4$), and concentrated in vacuo. The crude product was chromatographed (SiO$_2$; stepwise gradient from 10-20-30-50% solvent B, where solvent A=hexanes and solvent B=EtOAc) to give Part A compound (4.599 g; 30%) as an off-white powder.

B.

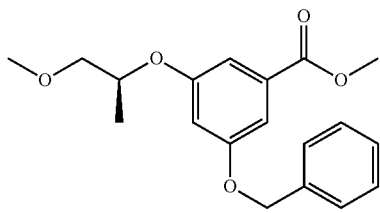

To a 0° C. solution of Part A compound (3.130 g; 12.12 mmol) in THF (52.7 mL) were added (R)-1-methoxypropan-2-ol (1.64 g; 18.18 mmol) and Ph$_3$P (4.77 g; 18.18 mmol), followed by the slow addition of DIAD (3.53 mL; 18.18 mmol) via syringe pump. The reaction mixture was stirred at 25° C. for 16 h under Ar, then was diluted with water and extracted with EtOAc (3×). The combined organic extracts were washed with 1N aqueous NaOH and brine, dried (MgSO$_4$) and concentrated in vacuo. The crude product was chromatographed (SiO$_2$; stepwise gradient from 5-10-30-50% solvent B, where solvent A=hexanes and solvent B=EtOAc) to give Part B compound (2.892 g; 53%) as a clear, colorless oil.

C.

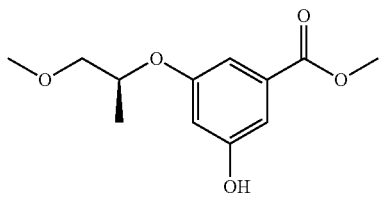

A flask containing Part B compound (2.892 g; 8.75 mmol) in MeOH (109 mL) was evacuated and flushed with Ar. 10% Pd/C (0.931 g; 0.875 mmol) was added followed by evacuation of the flask and refilling with H$_2$ (g; 1 atmosphere). The reaction was stirred for 2 days under H$_2$. The reaction mixture was filtered and the catalyst was washed with EtOAc. The combined filtrates were concentrated in vacuo to give Part C compound (2.075 g; 83%) as a clear, colorless oil.

D.

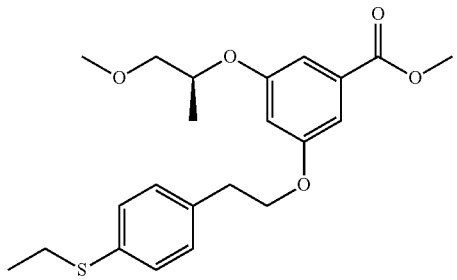

To a 0° C. solution of Part C compound (0.125 g; 0.519 mmol) in THF (2.60 mL) were added 2-(4-(ethylthio)phenyl) ethanol (0.208 g; 1.142 mmol) and Ph$_3$P (0.299 g; 1.142 mmol), followed by the slow addition of DIAD (0.222 mL; 1.142 mmol). The reaction mixture was stirred at 25° C. for 16 h under Ar. The reaction mixture was diluted with water and extracted with EtOAc (3×). The combined organic extracts were washed with 1N aqueous NaOH and brine, dried (MgSO$_4$) and concentrated in vacuo. The residue was chromatographed (SiO$_2$; stepwise gradient from 5-10-20-30-50% solvent B, where solvent A=hexanes and solvent B=EtOAc) to give Part D compound (0.121 g; 49%) as a clear, yellow oil.

E.

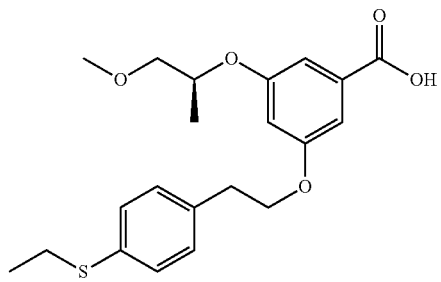

To a solution of Part D compound (0.1208 g; 0.299 mmol) in THF (2.47 mL) and water (0.25 mL) was added LiOH.H$_2$O (0.014 g; 0.597 mmol). The reaction mixture was stirred at 45° C. for 1 h in a sealed vial, then an additional equivalent of LiOH.H$_2$O was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO$_4$) and concentrated in vacuo to give Part E compound (0.1082 g; 76%) as a clear, colorless oil.

F.

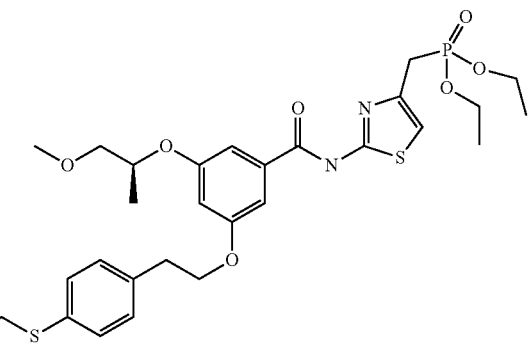

To a solution of Part E compound (0.160 g; 0.411 mmol) in DMF (2.05 mL) were added HOAT (0.064 g; 0.47 mmol), Example 13 Part E compound (0.123 g; 0.493 mmol), and DIPEA (0.08 mL; 0.47 mmol), and lastly, EDCI (0.091 g; 0.47 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$) and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:

CH₃CN:TFA and solvent B=90:10:0.1 CH₃CN:H₂O:TFA) to give the title compound (80.4 mg; 31%) as a clear, colorless oil. [M+H]⁺=623.2.

Example 125

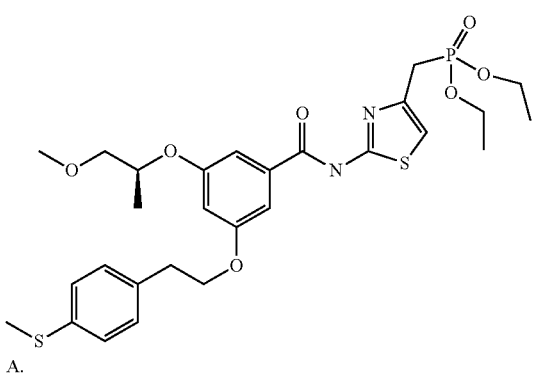

A.

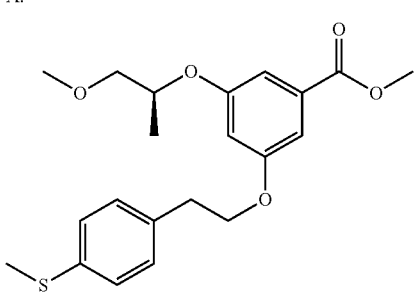

To a 0° C. solution of Example 124 Part C compound (0.125 g; 0.519 mmol) in THF (2.60 mL) was added 2-(4-(methylthio)phenyl)ethanol (0.208 g; 1.142 mmol) and Ph₃P (0.299 g; 1.142 mmol), followed by the slow addition of DIAD (0.222 mL; 1.142 mmol). The reaction mixture was stirred at 25° C. for 16 h under Ar, then was diluted with water and extracted with EtOAc (3×). The combined organic extracts were washed with 1N aqueous NaOH and brine, dried (MgSO₄) and concentrated in vacuo. The crude product was chromatographed (SiO₂; step gradient from 5-10-20-30-50% solvent B, where solvent A=hexanes and solvent B=EtOAc) to give Part A compound (0.121 g; 49%) as a clear, yellow oil.

B.

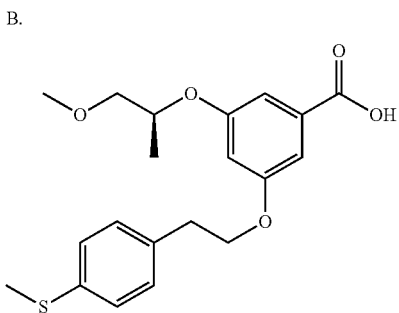

To a solution of Part A compound (0.1208 g; 0.299 mmol) in THF (2.47 mL) and water (0.25 mL) was added LiOH.H₂O (0.014 g; 0.597 mmol). The reaction mixture was stirred at 45° C. for 1 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄) and concentrated in vacuo to give Part B compound (0.1082 g; 76%) as a clear, colorless oil.

C.

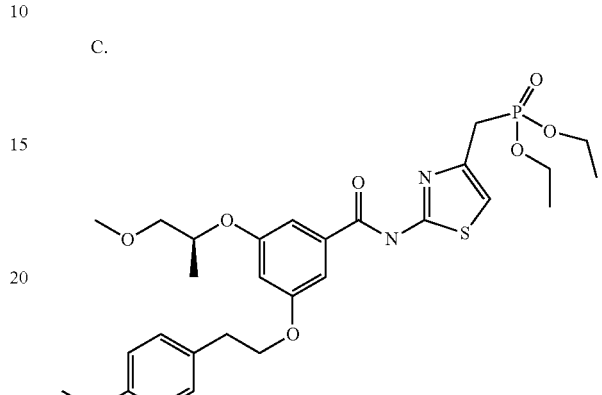

To a solution of Example 13 Part E compound (0.13 g; 0.51 mmol) in DMF (2.13 mL) were added HOAT (0.067 g; 0.49 mmol), Part B compound (0.16 g; 0.43 mmol), DIPEA (0.63 mL; 0.49 mmol), and, lastly, EDCI (0.094 g; 0.49 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O: CH₃CN:TFA and solvent B=90:10:0.1 CH₃CN:H₂O:TFA) to give the title compound (47.0 mg; 17%) as a clear, colorless oil. [M+H]⁺=609.1.

Example 126

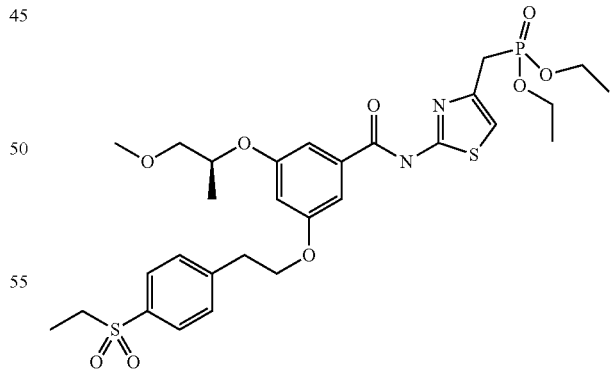

To Example 124 Part F compound (0.04 g; 0.07 mmol) in iPrOH (1.46 mL) and water (0.73 mL) was added oxone (0.09 g; 0.15 mmol). The reaction mixture was stirred for 16 h at 25° C., then was filtered and extracted with EtOAc. The filtrate was partitioned between water and brine. The organic layer was dried (MgSO₄) and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:

CH₃CN:TFA and solvent B=90:10:0.1 CH₃CN:H₂O:TFA) to give the title compound (48.0 mg; 55%) as a white solid. [M+H]⁺=655.3; ¹H NMR (400 MHz, CDCl₃): δ 1.16-1.29 (m, 12H), 2.98-3.08 (m, J=7.33, 7.33, 7.33 Hz, 2H), 3.08-3.18 (m, J=6.32, 6.32 Hz, 2H), 3.22 (s, 1H), 3.28 (s, 1H), 3.33 (s, 3H), 3.41-3.54 (m, 2H), 4.01-4.13 (m, 4H), 4.24 (t, J=6.32 Hz, 2H), 4.61-4.70 (m, J=10.17, 6.32 Hz, 1H), 6.64-6.70 (m, 1H), 6.93-6.97 (m, J=3.30 Hz, 1H), 7.29 (d, J=17.59 Hz, 2H), 7.42 (d, J=8.24 Hz, 2H), 7.78 (d, J=8.25 Hz, 2H).

Example 127

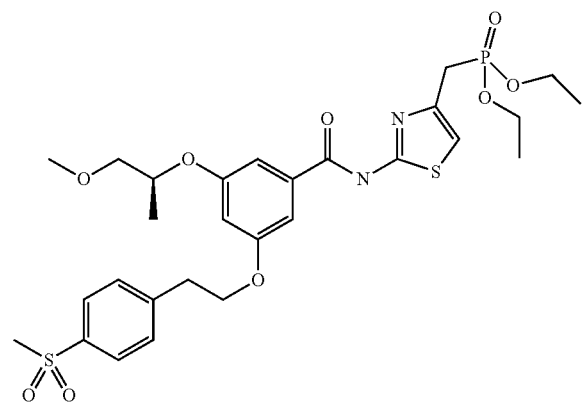 [SMILES: CCOP(=O)(Cc1csc(NC(=O)c2cc(OCCc3ccc(S(C)(=O)=O)cc3)cc(O[C@@H](C)COC)c2)n1)OCC]

To Example 125 Part C compound (0.04 g; 0.07 mmol) in iPrOH (1.46 mL) and water (0.73 mL) was added oxone (0.09 g; 0.15 mmol). The reaction mixture was stirred for 16 h at 25° C., then was filtered and rinsed with EtOAc. The filtrate was washed with water and brine, dried (MgSO₄) and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O: CH₃CN:TFA and solvent B=90:10:0.1 CH₃CN:H₂O:TFA) to give the title compound (14.2 mg; 33%) as a white solid. [M+H]⁺=641.3; ¹H NMR (400 MHz, CDCl₃): δ 1.21-1.30 (m, J=7.42, 7.42 Hz, 9H), 2.97 (s, 3H), 3.12 (t, J=6.05 Hz, 2H), 3.26 (s, 1H), 3.29-3.36 (m, 4H), 3.41-3.55 (m, 2H), 4.03-4.16 (m, 4H), 4.25 (t, J=6.32 Hz, 2H), 4.60-4.72 (m, 1H), 6.62-6.71 (m, 1H), 6.91-7.01 (m, J=3.85 Hz, 1H), 7.32 (d, J=16.49 Hz, 2H), 7.43 (d, J=8.25 Hz, 2H), 7.81 (d, J=8.24 Hz, 2H).

Example 128

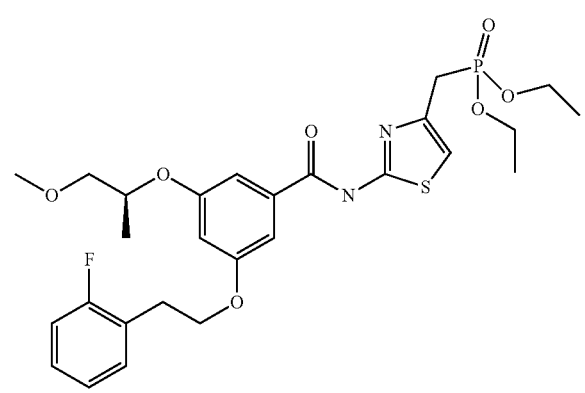 [SMILES: CCOP(=O)(Cc1csc(NC(=O)c2cc(OCCc3ccccc3F)cc(O[C@@H](C)COC)c2)n1)OCC]

A.

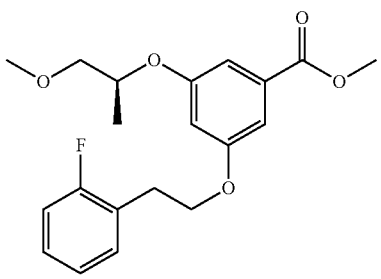

To Example 124 Part C compound (0.100 g; 0.416 mmol) was added 2-(2-fluorophenyl)ethanol (0.24 g; 1.67 mmol in toluene; 2.08 mL), followed by a suspension of Example 97 Part B compound (0.68 g; 1.67 mmol) in CH₂Cl₂ (7.6 mL). The reaction mixture was stirred for 16 h at 25° C., then was diluted with water and extracted with EtOAc (3×). The combined organic extracts were washed with 1N aqueous NaOH and brine, dried (MgSO₄) and concentrated in vacuo. The crude product was chromatographed (SiO₂; step gradient from 10-20-30% solvent B, where solvent A=hexanes and solvent B=EtOAc) to give Part A compound (0.146 g; 90%).

B.

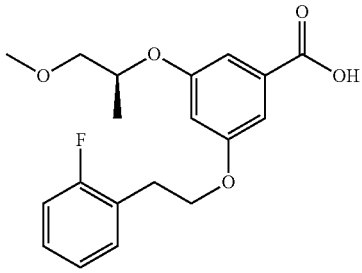

To a solution of Part A compound (0.100 g; 0.27 mmol) in THF (2.23 mL) and water (0.22 mL) was added LiOH.H₂O (0.013 g; 0.54 mmol). The reaction mixture was stirred at 45° C. for 1 h in a sealed vial, then an additional equivalent of LiOH.H₂O was added. The reaction mixture was stirred at 45° C. for 16 h, then cooled to RT. Volatiles were removed in vacuo and the remaining aqueous solution was acidified with 0.5N aqueous HCl to pH<2. The aqueous layer was re-extracted with EtOAc (3×). The combined organic extracts were washed with brine, dried (MgSO₄) and concentrated in vacuo to give Part B compound (0.107 g; 100%).

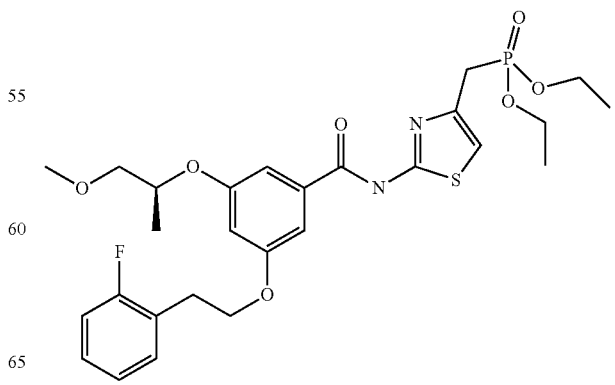

To a solution of Example 13 Part E compound (0.073 g; 0.29 mmol) in DMF (1.21 mL) were added HOAT (0.038 g; 0.278 mmol), Part B compound (0.084 g; 0.242 mmol), and DIPEA (0.049 mL; 0.278 mmol) and, lastly, EDCI (0.053 g; 0.278 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$), and concentrated in vacuo. The residue was purified by preparative HPLC (YMC reverse phase ODS-5 μm 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (69.7 mg; 49%) as a clear, colorless oil. [M+H]$^+$=581.5; $^1$H NMR (400 MHz, CDCl$_3$) δ 1.21-1.26 (m, 9H), 3.06 (t, J=6.87 Hz, 2H), 3.21 (s, 1H), 3.26 (s, 1H), 3.31-3.35 (m, 3H), 3.41-3.53 (m, 2H), 3.98-4.10 (m, 4H), 4.18 (t, J=6.60 Hz, 2H), 4.61-4.71 (m, 1H), 6.63-6.70 (m, 1H), 6.84-7.06 (m, 3H), 7.10-7.17 (m, 1H), 7.18-7.25 (m, J=12.64 Hz, 3H), 7.26-7.30 (m, 1H).

Example 129

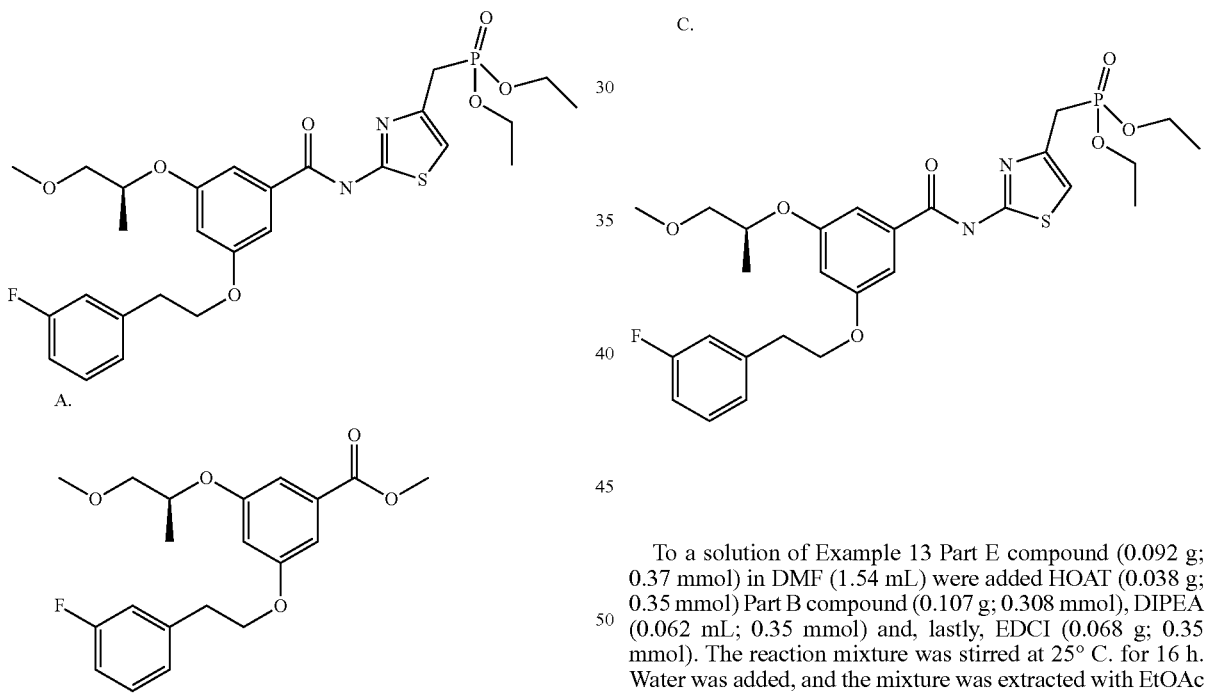

To Example 124 Part C compound (0.100 g; 0.416 mmol) were added 2-(3-fluorophenyl)ethanol (0.24 g; 1.67 mmol in toluene (2.08 mL) followed by a suspension of Example 97 Part B compound (0.68 g; 1.67 mmol) in CH$_2$Cl$_2$ (7.6 mL). The reaction mixture was stirred for 16 h at 25° C., then was diluted with water and extracted with EtOAc (3×). The combined organic extracts were washed with 1N aqueous NaOH and brine, dried (MgSO$_4$), and concentrated in vacuo. The crude product was chromatographed (SiO$_2$; step gradient from 10-20-30% solvent B, where solvent A=hexanes and solvent B=EtOAc) to give Part A compound (0.146 g; 90%).

B.

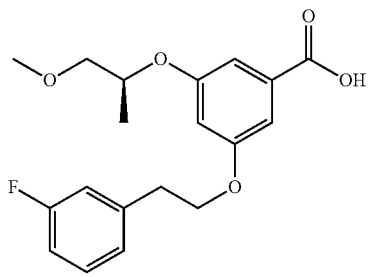

To a solution of Part A compound (0.100 g; 0.27 mmol) in THF (2.23 mL) and water (0.22 mL) was added LiOH.H$_2$O (0.013 g; 0.54 mmol). The reaction mixture was stirred at 45° C. for 1 h in a sealed vial, then an additional equivalent of LiOH.H$_2$O was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO$_4$), and concentrated in vacuo to give Part B compound (0.107 g; 100%).

C.

To a solution of Example 13 Part E compound (0.092 g; 0.37 mmol) in DMF (1.54 mL) were added HOAT (0.038 g; 0.35 mmol) Part B compound (0.107 g; 0.308 mmol), DIPEA (0.062 mL; 0.35 mmol) and, lastly, EDCI (0.068 g; 0.35 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$) and concentrated in vacuo. The residue was purified by preparative HPLC (YMC reverse phase ODS-5 μm 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (78.5 mg; 44%) as a clear, colorless oil. [M+H]$^+$=581.1; $^1$H NMR (400 MHz, CDCl$_3$) δ 1.17-1.28 (m, 9H), 3.01 (t, J=6.32 Hz, 2H), 3.24 (s, 1H), 3.26-3.36 (m, 4H), 3.42-3.54 (m, 2H), 4.00-4.14 (m, 4H), 4.19 (t, J=6.32 Hz, 2H), 4.62-4.73 (m, 1H), 6.64-6.70 (m, 1H), 6.79-6.88 (m, J=8.52, 8.52 Hz, 1H), 6.88-7.02 (m, 3H), 7.12-7.22 (m, 1H), 7.25-7.30 (m, 1H), 7.28 (s, 1H), 7.33 (s, 1H), 7.31-7.36 (m, 1H).

Example 130

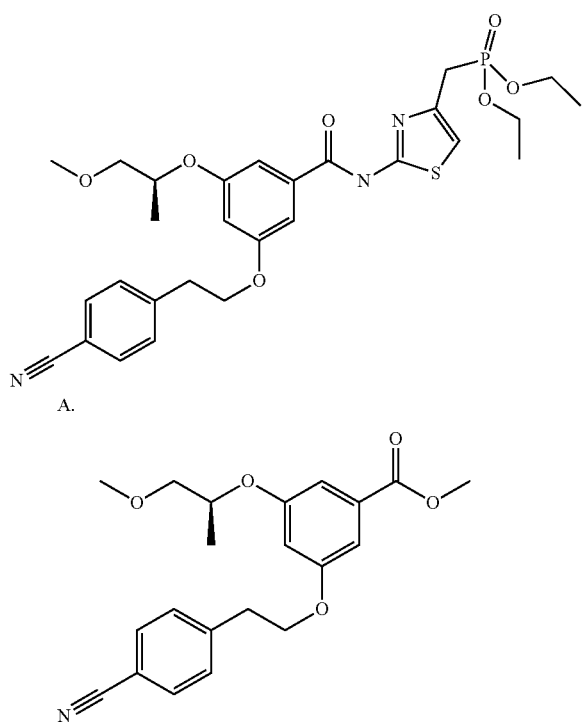

A.

To Example 124 Part C compound (0.100 g; 0.416 mmol) was added 4-(2-hydroxyethyl)benzonitrile (0.09 g; 0.62 mmol in toluene (2.08 mL) followed by a suspension of Example 97 Part B compound (0.26 g; 0.62 mmol) in CH$_2$Cl$_2$ (7.14 mL). The reaction mixture was stirred for 16 h at 25° C., then was diluted with water and extracted with EtOAc (3×). The combined organic extracts were washed with 1 N aqueous NaOH and brine, dried (MgSO$_4$) and concentrated in vacuo. The crude product was chromatographed (SiO$_2$; stepwise gradient from 5-10-20% solvent B, where solvent A=hexanes and solvent B=EtOAc) to give Part A compound (0.100 g; 63%).

B.

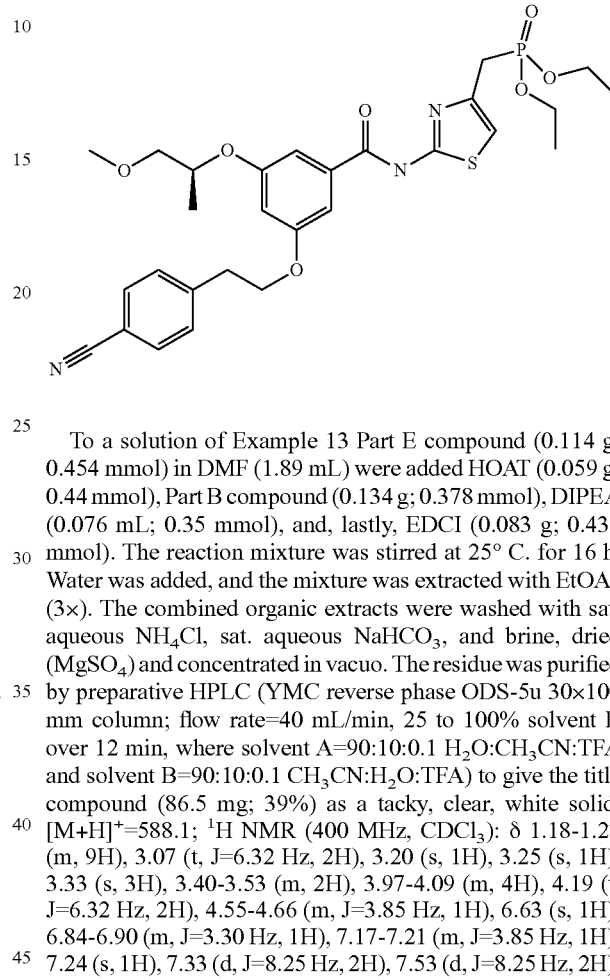

To a solution of Part A compound (0.15 g; 0.40 mmol) in THF (3.27 mL) and water (0.33 mL) was added LiOH.H$_2$O (0.019 g; 0.79 mmol). The reaction mixture was stirred at 45° C. for 1 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO$_4$), and concentrated in vacuo to give Part B compound (0.140 g; 85%).

C.

To a solution of Example 13 Part E compound (0.114 g; 0.454 mmol) in DMF (1.89 mL) were added HOAT (0.059 g; 0.44 mmol), Part B compound (0.134 g; 0.378 mmol), DIPEA (0.076 mL; 0.35 mmol), and, lastly, EDCI (0.083 g; 0.435 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$) and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (86.5 mg; 39%) as a tacky, clear, white solid. [M+H]$^+$=588.1; $^1$H NMR (400 MHz, CDCl$_3$): δ 1.18-1.27 (m, 9H), 3.07 (t, J=6.32 Hz, 2H), 3.20 (s, 1H), 3.25 (s, 1H), 3.33 (s, 3H), 3.40-3.53 (m, 2H), 3.97-4.09 (m, 4H), 4.19 (t, J=6.32 Hz, 2H), 4.55-4.66 (m, J=3.85 Hz, 1H), 6.63 (s, 1H), 6.84-6.90 (m, J=3.30 Hz, 1H), 7.17-7.21 (m, J=3.85 Hz, 1H), 7.24 (s, 1H), 7.33 (d, J=8.25 Hz, 2H), 7.53 (d, J=8.25 Hz, 2H).

Example 131

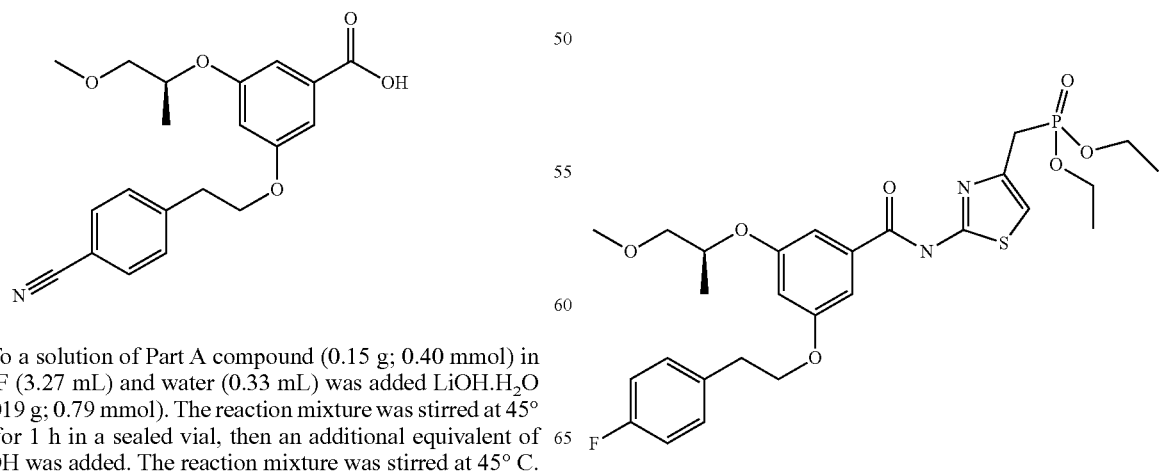

A.

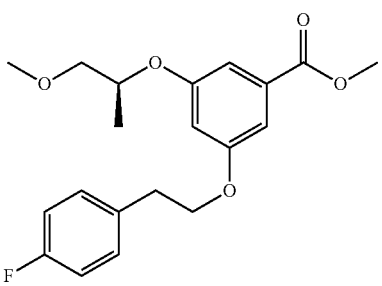

To Example 124 Part C compound (0.100 g; 0.416 mmol) were added a solution of 2-(4-fluorophenyl)ethanol (0.58 g; 4.16 mmol) in toluene (2.18 mL) and a suspension of Example 97 Part B compound (1.71 g; 4.16 mmol) in CH$_2$Cl$_2$ (7.60 mL). The reaction mixture was stirred for 16 h at 25° C., then was diluted with water and extracted with EtOAc (3×). The combined organic extracts were washed with 1N aqueous NaOH and brine, dried (MgSO$_4$) and concentrated in vacuo. The crude product was chromatographed (SiO$_2$; step gradient from 5-10-15-20% solvent B, where solvent A=hexanes and solvent B=EtOAc) to give Part A compound (0.137 g; 86%).

B.

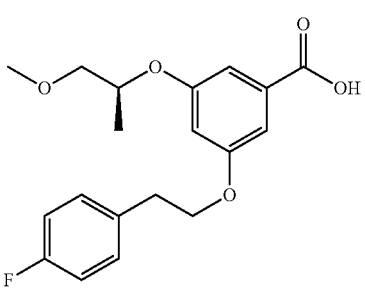

To a solution of Part A compound (0.14 g; 0.38 mmol) in THF (3.27 mL) and water (0.33 mL) was added LiOH.H$_2$O (0.010 g; 0.38 mmol). The reaction mixture was stirred at 45° C. for 1 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH less than 2. The aqueous layer was re-extracted with EtOAc (3×). The combined organic extracts were washed with brine, dried (MgSO$_4$), and concentrated in vacuo to give Part B compound (0.122 g; 78%).

C.

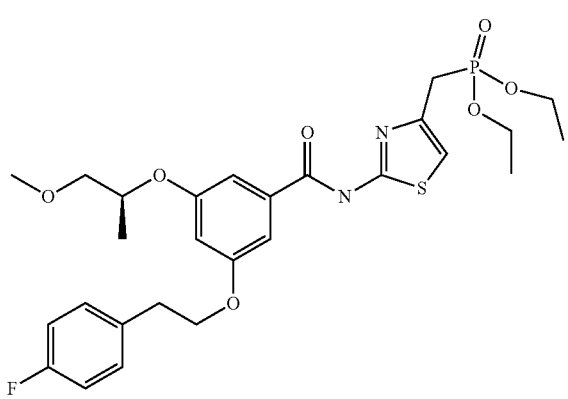

To a solution of Example 13 Part E compound (0.106 g; 0.422 mmol) in DMF (1.76 mL) were added HOAT (0.055 g; 0.404 mmol), Part B compound (0.122 g; 0.351 mmol), DIPEA (0.071 mL; 0.404 mmol), and, lastly, EDCI (0.077 g; 0.404 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$) and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (80.0 mg; 39%) as a clear, pale yellow oil. [M+H]$^+$=581.2; $^1$H NMR (400 MHz, CDCl$_3$): δ 1.21-1.33 (m, 9H), 3.06 (t, 2H), 3.25 (s, 1H), 3.31 (s, 1H), 3.39 (s, 3H), 3.45-3.60 (m, 2H), 4.00-4.15 (m, 4H), 4.19 (t, 2H), 4.60-4.70 (m, 1H), 6.65-6.72 (m, 1H), 6.88-6.94 (m, 1H), 6.99 (t, 2H), 7.13-7.27 (m, 4H), 11.77 (s, 1H).

Example 132

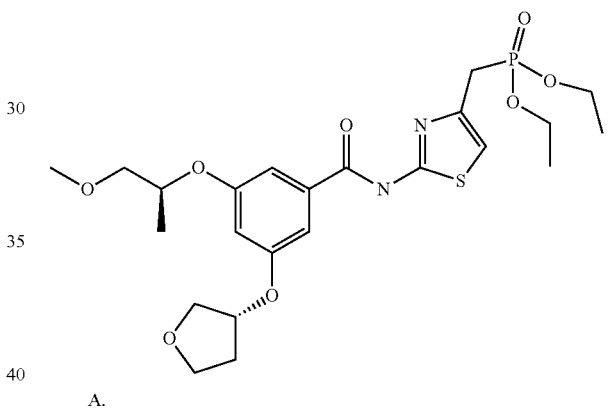

A.

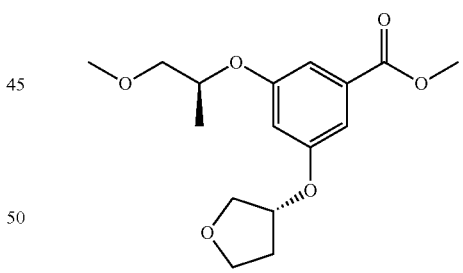

To a cold solution (0° C.) of Example 124 Part C compound (0.100 g; 0.416 mmol) in THF (2.08 mL) were added (S)-(+)-3-Hydroxytetrahydrofuran (0.074 mL; 0.916 mmol) and Ph$_3$P (0.24 g; 0.916 mmol), followed by the slow addition of DIAD (0.178 mL; 0.916 mmol). The reaction mixture was stirred at 25° C. for 16 h under at atmosphere of Ar. The reaction mixture was diluted with water and extracted with EtOAc (3×). The combined organic extracts were washed with 1N aqueous NaOH and brine, dried (MgSO$_4$), and concentrated in vacuo. The crude product was chromatographed (SiO$_2$; stepwise gradient from 10-15-20% solvent B, where solvent A=hexanes and solvent B=EtOAc) to give Part A compound (0.105 g; 75%).

B.

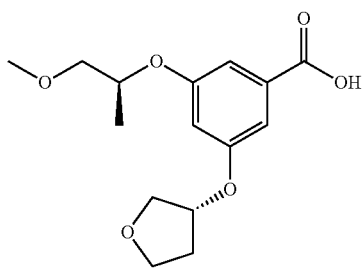

To a solution of Part A compound (0.105 g; 0.337 mmol) in THF (2.79 mL) and water (0.279 mL) was added LiOH.H$_2$O (0.028 g; 0.674 mmol). The reaction mixture was stirred at 45° C. for 1 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO$_4$), and concentrated in vacuo to give Part B compound (0.0964 g; 97%).

C.

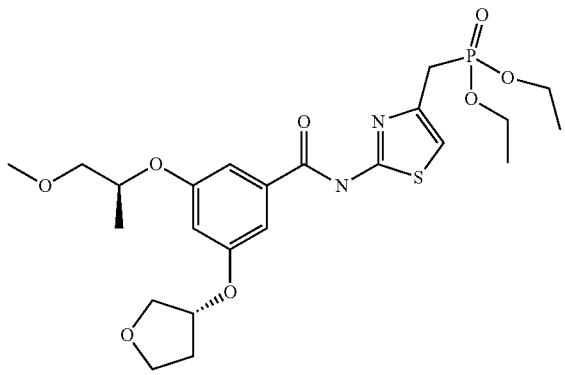

To a solution of Example 13 Part E compound (0.098 g; 0.390 mmol) in DMF (1.63 mL) were added HOAT (0.051 g; 0.374 mmol), Part B compound (0.096 g; 0.325 mmol), DIPEA (0.065 mL; 0.374 mmol), and, lastly, EDCI (0.072 g; 0.374 mmol). The reaction mixture was stirred at 25° C. for 16 h. Water was added, and the mixture was extracted with EtOAc (3×). The combined organic extracts were washed with sat.aqueous NH$_4$Cl, sat. aqueous NaHCO$_3$, and brine, dried (MgSO$_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (84.3 mg; 49%) as a clear, colorless oil. [M+H]$^+$=529.1; $^1$H NMR (400 MHz, CDCl$_3$): δ 1.19-1.34 (m, 9H), 2.06-2.30 (m, 2H), 3.25 (s, 1H), 3.30 (s, 1H), 3.39 (s, 3H), 3.43-3.61 (m, 2H), 3.84-4.00 (m, 4H), 4.00-4.13 (m, 4H), 4.54-4.64 (m, 1H), 4.91-5.00 (m, 1H), 6.62-6.70 (m, 1H), 6.80-6.88 (m, J=3.85 Hz, 1H), 7.06 (s, 1H), 7.13 (s, 1H), 10.53 (s, 1H).

Example 133

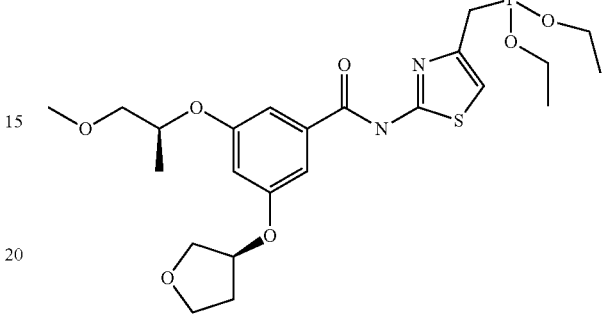

A.

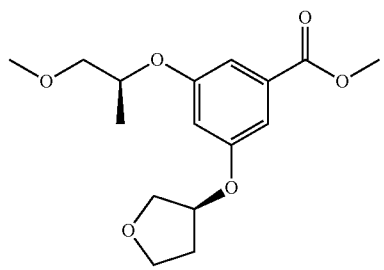

To a 0° C. solution of Example 124 Part C compound (0.100 g; 0.416 mmol) in THF (2.08 mL) were added (R)-(−)-3-hydroxytetrahydrofuran (0.033 mL; 0.416 mmol) and Ph$_3$P (0.24 g; 0.916 mmol), followed by the slow addition of DIAD (0.178 mL; 0.916 mmol). The reaction mixture was stirred at 25° C. for 16 h under Ar, then was diluted with water and extracted with EtOAc (3×). The combined organic extracts were washed with 1N aqueous NaOH and brine, dried (MgSO$_4$), and concentrated in vacuo. The crude product was chromatographed (SiO$_2$; stepwise gradient from 10-15-20% solvent B, where solvent A=hexanes and solvent B=EtOAc) to give Part A compound (0.088 g; 62%).

B.

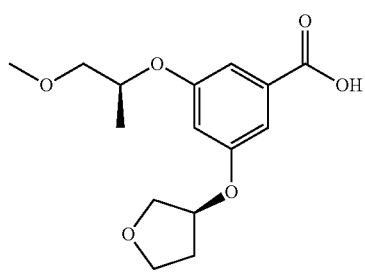

To a solution of Part A compound (0.088 g; 0.282 mmol) in THF (2.33 mL) and water (0.233 mL) was added LiOH.H$_2$O (0.024 g; 0.565 mmol). The reaction mixture was stirred at 45° C. for 1 h in a sealed vial, then an additional equivalent of LiOH was added. The reaction mixture was stirred at 45° C.

for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄) and concentrated in vacuo to give Part B compound (0.0654 g; 74%).

C.

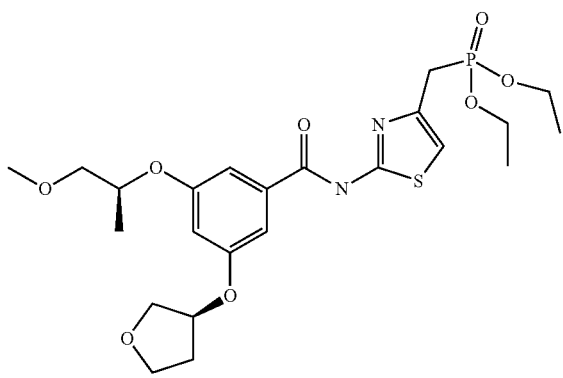

To a solution of Example 13 Part E compound (0.066 g; 0.265 mmol) in DMF (1.10 mL) were added HOAT (0.035 g; 0.254 mmol), Part B compound (0.065 g; 0.221 mmol), DIPEA (0.044 mL; 0.254 mmol), and, lastly, EDCI (0.049 g; 0.254 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O: CH₃CN:TFA and solvent B=90:10:0.1 CH₃CN:H₂O:TFA) to give the title compound (50.5 mg; 43%) as a clear, colorless oil. [M+H]⁺=529.1; ¹H NMR (400 MHz, CDCl₃): δ 1.21-1.33 (m, 9H), 2.03-2.17 (m, 1H), 2.17-2.28 (m, 1H), 3.25 (s, 1H), 3.31 (s, 1H), 3.38 (s, 3H), 3.44-3.53 (m, 1H), 3.52-3.59 (m, 1H), 3.68 (s, 2H), 3.83-3.92 (m, 1H), 3.93-4.01 (m, 2H), 4.03-4.12 (m, 3H), 4.57-4.67 (m, 1H), 4.96-5.02 (m, J=2.20 Hz, 1H), 6.67 (s, 1H), 6.85-6.92 (m, J=3.85 Hz, 1H), 7.13 (s, 1H), 7.20 (s, 1H).

Example 134

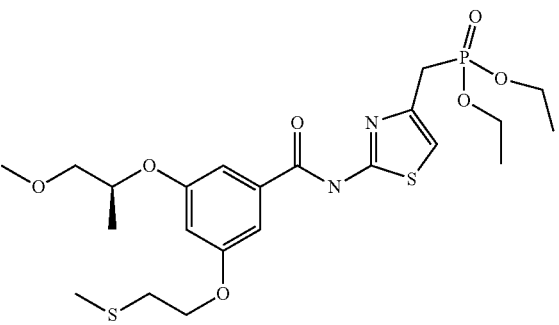

A.

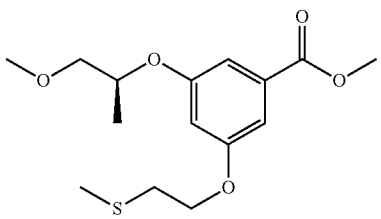

To a 0° C. solution of Example 124 Part C compound (0.125 g; 0.519 mmol) in THF (2.60 mL) were added 2-(methylthio)ethanol (0.105 mL; 1.14 mmol) and Ph₃P (0.30 g; 1.142 mmol), followed by the slow addition of DIAD (0.222 mL; 1.142 mmol). The reaction mixture was stirred at 25° C. for 16 h under Ar, then was diluted with water and extracted with EtOAc (3×). The combined organic extracts were washed with 1N aqueous NaOH and brine, dried (MgSO₄), and concentrated in vacuo. The crude product was chromatographed (SiO₂; step gradient from 20-30-50-60% solvent B, where solvent A=hexanes and solvent B=EtOAc) to give Part A compound (61.8 mg; 38%).

B.

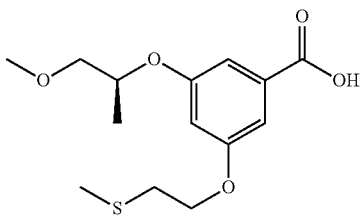

To a solution of Part A compound (0.062 g; 0.197 mmol) in THF (1.63 mL) and water (0.163 mL) was added LiOH.H₂O (0.016 g; 0.393 mmol). The reaction mixture was stirred at 45° C. for 1 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.052 g; 88%).

C.

To a solution of Example 13 Part E compound (0.059 g; 0.236 mmol) in DMF (0.98 mL) were added HOAT (0.031 g; 0.226 mmol), Part B compound (0.059 g; 0.196 mmol), DIPEA (0.034 mL; 0.196 mmol), and, lastly, EDCI (0.043 g; 0.226 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:CH₃CN:TFA and solvent B=90:10:0.1 CH₃CN:H₂O:TFA) to give the title compound (62.3 mg; 60%) as a clear, colorless oil. [M+H]⁺=533.4; ¹H NMR (400 MHz, CDCl₃): δ 1.23-1.31 (m, 9H), 2.15 (s, 3H), 3.27 (s, 1H), 3.31-3.37 (m, 4H), 3.44-3.56 (m, 2H), 3.99-4.15 (m, 4H), 4.19 (t, 2H), 4.65-4.77 (m, 1H), 6.69-6.74 (m, 1H), 6.95-7.00 (m, 1H), 7.28-7.33 (m, 1H), 7.35-7.40 (m, 1H).

Example 135

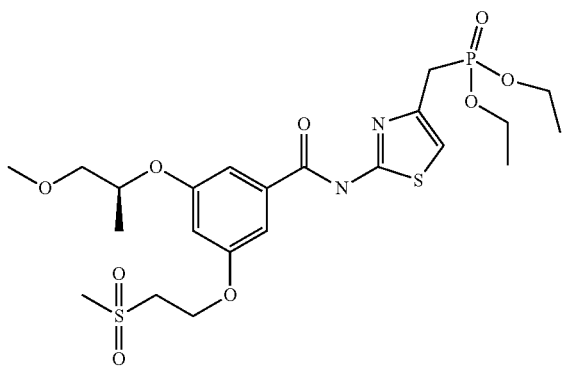 [SMILES: CCOP(=O)(Cc1csc(NC(=O)c2cc(OCCS(C)(=O)=O)cc(O[C@@H](C)COC)c2)n1)OCC]

To a 0° C. solution of Example 134 Part C compound (0.040 g; 0.075 mmol) in CH₂Cl₂ (0.75 mL) was added mCPBA (0.026 g; 0.15 mmol). The reaction mixture was stirred for 1 h at 0° C., then was warmed to RT. The reaction mixture was filtered, quenched with sat. aqueous NaHCO₃, and extracted with CH₂Cl₂ (3×). The combined organic extracts were washed with brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:CH₃CN:TFA and solvent B=90:10:0.1 CH₃CN:H₂O:TFA) to give the title compound (10.6 mg; 25%) as a clear, colorless oil. [M+H]⁺=565.2; ¹H NMR (400 MHz, CDCl₃): δ 1.26-1.34 (m, 9H), 3.05 (s, 3H), 3.29 (s, 1H), 3.34 (s, 1H), 3.39 (s, 4H), 3.43 (t, 3H), 3.49-3.60 (m, 2H), 4.07-4.18 (m, 4H), 4.52 (t, J=10.44 Hz, 3H), 4.69-4.79 (m, 1H), 6.72-6.78 (m, 1H), 6.99-7.05 (m, 1H), 7.40 (s, 1H), 7.45 (s, 1H).

Example 136

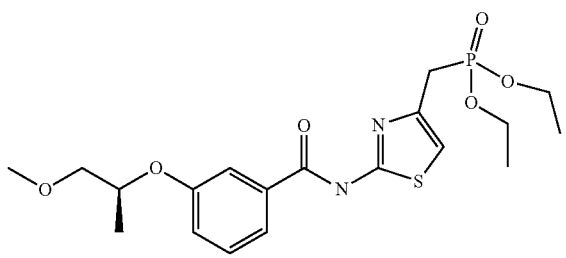

-continued

A.

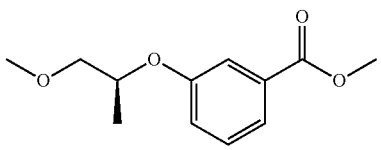

To a cold solution (0° C.) of 2-hydroxy-methylbenzoate (0.20 g; 1.31 mmol) in THF (5.70 mL) were added (R)-(−)-1-methoxy-2-propanol (0.178 g; 1.97 mmol) and Ph₃P (0.517 g; 1.97 mmol), followed by the slow addition of DIAD (0.398 g; 1.97 mmol). The reaction mixture was stirred at 25° C. for 16 h under Ar, then was diluted with water and extracted with EtOAc (3×). The combined organic extracts were washed with 1N aqueous NaOH and brine, dried (MgSO₄), and concentrated in vacuo. The residue was chromatographed (SiO₂; stepwise gradient from 10-20-30% solvent B, where solvent A=hexanes and solvent B=EtOAc) to give Part A compound (0.219 g; 74%).

B.

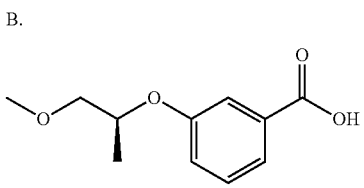

To a solution of Part A compound (0.219 g; 0.975 mmol) in THF (3.75 mL) and water (1.19 mL) was added LiOH.H₂O (0.049 g; 1.07 mmol). The reaction mixture was stirred at 45° C. for 1 h in a sealed vial, then an additional equivalent of LiOH was added. The reaction mixture was stirred at 50° C. for 2 h, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.221 g; 100%).

C.

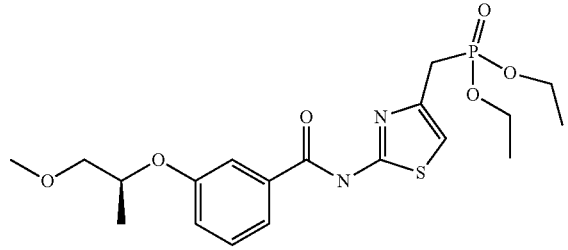

To a solution of Example 13 Part E compound (0.043 g; 0.171 mmol) in DMF (0.55 mL) were added HOAT (0.022 g; 0.164 mmol), Part B compound (0.030 g; 0.143 mmol), DIPEA (0.029 mL; 0.164 mmol), and, lastly, EDCI (0.031 g; 0.164 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5

μm, 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (17.3 mg; 27%) as a tacky, pale yellow oil. [M+H]$^+$=443.3; $^1$H NMR (400 MHz, CDCl$_3$): δ 1.22-1.30 (m, 9H), 3.30 (s, 1H), 3.35 (s, 3H), 3.35 (s, 4H), 3.47-3.58 (m, 2H), 4.01-4.16 (m, 4H), 4.75-4.83 (m, 1H), 6.96-7.00 (m, J=3.85 Hz, 1H), 7.14-7.18 (m, J=8.24, 2.20 Hz, 1H), 7.37 (t, J=7.97 Hz, 1H), 7.70 (d, J=7.70 Hz, 2H), 7.70 (d, J=7.70 Hz, 1H).

Example 137

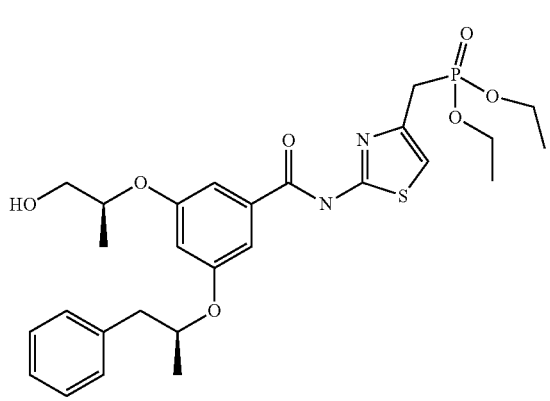

A.

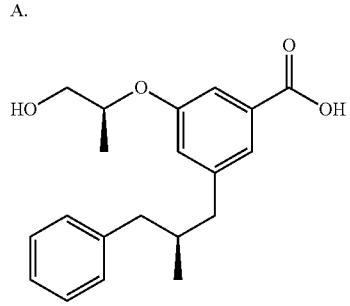

To a solution of Example 33 Part A acid (0.058 g; 0.17 mmol) in Et$_2$O (1.30 mL) under Ar was added TMSI (0.203 g; 1.01 mmol). The reaction mixture was stirred at 25° C. for 16 h, then was cooled to −40° C., cautiously quenched with water, and concentrated in vacuo. The residue was diluted with EtOAc and 1N aqueous HCl. The organic layer was washed with 10% (w/v) aqueous Na$_2$S$_2$O$_3$, washed with brine, dried (MgSO$_4$), and concentrated in vacuo to give Part A compound (0.056 g; 99%) as a yellow oil.

B.

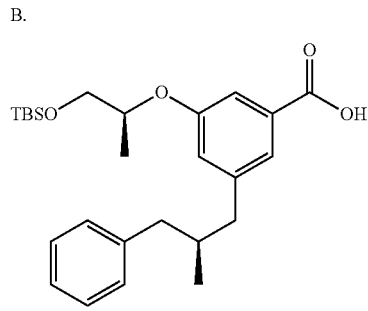

A solution of TBSCl (0.076 g; 0.504 mmol) in DMF (0.37 mL) was added to Part A compound (0.056 g; 0.17 mmol). Imidazole (0.069 g; 1.01 mmol) was added, and the reaction mixture was stirred for 2 h at 25° C., then was partitioned between EtOAc and sat. aqueous NH$_4$Cl. The organic phase was washed with sat. aqueous NH$_4$Cl and brine, dried (MgSO$_4$), and concentrated in vacuo. The residue was chromatographed (SiO$_2$; stepwise gradient from 20-25-30% solvent B, where solvent A=hexanes and solvent B=EtOAc) to give Part B compound (0.057 g; 76%).

C.

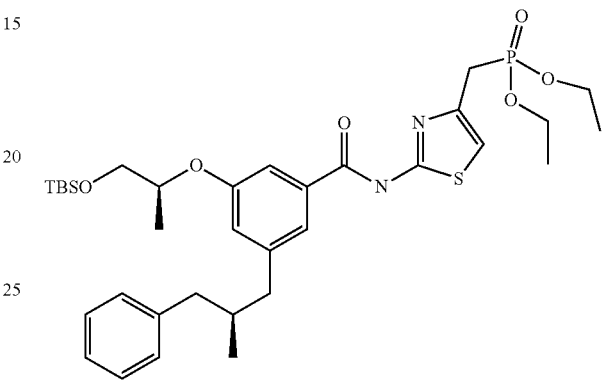

To a solution of Example 13 Part E compound (0.038 g; 0.152 mmol) in DMF (0.49 mL) were added HOAT (0.020 g; 0.146 mmol), Part B compound (0.057 g; 0.127 mmol), DIPEA (0.026 mL; 0.146 mmol), and, lastly, EDCI (0.028 g; 0.146 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine. The organic layer was dried (MgSO$_4$), and concentrated in vacuo to give Part C compound (0.063 g; 74%) as a clear, gold oil.

D.

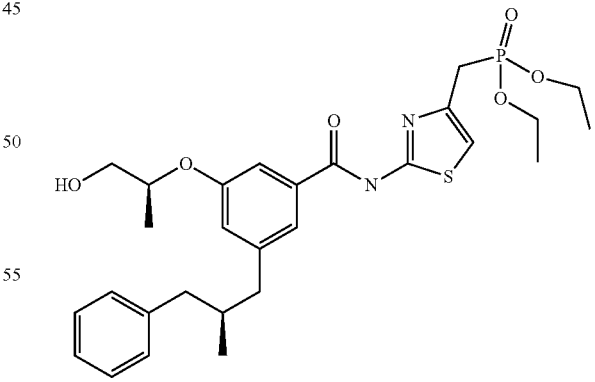

To a 0° C. solution of Part C compound (0.063; 0.094 mmol) in THF (0.47 mL) was added TBAF (0.090 mL of a 1 M solution; 0.094 mmol). The reaction was stirred for 1 h at 0° C. and an addition equivalent of TBAF (0.090 mL of a 1 M solution; 0.094 mmol) was added. The reaction was stirred at 0° C. for another 1 h, then was concentrated in vacuo. The residue was partitioned between EtOAc and brine. The organic layer was washed with brine, dried (MgSO$_4$), and concentrated in vacuo. The residue was purified by preparative HPLC (YMC reverse phase ODS-5 μm 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (23.6 mg; 45%) as a clear, colorless oil. [M+H]$^+$=563.5; $^1$H NMR (400 MHz, CDCl$_3$): δ 1.16-1.31 (m, J=11.82, 6.32 Hz, 12H), 1.98 (s, 1H), 2.77-2.87 (m, J=13.74 Hz, 1H), 2.93-3.02 (m, J=13.74 Hz, 1H), 3.27 (s, 1H), 3.32 (s, 1H), 3.61-3.69 (m, 1H), 3.69-3.76 (m, 1H), 4.01-4.14 (m, 4H), 4.60-4.72 (m, 2H), 6.62-6.66 (m, J=2.20, 2.20 Hz, 1H), 6.96 (d, J=3.85 Hz, 1H), 7.09-7.24 (m, 5H), 7.28 (s, 1H) 7.32 (s, 1H).

Example 138

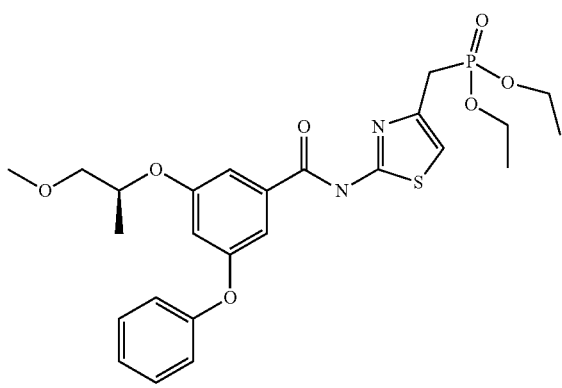

A.

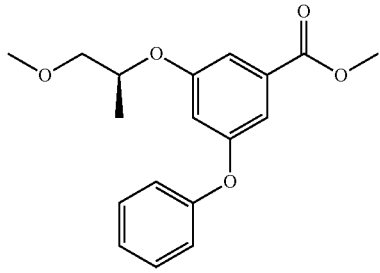

A solution of Example 124 Part C compound (0.100 g; 0.416 mmol), phenylboronic acid (0.102 g; 0.832 mmol), copper (II) acetate (0.151 g; 0.832 mmol), Et$_3$N (0.211 g; 2.08 mmol), and freshly activated 4 Å molecular sieves (1.2 g) in CH$_2$Cl$_2$ (8.32 mL) was stirred at 25° C. for 16 h. Additional solvent (8 mL), two equivalents each of boronic acid, copper (II) acetate, and Et$_3$N were added after 2 days. After a total of 5 days, 70% conversion was observed. The reaction mixture was filtered and washed with CH$_2$Cl$_2$. The combined filtrates were concentrated in vacuo, and the residue was partitioned between EtOAc and 1N aqueous HCl. The organic layer was washed with sat. aqueous NaHCO$_3$ and brine, dried (MgSO$_4$), and concentrated in vacuo. The crude product was chromatographed (SiO$_2$; step gradient from 10-20-30% solvent B, where solvent A=hexanes and solvent B=EtOAc) to give Part A compound (70.2 mg; 83% yield based on recovered starting material).

B.

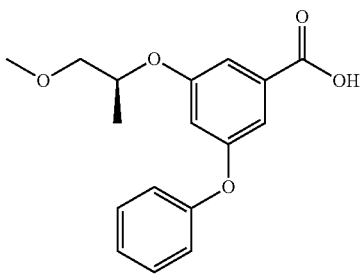

To a solution of Part A compound (0.070 g; 0.222 mmol) in THF (0.85 mL) and water (0.27 mL) was added LiOH.H$_2$O (0.010 g; 0.244 mmol). The reaction mixture was stirred at 45° C. for 1 h in a sealed vial, then an additional equivalent of LiOH.H$_2$O was added. The reaction mixture was stirred at 45° C. for an additional 3 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO$_4$), and concentrated in vacuo to give Part B compound (0.060 g; 90%).

C.

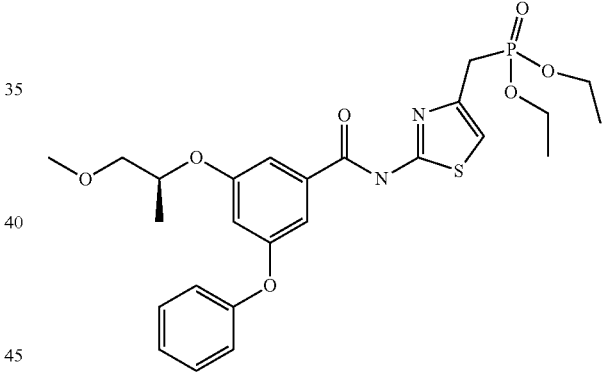

To a solution of Example 13 Part E compound (0.030 g; 0.119 mmol) in DMF (0.38 mL) were added HOAT (0.016 g; 0.114 mmol), Part B compound (0.03 g; 0.099 mmol), DIPEA (0.020 mL; 0.114 mmol), and, lastly, EDCI (0.022 g; 0.114 mmol). The reaction mixture was stirred at 25° C. for 16 h. An additional equivalent of Example 13 Part E compound was added, and the reaction mixture stirred at 25° C. for a further 16 h with no further conversion. Water was added, and the mixture was extracted with EtOAc (3×). The combined organic extracts were washed with sat. aqueous NH$_4$Cl, sat. aqueous NaHCO$_3$, and brine, dried (MgSO$_4$), and concentrated in vacuo. The residue was purified by preparative HPLC (YMC reverse phase ODS-5 μm 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (0.010 mg; 20%) as a tacky, yellow glass. [M+H]$^+$=535.5; $^1$H NMR (400 MHz, CDCl$_3$): δ 1.21-1.31 (m, 9H), 3.26 (s, 1H), 3.29-3.36 (m, 4H), 3.46-3.53 (m, 2H), 4.02-4.15 (m, 4H), 4.73-4.87 (m, 1H), 6.74-6.81 (m, 1H), 6.92-7.02 (m, 3H), 7.09 (t, J=7.42 Hz, 1H), 7.25-7.34 (m, 3H), 7.48 (s, 1H).

Example 139

A.

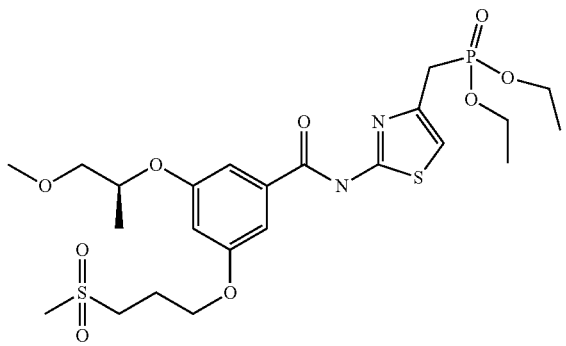

To a 0° C. solution of Example 124 Part C compound (0.110 g; 0.458 mmol) in THF (2.29 mL) were added 3-(methylthio)propan-1-ol (0.107 mL; 1.01 mmol) and Ph$_3$P (0.265 g; 1.01 mmol), followed by the slow addition of DIAD (0.195 mL; 1.01 mmol). The reaction mixture was stirred at 25° C. for 16 h under Ar, then was diluted with water and extracted with EtOAc (3×). The combined organic extracts were washed with 1N aqueous NaOH and brine, dried (MgSO$_4$), and concentrated in vacuo. The crude product was chromatographed (SiO$_2$; stepwise gradient from 10-20% solvent B, where solvent A=hexanes and solvent B=EtOAc) to give Part A compound (0.110 g; 73%).

B.

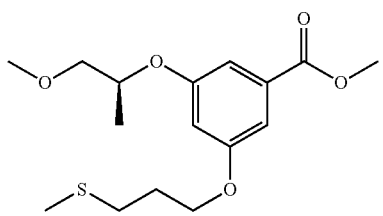

To a 0° C. solution of Part A compound (0.110 g; 0.334 mmol) in CH$_2$Cl$_2$ (3.34 mL) was added mCPBA (0.115 g; 0.67 mmol). The reaction mixture was stirred for 1 h at 0° C., then sat. aqueous NaHCO$_3$ was added and the mixture was extracted with CH$_2$Cl$_2$ (3×). The combined organic extracts were washed with brine, dried (MgSO$_4$), and concentrated in vacuo to give Part B compound (0.161 g; 88%).

C.

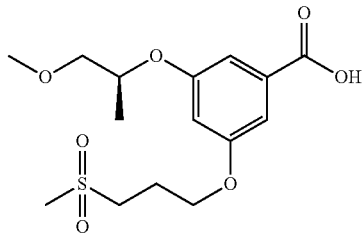

To a solution of Part C compound (0.162 g; 0.450 mmol) in THF (1.73 mL) and water (0.549 mL) was added LiOH.H$_2$O (0.021 g; 0.495 mmol). The reaction mixture was stirred at 45° C. for 1 h in a sealed vial, then an additional equivalent of LiOH was added. The reaction mixture was stirred at 45° C. for 16 h, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO$_4$), and concentrated in vacuo to give Part C compound (0.147 g; 94%).

D.

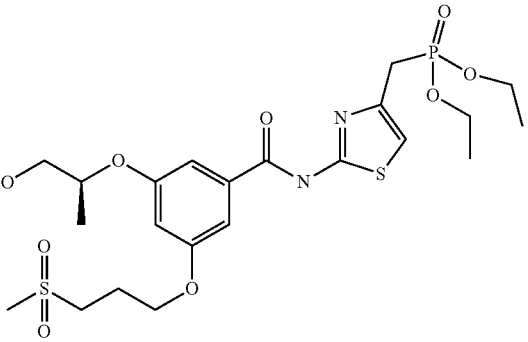

To a solution of Example 13 Part E compound (0.026 g; 0.104 mmol) in DMF (0.33 mL) were added HOAT (0.014 g; 0.100 mmol), Part C compound (0.030 g; 0.087 mmol), DIPEA (0.017 mL; 0.100 mmol), and, lastly, EDCI (0.019 g; 0.100 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (8 mg, 16% yield) as a white solid lyophilate. [M+H]$^+$=579.4; $^1$H NMR (400 MHz, CDCl$_3$): δ 1.14-1.28 (m, 9H), 2.20-2.33 (m, 2H), 2.89 (s, 3H), 3.13-3.26 (m, 4H), 3.33 (s, 3H), 3.40-3.54 (m, 2H), 3.92-4.05 (m, 4H), 4.05-4.12 (m, J=5.77, 5.77 Hz, 2H), 4.53-4.63 (m, 1H), 6.61-6.65 (m, 1H), 6.78-6.86 (m, J=3.85 Hz, 1H), 7.14 (s, 1H), 7.19 (s, 1H).

Example 140

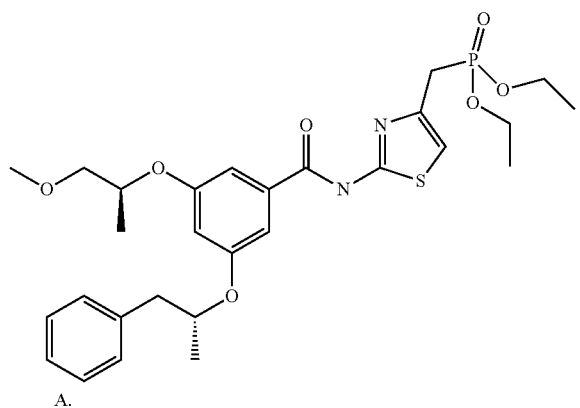

A.

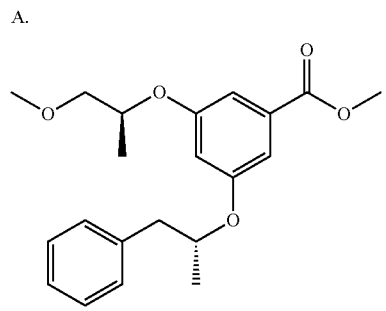

To a 0° C. solution of Example 124 Part C compound (0.110 g; 0.458 mmol) in THF (2.29 mL) were added (S)-(+)-1-phenyl-2-propanol (0.138 mL; 1.01 mmol) and Ph₃P (0.265 g; 1.01 mmol), followed by the slow addition of DIAD (0.195 mL; 1.01 mmol). The reaction mixture was stirred at 25° C. for 16 h under Ar, then was diluted with water and extracted with EtOAc (3×). The combined organic extracts were washed with 1N aqueous NaOH and brine, dried (MgSO₄), and concentrated in vacuo. The residue was chromatographed (SiO₂; stepwise gradient from 5-10% solvent B, where solvent A=hexanes and solvent B=EtOAc) to give Part A compound (0.133 g; 81%).

B.

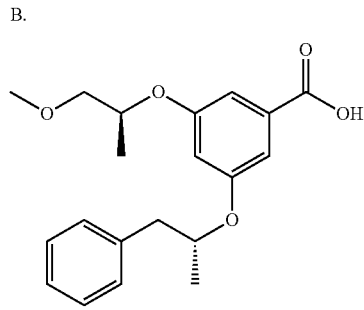 [SMILES: COC[C@H](C)Oc1cc(O[C@H](C)Cc2ccccc2)cc(C(=O)O)c1]

To a solution of Part A compound (0.133 g; 0.371 mmol) in THF (1.43 mL) and water (0.45 mL) was added LiOH.H₂O (0.017 g; 0.408 mmol). The reaction mixture was stirred at 45° C. for 1 h in a sealed vial, then an additional equivalent of LiOH was added. The reaction mixture was stirred at 45° C. for 16 h, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.123 g; 96%).

C.

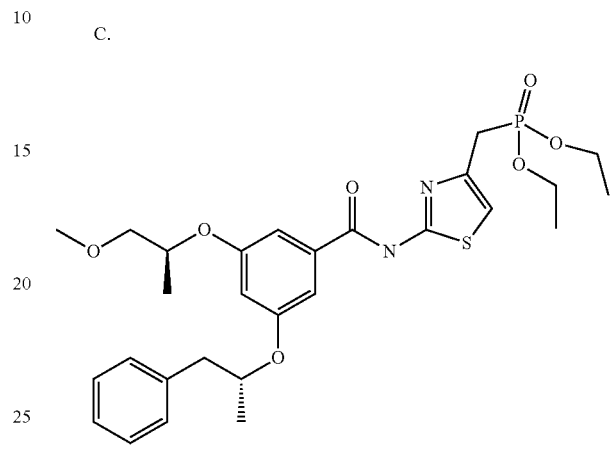

To a solution of Example 13 Part E compound (0.026 g; 0.105 mmol) in DMF (0.34 mL) were added HOAT (0.014 g; 0.100 mmol), Part B compound (0.030 g; 0.087 mmol), DIPEA (0.017 mL; 0.100 mmol), and, lastly, EDCI (0.019 g; 0.100 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:CH₃CN:TFA and solvent B=90:10:0.1 CH₃CN:H₂O:TFA) to give the title compound (16.4 mg; 33%) as a clear, colorless oil. [M+H]⁺=577.4; ¹H NMR (400 MHz, CDCl₃): δ 1.04-1.32 (m, 12H), 2.65-2.86 (m, J=13.74 Hz, 1H), 2.88-3.06 (m, 1H), 3.10-3.25 (m, J=20.89 Hz, 2H), 3.32 (s, 3H), 3.36-3.55 (m, 2H), 3.85-4.05 (m, J=7.15 Hz, 4H), 4.34-4.63 (m, 2H), 6.41-6.66 (m, 1H), 6.67-6.81 (m, 1H), 6.95-7.07 (m, 2H), 7.08-7.29 (m, 5H), 10.44 (s, 1H), 10.44 (s, 1H).

Example 141

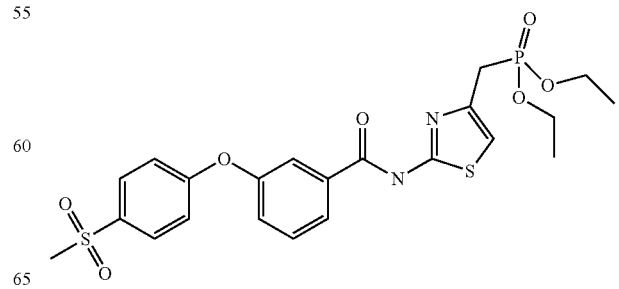

A.

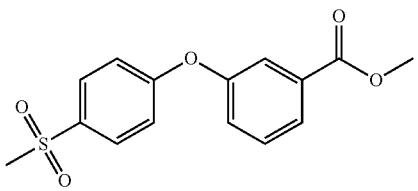

To a solution of 3-hydroxy-methylbenzoate (0.500 g; 3.29 mmol) in DMF (8.23 mL) were added $K_2CO_3$ (0.908 g; 6.57 mmol) and fluoro-4-(methylsulfonyl)benzene (0.573 g; 3.29 mmol). The reaction mixture was stirred at 120° C. for 2 days under Ar, then cooled to RT. Volatiles were removed in vacuo. The residue was partitioned between sat. aqueous $NaHCO_3$ and EtOAc. The organic layer was washed with 1N aqueous HCl and brine, dried ($MgSO_4$), and concentrated in vacuo. The residue was chromatographed ($SiO_2$; stepwise gradient from 20-30-40% solvent B, where solvent A=hexanes and solvent B=EtOAc) to give Part A compound (0.583 g; 58%).

B.

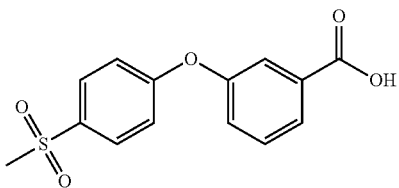

To a solution of Part A compound (0.200 g; 0.653 mmol) in THF (2.51 mL) and water (0.80 mL) was added $LiOH.H_2O$ (0.030 g; 0.718 mmol). The reaction mixture was stirred at 45° C. for 1 h in a sealed vial, then an additional equivalent of LiOH was added. The reaction mixture was stirred at 50° C. for 2 h, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried ($MgSO_4$), and concentrated in vacuo to give Part B compound (0.176 g; 92%).

C.

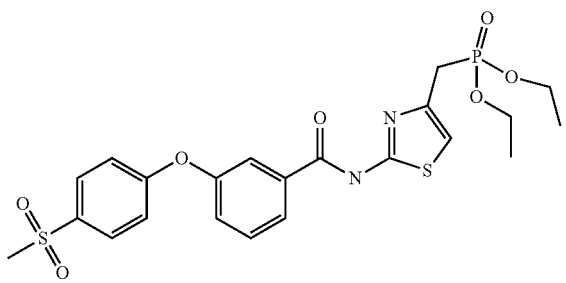

To a solution of Example 13 Part E compound (0.309 g; 0.124 mmol) in DMF (0.40 mL) were added HOAT (0.016 g; 0.118 mmol), Part B compound (0.030 g; 0.103 mmol), DIPEA (0.021 mL; 0.118 mmol), and, lastly, EDCI (0.023 g; 0.118 mmol). The reaction mixture was stirred at 25° C. for 16 h. Water was added, and the mixture was extracted with EtOAc (3×). The combined organic extracts were washed with sat. aqueous $NH_4Cl$, sat. aqueous $NaHCO_3$, and brine, dried ($MgSO_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 $H_2O$:$CH_3CN$:TFA and solvent B=90:10:0.1 $CH_3CN$:$H_2O$:TFA) to give the title compound (14.7 mg; 27%) as a tacky, white solid. $[M+H]^+$=525.3; $^1H$ NMR (400 MHz, $CDCl_3$): δ 1.20 (t, J=7.15 Hz, 6H), 2.99 (s, 3H), 3.21 (s, 1H), 3.26 (s, 1H), 3.95-4.08 (m, 4H), 6.85-6.92 (m, J=3.30 Hz, 1H), 7.00-7.10 (m, J=8.79 Hz, 2H), 7.24-7.32 (m, J=7.70 Hz, 1H), 7.53 (t, J=7.97 Hz, 1H), 7.77 (s, 1H), 7.74-7.80 (m, 1H), 7.84 (d, J=8.79 Hz, 2H), 7.92 (d, J=7.70 Hz, 1H).

Example 142

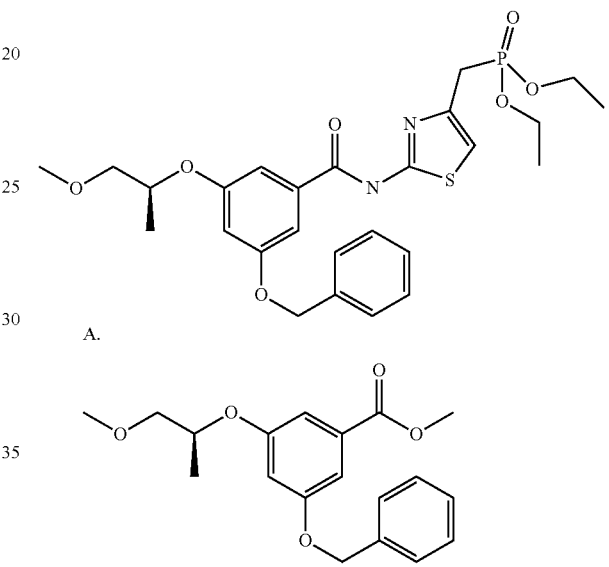

A.

To a 0° C. solution of Example 124 Part C compound (0.110 g; 0.458 mmol) in THF (2.29 mL) were added benzyl alcohol (0.109 mL; 1.01 mmol) and $Ph_3P$ (0.265 g; 1.01 mmol), followed by the slow addition of DIAD (0.195 mL; 1.01 mmol). The reaction mixture was stirred at 25° C. for 16 h under Ar, then was diluted with water and extracted with EtOAc (3×). The combined organic extracts were washed with 1N aqueous NaOH and brine, dried ($MgSO_4$), and concentrated in vacuo. The residue was chromatographed ($SiO_2$; step gradient from 10-15-20% solvent B, where solvent A=hexanes and solvent B=EtOAc) to give Part A compound (0.160 g; 100%).

B.

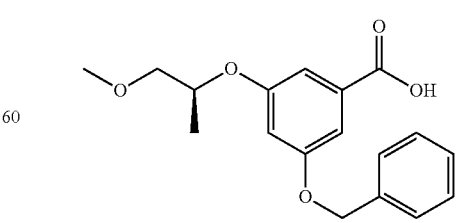

To a solution of Part A compound (0.160 g; 0.483 mmol) in THF (1.86 mL) and water (0.59 mL) was added $LiOH.H_2O$ (0.022 g; 0.532 mmol). The reaction mixture was stirred at 45° C. for 2 h in a sealed vial, then an additional equivalent of LiOH was added. The reaction mixture was stirred at 45° C. for 16 h, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.137 g; 90%).

C.

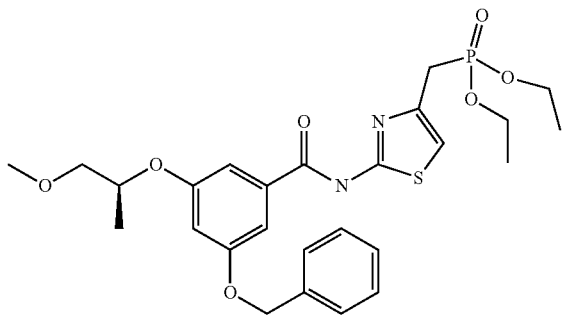

To a solution of Example 13 Part E compound (0.029 g; 0.114 mmol) in DMF (0.37 mL) were added HOAT (0.015 g; 0.109 mmol), Part B compound (0.030 g; 0.095 mmol), DIPEA (0.019 mL; 0.109 mmol), and, lastly, EDCI (0.021 g; 0.109 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:CH₃CN:TFA and solvent B=90:10:0.1 CH₃CN:H₂O:TFA) to give the title compound (18.6 mg; 36%) as a clear, colorless oil. [M+H]⁺=549.2; ¹H NMR (400 MHz, CDCl₃): δ 1.13-1.29 (m, 9H), 3.19 (s, 1H), 3.24 (s, 2H), 3.33 (s, 3H), 3.39-3.46 (m, 1H), 3.46-3.53 (m, 1H), 3.89-4.04 (m, 4H), 4.48-4.58 (m, J=3.85 Hz, 1H), 5.01 (s, 2H), 6.69-6.74 (m, 1H), 6.75-6.80 (m, J=3.85 Hz, 1H), 7.11 (s, 1H), 7.23-7.38 (m, 5H).

Example 143

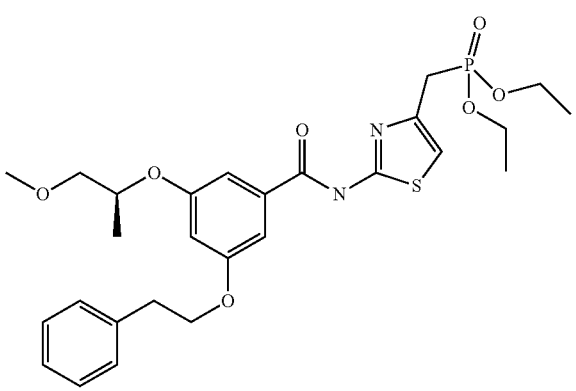

-continued

A.

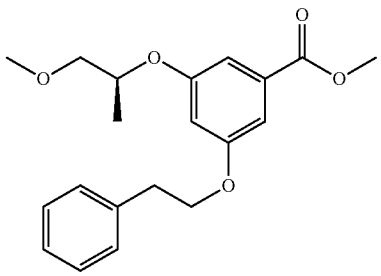

To a 0° C. solution of Example 124 Part C compound (0.110 g; 0.458 mmol) in THF (2.29 mL) were added 2-phenylethanol (0.121 mL; 1.01 mmol) and Ph₃P (0.265 g; 1.01 mmol), followed by the slow addition of DIAD (0.195 mL; 1.01 mmol). The reaction mixture was stirred at 25° C. for 16 h under Ar, then was diluted with water and extracted with EtOAc (3×). The combined organic extracts were washed with 1N aqueous NaOH and brine, dried (MgSO₄), and concentrated in vacuo. The residue was chromatographed (SiO₂; stepwise gradient from 10-15-20% solvent B, where solvent A=hexanes and solvent B=EtOAc) to give Part A compound (0.127 g; 81%).

B.

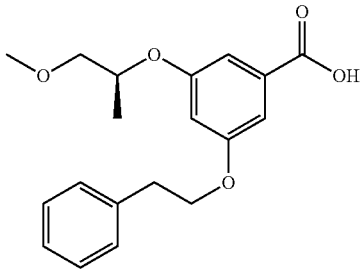

To a solution of Part A compound (0.127 g; 0.370 mmol) in THF (1.42 mL) and water (0.45 mL) was added LiOH.H₂O (0.017 g; 0.407 mmol). The reaction mixture was stirred at 45° C. for 2 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.112 g; 91%).

C.

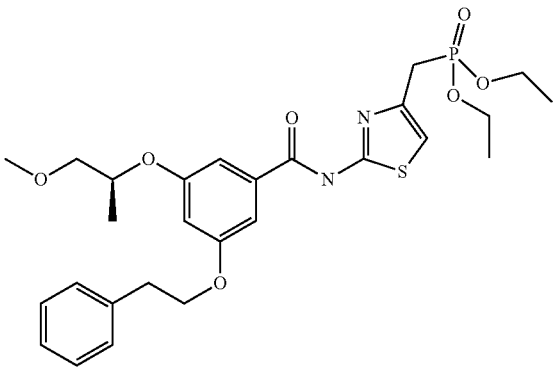

To a solution of Example 13 Part E compound (0.027 g; 0.109 mmol) in DMF (0.35 mL) were added HOAT (0.014 g; 0.104 mmol), Part B compound (0.030 g; 0.091 mmol), DIPEA (0.018 mL; 0.104 mmol), and, lastly, EDCI (0.020 g; 0.104 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (24.5 mg; 48%) as a clear, colorless oil. [M+H]$^+$=563.2; $^1$H NMR (400 MHz, CDCl$_3$): δ 1.16-1.28 (m, 6H), 3.02 (t, J=6.60 Hz, 2H), 3.20 (s, 1H), 3.25 (s, 1H), 3.33 (s, 3H), 3.41-3.54 (m, 2H), 3.96-4.08 (m, 4H), 4.16 (t, J=6.87 Hz, 2H), 4.57-4.67 (m, 1H), 6.63-6.69 (m, 1H), 6.83-6.89 (m, J=3.85 Hz, 1H), 7.13-7.28 (m, 7H).

Example 144

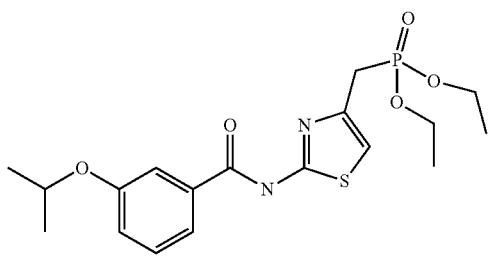 [SMILES: CCOP(=O)(Cc1csc(NC(=O)c2cccc(OC(C)C)c2)n1)OCC]

To a solution of Example 13 Part E compound (0.100 g; 0.400 mmol) in DMF (2.0 mL) were added HOAT (0.052 g; 0.383 mmol), 3-isopropoxybenzoic acid (0.060 g; 0.333 mmol), DIPEA (0.07 mL; 0.383 mmol), and, lastly, EDCI (0.073 g; 0.383 mmol). The reaction mixture was stirred at 25° C. for 16 h. Water was added, and the mixture was extracted with EtOAc (3×). The combined organic extracts were washed with 0.5N aqueous HCl and brine, dried (MgSO$_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (9.4 mg; 7%) as a clear, colorless oil. [M+H]$^+$=413.1; $^1$H NMR (400 MHz, CDCl$_3$): δ 1.21-1.34 (m, J=7.15, 7.15 Hz, 12H), 3.26 (s, 1H), 3.31 (s, 1H), 4.00-4.14 (m, 4H), 4.68-4.80 (m, 1H), 6.91-6.99 (m, 1H), 7.04-7.12 (m, J=8.25 Hz, 1H), 7.31-7.41 (m, 1H), 7.62-7.72 (m, 2H).

Example 145

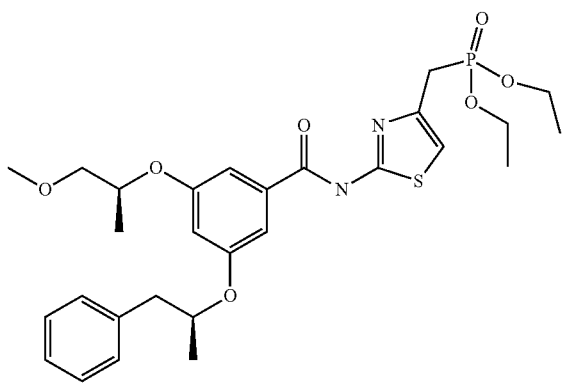 [SMILES: CCOP(=O)(Cc1csc(NC(=O)c2cc(O[C@@H](C)COC)cc(O[C@@H](C)Cc3ccccc3)c2)n1)OCC]

To a solution of Example 13 Part E compound (0.027 g; 0.105 mmol) in DMF (0.34 mL) were added HOAT (0.013 g; 0.093 mmol), Example 33 Part A acid (0.030 g; 0.087 mmol), DIPEA (0.016 mL; 0.093 mmol), and, lastly, EDCI (0.018 g; 0.932 mmol). The reaction mixture was stirred at 25° C. for 16 h. Water was added, and the mixture was extracted with EtOAc (3×). The combined organic extracts were washed with sat. aqueous NH$_4$Cl, sat. aqueous NaHCO$_3$, and brine, dried (MgSO$_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H$_2$O:CH$_3$CN:TFA and solvent B=90:10:0.1 CH$_3$CN:H$_2$O:TFA) to give the title compound (35.2 mg; 70%) as a clear, colorless oil. [M+H]$^+$=577.2; $^1$H NMR (400 MHz, CDCl$_3$): δ 1.21-1.37 (m, 12H), 2.82-2.93 (m, J=14.02, 5.22 Hz, 1H), 2.99-3.09 (m, 1H), 3.32-3.48 (m, 5H), 3.51-3.66 (m, 2H), 4.06-4.26 (m, 4H), 4.68-4.84 (m, 2H), 6.68-6.77 (m, 1H), 6.96-7.07 (m, J=3.85 Hz, 1H), 7.13-7.41 (m, 7H), 10.77 (s, 1H).

Example 146

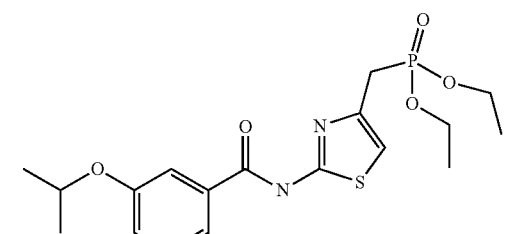

A.

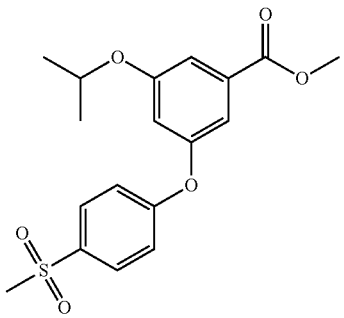

To a 0° C. solution of Example 26 Part A compound (0.166 g; 0.515 mmol) in THF (2.60 mL) were added iPrOH (0.087 mL; 1.13 mmol) and Ph$_3$P (0.30 g; 1.13 mmol), followed by the slow addition of DIAD (0.219 mL; 1.13 mmol). The reaction mixture was stirred at 25° C. for 16 h under Ar, then was diluted with water and extracted with EtOAc (3×). The combined organic extracts were washed with 1N aqueous NaOH and brine, dried (MgSO$_4$), and concentrated in vacuo. The residue was chromatographed (SiO$_2$; stepwise gradient from 20-40% solvent B, where solvent A=hexanes and solvent B=EtOAc) to give Part A compound (0.258 g; >100%, contaminated with reduced DIAD).

B.

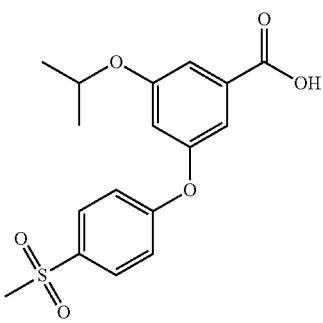

To a solution of Part A compound (0.189 g; 0.515 mmol) in THF (3.22 mL) and water (0.62 mL) was added LiOH.H₂O (0.024 g; 0.567 mmol). The reaction mixture was stirred at 45° C. for 1 h in a sealed vial, then an additional equivalent of LiOH was added. The reaction mixture was stirred at 45° C. for 16 h, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.214 g; >100%, contaminated with reduced DIAD).

C.

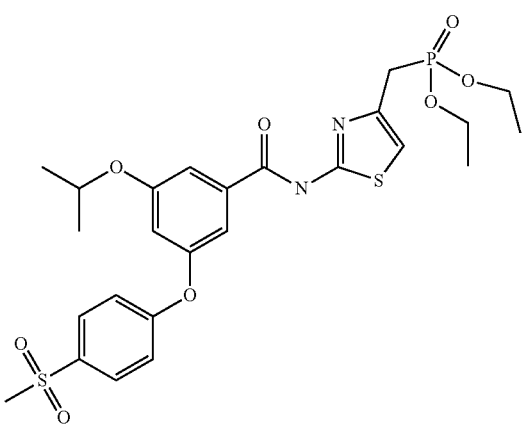

To a solution of Example 13 Part E compound (0.043 g; 0.17 mmol) in DMF (0.55 mL) were added HOAT (0.022 g; 0.164 mmol), Part B compound (0.050 g; 0.143 mmol), DIPEA (0.029 mL; 0.164 mmol), and, lastly, EDCI (0.031 g; 0.164 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:CH₃CN:TFA and solvent B=90:10:0.1 CH₃CN:H₂O:TFA) to give the title compound (37.5 mg; 60%) as a clear, colorless oil. [M+H]⁺=583.1; ¹H NMR (400 MHz, CDCl₃): δ 1.17-1.38 (m, 12H), 3.04 (s, 3H), 3.27 (s, 1H), 3.32 (s, 1H), 3.99-4.14 (m, 4H), 4.64-4.77 (m, 1H), 6.79-6.83 (m, 1H), 6.88-6.96 (m, J=3.30 Hz, 1H), 7.07-7.15 (m, J=8.79 Hz, 2H), 7.30-7.36 (m, 1H), 7.47-7.54 (m, 1H), 7.84-7.92 (m, J=8.79 Hz, 2H).

Example 147

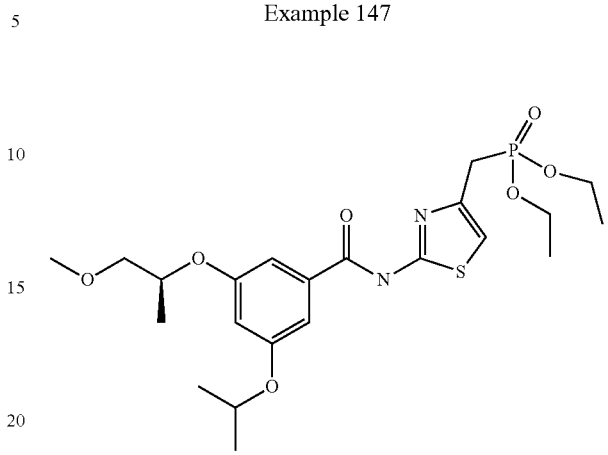

A.

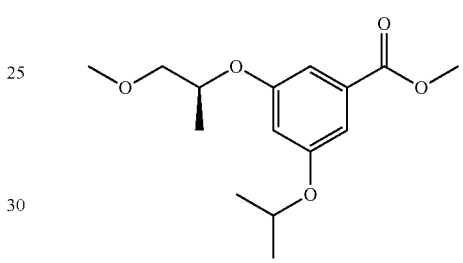

To a 0° C. solution of Example 124 Part C compound (0.100 g; 0.416 mmol) in THF (2.08 mL) were added iPrOH (0.019 mL; 0.916 mmol) and Ph₃P (0.240 g; 0.916 mmol), followed by the slow addition of DIAD (0.177 mL; 0.916 mmol). The reaction mixture was stirred at 25° C. for 16 h under Ar, then was diluted with water and extracted with EtOAc (3×). The combined organic extracts were washed with 1N aqueous NaOH and brine, dried (MgSO₄), and concentrated in vacuo. The residue was chromatographed (SiO₂; stepwise gradient from 5-10% solvent B, where solvent A=hexanes and solvent B=EtOAc) to give Part A compound (82.2 mg; 70%).

B.

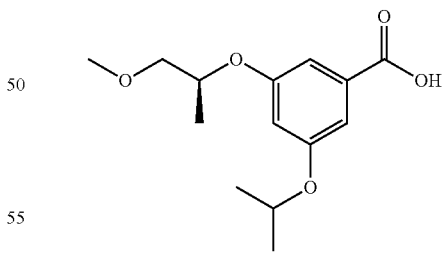

To a solution of Part A compound (0.082 g; 0.291 mmol) in THF (1.82 mL) and water (0.45 mL) was added LiOH.H₂O (0.014 g; 0.32 mmol). The reaction mixture was stirred at 45° C. for 3 h in a sealed vial, then an additional equivalent of LiOH. The reaction mixture was stirred at 45° C. for 16 h, then was cooled to RT. Volatiles were removed in vacuo, and the remaining aqueous solution was acidified with 0.5N aqueous HCl to pH<2. The aqueous layer was back extracted with EtOAc (3×). The combined organic extracts were washed with brine, dried (MgSO₄), and concentrated in vacuo to give Part B compound (83.0 mg; 100%).

C.

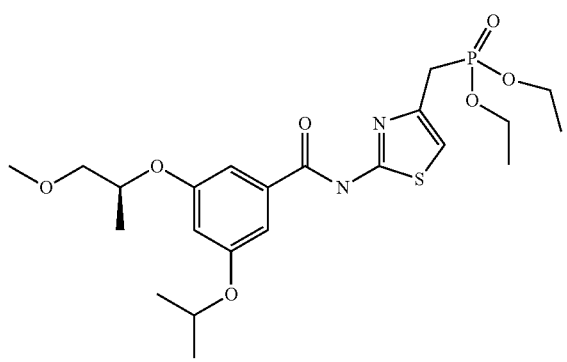

To a solution of Example 13 Part E compound (0.034 g; 0.134 mmol) in DMF (0.43 mL) were added HOAT (0.018 g; 0.129 mmol), Part B compound (0.030 g; 0.112 mmol), DIPEA (0.023 mL; 0.129 mmol), and, lastly, EDCI (0.025 g; 0.129 mmol). The reaction mixture was stirred at 25° C. for 16 h. Water was added, and the mixture was extracted with EtOAc (3×). The combined organic extracts were washed with sat. aqueous $NH_4Cl$, sat. aqueous $NaHCO_3$, and brine, dried ($MgSO_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 $H_2O$:$CH_3CN$:TFA and solvent B=90:10:0.1 $CH_3CN$:$H_2O$:TFA) to give the title compound (28.0 mg; 50%) as a clear, colorless oil. $[M+H]^+$=501.0; $^1H$ NMR (400 MHz, $CDCl_3$): δ 1.20-1.30 (m, 15H), 3.22 (s, 1H), 3.27 (s, 1H), 3.34 (s, 3H), 3.42-3.56 (m, 2H), 4.00-4.12 (m, 4H), 4.56-4.70 (m, 2H), 6.64-6.69 (m, 1H), 6.88-6.95 (m, J=3.30 Hz, 1H), 7.21-7.28 (m, J=8.24 Hz, 2H).

Example 148

A.

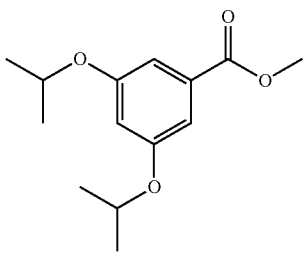

To a cold solution (0° C.) of 3,5-dihydroxy-methylbenzoate (1.00 g; 5.95 mmol) in THF (29.8 mL) were added iPrOH (0.787 mL; 13.10 mmol) and $Ph_3P$ (3.43 g; 13.10 mmol), followed by the slow addition of DIAD (2.58 mL; 13.1 mmol). The reaction mixture was stirred at 25° C. for 16 h under Ar, then was diluted with water and extracted with EtOAc (3×). The combined organic extracts were washed with 1N aqueous NaOH and brine, dried ($MgSO_4$), and concentrated in vacuo. The crude product was chromatographed ($SiO_2$; stepwise gradient from 10-20-30% solvent B, where solvent A=hexanes and solvent B=EtOAc) to give Part A compound (1.27 g; 85%).

B.

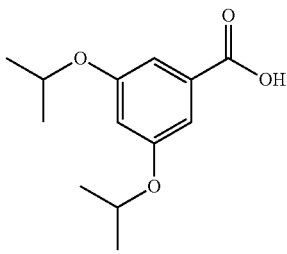

To a solution of Part A compound (0.300 g; 1.19 mmol) in THF (7.44 mL) and water (1.45 mL) was added $LiOH·H_2O$ (0.055 g; 1.31 mmol). The reaction mixture was stirred at 45° C. for 3 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried ($MgSO_4$), and concentrated in vacuo to give Part B compound (0.290 g; 100%).

C.

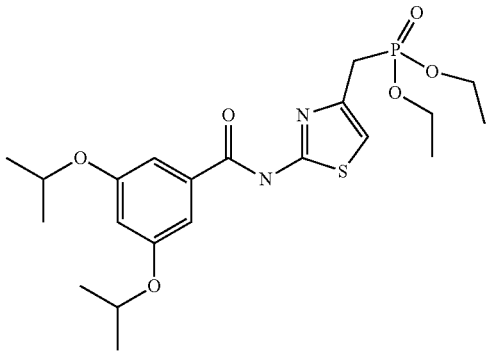

To a solution of Example 13 Part E compound (0.167 g; 0.668 mmol) in DMF (2.14 mL) were added HOAT (0.087 g; 0.641 mmol), Part B compound (0.133 g; 0.557 mmol), DIPEA (0.116 mL; 0.641 mmol), and, lastly, EDCI (0.123 g; 0.668 mmol). The reaction mixture was stirred at 25° C. for 16 h. Water was added, and the mixture was extracted with EtOAc (3×). The combined organic extracts were washed with sat. aqueous $NH_4Cl$, sat. aqueous $NaHCO_3$, and brine, dried ($MgSO_4$), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:CH₃CN:TFA and solvent B=90:10:0.1 CH3CN:H₂O:TFA) to give the title compound (95.1 mg; 36%) as a white solid. [M+H]⁺=471.5; ¹H NMR (400 MHz, CDCl₃): δ 1.24-1.37 (m, 18H), 3.27 (s, 1H), 3.32 (s, 1H), 4.01-4.19 (m, 4H), 4.58-4.72 (m, 2H), 6.65 (s, 1H), 6.92-7.00 (m, J=3.85 Hz, 1H), 7.21-7.27 (m, 2H).

Example 149

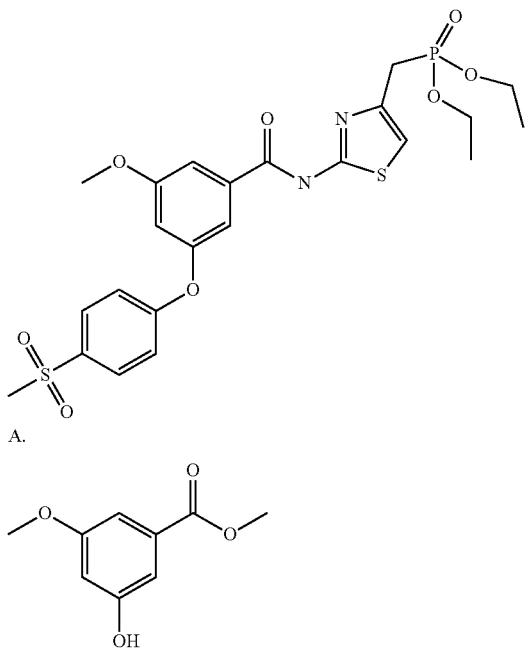

A.

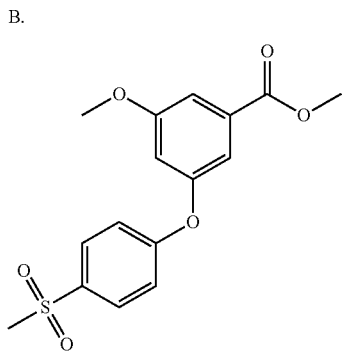

B.

To a solution of methyl 3,5-dihydroxybenzoate (1.75 g; 10.41 mmol) in acetone (14 mL was added K₂CO₃ (2.88 g; 20.82 mmol) and nBu₄NI (384 mg; 1.04 mmol), followed by dimethyl sulfate (985 μL; 10.41 mmol). The reaction mixture was heated at reflux (~65° C.) for 3 h, then was cooled to RT. The mixture was filtered, and the filtrate was concentrated in vacuo. The residue was chromatographed (SiO₂; continuous gradient from 0 to 45% solvent B over 40 min, where solvent A=hexanes and solvent B=EtOAc) to give Part A compound (0.74 g; 39%) as a white solid.

To a mixture of Part A compound (75 mg; 0.412 mmol), 4-fluorophenyl methyl sulfone (72 mg; 0.412 mmol) and K₂CO₃ (114 mg; 0.824 mmol) was added DMF (1.6 mL). The reaction mixture was heated at 120° C. for 5 h, then was cooled to RT. The mixture was partitioned between EtOAc (10 mL) and H₂O (10 mL). The organic phase was washed with brine (5 mL), dried (MgSO₄), and concentrated in vacuo. The residue was chromatographed (SiO₂; continuous gradient from 0 to 80% solvent B over 12 min, where solvent A=hexanes and solvent B=EtOAc) to give Part B compound (119 mg; 86%) as a colorless syrup.

C.

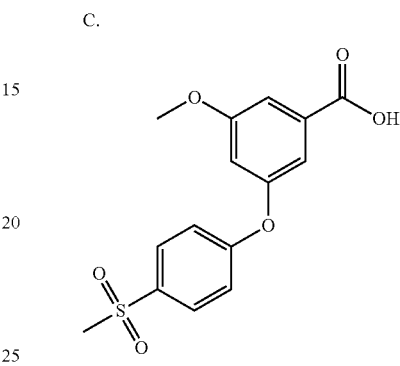

To a solution of Part B compound (118 mg; 0.351 mmol) in THF (0.47 mL), MeOH (0.47 mL), and H₂O (0.47 mL) was added LiOH.H₂O (44 mg; 1.053 mmol). After 1 h of stirring, the mixture was partitioned between EtOAc (6 mL) and 0.5 N aqueous HCl (6 mL). The aqueous phase was extracted with EtOAc (6 mL). The combined organic extracts were washed with brine (6 mL), dried (MgSO₄), and concentrated in vacuo to give Part C compound (94 mg; 83%) as a white solid.

D.

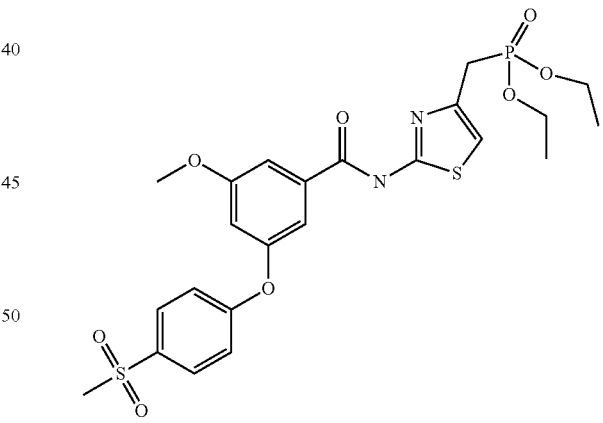

To a solution of Example 13 Part E compound (0.038 g; 0.150 mmol) in DMF (0.48 mL) were added HOAT (0.020 g; 0.144 mmol), Part C compound (0.040 g; 0.125 mmol), DIPEA (0.025 mL; 0.144 mmol), and, lastly, EDCI (0.028 g; 0.144 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 25 to 100% solvent B over 12 min, where solvent A=90:10:0.1 H₂O:

CH₃CN:TFA and solvent B=90:10:0.1 CH₃CN:H₂O:TFA) to give the title compound (27.6 mg; 40%) as a white solid. [M+H]⁺=555.4; ¹H NMR (400 MHz, CDCl₃): δ 1.20 (t, J=7.15 Hz, 6H), 3.01 (s, 3H), 3.24 (s, 1H), 3.30 (s, 1H), 3.83 (s, 3H), 3.94-4.09 (m, 4H), 6.73-6.87 (m, 2H), 7.08 (d, J=8.79 Hz, 2H), 7.22-7.28 (m, 1H), 7.36-7.43 (m, 1H), 7.86 (d, J=8.79 Hz, 2H).

Example 150

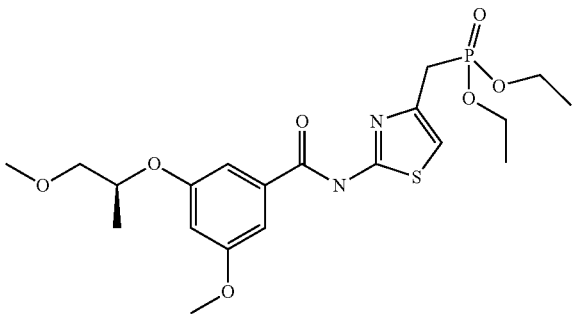

A.

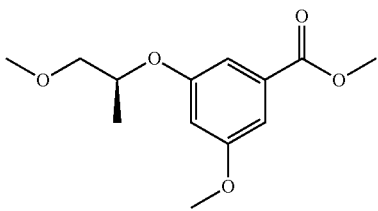

To a 0° C. mixture of Example 149 Part A compound (100 mg; 0.549 mmol), R-(−)-1-methoxy-2-propanol (70 μL; 0.714 mmol), and polymer-bound PPh₃ (0.47 g; 1.43 mmol) in THF (2 mL) was added dropwise a solution of DIAD (162 μL; 0.823 mmol) in THF (0.20 mL). The reaction was stirred at RT for 18 h, then was filtered. The resin was rinsed with THF (2×4 mL), and the combined filtrates were concentrated in vacuo. The residue was chromatographed (SiO₂; continuous gradient from 0 to 45% solvent B over 20 min, where solvent A=hexanes and solvent B=EtOAc) to give Part A compound (78 mg; 56%) as a colorless oil.

B.

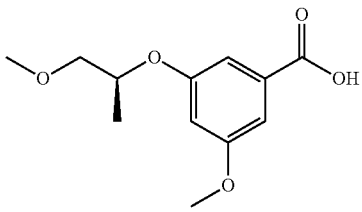

To a solution of Part A compound (74 mg; 0.291 mmol) in THF (0.39 mL), MeOH (0.39 mL), and H₂O (0.39 mL) was added LiOH.H₂O (37 mg; 0.873 mmol). The reaction was stirred for 1 h, then was partitioned between EtOAc (5 mL) and 0.5 N aqueous HCl (5 mL). The aqueous phase was extracted with EtOAc (5 mL). The combined organic extracts were washed with brine (5 mL), dried (MgSO₄), and concentrated in vacuo to give Part B compound (68 mg; 97%) as a colorless syrup

C.

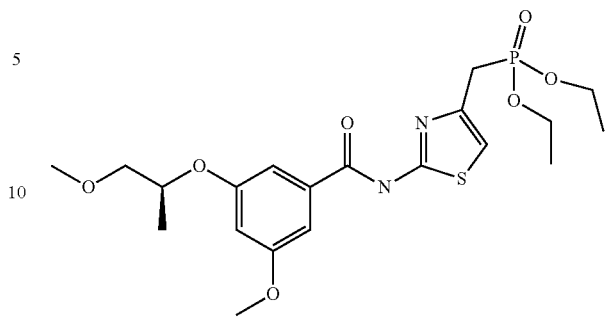

To a solution of Example 13 Part E compound (0.041 g; 0.164 mmol) in DMF (0.52 mL) were added HOAT (0.087 g; 0.641 mmol), Part B compound (0.033 g; 0.137 mmol), and DIPEA (0.028 mL; 0.158 mmol), and, lastly, EDCI (0.030 g; 0.158 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5 μm 30×100 mm column; flow rate=40 mL/min, 25 to 100% solvent B over 12 min, where solvent A=90:10:0.1 H₂O: CH₃CN:TFA and solvent B=90:10:0.1 CH₃CN:H₂O:TFA) to give the title compound (38.1 mg; 59%) as a clear, colorless oil. [M+H]⁺=473.4; ¹H NMR (400 MHz, CDCl₃): δ 1.20-1.30 (m, 9H), 3.23 (s, 1H), 3.28 (s, 1H), 3.35 (s, 3H), 3.43-3.55 (m, 2H), 3.80 (s, 3H), 4.01-4.12 (m, 4H), 4.60-4.72 (m, 1H), 6.66-6.72 (m, 1H), 6.89-6.94 (m, J=3.30 Hz, 1H), 7.21-7.25 (m, 1H), 7.25-7.29 (m, 1H).

Example 151

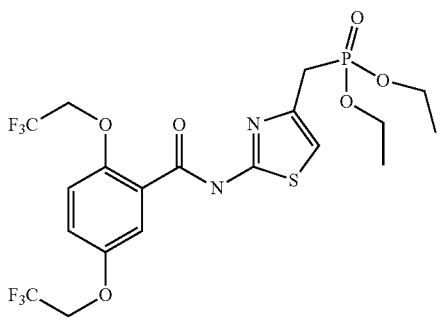

A.

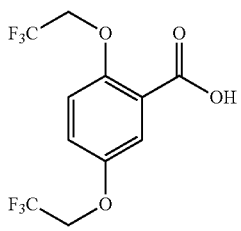

To a solution of methyl 2,5-bis(2,2,2-trifluoroethoxy)benzoate (0.029 g; 1.20 mmol) in THF (2.49 mL) and water (0.25 mL) was added LiOH.H₂O (0.100 g; 0.301 mmol). The reaction mixture was stirred at 45° C. for 3 h in a sealed vial, then an additional equivalent of LiOH was added. The reaction mixture was stirred at 45° C. for 16 h, then was cooled to RT. The solvent was removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part A compound (0.0954 g; 99%).

B.

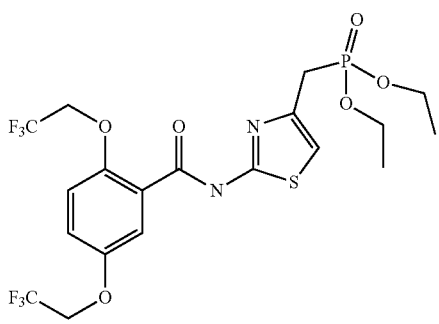 [SMILES: CCOP(=O)(Cc1csc(NC(=O)c2cc(OCC(F)(F)F)ccc2OCC(F)(F)F)n1)OCC]

To a solution of Example 13 Part E compound (0.029 g; 0.114 mmol) in DMF (0.476 mL) were added HOAT (0.015 g; 0.11 mmol), Part A compound (0.030 g; 0.095 mmol), DIPEA (0.019 mL; 0.110 mmol), and, lastly, EDCI (0.021 g; 0.110 mmol). The reaction mixture was stirred at 25° C. for 16 h. Water was added, and the mixture was extracted with EtOAc (3×). The combined organic extracts were washed with sat. aqueous NH₄Cl, sat. aqueous NaHCO₃, and brine, dried (MgSO₄), and concentrated in vacuo. The residue was purified by preparative HPLC (YMC reverse phase ODS-5u 30×100 mm column; flow rate=40 mL/min, 0 to 100% solvent B over 12 min, where solvent A=90:10:0.1 H₂O:CH₃CN:TFA and solvent B=90:10:0.1 CH₃CN:H₂O:TFA) to give the title compound (13.8 mg; 26%) as a white lyophilate. [M+H]⁺=551.2; ¹H NMR (400 MHz, CDCl₃) δ 1.23 (t, J=7.15 Hz, 6H), 3.23 (s, 1H), 3.28 (s, 1H), 3.94-4.10 (m, 4H), 4.27-4.39 (m, J=7.88, 7.88, 7.88 Hz, 2H), 4.46-4.58 (m, J=8.06, 8.06, 8.06 Hz, 2H), 6.81-6.86 (m, J=3.30 Hz, 1H), 6.93-6.98 (m, J=9.34 Hz, 1H), 7.12-7.18 (m, J=9.34, 3.30 Hz, 1H), 7.69-7.75 (m, J=3.30 Hz, 1H).

Example 152

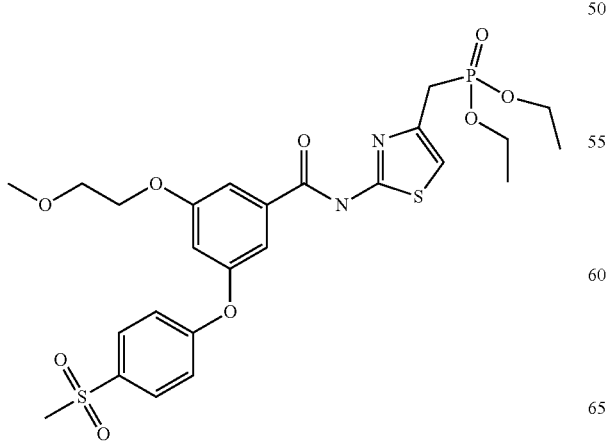

A.

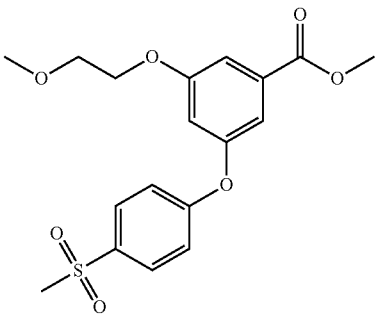

To Example 26 Part A compound (0.130 g; 0.403 mmol) were successively added 2-methoxyethanol (0.046 g; 0.605 mmol) in toluene (2.02 mL) and a suspension of Example 97 Part B compound (0.248 g; 0.605 mmol) in CH₂Cl₂ (1.1 mL). The reaction mixture was stirred for 16 h at 25° C., then was diluted with water and extracted with EtOAc (3×). The combined organic extracts were washed with 1N aqueous NaOH and brine, dried (MgSO₄), and concentrated in vacuo. The residue was chromatographed (SiO₂; step gradient from 50-60% solvent B, where solvent A=hexanes and solvent B=EtOAc) to give Part A compound (0.157 g; 93%).

B.

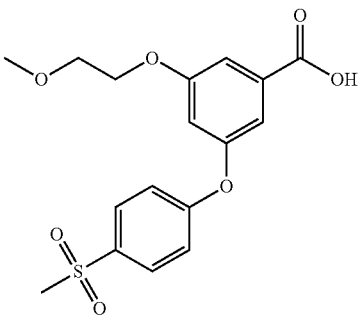

To a solution of Part A compound (0.157 g; 0.413 mmol) in THF (3.42 mL) and water (0.342 mL) was added LiOH.H₂O (0.020 g; 0.827 mmol). The reaction mixture was stirred at 45° C. for 3 h in a sealed vial, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.166 g; 100%).

C.

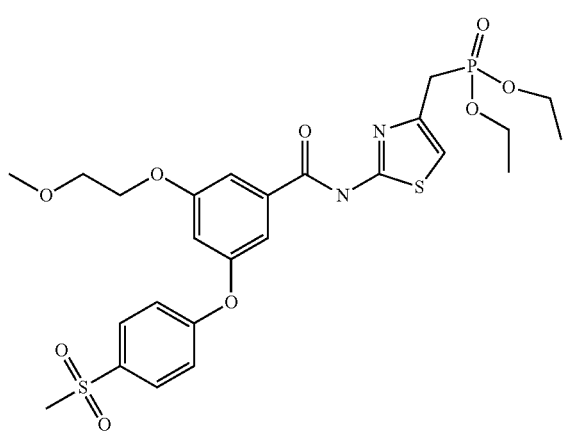

To a solution of Example 13 Part E compound (0.033 g; 0.130 mmol) in DMF (0.542 mL) were added HOAT (0.017 g; 0.125 mmol), Part B compound (0.040 g; 0.108 mmol), DIPEA (0.022 mL; 0.125 mmol), and, lastly, EDCI (0.024 g; 0.125 mmol). The reaction mixture was stirred at 25° C. for 5 h. Water was added, and the mixture was extracted with EtOAc (3×). The combined organic extracts were washed with sat. aqueous NH$_4$Cl, sat. aqueous NaHCO$_3$, and brine, dried (MgSO$_4$), and concentrated in vacuo. The residue was purified by preparative HPLC (YMC reverse phase ODS-5 μm 30×100 mm column; flow rate=40 mL/min, 0 to 100% solvent B over 12 min, where solvent A=90:10:0.1 H$_2$O:CH$_3$CN:TFA and solvent B=90:10:0.1 CH$_3$CN:H$_2$O:TFA) to give the title compound (34.4 mg; 51%) as a white lyophilate. [M+H]$^+$=599.2; $^1$H NMR (400 MHz, CDCl$_3$): δ 1.25 (t, J=6.87 Hz, 6H), 3.00 (s, 3H), 3.24 (s, 1H), 3.29 (s, 1H), 3.39 (s, 3H), 3.67-3.77 (m, 2H), 4.00-4.15 (m, 4H), 4.18-4.28 (m, 2H), 6.86-6.93 (m, 1H), 6.94-7.00 (m, J=3.30 Hz, 1H), 7.04-7.12 (m, J=8.79 Hz, 2H), 7.38-7.45 (m, 1H), 7.58-7.64 (m, 1H), 7.81-7.88 (m, J=8.79 Hz, 2H).

Example 153

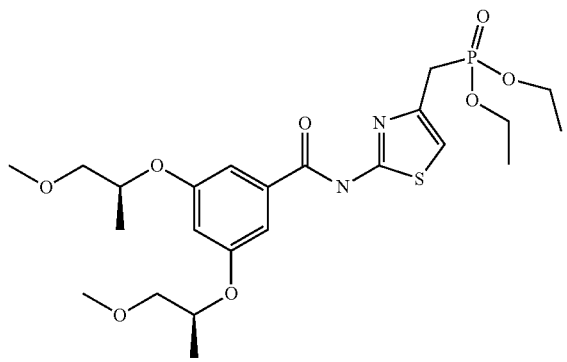

A.

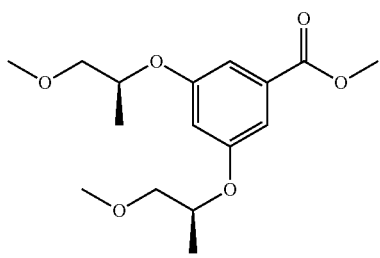

To methyl-3,5-dihydroxybenzoate (0.100 g; 0.595 mmol) were added (R)-1-methoxy-propan-2-ol (0.134 g; 1.487 mmol in toluene (2.97 mL), followed by a suspension of Example 97 Part B compound (0.610 g; 1.487 mmol) in CH$_2$Cl$_2$ (2.72 mL). The reaction mixture was stirred for 2 days at 25° C., then at 45° C. for 2 days, then was cooled to RT. The reaction mixture was diluted with water and extracted with EtOAc (3×). The combined organic extracts were washed with 1N aqueous NaOH and brine, dried (MgSO$_4$), and concentrated in vacuo. The residue was chromatographed (SiO$_2$; stepwise gradient from 10-20% solvent B, where solvent A=hexanes and solvent B=EtOAc) to give Part A compound (0.080 g; 40%).

B.

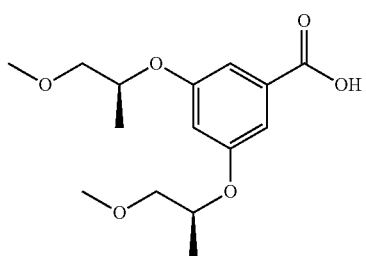

To a solution of Part A compound (0.080 g; 0.257 mmol) in THF (2.13 mL) and water (0.213 mL) was added LiOH.H$_2$O (0.012 g; 0.514 mmol). The reaction mixture was stirred at 45° C. for 3 h in a sealed vial, then an additional equivalent of LiOH was added. The reaction mixture was stirred at 45° C. for 16 h, then was cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO$_4$), and concentrated in vacuo to give Part B compound (0.082 g; 100%).

C.

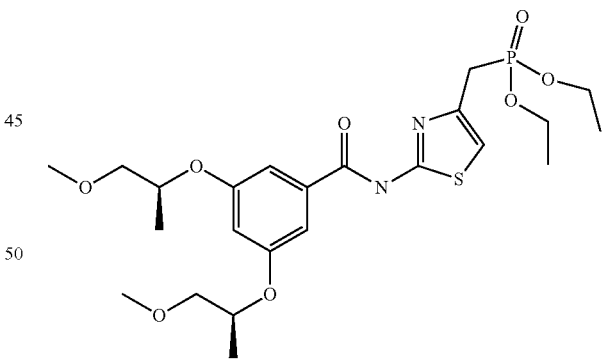

To a solution of Example 13 Part E compound (0.036 g; 0.142 mmol) in DMF (0.592 mL) were added HOAT (0.019 g; 0.136 mmol), Part B compound (0.035 g; 0.118 mmol), and DIPEA (0.024 mL; 0.136 mmol) and, lastly, EDCI (0.026 g; 0.136 mmol). The reaction mixture was stirred at 25° C. for 15 h. Water was added, and the mixture was extracted with EtOAc (3×). The combined organic extracts were washed with sat. aqueous NH$_4$Cl, sat. aqueous NaHCO$_3$, and brine, dried (MgSO$_4$), and concentrated in vacuo. The residue was purified by preparative HPLC (YMC reverse phase ODS-5u 30×100 mm column; flow rate=40 mL/min, 0 to 100% solvent B over 12 min, where solvent A=90:10:0.1 H$_2$O:

CH₃CN:TFA and solvent B=90:10:0.1 CH₃CN:H₂O:TFA) to give the title compound (28.2 mg; 45%) as a clear, colorless oil. [M+H]⁺=531.3; ¹H NMR (400 MHz, CDCl₃) δ 1.22-1.29 (m, J=6.87, 6.87 Hz, 12H), 3.28 (s, 1H), 3.32-3.38 (m, 7H), 3.44-3.56 (m, 4H), 4.06-4.16 (m, 4H), 4.64-4.73 (m, 2H), 6.70-6.76 (m, 1H), 6.94-7.00 (m, J=3.85 Hz, 1H), 7.32-7.35 (m, J=2.20 Hz, 2H).

Example 154

A.

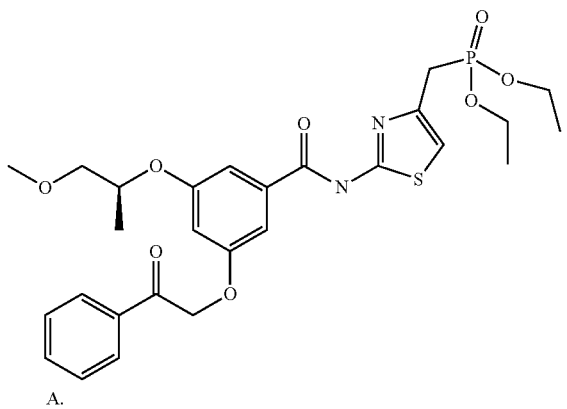

To a solution of Example 134 compound (0.298 g; 0.560 mmol) in iPrOH (12.43 mL) and water (6.22 mL) was added oxone (0.791 g; 1.287 mmol). The reaction mixture was stirred for 16 h at 25° C., then was filtered and extracted with EtOAc. The combined filtrates were washed with water and brine, dried (MgSO₄), and concentrated in vacuo to give Part A compound (0.206 g; 38%).

B.

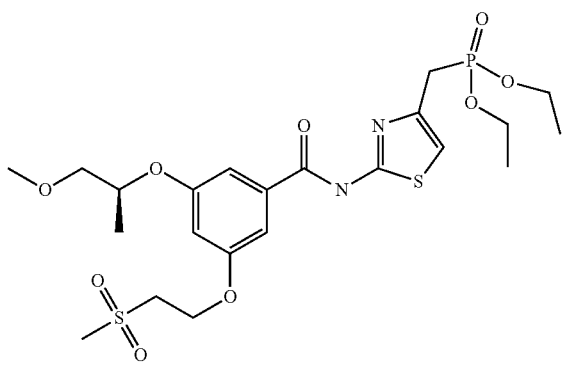

To a solution of Part A compound (0.070 g; 0.125 mmol) in THF (1.03 mL) and water (0.103 mL) was added LiOH.H₂O (0.006 g; 0.249 mmol). The reaction mixture was stirred at 45° C. for 1 h in a sealed vial, then two more equivalents of LiOH.H₂O were added. The reaction mixture was stirred at 45° C. for 20 minutes, then cooled to RT. Volatiles were removed in vacuo, and the remaining aqueous solution was acidified with 0.5N aqueous HCl to pH<2. The aqueous layer was re-extracted with EtOAc (3×). The combined organic extracts were washed with brine, dried (MgSO₄), and concentrated in vacuo to give Part B compound (0.082 g; 87%).

C.

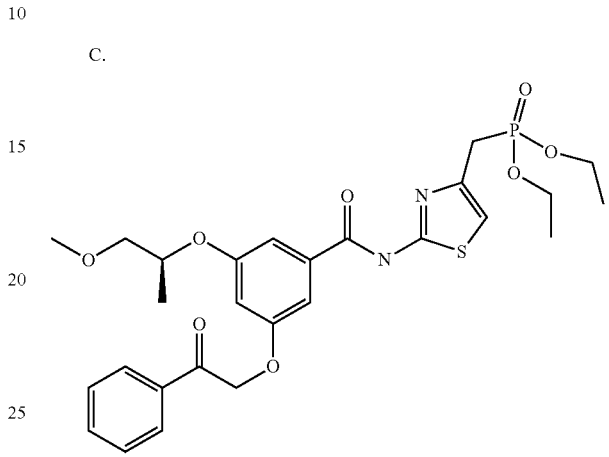

To a 0° C. solution of the Part B compound (0.020 g; 0.044 mmol) in NMP (0.146 mL) was added 1M LiHMDS in THF (0.087 mL; 0.087 mmol). After 15 min, 2-bromo-1-phenylethanone (0.017 g; 0.087 mmol) was added. The reaction mixture was allowed to warm to RT and stirred at RT for 15 h, then was partitioned between sat. aqueous NH₄Cl and EtOAc. The organic layer was washed with water (2×) and brine, dried (MgSO₄), and concentrated in vacuo. The residue was purified by preparative HPLC (YMC reverse phase ODS-5u 30×100 mm column; flow rate=40 mL/min, 0 to 100% solvent B over 12 min, where solvent A=90:10:0.1 H₂O:CH₃CN:TFA and solvent B=90:10:0.1 CH₃CN:H₂O:TFA) to give the title compound (6.0 mg; 24%) as a yellow oil. [M+H]⁺=577.3; ¹H NMR (400 MHz, CDCl₃) δ 1.05-1.12 (m, J=6.05 Hz, 3H), 1.24 (t, 6H), 3.06 (s, 1H), 3.11 (s, 1H), 3.23-3.35 (m, 4H), 3.36-3.42 (m, 1H), 3.93-4.10 (m, 4H), 4.24-4.35 (m, 1H), 5.92-5.99 (m, J=4.40 Hz, 2H), 6.41-6.48 (m, 1H), 6.50-6.57 (m, 1H), 7.11 (s, 1H), 7.19 (s, 1H), 7.44-7.54 (m, J=7.70 Hz, 2H), 7.56-7.66 (m, J=7.15 Hz, 1H), 7.99-8.08 (m, J=8.25 Hz, 2H).

Example 155

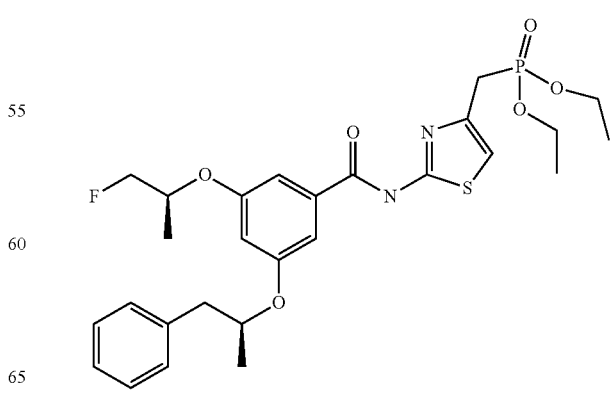

To a 0° C. solution of Example 137 compound (0.021 g; 0.036 mmol) in anhydrous CH$_2$Cl$_2$ (0.369 mL) was added DAST (0.005 mL; 0.036 mmol). The reaction mixture was stirred for 2 h at 0° C., followed by careful addition of sat. aqueous NaHCO$_3$ and stirred for 5 min, then was partitioned between sat. aqueous NaHCO$_3$ and CH$_2$Cl$_2$. The aqueous layer was re-extracted with CH$_2$Cl$_2$ (3×). The combined organic extracts were washed with brine, dried (MgSO$_4$), and concentrated in vacuo. The residue was purified twice by preparative HPLC (YMC reverse phase ODS-5u 30×100 mm column; flow rate=40 mL/min, 20 to 100% solvent B over 12 min, where solvent A=90:10:0.1 H$_2$O:CH$_3$CN:TFA and solvent B=90:10:0.1 CH$_3$CN:H$_2$O:TFA) to give the title compound (6.0 mg; 29%) as a clear, colorless oil. [M+H]$^+$=565.2; $^1$H NMR (400 MHz, CDCl$_3$) δ 1.22-1.32 (m, 12H), 2.75-2.87 (m, J=13.74, 5.50 Hz, 2H), 2.92-3.03 (m, J=13.74, 6.60 Hz, 1H), 3.29 (s, 1H), 3.34 (s, 1H), 4.06-4.17 (m, 4H), 4.33-4.45 (m, 1H), 4.45-4.57 (m, 1H), 4.63-4.74 (m, 1H), 4.74-4.87 (m, 1H), 6.64-6.69 (m, J=2.20, 2.20 Hz, 1H), 6.94-7.00 (m, J=3.30 Hz, 1H), 7.12-7.24 (m, 5H), 7.30 (s, 1H), 7.33 (s, 1H).

Example 156

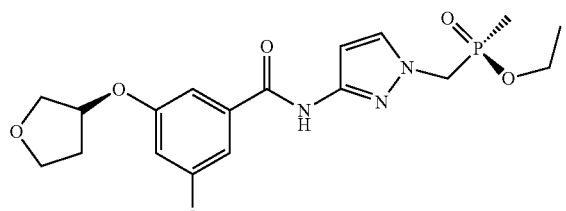

A.

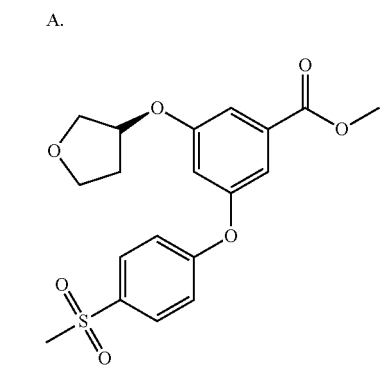

To a suspension of Example 97 Part B compound (1.4 g, 3.5 mmol) in DCM (6 mL) was added a solution of Example 26 Part A compound (141 mg, 0.44 mmol) and (R)-(−)-3-hydroxytetrahydrofuran (0.081 mL, 1.00 mmol) in toluene (2 mL). The reaction was stirred at RT for 15 h, then was diluted with EtOAc (10 mL) and washed with water and brine. The organic layer was dried (MgSO$_4$), and concentrated in vacuo. The residue was chromatographed (SiO$_2$; 40 g, 19 min continuous gradient, from 100% Hexane/0% EtOAc to 0% Hexanes/100% EtOAc) to provide Part A compound (254 mg, 148% yield, mixed with Ph$_3$PO) as a colorless oil.

B.

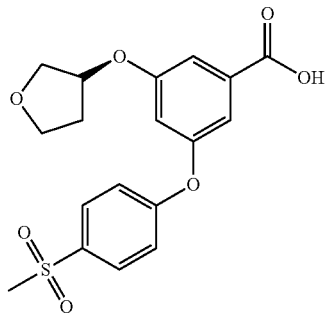

To a solution of Part A compound (254 mg, 0.65 mmol) in THF (2 mL) was added 1N aqueous NaOH (1 mL, 1.00 mmol). The reaction was stirred at RT for 15 h, then was diluted with EtOAc (6 mL) and acidified with 1N aqueous HCl (0.5 mL). The organic layer was washed with brine, dried (MgSO$_4$), and concentrated in vacuo. The residue was purified by preparative HPLC (Phenomenex Luna AXIA 30×100 mm column; flow rate=40 mL/min, 30 to 100% solvent B over 10 min, where solvent A=90:10:0.1 H$_2$O:MeOH:TFA and solvent B=90:10:0.1 MeOH:H$_2$O:TFA) to give Part B compound (90 mg, 37% yield) as a colorless oil.

C.

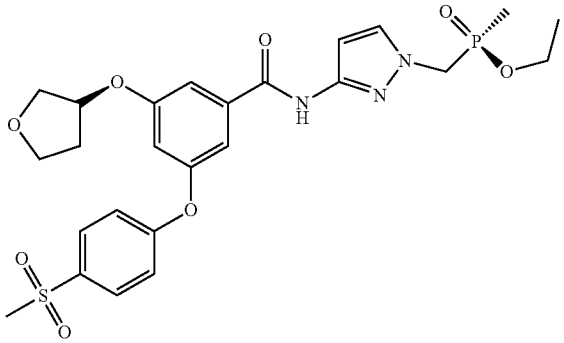

To a solution of Part B compound (25 mg, 0.066 mmol) in DMF (1 mL) were added Example 60 Part D2 amine (26.8 mg, 0.13 mmol), EDCI (25.3 mg, 0.13 mmol), HOBT (20.2 mg, 0.13 mmol), and DIPEA (0.035 mL, 0.20 mmol). The reaction was stirred at RT for 24 h. The reaction was purified directly by preparative HPLC (Phenomenex Luna AXIA 30×100 mm column; flow rate=40 mL/min, 30 to 100% solvent B over 10 min, where solvent A=90:10:0.1 H$_2$O:MeOH: TFA and solvent B=90:10:0.1 MeOH:H$_2$O:TFA) to provide the title compound (24.6 mg, 66% yield) as a white solid. [M+H]$^+$=564.3; $^1$H NMR (500 MHz, CDCl$_3$) δ 9.63 (1H, s), 7.92 (2H, d, J=8.80 Hz), 7.52 (1H, d, J=2.20 Hz), 7.33 (1H, s), 7.27 (1H, s), 7.09-7.18 (2H, m), 7.01 (1H, d, J=2.20 Hz), 6.71-6.86 (1H, m), 5.01-5.14 (1H, m), 4.37-4.60 (2H, m), 4.07-4.22 (2H, m), 3.96-4.05 (3H, m), 3.84-3.96 (1H, m), 3.07 (3H, s), 2.05-2.38 (2H, m), 1.55 (3H, d, J=14.85 Hz), 1.34 (3H, t, J=7.15 Hz).

Example 157

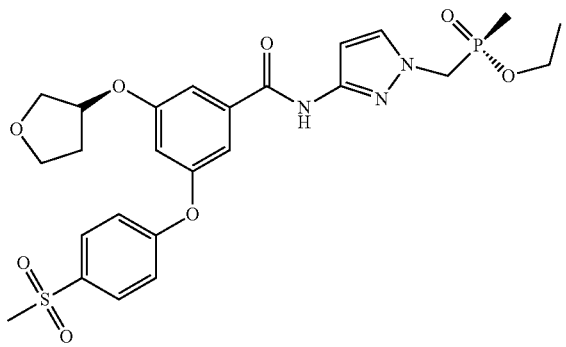

The title compound (27.4 mg, 73.6% yield; white solid) was synthesized from Example 60 Part D1 amine using the procedure employed in Example 156. [M+H]$^+$=564.3; $^1$H NMR (500 MHz, CDCl$_3$) δ 9.58 (1H, s), 7.92 (2H, d, J=8.25 Hz), 7.52 (1H, s), 7.31 (1H, s), 7.26 (1H, s), 7.14 (2H, d, J=8.25 Hz), 7.01 (1H, s), 6.80 (1H, s), 5.01-5.13 (1H, m), 4.41-4.60 (2H, m), 4.06-4.21 (2H, m), 3.96-4.05 (3H, m), 3.86-3.96 (1H, m), 3.07 (3H, s), 2.09-2.35 (2H, m), 1.55 (3H, d, J=14.30 Hz), 1.27-1.39 (3H, m).

Example 158

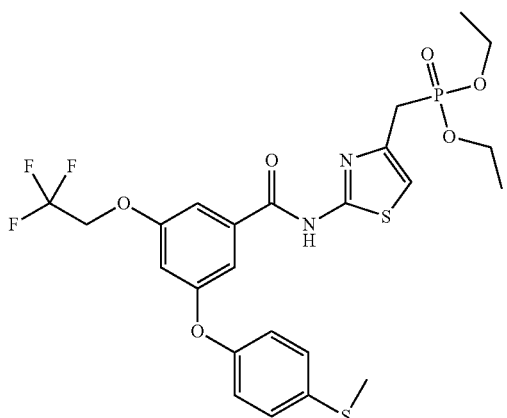

A.

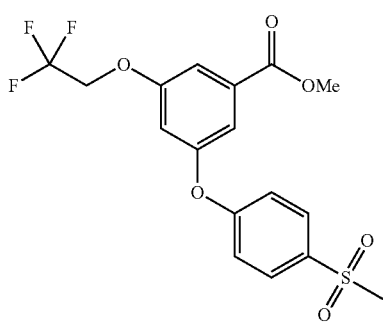

To a RT solution of Example 26 Part A compound (117.8 mg, 0.365 mmol) in NMP (1.8 mL) under Ar was added Cs$_2$CO$_3$ (357 mg, 1.096 mmol), followed by dropwise addition of 2,2,2-trifluoroethyl methanesulfonate (0.075 mL, 0.640 mmol). The mixture was stirred at 60° C. for 18 h, after which more 2,2,2-trifluoroethyl methanesulfonate (0.043 mL, 0.365 mmol) was added. The reaction was heated to 80° C. for 29 h, then was cooled to RT. The reaction was diluted with water and stirred for 1 h, then was partitioned between EtOAc and saturated aqueous NaHCO$_3$. The organic layer was washed with water (2×), and the combined aqueous layers were back extracted with EtOAc. The combined organic extracts were washed with brine, dried (Na$_2$SO$_4$), and concentrated in vacuo. The residue was chromatographed (12 g SiO$_2$, eluting from 0-10% EtOAc:CH$_2$Cl$_2$, then flushing with 90% EtOAc) to give Part A compound (44 mg, 29%) as a colorless oil.

B.

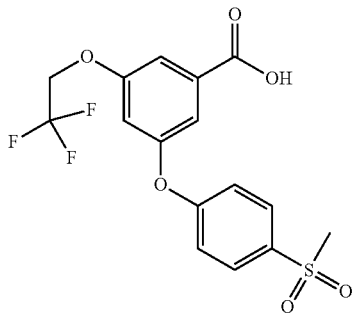

To a RT solution of Part A ester (44 mg, 0.109 mmol) in THF (0.8 mL) and MeOH (0.4 mL) under Ar was added 4N aqueous LiOH.H$_2$O (0.2 mL, 0.800 mmol). A precipitate formed immediately, and the reaction was stirred at RT for 6.5 h, then was diluted with MeOH, and volatiles were removed in vacuo. The residue was dissolved in water and acidified with 1N aqueous HCl. The aqueous layer was extracted with EtOAc; the organic layer was washed with brine, dried (Na$_2$SO$_4$), and concentrated in vacuo to give Part B acid (38.6 mg, 91%) as a colorless solid.

C.

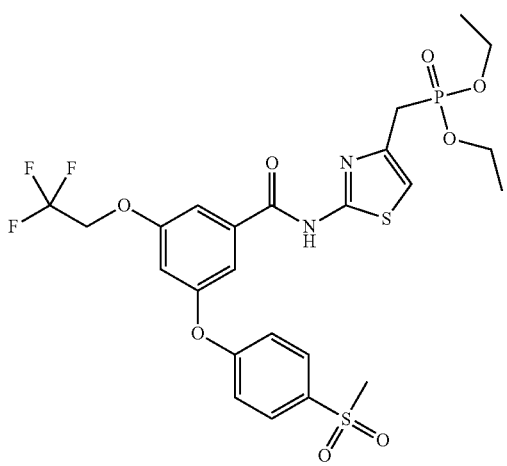

To a RT suspension of Part B acid (20 mg, 0.051 mmol) in CH$_2$Cl$_2$ (0.3 mL) under Ar were added HATU (36 mg, 0.095 mmol), and a solution of Example 13 Part E compound (18.6 mg, 0.074 mmol) in CH$_2$Cl$_2$ (0.3 mL), followed by DIPEA (0.036 mL, 0.205 mmol). The reaction was stirred at RT for 42 h, then EtOAc and sat. aqueous NaHCO$_3$ were added. The reaction was stirred for 1 h, then was partitioned between EtOAc and sat. aqueous NaHCO$_3$. The organic layer was washed with sat. aqueous NaHCO$_3$, brine, dried (Na$_2$SO$_4$), and concentrated in vacuo. The residue was purified by preparative HPLC (Phenomenex Luna 5 µm 21.2×100 mm column, detection at 220 nm; flow rate=20 mL/min; continuous gradient from 50% A to 100% B over 10 min+2 min hold time at 100% B, where A=90:10:0.1 H$_2$O:MeOH:TFA and B=90:10:0.1 MeOH:H$_2$O:TFA) to give one clean fraction. The desired fraction was passed through a MeOH treated cartridge of Polymer Lab StratoSpheres TM SPE PL-HCO$_3$ MP SPE resin (500 mg), washing well with MeOH. The filtrate was concentrated in vacuo, then azeotroped several times with MeOH. The residue was taken up in CH$_2$Cl$_2$/MeOH; solids were filtered off, and the filtrate was concentrated in vacuo to give the title compound (14.8 mg, 46%) as a tan colored solid. [M+H]$^+$=623.2; $^1$H NMR (400 MHz, CDCl$_3$) δ 1.24 (t, J=7.15 Hz, 6H), 3.09 (s, 3H), 3.46 (d, J=21.5 Hz, 2H), 3.99-4.10 (m, 4H), 4.48 (q, J=7.70 Hz, 2H), 6.83 (d, J=3.30 Hz, 1H), 6.92 (s, 1H), 7.16 (d, J=8.79 Hz, 2H), 7.46 (s, 1H), 7.58 (s, 1H), 7.95 (d, J=8.79 Hz, 2H), $^{19}$F NMR (400 MHz, CDCl$_3$): δ−73.66.

Example 159

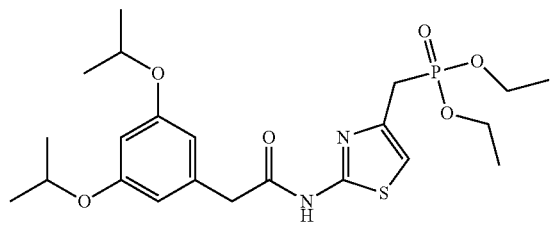 [SMILES: CCOP(=O)(Cc1csc(NC(=O)Cc2cc(OC(C)C)cc(OC(C)C)c2)n1)OCC]

The title compound (20 mg, 51% yield, yellow oil) was prepared employing the same general sequence as described in the synthesis of Example 74. [M+H]$^+$=485.18; $^1$H NMR (400 MHz, CDCl$_3$) δ ppm 6.94 (1H, d, J=3.95 Hz), 6.52 (2H, d, J=2.20 Hz), 6.35 (1H, t, J=2.20 Hz), 4.49-4.57 (2H, m), 4.10-4.19 (4H, m), 3.78 (2H, s), 3.25-3.34 (2H, m), 1.27-1.36 (18H, m).

Example 160

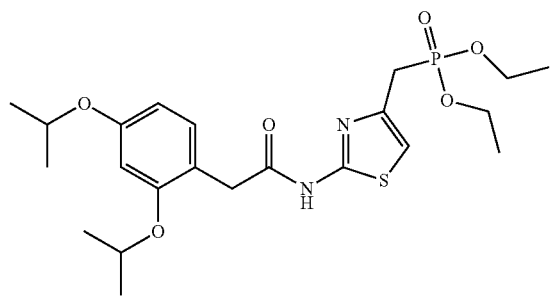 [SMILES: CCOP(=O)(Cc1csc(NC(=O)Cc2ccc(OC(C)C)cc2OC(C)C)n1)OCC]

The title compound (15 mg, 45% yield, yellow oil) was prepared employing the same general sequence as described in the synthesis of Example 74. [M+H]$^+$=485.18; $^1$H NMR (400 MHz, CDCl$_3$) δ 7.12 (1H, d, J=8.79 Hz), 6.88 (1H, d, J=3.95 Hz), 6.41-6.46 (2H, m), 4.47-4.57 (1H, m), 4.07-4.17 (4H, m), 3.75 (2H, s), 3.24-3.34 (2H, m), 1.23-1.37 (18H, m).

Example 161

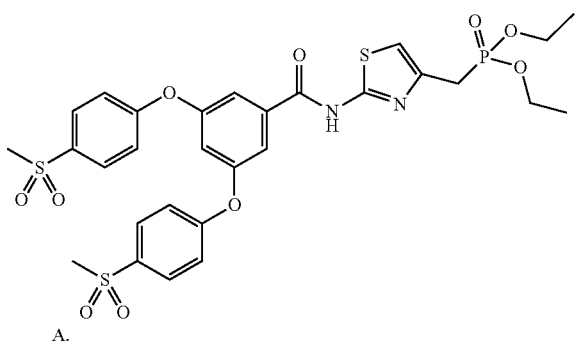

A.

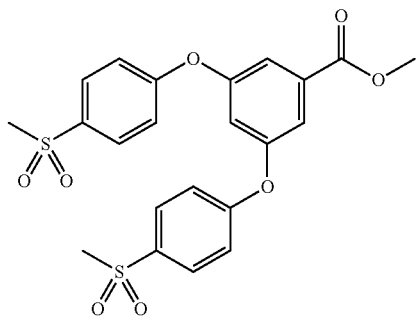

A solution of methyl 3,5-dihydroxybenzoate (2.5 g, 14.9 mmol), 1-fluoro-4-(methylsulfonyl)benzene (5.18 g, 29.8 mmol), and anhydrous K$_2$CO$_3$ (8.23 g, 59.6 mmol) in dry DMF (100 mL) was heated at 120'C for 10 h, then was cooled to RT and filtered. The solid was washed with CH$_2$Cl$_2$ (100 mL), and the combined filtrate was concentrated in vacuo. The residue was chromatographed (SiO$_2$; 80 g; continuous gradient from 100% hexane to 100% EtOAc over 40 min) to provide Part A compound (6.1 g, 86% yield) as a white solid. [M+H]$^+$=477.

B.

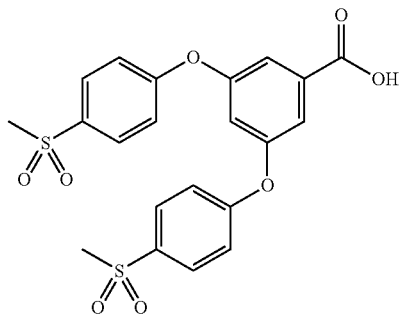

A solution of Part A compound (2.3 g, 4.83 mmol), and LiOH.H$_2$O (4.1 g, 97.5 mmol) in THF (10 mL)/H$_2$O (5 mL) was stirred for 2 h at RT. The reaction was acidified to pH 1 with 1N aqueous HCl, and extracted with EtOAc (3×15 mL). The combined organic extracts were washed with brine (30 mL), dried (MgSO$_4$) and concentrated in vacuo to give Part B compound (2.2 g, 99% yield) as a white solid. [M−H]=461.

C.

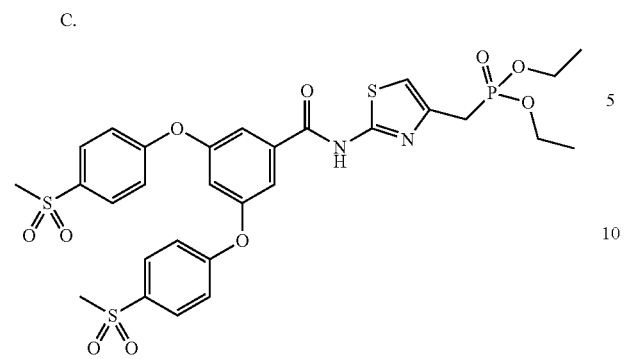

To a suspension of the Part B compound (50 mg, 0.11 mmol) in $CH_2Cl_2$ (3 mL) were added Example 13 Part E compound (27 mg, 0.11 mmol), $Et_3N$ (30 μL, 0.22 mmol), and BOP (72 mg, 0.16 mmol). The reaction was stirred for 16 h, then was diluted with $H_2O$ (1 mL), and extracted with $CH_2Cl_2$ (3×5 mL). The combined organic extracts were washed with brine (3 mL), dried ($MgSO_4$), and concentrated in vacuo. The residue was purified by preparative HPLC (YMC reverse phase ODS-A-5 μm 30×250 mm column; flow rate=25 mL/min, 20 to 100% solvent B over 30 min, hold to 40 min, where solvent A=90:10:0.1 $H_2O$:MeOH:TFA and solvent B=90:10:0.1 MeOH:$H_2O$:TFA) to afford the title compound (50 mg, 65% yield) as a white solid. $[M+H]^+=695$; $^1H$ NMR (500 MHz, $CDCl_3$): δ 7.95 (d, J=8.8 Hz, 4H), 7.65 (d, J=2.2 Hz, 2H), 7.20 (d, J=8.8 Hz, 4H), 7.09 (t, J=2.2 Hz, 1H), 7.01 (d, J=3.3 Hz, 1H), 4.11 (m, 4H), 3.28 (d, J=22.0 Hz, 2H), 3.06 (s, 6H), 1.28 (t, J=6.9 Hz, 6H).

Example 162

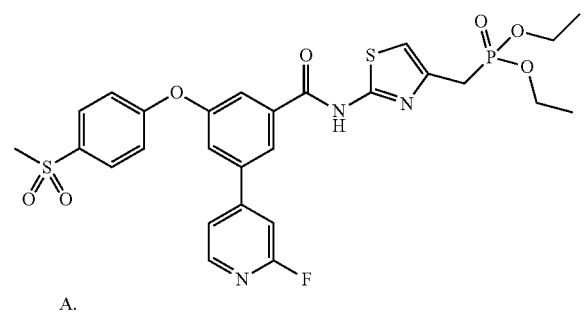

A.

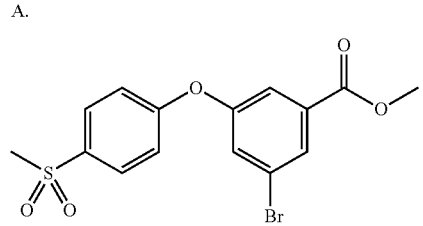

A solution of methyl 3-bromo-5-hydroxybenzoate (2.13 g, 9.21 mmol), 1-fluoro-4-(methylsulfonyl)benzene (1.93 g, 11.1 mmol), and anhydrous $K_2CO_3$ (2.55 g, 18.42 mmol) in dry DMF (15 mL) was heated at 120'C for 20 h, then was cooled to RT and filtered. The solids were washed with $CH_2Cl_2$ (100 mL), and the combined filtrates were concentrated in vacuo. The residue was chromatographed ($SiO_2$; 80 g; continuous gradient from 100% hexane to 100% EtOAc over 40 min) to provide Part A compound (1.64 g, 48% yield) as a white solid. $[M-H]=370$.

B.

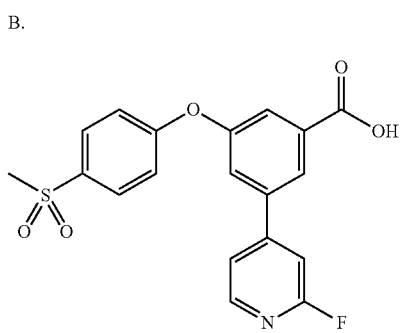

A RT solution of Part A compound (124 mg, 0.322 mmol), 2-fluoropyridin-4-ylboronic acid (54.4 mg, 0.386 mmol), $K_2CO_3$ (89 mg, 0.644 mmol), and $(PPh_3)_4Pd$ (18.6 mg, 16 mmol) in DME (4 mL) and water (1 mL) was stirred under a stream of $N_2$ for 5 min. The mixture was then sealed and heated in an Emrys Optimizer® at 150° C. for 30 min. The reaction was cooled to RT and was acidified to pH 2 with 1N aqueous HCl. The mixture was partitioned between EtOAc (3 mL) and water (3 mL), and was extracted with EtOAc (3×10 mL). The combined organic extracts were dried ($MgSO_4$) and concentrated in vacuo. The residue was purified by preparative HPLC (YMC reverse phase ODS-A-5 μm 30×250 mm column; flow rate=25 mL/min, 20 to 100% solvent B over 30 min, then held for 10 min, where solvent A=90:10:0.1 $H_2O$:MeOH:TFA and solvent B=90:10:0.1 MeOH:$H_2O$:TFA) to afford the Part B compound (80 mg, 64%) as a white solid. $[M-H]=386$.

C.

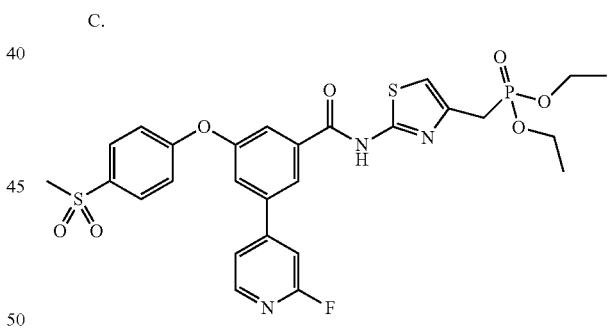

To a suspension of the Part B compound (20 mg, 0.052 mmol) in $CH_2Cl_2$ (2 mL) were added Example 13 Part E compound (13 mg, 0.052 mmol), $Et_3N$ (11 μL, 0.077 mmol), and BOP (27.4 mg, 0.062 mmol). The reaction was stirred for 16 h, then was diluted with $H_2O$ (1 mL) and extracted with $CH_2Cl_2$ (3×5 mL). The combined organic extracts were washed with brine (3 mL), dried ($MgSO_4$) and concentrated in vacuo. The residue was purified by preparative HPLC (YMC reverse phase ODS-A-5 μm 30×250 mm column; flow rate=25 mL/min, 20 to 100% solvent B over 30 min, hold to 40 min, where solvent A=90:10:0.1 $H_2O$:MeOH:TFA and solvent B=90:10:0.1 MeOH:$H_2O$:TFA) to afford the title compound (27 mg, 84% yield) as a white solid. $[M+H]^+=620$; $^1H$ NMR (500 MHz, $CD_3OD$): δ 8.32-8.29 (m, 2H), 8.0 (d, J=8.8 Hz, 2H), 7.85-7.82 (m, 2H), 7.72-7.69 (m, 1H), 7.51 (s, 1H), 7.30 (d, J=8.8 Hz, 2H), 7.00 (d, J=3.8 Hz, 1H), 4.12-4.05 (m, 4H), 3.37 (d, J=21.4 Hz, 2H), 3.13 (s, 3H), 1.28 (t, J=6.8 Hz, 6H).

Example 163

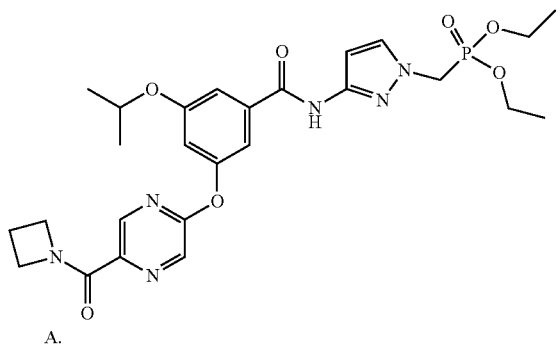

A.

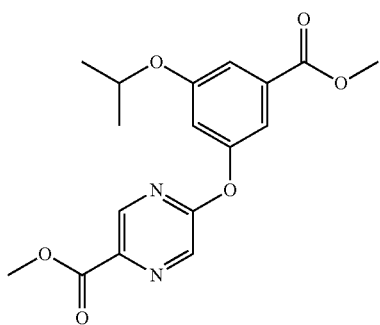

A solution of methyl 3-hydroxy-5-isopropoxybenzoate (*Bioorg. Med. Chem. Lett.* 2005, 15:2103) (609 mg, 2.90 mmol), methyl 5-chloropyrazine-2-carboxylate (500 mg, 2.90 mmol), and $K_2CO_3$ (1.20 mg, 8.69 mmol) in $CH_3CN$ (20 mL) was heated to 80° C. for 2 h under Ar. The reaction was cooled to RT, diluted with $CH_2Cl_2$ (50 mL), filtered and the filtrate was concentrated in vacuo. The residue was chromatographed ($SiO_2$; 40 g; continuous gradient from 100% hexane to 100% EtOAc over 40 min) to provide Part A compound (1.005 g, 100% yield) as a colorless oil. [M+H]$^+$=347.

B.

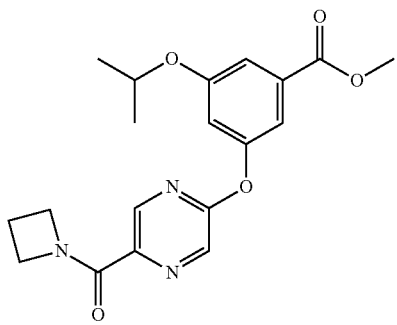

A mixture of Part B compound (1.005 g, 2.9 mmol), azetidine hydrochloride (326 mg, 3.48 mmol), $Et_3N$ (0.485 mL, 3.48 mmol), and $MgCl_2$ (332 mg, 3.48 mmol) was stirred at RT for 5 h. More azetidine hydrochloride (326 mg, 3.48 mmol), $Et_3N$ (0.485 mL, 3.48 mmol), and $MgCl_2$ (332 mg, 3.48 mmol) were added. The reaction was stirred at RT for 30 min, then was stored at 0° C. overnight, then diluted with $CH_2Cl_2$ (50 mL), filtered, and the filtrate was concentrated in vacuo. The residue was chromatographed ($SiO_2$; 40 g; continuous gradient from 100% hexane to 100% EtOAc over 40 min) to provide Part B compound (267 mg, 25% yield) as a colorless oil. [M+H]$^+$=372.

C.

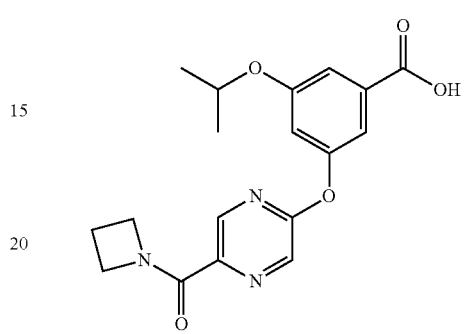

A solution of Part B compound (267 mg, 0.72 mmol) and $LiOH \cdot H_2O$ (90 mg, 2.16 mmol) in THF (4 mL)/$H_2O$ (4 mL) was stirred for 5 h at RT. The reaction was acidified to pH 2 with 1N aqueous HCl, then was extracted with EtOAc (3×10 mL). The combined organic extracts were washed with brine (10 mL), dried ($MgSO_4$) and concentrated in vacuo to give Part C compound (200 mg, 78% yield) as a white solid. [M+H]$^+$=358.

D.

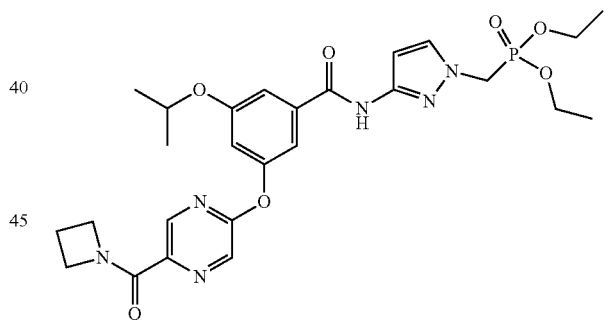

To a suspension of the Part C compound (14 mg, 0.039 mmol) in $CH_2Cl_2$ (1.5 mL) were added Example 32 Part A compound (9.1 mg, 0.039 mmol), $Et_3N$ (11 μL, 0.078 mmol), and BOP (34.7 mg, 0.078 mmol). The reaction was stirred for 16 h at RT, then was diluted with $H_2O$ (1 mL) and extracted with $CH_2Cl_2$ (3×5 mL). The combined organic extracts were washed with brine (3 mL), dried ($MgSO_4$), and concentrated in vacuo. The residue was purified by preparative HPLC (YMC reverse phase ODS-A-5u 30×250 mm column; flow rate=25 mL/min, 20 to 100% solvent B over 30 min, hold to 40 min, where solvent A=90:10:0.1 $H_2O$:MeOH:TFA and solvent B=90:10:0.1 MeOH:$H_2O$:TFA) to afford the title compound (9.5 mg, 43% yield) as a white solid. [M+H]$^+$=573; $^1$H NMR (500 MHz, CDCl$_3$): δ 9.11 (s, 1H), 8.84 (s, 1H), 8.33 (s, 1H), 7.48 (s, 1H), 7.35 (s, 1H), 7.27 (s, 1H), 6.95 (d, J=2.2 Hz, 1H), 6.87 (d, J=2.2 Hz, 1H), 4.70-7.62

(m, 3H), 4.44 (d, J=8.0 Hz, 2H), 4.26 (t, J=7.7 Hz, 2H), 4.15-4.05 (m, 4H), 2.41-2.34 (m, 2H), 1.35 (d, J=6.1 Hz, 6H), 1.29 (t, J=7.2 Hz, 6H).

Example 164

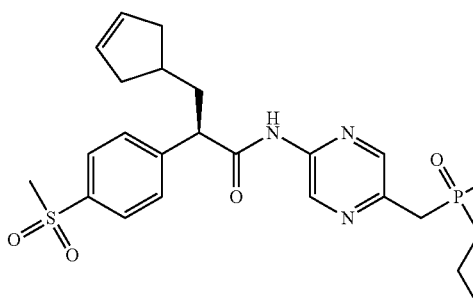

A.

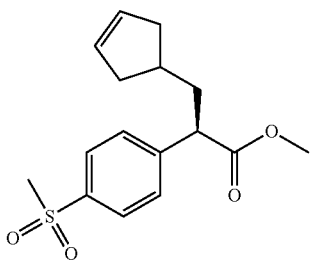

To a −70° C. solution of LDA (2.9 mL, 5.79 mmol, 2N in THF) and DMPU (1.75 mL, 5.79 mmoL) in THF (5.1 mL) was slowly added methyl 2-(4-(methylsulfonyl)phenyl)acetate (1.27 g, 5.55 mmol) (see WO 00/58293), keeping the temperature below −65° C. The reaction was stirred at −70° C. for 1 h and 4-(iodomethyl)cyclopent-1-ene (1.38 g, 6.58 mmol) was added, keeping the temperature below −60° C. The reaction mixture was stirred at −70° C. for 30 min and then was warmed to RT and was stirred for 18 h. The reaction was cooled in an ice bath and was quenched with sat. aqueous NH$_4$Cl (20 mL). Volatiles were removed in vacuo, and the mixture was extracted with EtOAc (2×). The combined organic layer was washed with Brine, dried (MgSO4), filtered, and concentrated in vacuo. The residue was chromatographed (SiO$_2$) to give the Part A compound (880 mg, 51% yield) as a white solid.

B.

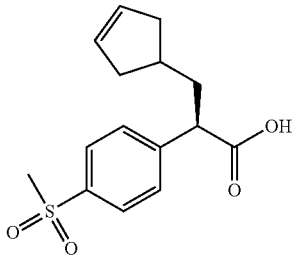

To a 0° C. solution of Part A compound (880 mg, 2.85 mmol) in MeOH (8 mL) and THF (4 mL) was added 1N aqueous NaOH (6 mL). The reaction was slowly warmed to RT and was stirred at RT for 18 h. Volatiles were removed in vacuo, and the reaction was diluted with water, acidified with 2N aqueous HCl (5 mL), and extracted with EtOAc. The organic layer was washed with brine, dried (MgSO$_4$), filtered, and concentrated in vacuo to give the Part B compound (830 mg, 96% yield) as a white solid.

C.

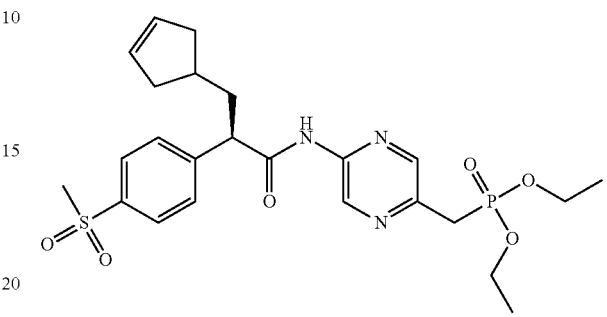

To a 0° C. solution of Part B compound (29.4 mg, 0.1 mmol) in CH$_2$Cl$_2$ (0.5 mL) under Ar was added oxalyl chloride (0.065 mL, 0.13 mmol, 2M in CH$_2$Cl$_2$) and DMF (3 μL). The reaction was stirred at 0° C. for 1 h and was then warmed to RT and was stirred for 2 h. Volatiles were removed in vacuo. To a 0° C. solution of the acid chloride residue in CH$_2$Cl$_2$ (0.5 mL) under Ar was added a solution of pyridine (32.3 μL, 0.4 mmol) in CH$_2$Cl$_2$ (0.25 mL), followed by the addition of Example 7 Part B compound (27 mg, 0.11 mmol). The reaction was a stirred at RT for 18 h and was directly purified by column chromatography (SiO$_2$, O-10% MeOH: CH$_2$Cl$_2$). The desired product and the Part B acid co-eluted, so the mixture was extracted with CH$_2$Cl$_2$. The organic layer was washed with 0.5 N aqueous HCl, water, sat. aqueous NaHCO$_3$, and brine. The organic layer was dried (MgSO$_4$), filtered, and concentrated in vacuo to give the title compound (29 mg, 56% yield) as an oil. [M+H]$^+$=522.2.

Example 165

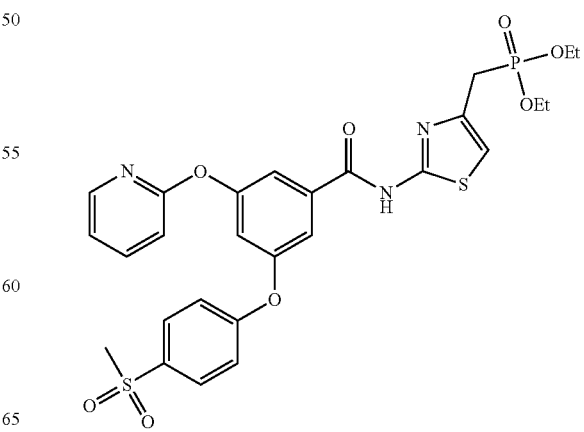

A.

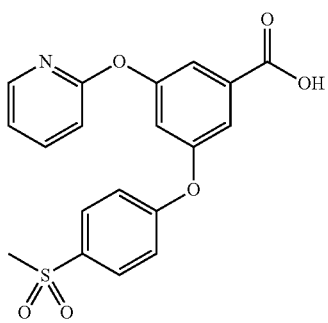

To a solution of Example 26 Part A compound (80 mg, 0.248 mmol) in DMF (1 mL), were added 2-chloropyridine (0.047 mL, 0.496 mmol) and K₂CO₃ (103 mg, 0.745 mmol). The reaction mixture was stirred at 120° C. for 40 h, then was cooled to RT and filtered. The filtrate was diluted with MeOH, then was purified by preparative HPLC (Phenomenex Luna AXIA 30×100 mm column; detection at 220 nm; flow rate=40 mL/min.; continuous gradient from 80% A to 100% B over 10 min., where A=10% MeOH/90% H₂O/0.1% TFA and B=90% MeOH/10% H₂O/0.1% TFA) to give Part A compound (26 mg, 27%) as a white solid.

B.

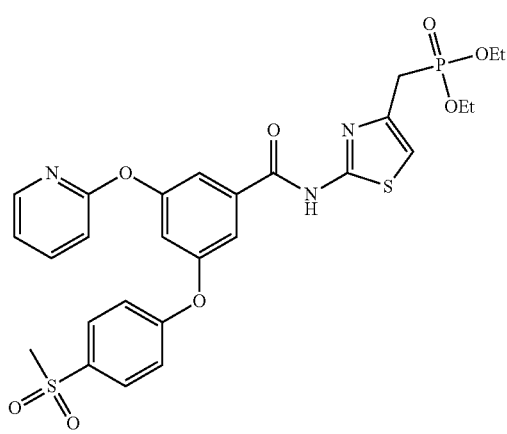 [SMILES: CCOP(=O)(Cc1csc(NC(=O)c2cc(Oc3ccc(S(C)(=O)=O)cc3)cc(Oc3ncccn3)c2)n1)OCC]

To a solution of Part A compound (26 mg, 0.067 mmol) in DMF (1 mL), was added Example 13 Part E compound (33.8 mg, 0.135 mmol), EDCI (25.9 mg, 0.135 mmol), HOBT (20.66 mg, 0.135 mmol), and DIPEA (0.035 mL, 0.202 mmol). The reaction mixture was stirred at RT for 2 days. The reaction mixture was purified directly by preparative HPLC (Phenomenex Luna AXIA 30×100 mm column; detection at 220 nm; flow rate=40 mL/min.; continuous gradient from 70% A to 100% B over 10 min., where A=10% MeOH/90% H₂O/0.1% TFA and B=90% MeOH/10% H₂O/0.1% TFA) to give the title compound (11 mg, 26% yield) as a yellow oil. [M+H]⁺=618.3; ¹H NMR (500 MHz, CDCl₃): δ 8.24 (1H, d, J=4.95 Hz), 7.95 (2H, d, J=8.80 Hz), 7.78-7.84 (2H, m), 7.71 (1H, s), 7.20-7.25 (3H, m), 7.13 (1H, dd, J=6.87, 4.67 Hz), 7.07 (1H, d, J=8.25 Hz), 7.04 (1H, d, J=3.85 Hz), 4.10-4.21 (4H, m), 3.34 (2H, d, J=21.44 Hz), 3.07 (3H, s), 1.32 (6H, t, J=6.87 Hz).

Example 166

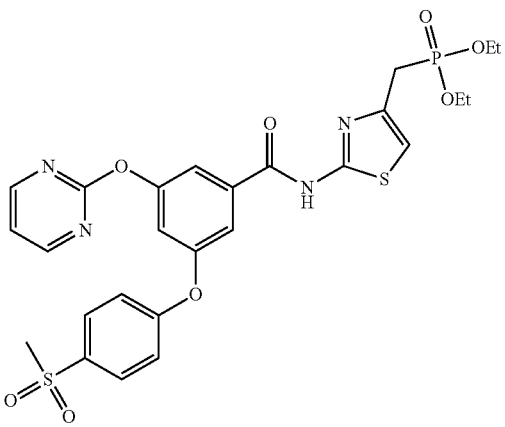

The title compound (5 mg, 24% yield, yellow oil) was prepared from 2-chloropyrimidine following the same general procedure as used for the synthesis of Example 165. [M+H]⁺=619.3; ¹H NMR (500 MHz, CDCl₃): δ 8.63 (2H, d, J=4.95 Hz), 7.88-7.99 (3H, m), 7.78 (1H, s), 7.27-7.28 (1H, m), 7.24 (2H, d, J=9.35 Hz), 7.15 (1H, t, J=4.95 Hz), 7.05 (1H, d, J=3.30 Hz), 4.11-4.21 (4H, m), 3.34 (2H, d, J=21.44 Hz), 3.08 (3H, s), 1.32 (6H, t, J=7.15 Hz).

Example 167

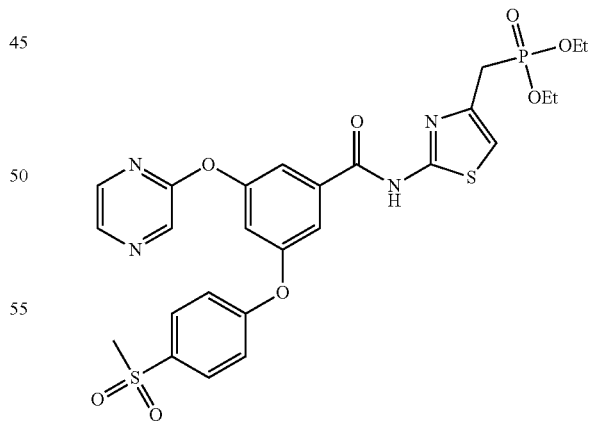

The title compound (11.5 mg, 30% yield, yellow solid) was prepared from 2-chloropyrazine following the same general procedure as used for the synthesis of Example 165. [M+H]⁺=619.3; ¹H NMR (500 MHz, CDCl₃): δ 8.54 (1H, s), 8.37 (1H, d, J=2.75 Hz), 8.16 (1H, s), 7.96 (2H, d, J=8.80 Hz), 7.89 (1H, s), 7.77 (1H, s), 7.25-7.27 (1H, m), 7.24 (2H, d, J=8.80 Hz), 7.05 (1H, d, J=3.85 Hz), 4.10-4.21 (4H, m), 3.34 (2H, d, J=21.44 Hz), 3.08 (3H, s), 1.32 (6H, t, J=6.87 Hz).

Example 168

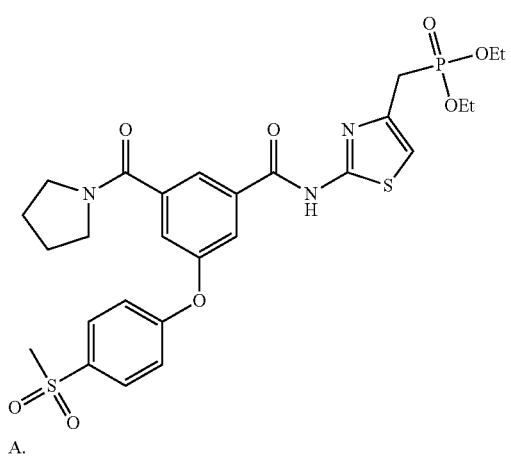

A.

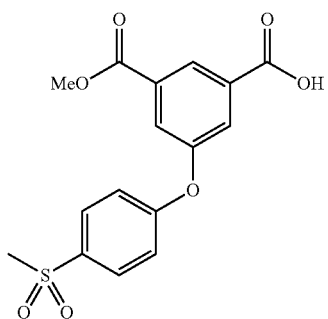

To a solution of dimethyl 5-hydroxyisophthalate (198 mg, 0.942 mmol) in DMF (2 mL), was added 1-fluoro-4-(methylsulfonyl)benzene (197 mg, 1.130 mmol) and K₂CO₃ (391 mg, 2.83 mmol). The reaction mixture was stirred at 120° C. for 41 h, then was cooled to RT and filtered. The filtrate was diluted with MeOH, then was purified by preparative HPLC (Phenomenex Luna AXIA 30×100 mm column; detection at 220 nm; flow rate=40 mL/min.; continuous gradient from 80% A to 100% B over 10 min., where A=10% MeOH/90% H₂O/0.1% TFA and B=90% MeOH/10% H₂O/0.1% TFA) to provide Part A compound (176 mg, 53% yield) as a white solid. [M+H]⁺=351.2.

B.

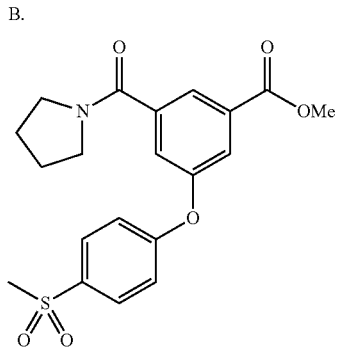

To a solution of Part A compound (85 mg, 0.243 mmol) in CH₂Cl₂ (1.0 ml) was added oxalyl chloride (0.243 mL, 0.485 mmol) and DMF (5.64 µL, 0.073 mmol). The mixture was stirred at RT for 1 h, then was concentrated in vacuo. The crude acid chloride was taken up in THF (1.0 mL), and pyrrolidine (0.041 mL, 0.485 mmol) and pyridine (0.059 mL, 0.728 mmol) were added. The reaction mixture was stirred at RT for 3 h, then was diluted with EtOAc (10 mL), washed with H₂O and brine, dried (MgSO₄), and concentrated in vacuo. The residue was purified by preparative HPLC (Phenomenex Luna AXIA 30×100 mm column; detection at 220 nm; flow rate=40 mL/min.; continuous gradient from 70% A to 100% B over 10 min., where A=10% MeOH/90% H₂O/0.1% TFA and B=90% MeOH/10% H₂O/0.1% TFA) to provide Part B compound (93 mg, 95% yield) as a colorless oil. [M+H]⁺=404.3.

C.

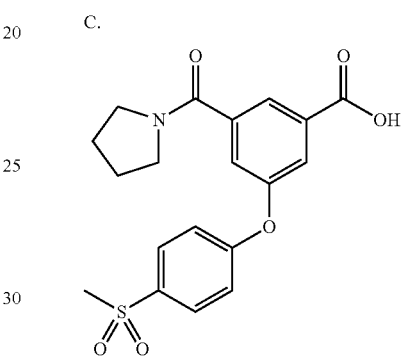

To a solution of art B compound (8.5 mg, 0.021 mmol) in THF (1 mL), was added 1N aqueous NaOH (0.063 mL, 0.063 mmol). The reaction mixture was stirred at RT for 15 h and was diluted with EtOAc (6 mL), acidified with 1N aqueous HCl (0.050 mL), and separated. The organic layer was washed with brine, dried (MgSO₄), and concentrated in vacuo to give crude Part C compound (10 mg) as a white solid, which was used in the next step without further purification. [M+H]⁺=390.2.

D.

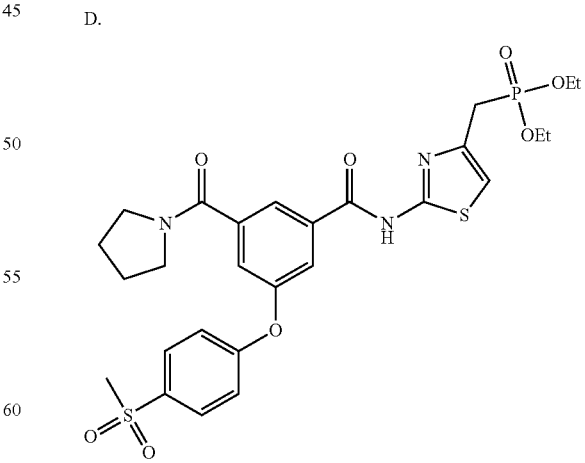

To a solution of Part C compound (10 mg, 0.026 mmol) in DMF (1 mL), was added Example 13 Part E compound (12.9 mg, 0.051 mmol), EDCI (9.9 mg, 0.051 mmol), HOBT (7.9 mg, 0.051 mmol), and DIPEA (0.013 mL, 0.077 mmol). The reaction mixture was stirred at RT for 4 days, then was purified directly by preparative HPLC (Phenomenex Luna AXIA 30×100 mm column; detection at 220 nm; flow rate=40 mL/min.; continuous gradient from 70% A to 100% B over 10 min., where A=10% MeOH/90% H₂O/0.1% TFA and B=90% MeOH/10% H₂O/0.1% TFA) to provide the title compound (3 mg, 23% yield over 2 steps) as a white solid. [M+H]⁺=622.3; ¹H NMR (500 MHz, CDCl₃): δ 8.18 (1H, s), 7.89-8.00 (3H, m), 7.55 (1H, s), 7.19 (2H, d, J=8.80 Hz), 7.05 (1H, d, J=3.30 Hz), 4.05-4.23 (4H, m), 3.50-3.74 (4H, m), 3.35 (2H, d, J=21.44 Hz), 3.09 (3H, s), 1.85-2.04 (4H, m), 1.32 (6H, t, J=7.15 Hz).

Example 169

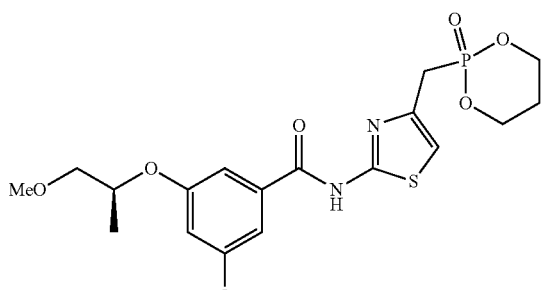

A.

To a solution of Example 13 Part A compound (377 mg, 1.08 mmol) in CH₂Cl₂ (5 mL) at RT under Ar was added TMSBr (0.307 mL, 2.37 mmol). After stirring at RT for 15 h, the reaction mixture was concentrated in vacuo under scrupulously dry conditions to provide Part A compound as a colorless oil, which was used in the next step without further purification.

B.

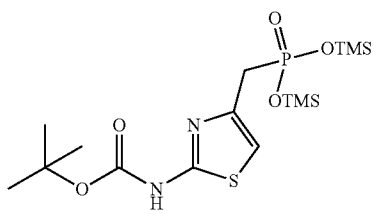

To a solution of Part A compound in dry CH₂Cl₂ (5 mL; protected from the atmosphere by a CaCl₂-filled drying tube) was added oxalyl chloride (0.207 mL, 2.37 mmol) and DMF (8 μL, 0.1 mmol). Considerable foaming was observed, eventually resulting in the formation of a beige precipitate. After stirring at RT for 3 h, the reaction mixture was concentrated in vacuo and the residue was taken up in THF (12 mL) and cooled to –65° C. under Ar. To this slurry was added a solution of 1,3-propanediol (0.086 mL, 1.18 mmol) in MeCN (6 mL) over 2 min and stirred for 5 min at –65° C. Pyridine (0.183 mL, 2.26 mmol) was then added over 1 min, and the reaction mixture was allowed to warm to RT and stirred for 16 h at RT. The mixture was partitioned between EtOAc and 5% aqueous NaHSO₄ (25 mL each). The organic phase was dried (Na₂SO₄) and concentrated in vacuo. The residue was purified by preparative HPLC (Phenomenex Luna 21.2×100 mm column; detection at 254 nm; flow rate=20 mL/min.; continuous gradient from 0% A to 100% B over 10 min, where A=10% MeCN/90% H₂O/0.1% TFA and B=90% MeCN/10% H₂O/0.1% TFA) to provide Part B compound (71 mg, 20% yield) as a white amorphous solid. [M+H]⁺=335.

C.

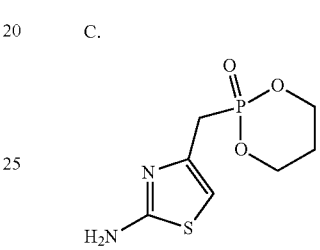

To a stirred solution of Part B compound (71 mg, 0.21 mmol) in dry CH₂Cl₂ (2 mL; protected from the atmosphere by a CaCl₂-filled drying tube) at RT was added TFA (0.5 mL). The reaction was stirred for 4 h at RT, then was concentrated in vacuo. The residue was dissolved in MeOH and eluted through a StratoSpheres™ SPE PL-HCO₃ MP ion exchange cartridge (0.9 meq capacity) with MeOH. Concentration of the eluent in vacuo provided Part C compound as a white amorphous solid (43 mg, 86% yield). [M+H]⁺=235.

D.

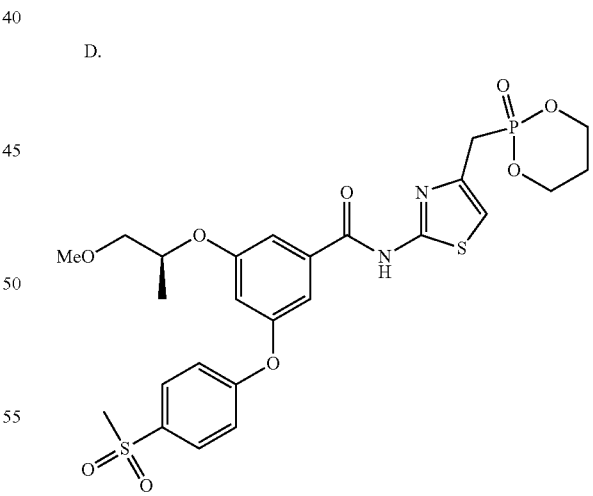

To a stirred slurry of Example 26C compound (69 mg, 0.18 mmol) in CH₂Cl₂ (2 mL) at RT under Ar were successively added HOAt (25 mg, 0.18 mmol) and EDC (35 mg, 0.18 mmol). A clear solution formed within 5 min. After 30 min, this solution was added to a slurry of Part C compound in THF (2 mL) at RT under Ar, followed by iPr₂NEt (0.016 mL, 0.43 mmol) and DMAP (2.6 mg, 0.02 mmol). After stirring for 18 h at RT, analytical HPLC indicated that no product had formed. The reaction mixture was concentrated in vacuo and taken up in dry MeCN (3 mL), then was heated to reflux under Ar, whereupon a solution formed. After 2 h at reflux, analytical HPLC indicated that almost all the amine had been consumed. The reaction mixture was cooled to RT and concentrated in vacuo. The residue was partitioned between EtOAc and saturated aqueous NaHCO$_3$ (20 mL each). The organic phase was washed with brine and aqueous 10% NaHSO$_3$, dried (Na$_2$SO$_4$) and concentrated in vacuo. Purification of the oily residue by preparative HPLC (Phenomenex Luna 21.2× 100 mm column; detection at 220 nm; flow rate=20 mL/min.; continuous gradient from 0% A to 100% B over 10 min., where A=10% MeCN/90% H$_2$O/0.1% TFA and B=90% MeCN/10% H$_2$O/0.1% TFA) provided the title compound (35 mg, 28% yield) as a white amorphous solid. [M+H]$^+$=597. $^1$H NMR (400 MHz, CDCl$_3$): δ 7.92 (2H, d, J=7.1 Hz), 7.59 (1H, s), 7.42 (1H, s), 7.17 (2H, d, J=8.80 Hz), 6.85 (2H, m), 4.73 (1H, m), 4.35 (2H, m), 4.12 (2H, m), 3.66-3.51 (3H, m), 3.41 (3H, s), 3.07 (3H, s), 1.92-1.72 (2H, m), 1.34 (3H, d, J=6.0 Hz).

ASSAYS FOR GLUCOKINASE ACTIVATION

The compounds of formula I of the invention activate glucokinase. Assays which may be used in testing the compounds of formula I of the invention in activating glucokinase are known in the art such as disclosed in U.S. Pat. Nos. 6,320,050, 6,384,200 and 6,610,846 and WO 2004/052869 and in Castellano, A. L., Dong, H., Fyfe, M. C. T., Gardner, L. S., Kamikozawa, Y. et al. (2005) "Glucokinase activating ureas", *Bioorg. Med. Chem. Letters*, 15:1501-1504, and Grimsby, J., Sarabu, R., Corbett, W. L., Haynes, N-E., Bizzarro, F. T., Coffey, J. W., Guertin, K. R., Hilliard, D. W., Kester, R. F., Mahaney, P. E., Marcus, L., Qi, L., Spence, C. L., Tengi, J., Magnuson, M. A., Chu, C. A., Dvorozniak, M. T., Matschinsky, F. M., Grippo, J. F. (2003) "Allosteric Activators of Glucokinase: Potential Role in Diabetes Therapy", *Science*, 301:370-373.

In general, compounds of the present invention, such as particular compounds disclosed in the following examples, have been identified to enhance the activity of glucokinase at concentrations equivalent to, or more potently than, 100 μM, preferably 10 μM, more preferably 1 μM, thereby demonstrating compounds of the present invention as especially effective enhancers of activity of glucokinase. Potencies can be calculated and expressed as either EC$_{50}$ (concentration to achieve 50% of full activation) and/or the maximum percentage activation above background, and refer to activity measured employing the assay system described above.

ASSAY AND BIOLOGICAL DATA

Compounds of formula I of the invention, including compounds described in the Examples hereof, have been tested in the following assay and have shown to be activators of glucokinase.

Glucokinase Tandem Enzymatic Assay

Enzymatic activity of human glucokinase (GK) was measured by incubating GK, ATP, and glucose for discrete time periods followed by quenching with EDTA (ethylenediamine tetra-acetic acid). Relative amounts of product glucose-6-phosphate (G6P) were measured by then running a detection assay using G6P dehydrogenase and measuring the conversion of ThioNAD (thio-nicotinamide adenine dinucleotide) to ThioNADH (thio-dihydronicotinamide adenine dinucleotide) at a wavelength of 405 nm. This 'uncoupled' enzymatic reaction is denoted as the GK 'tandem' assay. Activation of GK by compounds can be assessed using this assay. The GK tandem assay protocol described below was followed using a range of activator compound concentrations from 0 to 100 μM at 5 and 12 mM of glucose. Human full-length glucokinase (GK, 15 nM) was incubated with 5 or 12 mM glucose in a 384 well black microtiter plate with a clear bottom. To initiate the GK reaction, magnesium-ATP (3 mM final concentration) was added to GK in buffer (final buffer conditions of 25 mM HEPES buffer, pH 7.1, containing 1 mM dithiothreitol and 5% DMSO). The total reaction volume was 20 μL. The reaction was allowed to proceed for ten minutes and was then quenched with 5 μL EDTA; 45 mM final). The components of the detection reaction, ThioNAD and G6PDH (glucose-6-phosphate dehydrogenase) (final concentrations of 650 μM and 3.33 Units, respectively), were then added together in a volume of 25 μL, (to give a total volume of 50 μL). Absorbance measurements were made at 405 nm on a Spectramax Plus 384 absorbance plate reader (Molecular Devices). Absorbance was read, background glucose-6-phosphate levels were subtracted, after which activation was calculated as a percentage of control activity. Control activity was determined using GK in the presence of vehicle (DMSO), with background glucose-6-phosphate subtracted. Background glucose-6-phosphate was determined by pre-quenching GK with EDTA prior to reaction initiation with ATP.

Expression and Purification of Human GK

Full-length human hepatic GK (untagged) was expressed in BL21 STAR (DE3)pLysS cells (Invitrogen) at 25° C. as described by Mookhtiar et al. (1). The protein was purified essentially as described by Lange (2) with a slight modification. Briefly, cell pellets were lysed via three rounds of freezing and thawing, centrifuged at 15000 g for clarification, and precipitated with 40-65% (NH4)2SO4. The resulting pellet was resuspended in buffer, dialyzed, and applied directly to a Q-Sepharose (Sigma) column followed by elution with a linear 100-600 mM KCl gradient. GK containing fractions were pooled, dialyzed overnight vs. 25 mM Hepes pH 7.2/1 mM MgCl2/1 mM EDTA/0.1 M KCl/1 mM DTT, then dialyzed again with same buffer with 10% glycerol added.

REFERENCES

1. Mookhtiar, K. A., Kalinowski, S. S., Brown, K. S., Tsay, Y. H., Smith-Monroy, C., and Robinson, G. W. (1996) "Heterologous expression and characterization of rat liver glucokinase regulatory protein", *Diabetes*, 45:1670-1677.
2. Lange, A. J., Xu, L. Z., Van Poelwijk, F., Lin, K., Granner, D. K., and Pilkis, S. J. (1991) "Expression and site-directed mutagenesis of hepatic glucokinase", *Biochem. J.*, 277: 159-163.

Biological data for select Examples are shown in the table below.

| Example No. | EC$_{50}$ (nM) with Human Glucokinase @ 12 mM Glucose |
|---|---|
| 169 | 9 |
| 51 | 15 |
| 82 | 18 |
| 137 | 21 |
| 50 | 22 |
| 122 | 23 |
| 145 | 24 |
| 33 | 26 |

-continued

| Example No. | EC$_{50}$ (nM) with Human Glucokinase @ 12 mM Glucose |
|---|---|
| 37 | 34 |
| 163 | 38 |
| 54 | 49 |
| 32 | 65 |
| 29 | 98 |
| 148 | 178 |
| 22 | 402 |
| 112 | 428 |
| 113 | 437 |
| 139 | 467 |
| 116 | 469 |
| 134 | 476 |
| 84 | 492 |
| 56 | 534 |
| 44 | 564 |

For other Examples, the EC$_{50}$ values could not be calculated from the activation curves, so the maximal activation data (expressed as a % of basal activation) for some select Examples are shown in the table below.

| Example No. | Maximal activation (%) Human Glucokinase @ 12 mM Glucose |
|---|---|
| 121 | 126% |
| 65 | 162% |
| 35 | 133% |
| 79 | 133% |
| 86 | 141% |
| 123 | 135% |
| 74 | 142% |
| 23 | 150% |

In Vivo Studies: Oral Glucose Tolerance Test (OGTT)

Oral glucose tolerance tests were carried out on male DIO (diet-induced obese) C57BL/6J mice fed a high fat diet (60% kcal from fat) for 26 weeks prior to experimentation. Mice were fasted overnight before use for experiments. A test compound or vehicle (either: 1) 40% PEG 400+10% Cremophore+50% water or 2) 10% dimethyl acetamide+10% ethanol+10% Cremophore+70% water) was given orally 60 min before oral administration of a glucose solution at a dose of 2 g/kg body weight (oral glucose tolerance test; OGTT). Blood glucose levels were measured from tail-bled samples taken at different time points before and after administration of glucose (time course of 2 hours). A time curve of the blood glucose was generated and the change from baseline area-under-the curve (ΔAUC) from 0-120 min was calculated (the time glucose administration being time zero).

The examples in the table below reduced glucose AUC levels in an OGTT test in DIO mice as described above.

| Example No. | Reduction in Glucose AUC at 30 mg/kg dose |
|---|---|
| 37 | 88% |
| 148 | 60% |
| 145 | 71% |
| 54 | 68-82% |
| 29 | 66-78% |
| 44 | 62-80 |
| 32 | 79% @ 30 μmol/kg |
| 82 | 44% @ 10 μmol/kg |

What is claimed is:

1. A method for modulating glucokinase activity, which comprises administering to a mammalian patient in need thereof a therapeutically effective amount of a compound having the structure:

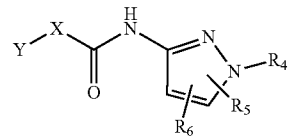

or a pharmaceutically acceptable salt thereof, wherein:
R$_4$ is selected from the group consisting of:
—(CH$_2$)$_n$—Z—(CH$_2$)$_m$—PO(OR$_7$)(OR$_8$),
—(CH$_2$)$_n$Z—(CH$_2$)$_m$—PO(OR$_7$)R$_9$, and
—(CH$_2$)$_n$Z—(CH$_2$)$_m$—PO—(R$_9$)R$_{10}$;
R$_7$ and R$_8$ are independently alkyl, or
R$_7$ and R$_8$ can be cyclized into a ring

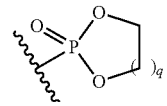

where q=1, 2, or 3;
R$_9$ and R$_{10}$ are independently selected from the group consisting of alkyl, aryl, arylalkyl, heteroaryl, and heteroarylalkyl;
or R$_9$ and R$_{10}$ can be cyclized into a ring

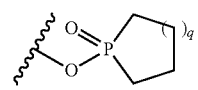

where q=1, 2, or 3, or

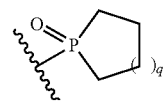

where q=1, 2, or 3;
or R$_7$ and R$_9$ can be cyclized into a ring

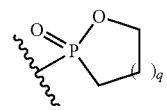

where q=1, 2, or 3 or

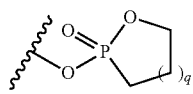

where q=1, 2, or 3;

Z is a single bond, alkylene, or alkenylene wherein said alkylene or alkenylene may be optionally substituted with hydroxy, alkoxy, aminoalkyl, aminoaralkyl, aminoheteroaralkyl, aminoaryl, aminoheteroaryl, or carboxy;

m is zero, 1, or 2;

n is 1 or 2;

$R_5$ and $R_6$ are independently selected from the group consisting of hydrogen, alkyl, halogen and carboxy;

X is a single bond;

Y is $R_3$—$(CH_2)_s$—;

s is zero; and $R_3$ is phenyl substituted with zero, 1, or 2 substituent groups independently selected:
  (a) —$OR^a$ wherein $R^a$ is:
    (i) alkyl, wherein said alkyl may be further substituted with at least one of halo, alkoxy or phenyl;
    (ii) phenyl, optionally substituted with —$SO_2R^c$ wherein $R^c$ is alkyl;
    (iii) a 4- to 7-membered heterocyclo optionally substituted with —$SO_2R^c$ wherein $R^c$ is alkyl;
    (iv) pyridinyl or pyrazinyl, optionally substituted with —C(=O)$NR^dR^b$ or —$SO_2R^c$ wherein $R^d$ and $R^b$ may join together with the N to which they are attached to form a 4- to 7-membered heterocyclo and $R^c$ is alkyl; and/or
  (b) —C(=O)$R^a$ wherein $R^a$ is a 4- to 7-membered heterocyclo.

2. The method according to claim 1 where, in said compound or a pharmaceutically acceptable salt, thereof:
  $R_3$ is phenyl substituted with zero, 1, or 2 substituent groups selected from —$OR^a$ wherein each $R^a$ is independently selected from:
    (i) alkyl, wherein said alkyl may be further substituted with at least one of halo, alkoxy or phenyl;
    (ii) phenyl, optionally substituted with —$SO_2R^c$ wherein $R^c$ is alkyl; or
    (iii) pyridinyl or pyrazinyl, optionally substituted with —C(=O)$NR^dR^b$ or —$SO_2R^c$ wherein $R^d$ and $R^b$ may join together with the N to which they are attached to form a 4- to 7-membered heterocyclo and $R^c$ is alkyl.

3. The method according to claim 2 where, in said compound or a pharmaceutically acceptable salt thereof, $R_4$ is —$(CH_2)_nZ$—$(CH_2)_m$—$PO(OR_7)R_9$.

4. The method according to claim 2 where, in said compound or a pharmaceutically acceptable salt thereof, $R_4$ is —$(CH_2)_nZ$—$(CH_2)_m$—PO—$(R_9)R_{10}$.

5. The method according to claim 2 where, in said compound or a pharmaceutically acceptable salt thereof, $R_4$ is —$(CH_2)_n$—Z—$(CH_2)_m$—PO($OR_7$)($OR_8$).

6. The method according to claim 5 where, in said compound or a pharmaceutically acceptable salt thereof,
  Z is a single bond;
  m is zero;
  n is 1 or 2;
  $R_7$ is alkyl; and
  $R_8$ is alkyl.

7. The method according to claim 5 wherein said compound has the structure:

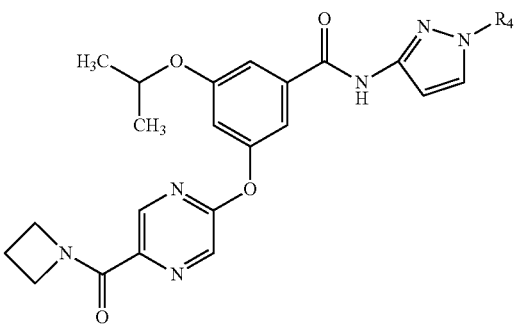

or a pharmaceutically acceptable salt thereof.

8. The method according to claim 7 where, in said compound or a pharmaceutically acceptable salt thereof, $R_4$ is —$(CH_2)_nZ$—$(CH_2)_m$—$PO(OR_7)R_9$.

9. The method according to claim 7 where, in said compound or a pharmaceutically acceptable salt thereof, $R_4$ is —$(CH_2)_nZ$—$(CH_2)_m$—PO—$(R_9)R_{10}$.

10. The method according to claim 7 where, in said compound or a pharmaceutically acceptable salt thereof, $R_4$ is —$(CH_2)_n$—Z—$(CH_2)_m$—PO($OR_7$)($OR_8$).

11. The method according to claim 10 where, in said compound or a pharmaceutically acceptable salt thereof,
  Z is a single bond;
  m is zero;
  n is 1 or 2;
  $R_7$ is alkyl; and
  $R_8$ is alkyl.

12. The method according to claim 1 wherein said disease is Type II diabetes.

13. The method according to claim 1 where, in said compound or a pharmaceutically acceptable salt thereof, Y—X—CO— is:

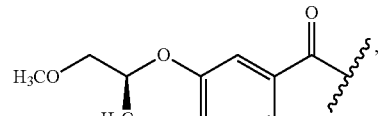

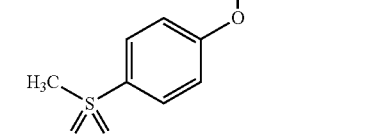

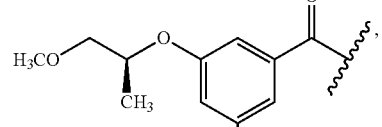

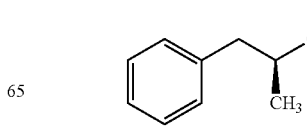

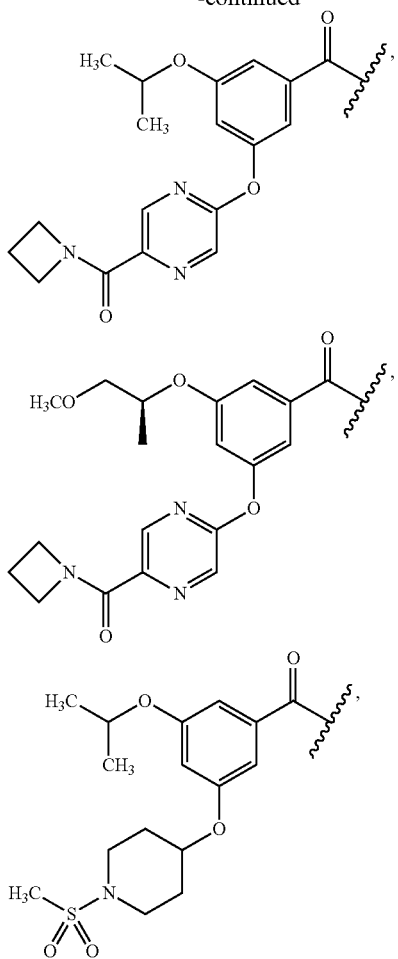
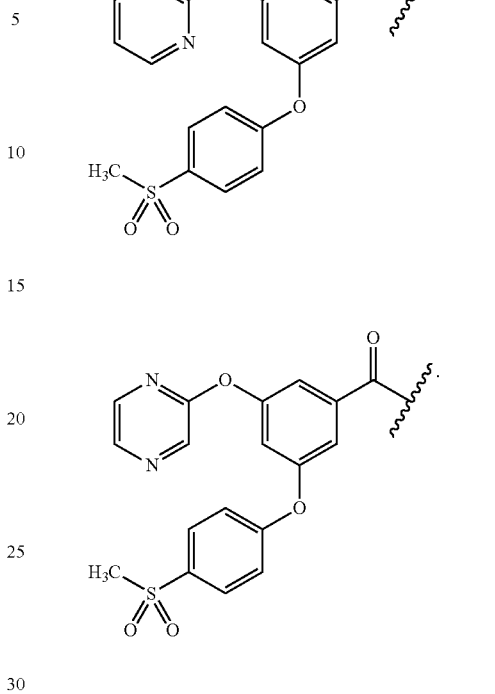
14. The method according to claim 1 wherein said compound has the structure:
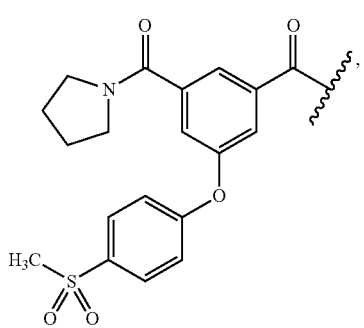
or a pharmaceutically acceptable salt thereof, wherein:
wherein $R_4$ is:
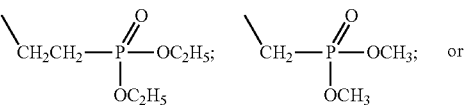
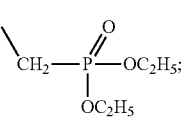
and $R^a$ is $C_{1-4}$-alkyl.

15. The method according to claim 1, wherein said compound is:

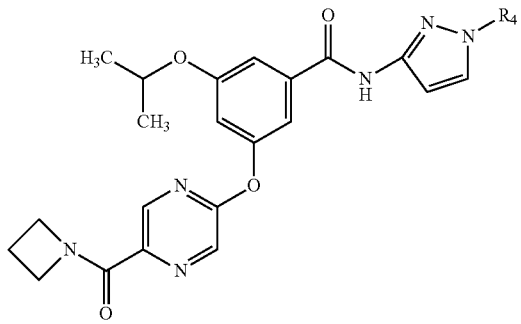

or a pharmaceutically acceptable salt thereof, wherein $R_4$ is:

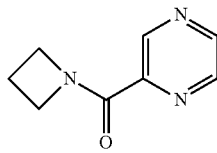

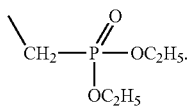

16. The method according to claim 1 wherein said compound is:

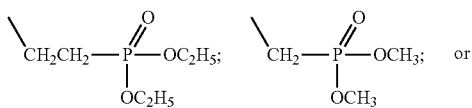

or a pharmaceutically acceptable salt thereof.

17. A method for modulating glucokinase activity, which comprises administering to a human in need thereof a compound having the structure:

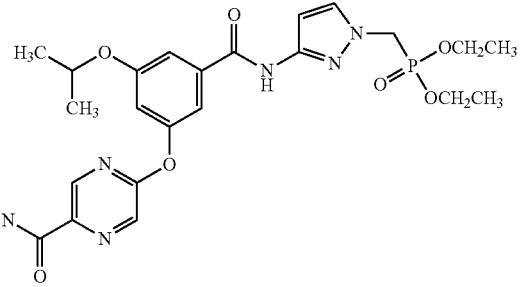

or a pharmaceutically acceptable salt thereof.

18. The method of claim 1 wherein a therapeutically effective amount of said compound is administered.

* * * * *

UNITED STATES PATENT AND TRADEMARK OFFICE
CERTIFICATE OF CORRECTION

| | | |
|---|---|---|
| PATENT NO. | : 8,614,332 B2 | Page 1 of 1 |
| APPLICATION NO. | : 13/397123 | |
| DATED | : December 24, 2013 | |
| INVENTOR(S) | : Denis E. Ryono et al. | |

It is certified that error appears in the above-identified patent and that said Letters Patent is hereby corrected as shown below:

<u>In the Claims:</u>

Claim 7:

Column 280, line 1, change "claim 5" to -- claim 1 --.

Claim 18:

Column 284, line 36, change "claim 1" to -- claim 17 --.

Signed and Sealed this
Second Day of September, 2014

Michelle K. Lee
*Deputy Director of the United States Patent and Trademark Office*